US012624081B2

(12) United States Patent (10) Patent No.: US 12,624,081 B2
Posey et al. (45) Date of Patent: *May 12, 2026

(54) Tn-MUC1 CHIMERIC ANTIGEN RECEPTOR (CAR) T CELL THERAPY

(71) Applicant: THE TRUSTEES OF THE UNIVERSITY OF PENNSYLVANIA, Philadelphia, PA (US)

(72) Inventors: Avery D. Posey, Philadelphia, PA (US); Carl H. June, Merion Station, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 1296 days.

This patent is subject to a terminal disclaimer.

(21) Appl. No.: 17/370,655

(22) Filed: Jul. 8, 2021

(65) Prior Publication Data

US 2021/0338733 A1 Nov. 4, 2021

Related U.S. Application Data

(63) Continuation of application No. 16/830,554, filed on Mar. 26, 2020, now Pat. No. 11,090,336.

(60) Provisional application No. 62/881,269, filed on Jul. 31, 2019, provisional application No. 62/824,532, filed on Mar. 27, 2019.

(51) Int. Cl.

| | |
|---|---|
| *C07K 14/725* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *A61K 31/675* | (2006.01) |
| *A61K 31/7076* | (2006.01) |
| *A61K 45/06* | (2006.01) |

(52) U.S. Cl.
CPC .......... *C07K 14/7051* (2013.01); *A61K 40/11* (2025.01); *A61K 40/31* (2025.01); *A61K 40/4211* (2025.01); *A61K 40/4257* (2025.01); *A61P 35/00* (2018.01); *C07K 14/70507* (2013.01); *C07K 14/70517* (2013.01); *C07K 14/70596* (2013.01); *A61K 31/675* (2013.01); *A61K 31/7076* (2013.01); *A61K 45/06* (2013.01); *A61K 2239/31* (2023.05); *A61K 2239/38* (2023.05); *A61K 2239/48* (2023.05); *A61K 2239/49* (2023.05); *A61K 2239/54* (2023.05); *A61K 2239/55* (2023.05); *A61K 2239/59* (2023.05)

(58) Field of Classification Search
CPC ........................... A61K 35/17; C07K 14/7051
See application file for complete search history.

(56) References Cited

U.S. PATENT DOCUMENTS

| | | | |
|---|---|---|---|
| 4,444,887 | A | 4/1984 | Hoffmann |
| 4,716,111 | A | 12/1987 | Osband et al. |
| 4,797,368 | A | 1/1989 | Carter et al. |
| 4,956,778 | A | 9/1990 | Naito |
| 5,091,513 | A | 2/1992 | Huston et al. |
| 5,132,405 | A | 7/1992 | Huston et al. |
| 5,139,941 | A | 8/1992 | Muzyczka et al. |
| 5,350,674 | A | 9/1994 | Boenisch et al. |
| 5,413,923 | A | 5/1995 | Kucherlapati et al. |
| 5,545,806 | A | 8/1996 | Lonberg et al. |
| 5,569,825 | A | 10/1996 | Lonberg et al. |
| 5,585,362 | A | 12/1996 | Wilson et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,814,318 | A | 9/1998 | Lonberg et al. |
| 5,858,358 | A | 1/1999 | June et al. |
| 5,883,223 | A | 3/1999 | Gray |
| 5,939,598 | A | 8/1999 | Kucherlapati et al. |
| 5,993,434 | A | 11/1999 | Dev et al. |
| 5,994,136 | A | 11/1999 | Naldini et al. |
| 6,013,516 | A | 1/2000 | Verma et al. |
| 6,181,964 | B1 | 1/2001 | Hofmann et al. |
| 6,233,482 | B1 | 5/2001 | Hofmann et al. |
| 6,241,701 | B1 | 6/2001 | Hofmann et al. |
| 6,326,193 | B1 | 12/2001 | Liu et al. |
| 6,352,694 | B1 | 3/2002 | June et al. |
| 6,516,223 | B2 | 2/2003 | Hofmann et al. |
| 6,534,055 | B1 | 3/2003 | June et al. |
| 6,567,694 | B2 | 5/2003 | Hayakawa et al. |
| 6,678,556 | B1 | 1/2004 | Nolan et al. |

(Continued)

FOREIGN PATENT DOCUMENTS

| | | |
|---|---|---|
| CN | 110526977 | 12/2019 |
| WO | 1990013644 | 11/1990 |

(Continued)

OTHER PUBLICATIONS

Bridgeman et al. (J.Immunol. Jun. 15, 2010; 184 (12): 6938-49).*

(Continued)

*Primary Examiner* — David J Blanchard

(74) *Attorney, Agent, or Firm* — Saul Ewing LLP; Alireza Behrooz; Kathryn Doyle

(57) ABSTRACT

<section type="abstract">Various TnMUC1-specific chimeric antigen receptors (CARs), nucleic acids encoding the same, and methods of using the same, are provided. Compositions and methods comprising a TnMUC1-specific CAR for treating MUC1-associated cancer in a subject in need thereof are provided.</section>

14 Claims, 39 Drawing Sheets

Specification includes a Sequence Listing.

(56)  References Cited

U.S. PATENT DOCUMENTS

| | | | |
|---|---|---|---|
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,171,264 | B1 | 1/2007 | Hofmann et al. |
| 7,172,869 | B2 | 2/2007 | June et al. |
| 7,173,116 | B2 | 2/2007 | Fewell et al. |
| 7,175,843 | B2 | 2/2007 | June et al. |
| 7,232,566 | B2 | 6/2007 | June et al. |
| 7,754,482 | B2 | 7/2010 | Riley et al. |
| 8,722,400 | B2 | 5/2014 | Riley et al. |
| 9,555,105 | B2 | 1/2017 | Riley et al. |
| 9,783,591 | B2 * | 10/2017 | June ..................... C12N 15/85 |
| 9,845,362 | B2 | 12/2017 | Mukherjee |
| 9,855,298 | B2 | 1/2018 | Bot et al. |
| 2004/0014645 | A1 | 1/2004 | Draghia-Akli et al. |
| 2004/0059285 | A1 | 3/2004 | Mathiesen et al. |
| 2004/0092907 | A1 | 5/2004 | Mathiesen et al. |
| 2005/0052630 | A1 | 3/2005 | Smith et al. |
| 2005/0070841 | A1 | 3/2005 | Mathiesen et al. |
| 2005/0196754 | A1 | 9/2005 | Drmanac et al. |
| 2006/0121005 | A1 | 6/2006 | Berenson et al. |
| 2007/0128708 | A1 | 6/2007 | Gamelin et al. |
| 2014/0050708 | A1 | 2/2014 | Powell |
| 2014/0219975 | A1 * | 8/2014 | June ..................... A61P 35/00 435/372.3 |
| 2014/0322212 | A1 | 10/2014 | Brogdon et al. |
| 2016/0130357 | A1 | 5/2016 | Mukherjee |
| 2017/0166652 | A1 | 6/2017 | Schreiber et al. |
| 2017/0204177 | A1 | 7/2017 | Wang et al. |
| 2017/0267778 | A1 | 9/2017 | Van Berkel et al. |
| 2018/0009895 | A1 | 1/2018 | Smith et al. |
| 2019/0055297 | A1 * | 2/2019 | Zhao ..................... C07K 19/00 |
| 2019/0216851 | A1 | 7/2019 | Xiao |
| 2019/0233511 | A1 | 8/2019 | Wang et al. |

FOREIGN PATENT DOCUMENTS

| | | | | |
|---|---|---|---|---|
| WO | 9110741 | A1 | 7/1991 | |
| WO | 9633735 | A1 | 10/1996 | |
| WO | 9634096 | A1 | 10/1996 | |
| WO | 9816654 | A1 | 4/1998 | |
| WO | 9824893 | A2 | 6/1998 | |
| WO | 9846645 | A2 | 10/1998 | |
| WO | 9850433 | A2 | 11/1998 | |
| WO | 0129058 | A1 | 4/2001 | |
| WO | 0196584 | A3 | 1/2003 | |
| WO | 2008040362 | A3 | 3/2009 | |
| WO | WO-2013019615 | A2 * | 2/2013 | .............. A61P 35/00 |
| WO | 2013126729 | A1 | 8/2013 | |
| WO | 2013126733 | A1 | 8/2013 | |
| WO | 2014087010 | A1 | 6/2014 | |
| WO | 2015120180 | | 8/2015 | |
| WO | 2015159076 | A1 | 10/2015 | |
| WO | 2016122738 | | 8/2016 | |
| WO | 2016203048 | | 12/2016 | |
| WO | 2017040945 | A1 | 3/2017 | |
| WO | 2017172981 | A2 | 10/2017 | |
| WO | 2018006882 | A1 | 1/2018 | |
| WO | 2018102795 | | 6/2018 | |
| WO | WO-2018191490 | A1 * | 10/2018 | ......... A61K 40/4269 |
| WO | 2019047885 | A1 | 3/2019 | |

OTHER PUBLICATIONS

Ma et al. (Prostate. Sep. 15, 2004; 61 (1): 12-25).*
Hudecek et al. (Clin. Cancer Res. Jun. 15, 2013; 19 (12): 3153-64).*
Long et al. (Nat. Med. Jun. 2015; 21 (6): 581-90).*

Künkele et al. (Cancer Immunol. Res. Apr. 2015; 3 (4): 368-79).*
Fujiwara et al. (Cells. May 9, 2020; 9 (5): 1182; pp. 1-17).*
Rudikoff et al. Proc. Natl. Acad. Sci. USA, 79(6):1979-1983, (Year: 1982).*
Colman P. M. Research in Immunology, 145:33-36, (Year: 1994).*
Bendig M. M. Methods: A Companion to Methods in Enzymology, 8:83-93, (Year: 1995).*
MacCallum et al (J. Mol. Biol., 262, 732-745, (Year: 1996).*
Casset et al. Biochemical and Biophysical Research Communications, 307:198-205, (Year: 2003).*
Boyerinas et al. Cancer Research, 77(13 Supplement: 602, (Year: 2017).*
Tay et al. Immunotherapy, 9(16), 1339-1349, (Year: 2017).*
International Search Report and Written Opinion dated Aug. 12, 2020—PCT/US2020/024825.
Andrulis , et al., "Expression of Mucin-1 in Multiple Myeloma and Its Precursors: Correlation With Glycosylation and Subcellular Localization", (2014) Histopathology, 64:799-806 Abstract.
Barrett , et al., "Treatment of Advanced Leukemia in Mice with mRNA Engineered T Cells", Human Gene Therapy 22, Dec. 2011, 1575-1586.
Berge , et al., "Selective Expansion of a Peripheral Blood CD8+ Memory T Cell Subset Expressing Both Granzyme B and L-Selectin During Primary Viral Infection in Renal Allograft Recipients.", Transplantation Proceedings, 30, 3975-3977 (1998).
Bridgman , et al., "CD3-zeta-based chimeric antigen receptors mediate T cell activation via cis- and trans-signalling mechanisms: implications for optimization of receptor structure for adoptive cell therapy", (2014) Clin Exp Immunol, 175(2):258-267.
Brocks , et al., "A Tnf Receptor Antagonistic scFv, Which Is Not Secreted in Mammalian Cells, Is Expressed as a Soluble Mono- And Bivalent scFv Derivative in Insect Cells", Immunotechnology 1997 3(3):173-84; Abstract.
Bruggerman , et al., "Designer Mice: The Production of Human Antibody Repertoires in Transgenic Animals.", 1993, Year in Immunol 7:33-40.
Carithers , et al., (2015) Biopreserve Biobank, 13(5):311-319.
Cascio , et al., "Abnormally Glycosylated MUC1 Establishes a Positive Feedback Circuit of Inflammatory Cytokines, Mediated by NF-kappa-B p65 and EzH2, in Colitis—", (2017) Oncotarget, 8(62):105284-98.
Clackson , et al., "Making antibody fragments using phage display libraries.", 1991, Nature 352:624-628.
Cloosen , et al., "Cancer Specific Mucin-1 Glycoforms Are Expressed on Multiple Myeloma", (2006) British Journal of Haematology, 135:513-516.
Cougot , et al., "'Cap-tabolism'.", Trends Biochem Sci. Aug. 2004;29(8):436-44. (Abstract).
Danthinne , et al., "Production of first generation adenovirus vectors: a review.", Gene Therapy (2000) 7(20): 1707-1714.
Duchosal , et al., "Immunization of hu-PBL-SCID mice and the rescue of human monoclonal Fab fragments through combinatorial libraries.", 1992, Nature 355:258-262.
Eisenhauer , et al., "New Response Evaluation Criteria in Solid Tumours: Revised RECIST Guideline (Version 1.1)", (2009) Eur J Cancer, 45(2):228-247 Abstract.
Elango , et al., "Optimized transfection of mRNA transcribed from a d(A/T) 100 tailcontaining vector.", Biochem Biophys Res Commun. May 13, 2005;330(3):958-66. (Abstract).
Fife , et al., "Inhibition of T cell activation and autoimmune diabetes using a B cell surface-linked CTLA-4 agonist", J Clin Invest 2006 116(8):2252-61.
Finn , et al., "Importance of MUC1 and Spontaneous Mouse Tumor Models for Understanding the Immunobiology of Human Adenocarcinomas", (2011) Immunol Research, 50(2-3):261-268 Abstract.
Garcia , et al., "Limits of the human-PBL-SCID Mice Model: Severe Restriction of the V Beta T-cell Repertoire of Engrafted Human T Cells", (1997) Blood, 89(1):329-336 Abstract.
Garland , et al., "The use of Teflon cell culture bags to expand functionally active CD8+ cytotoxic T lymphocytes.", Journal of Immunological Methods 227 (1999) 53-63.
Ghosh , et al., "Design of liposomes for circumventing the reticuloendothelial cells", 1991 Glycobiology 5: 505-10.

(56)          References Cited

OTHER PUBLICATIONS

Giavridis , et al., "CAR T cell-induced cytokine release syndrome is mediated by macrophages and abated by IL-1 blockade", (2018) Nature Medicine, 24:731-738.
Gillis , et al., "Contribution of human Fc-gamma-Rs to disease with evidence from human polymorphisms and transgenic animal studies", Front Immunol., May 3, 20140, 5:254.
Giomarelli , et al., "Inhibition of Thrombin-Induced Platelet Aggregation Using Human Single-Chain Fv Antibodies Specific for TREM-like transcript-1", Thromb Haemost 2007 97(6):955-63 Abstract.
Glaser , et al., "Novel antibody hinge regions for efficient production of CH2 domain-deleted antibodies", J. Biol. Chem., 2005, 280:41494-41503.
Griffith , et al., "Human anti-self antibodies with high specificity from phage display libraries", EMBO J., 12:725-734 (1993).
Haanen , et al., "Selective Expansion of Cross-reacitve CD8+ Memory T Cells by Viral Variants.", 1999, J Exp Med 190(9):1319-1328.
Hiermans , et al., "The VITAL Assay: A Versatile Fluorometric Technique for Assessing CTL- And NKT-mediated Cytotoxicity Against Multiple Targets in Vitro and in Vivo", J. Immunological Methods, 285(1): 25-40 (2004) Abstract.
Hermanson , et al., "Utilizing chimeric antigen receptors to direct natural killer cell activity.", Front. Immunol. (2015) 6: 195.
Ho , et al., "Inhibition of Cocaine Binding to the Human Dopamine Transporter by a Single Chain Anti-Idiotypic Antibody: Its Cloning, Expression and Functional Properties", BioChim Biophys Acta 2003 1638(3):257-66.
Hoogenboom , et al., "By-passing immunisation. Human antibodies from synthetic repertoires of germline VH gene segments arranged in vitro.", J Mol Biol Sep. 20, 1992;227(2):381-8. (Abstract).
Huck , et al., "Sequence of a human immunoglobulin gamma 3 heavy chain constant region gene: comparison with the other human C gamma genes.", Nucleic Acids Res. Feb. 25, 1986; 14(4): 1779-1789.
Hudecek , et al., "The non-signaling extracellular spacer domain of chimeric antigen receptors is decisive for in vivo antitumor activity", Cancer Immunol Res. 3(2), 2015, 125-135.
Huston , et al., "Protein engineering of antibody binding sites: Recovery of specific activity in an anti-digoxin single-chain Fv analogue produced in Escherichia coli.", 1988, Proc Natl Acad Sci USA 85:5879-5883.
Jakobovits , et al., "Analysis of homozygous mutant chimeric mice: Deletion of the immunoglobulin heavy-chain joining region blocks B-cell development and antibody production", Proc. Natl. Acad. Sci. 90, 1993, 2551-2555.
Jakobovits , et al., "Germ-line transmission and expression of a human-derived yeast artificial chromosome", Nature, 362:255-258 (1993).
Johnson , et al., "Human antibody engineering", Current Opinion in Structural Biology 3:564-571 (1993).
Ju , et al., "Chaperone mutation in Tn syndrome", (2005) Nature, 437(7063):1252.
Ju , et al., "Human Tumor Antigens Tn and Sialyl Tn Arise from Mutations in Cosmc", (2008) Cancer Res, 68 (6):1636-1646.
Ju , et al., "The Cosmc Connection to the Tn Antigen in Cancer", (2014) Cancer Biomark, 14(1):63-8.
Kochenderfer , et al., "Construction and Preclinical Evaluation of an anti-CD19 Chimeric Antigen Receptor", J. Immunotherapy, 32(7): 689-702 (2009).
Lavrsen , et al., "Aberrantly Glycosylated MUC1 Is Expressed on the Surface of Breast Cancer Cells and a Target for Antibody-Dependent Cell-Mediated Cytotoxicity", (2013) Glycoconjugates, 30(3):227-236 Abstract.
Ledbetter , et al., "Agonistic Activity of a CD40-specific Single-Chain Fv Constructed From the Variable Regions of mAb G28-5", Crit Rev Immunol 1997 17(5-6):427-55; Abstract.
Lee , et al., "ASTCT Consensus Grading for Cytokine Release Syndrome and Neurologic Toxicity Associated with Immune Effector Cells", Biol Blood Marrow Transplant 25 (2019) 625-638.

Marks , et al., "By-passing immunization. Human antibodies from V-gene libraries displayed on phage", J. Mol. Biol. 222:581-597 (1991).
Martin , et al., "Phase I trial of afatinib and 3-weekly trastuzumab with optimal anti-diarrheal management in patients with HER2-positive metastatic cancer", Cancer Chemother Pharmacol. 2018; 82(6): 979-986.
Mccafferty , et al., "Phage antibodies: filamentous phage displaying antibody variable domains", Nature, 348:552-553 (1990)93).
Mckinney , et al., "T cell exhaustion, costimulation and clinical outcome in autoimmunity and infection", (2015) Nature, 523:612.
Milone , et al., "Chimeric Receptors Containing CD137 Signal Transduction Domains Mediate Enhanced Survival of T Cells and Increased Antileukemic Efficacy In Vitro", 2009, Molecular Therapy 17(8):1453-1464.
Moosmayer , et al., "A Single-Chain TNF Receptor Antagonist Is an Effective Inhibitor of TNF Mediated Cytotoxicity", Ther Immunol 1995 2(10):31-40 Abstract.
Hutloff, et al., ICOS is an inducible T-cell co-stimulator structurally and functionally related to CD28, 1999 Nature 397:263-266.
Lázár-Molnár, E., et al., "Structure-guided development of a high-affinity human Programmed Cell Death-1: Implications for tumor immunotherapy", EBioMedicine, vol. 17, pp. 30-44, 2017.
Nakagawa, T. et al., "Development of next-generation adoptive immunollierapy uszng cytotoxic T-lymphocyte (CTL) expressing chimeric antigen-receptor (CAR)," Drug Delivery System, 28-1, pp. 35-44 (2013) (English language Abstract).
Extended European Search Report issued in App. No. EP20776961, dated Feb. 14, 2023, 18 pages.
Guedan, S. et al., "Combination of ICOS and 4-1BB in a Third Generation CAR Exhibits Enhanced T Cell Persistence and Increased Antitumor Effect" Molecular Therapy, vol. 23, Supplement 1, Abstract 719, p. S287, May 2015.
N/A, "Abstracts of the ASGCT 18th Annual Meeting", Molecular Therapy, US, (May 1, 2015), vol. 23, No. Suppl. 1., doi:10.1038/mt.2015.74, ISSN 1525-0016, pp. s1-s289, XP055310559.
Neelapu SS, Tummala S, Kebriaei P, et al.. Chimeric antigen receptor T-cell therapy—assessment and management of toxicities. Nat Rev Clin Oncol. 2018;15(1):47-62.
Nishikawa, et al., "Nonviral vectors in the new millennium: delivery barriers in gene transfer", Hum. Gene Ther., 12 (8):861-70 (2001) (abstract).
Norelli, et al., "Monocyte-derived IL-1 and IL-6 Are Differentially Required for Cytokine-Release Syndrome and Neurotoxicity Due to Car T Cells", (2018) Nature Medicine 24:739-748; Abstract.
Park, et al., "Are All Chimeric Antigen Receptors Created Equal?", J. Clin. Oncol. (2015) 33(6): 651-653 Abstract.
Peter, et al., "scFv Single Chain Antibody Variable Fragment as Inverse Agonist of the beta2-adrenergic Receptor", J Bioi Chem 2003 25278(38):36740-7.
Pinto, et al., "Identification of New Cancer Biomarkers Based on Aberrant Mucin Glycoforms by in Situ Proximity Ligation", (2012) J Cellular Mol Medicine, 16:1474-1484.
Posey, A. et al., "CD2, the First Identified T cell Co-Stimulator, Demonstrates More Effective Chimeric Antigen Receptor Activity Over CD28 and 4-1BB," Molecular Therapy, vol. 23, Supplement 1, Abstract 211, p. S83, May 2015.
Posey, A. et al., "Treating Epithelial and Metastatic Malignances with Glycoform-Specific Chimeric Antigen Receptors," Molecular Therapy, vol. 24, Supplement 1, Abstract 510, p. S203, May 2016.
Posey, Avery et al., "Engineered CAR T Cells Targeting the Cancer-Associated Tn-Glycoform of the Membrane Mucin MUC1 Control Adenocarcinoma", Immunity, Amsterdam, NL, (Jun. 21, 2016), vol. 44, No. 6, doi:10.1016/j.immuni.2016.05.014, ISSN 1074-7613, pp. 1-25, XP055570946.
Ren, et al., "Phyllodes Tumor of the Breast: Role of Axl and ST6GalNAcll in the Development of Mammary Phyllodes Tumors", (2014) Tumour Biol, 35(10):9603-9612 (Abstract).
Roder, et al., "The EBV-hybridoma technique", Methods Enzymol., 121:140-167 (1986).
Rooney, et al., "Modeling Cytokine Release Syndrome", (2018) Nature Medicine, 24:705-706; Abstract.

(56)  References Cited

OTHER PUBLICATIONS

Rosenberg, et al., "Use of Tumor-Infiltrating Lymphocytes and Interleukin-2 in the Immunotherapy of Patients with Metastatic Melanoma", New Eng. J. of Med. 319:1676-1680, 1988.

Shen , et al., "Engineering Peptide Linkers for scFv Immunosensors", Anal Chem. Mar. 15, 2008; 80(6): 1910-1917.

Shieh, et al., "Transgenic Expression of Single-Chain Anti-CTLA-4 Fv on Beta Cells Protects Nonobese Diabetic Mice from Autoimmune Diabetes", J Imunol 2009 183(4):2277-85.

Simon, "Optimal Two-Stage Designs for Phase II Clinical Trials", (1989) Control Clin Trials, 10:1-10 Abstract.

Simpson, et al., "Regulation of CD4 T Cell Activation and Effector Function by Inducible Costimulator (ICOS)", (2010) Curr. Opin. Immunol., 22:326-332. Abstract.

Siroy, A et al., "MUC1 is Expressed at High Frequency in Early-Stage Basal-Like Triple Negative Breast Cancer", Human Pathology, (Oct. 2013), vol. 44, No. 10, doi:10.1016/j.humpath.2013.04.010, pp. 2159-2166, XP028719927.

Sorensen, et al., "Chemoenzymatically synthesized multimeric Tn/STn MUC1 glycopeptides elicit cancer-specific anti-MUC1 antibody responses and override tolerance", (2006) Glycobiology, 16:96-107.

Spicer, et al., "Molecular Cloning and Analysis of the Mouse Homologue of the Tumor-Associated Mucin, MUC1, Reveals Conservation of Potential O-glycosylation Sites, Transmembrane, and Cytoplasmic Domains and a Loss of Minisatellite-Like Polymorphism", (1991) Journal of Biological Chemistry, 266:15099-15109.

Springer, et al., "T and Tn, General Carcinoma Autoantigens", (1984) Science, 224(4654):1198-1206 Abstract.

Stepinski, et al., "Synthesis and properties of mRNAs containing the novel "anti-reverse" cap analogs 7-methyl(3'-0-methyl) GpppG and 7-methyl(3'-deoxy)GpppG", RNA, 7:1468-95 (2001).

Stowell, et al., "Protein Glycosylation in Cancer", (2015) Annu Rev Pathol, 10:473-510.

Supplementary European Search Report issued in App. No. EP20776961, dated Nov. 8, 2022, 18 pages.

Tan, et al., "Influence of the hinge region on complement activation, C1q binding, and segmental flexibility in chimeric human immunoglobulins.", Proc Natl Acad Sci USA. Jan. 1990; 87(1): 162-166.

Tarp, et al., "Identification of a Novel Cancer-Specific Immunodominant Glycopeptide Epitope in the MUC1 Tandem Repeat", (2008) Glycobiology, 17(2):197-209.

Taylor-Papadimitriou, et al., "MUC1 and Cancer", Biochim Biophys Acta 1455 (2-3), 301-13 Oct. 8, 1999.

Tchou, et al., "Safety and Efficacy of Intratumoral Injections of Chimeric Antigen Receptor (CAR) T Cells in Metastatic Breast Cancer", (2017) Cancer Immunol Res 5, 1152-1161).

Teachey, et al., "Identification of Predictive Biomarkers for Cytokine Release Syndrome After Chimeric Antigen Receptor T-cell Therapy for Acute Lymphoblastic Leukemia", (2016) Cancer Discov, 6:664-679.

Toes, et al., "CD40-CD40Ligand Interactions and Their Role in Cytotoxic T Lymphocyte Priming and Anti-Tumor Immunity", (1998) Semin Immunol, 10(6):443-448 Abstract.

Tokarew Nicholas et al, "Teaching an old dog new tricks: next-generation CAR T cells", British Journal of Cancer, Nature Publishing Group UK, London, vol. 120, No. 1, doi:10.1038/S41416-018-0325-1, ISSN 0007-0920, (Jan. 1, 2019), pp. 26-37, (Nov. 9, 2018), XP036668683.

Topfer, et al., "DAP12-Based Activating Chimeric Antigen Receptor for NK Cell Tumor Immunotherapy", J. Immunol. (2015) 194(7): 3201-3212.

Uhlen, et al., "Proteomics. Tissue-based Map of the Human Proteome", (2015) Science, 347(6220) Abstract.

Ui-Tei, et al., Sensitive assay of RNA interference in Drosophila and Chinese hamster cultured cells using firefly luciferase gene as target., 2000 FEBS Letters 479: 79-82.

Vaughan, et al., "Human antibodies with sub-nanomolar affinities isolated from a large non-immunized phage display library", Nature Biotech., 14:309-14 (1996) (abstract).

Watanabe, et al., "Pancreatic Cancer Therapy With Combined Mesothelin-Redirected Chimeric Antigen Receptor T Cells and Cytokine-Armed Oncolytic Adenoviruses", JCI Insight 3 (7) Apr. 5, 2018. 18 pages.

Wei, X et al., "PSCA and MUC1 in non-small-cell lung cancer as targets of chimeric antigen receptor T cells", Oncoimmunology, vol. 6, No. 3, doi: 10.1080/2162402X.2017.1284722, (Mar. 15, 2017), p. e1284722, URL: http://dx.doi.org/10.1080/2162402X.2017.1284722, XP055603482.

Winterford, et al., "Ultrastructural Localization of Epithelial Mucin Core Proteins in Colorectal Tissues", J Histochem Cytochem 47 (8), 1063-74 Aug. 1999.

Xie, et al., "Direct Demonstration of MuSK Involvement in Acetylcholine Receptor Clustering Through Identification of Agonist ScFv", Nat Biotech 1997 15(8):768-71; Abstract.

Xue, et al., "Single-cell Multiplexed Cytokine Profiling of CD19 CAR-T Cells Reveals a Diverse Landscape of Polyfunctional Antigen-Specific Response", (2017) J Immunother Cancer, 5:85.

Yan, et al., "Engineering Upper Hinge Improves Stability and Effector Function of a Human IgG1.", J Biol Chem. Feb. 17, 2012;287(8):5891-7.

Zhang et al., "An NKp30-Based Chimeric Antigen Receptor Promotes T Cell Effector Functions and Antitumor Efficacy in Vivo" The Journal of Immunology (2012) vol. 189 No. 5 pp. 2290-2299.

Zhao, et al., "Characteristics of an scFv antibody fragment that binds to immunoglobulin G of Graves' disease patients and inhibits autoantibody-mediated thyroid-stimulating activity.", Hybridoma (Larchmt). Dec. 2008;27 (6):445-51. doi: 10.1089/hyb.2008.0045. Abstract.

Zhao, et al., "Multiple injections of electroporated autologous T cells expressing a chimeric antigen receptor mediate regression of human disseminated tumor", Cancer Res. Nov. 15, 2010; 70(22): 9053-9061.

Zhao, et al., "Structural design of engineered costimulation determines tumor rejection kinetics and persistence of CAR T cells", (2015) Cancer Cell, 28(4):415-428).

* cited by examiner

Phase 1 Arm 1: TnMUC1+ solid tumors CART-TnMUC1 administered i.v. in dose escalation cohorts (n~22)

Phase 1 Arm 2: TnMUC1+ Multiple Myeloma CART-TnMUC1 administered i.v. in dose escalation cohorts (n~18)

Phase 1a Expansion: TnMUC1+ platinum-resistant ovarian cancer. CART-TnMUC1 administered i.v. at the RP2D of Arm 1 (n~40)

Tn-MUC1 CHIMERIC ANTIGEN RECEPTOR (CAR) T CELL THERAPY

CROSS-REFERENCE TO RELATED APPLICATIONS

The present application is a continuation of U.S. patent application Ser. No. 16/830,554, filed Mar. 26, 2020, now U.S. Pat. No. 11,090,336, which is entitled to priority under 35 U.S.C. § 119 (e) to U.S. Provisional Patent Application 62/824,532, filed Mar. 27, 2019 and to U.S. Provisional Patent Application No. 62/881,269, filed Jul. 31, 2019, which are hereby incorporated by reference in their entireties.

SEQUENCE LISTING

The instant application contains a Sequence Listing which has been submitted electronically in ASCII format and is hereby incorporated by reference in its entirety. Said ASCII copy, created Jul. 8, 2021, is named "046483-7229US2_Sequence_Listing.txt" and is 107,268 bytes in size.

BACKGROUND OF THE INVENTION

Chimeric antigen receptor (CAR) T cells are effector immune cells that are genetically-modified to recognize a specific tumor-associated antigen and subsequently kill the tumor cell. While success with CAR T therapy has led to approval for use in hematologic malignancy, the effectiveness of CAR T therapy in the treatment of solid tumors, such as breast cancer, remains uncertain. There are several obstacles to CAR T therapy in solid tumors. Foremost, most of the identified and best-studied cell-surface antigens expressed by tumors are also expressed by normal tissue, resulting in non-specific targeting by CAR T cells (on-target, off-tumor activity). Second, solid tumors have a generally immunosuppressive tumor microenvironment, which may inhibit CAR T cell activity once the cells reach the tumor and recognize the antigen. Third, the durability of anti-tumor responses is highly correlated with the persistence of the adoptively-transferred cells and optimal persistence for CAR T cells in solid tumors has yet to match the persistence observed in hematopoietic malignancies.

Identifying tumor-specific antigens is essential in the continuing application of CAR T cell therapy to solid tumors. A need exists for novel compositions and methods that treat solid tumors, such as breast cancers. The present invention satisfies this need.

SUMMARY

Mucin 1 (MUC1) is a cell surface mucin that typically undergoes serial addition of glycans to form a hyperglycosylated protein (FIG. 1). The O-glycosylation process begins with GalNAc addition on serine and threonine residues. Elongation begins by addition of galactose by Core 1 synthase (composed of C1GalT1 and its chaperone C1GalT1C1 (Cosmc)) or GlcNAc addition by Core 3 synthase (B3GNT6). Aberrations in this serial glycosylation, such as epigenetic silencing of Cosmc, yield a hypoglycosylated product, Tn-MUC1, to which a sialic acid may be added by (ST6GALNAC-1) to form STn-MUC1.

The present disclosure is based on the discovery that CAR T cells directed against Tn-MUC1 demonstrated potent cytolytic activity against various cancer cell lines in vitro and significant tumor eradication in vivo. In one aspect, a modified immune cell or precursor cell thereof, comprising a chimeric antigen receptor (CAR) that specifically binds MUC1, wherein the CAR comprises: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a transmembrane domain; a costimulatory signaling domain; and an intracellular signaling domain, is provided.

In certain exemplary embodiments, the MUC1-specific antigen binding domain is specific for a glycoepitope of MUC1. In certain exemplary embodiments, the MUC1-specific antigen binding domain is specific for a truncated glycoepitope of MUC1.

In certain exemplary embodiments, the VH domain comprises the amino acid sequence set forth in SEQ ID NO: 5. In certain exemplary embodiments, the VL domain comprises the amino acid sequence set forth in SEQ ID NO: 6. In certain exemplary embodiments, the VH domain comprises the amino acid sequence set forth in SEQ ID NO: 5, and the VL domain comprises the amino acid sequence set forth in SEQ ID NO: 6. In certain exemplary embodiments, the MUC1-specific antigen binding domain comprises the amino acid sequence set forth in SEQ ID NO: 4.

In certain exemplary embodiments, the transmembrane domain comprises a transmembrane region of a protein selected from the group consisting of a type I transmembrane protein, an alpha, beta, or zeta chain of a T cell receptor, CD28, CD2, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), CD278 (ICOS), CD357 (GITR), Toll-like receptor 1 (TLR1), TLR2, TLR3, TLR4, TLR5, TLR6, TLR7, TLR8, and TLR9. In certain exemplary embodiments, the transmembrane domain comprises a CD8 transmembrane region. In certain exemplary embodiments, the transmembrane domain comprises the amino acid sequence set forth in SEQ ID NO: 7.

In certain exemplary embodiments, the costimulatory signaling domain comprises a costimulatory domain of a protein selected from the group consisting of a TNFR superfamily member, CD27, CD28, 4-1BB (CD137), OX40 (CD134), CD30, CD40, PD-1, ICOS, lymphocyte function-associated antigen-1 (LFA-1), CD2, CD5, CD7, LIGHT, NKG2C, B7-H3, a ligand that specifically binds with CD83, DAP10, DAP12, Lck, Fas, and any derivative or variant thereof. In certain exemplary embodiments, the costimulatory signaling domain is a CD2 costimulatory signaling domain. In certain exemplary embodiments, the costimulatory signaling domain comprises the amino acid sequence set forth in SEQ ID NO: 28.

In certain exemplary embodiments, the intracellular signaling domain comprises a signaling domain of a protein selected from the group consisting of CD3 zeta, FcγRIII, FcεRI, a cytoplasmic tail of an Fc receptor, an immunoreceptor tyrosine-based activation motif (ITAM) bearing cytoplasmic receptor, TCR zeta, FcR gamma, FcR beta, CD3 gamma, CD3 delta, CD3 epsilon, CD5, CD22, CD79a, CD79b, and CD66d. In certain exemplary embodiments, the intracellular signaling domain comprises a signaling domain of CD3 zeta. In certain exemplary embodiments, the intracellular signaling domain comprises the amino acid sequence set forth in SEQ ID NO: 30.

In certain exemplary embodiments, the CAR further comprises a leader sequence. In certain exemplary embodiments, the leader sequence is a CD8 leader sequence. In certain exemplary embodiments, the leader sequence comprises the amino acid sequence set forth in SEQ ID NO: 48.

In certain exemplary embodiments, the CAR further comprises a hinge domain. In certain exemplary embodiments, the hinge domain is from a protein selected from the group consisting of an Fc fragment of an antibody, a hinge region of an antibody, a CH2 region of an antibody, a CH3 region of an antibody, an artificial spacer sequence, a hinge comprising an amino acid sequence of CD8, and any combination thereof. In certain exemplary embodiments, the hinge domain is a CD8 hinge domain. In certain exemplary embodiments, the hinge domain comprises the amino acid sequence set forth in SEQ ID NO: 13.

In certain embodiments, the modified immune cell further comprises a dominant negative receptor and/or switch receptor.

In certain embodiments, wherein the dominant negative receptor is a truncated variant of a wild-type protein associated with a negative signal. In one embodiment, the truncated variant of a wild-type protein associated with a negative signal comprises the amino acid sequence set forth in SEQ ID NO:76.

In certain embodiments, the switch receptor comprises: a first domain, wherein the first domain is derived from a first polypeptide that is associated with a negative signal; and a second domain, wherein the second domain is derived from a second polypeptide that is associated with a positive signal. In one embodiment, the first domain comprises at least a portion of the extracellular domain of the first polypeptide that is associated with a negative signal, and the second domain comprises at least a portion of the intracellular domain of the second polypeptide that is associated with a positive signal. In one embodiment, the switch receptor further comprises a switch receptor transmembrane domain. In one embodiment, the switch receptor transmembrane domain comprises: the transmembrane domain of the first polypeptide that is associated with a negative signal; or the transmembrane domain of the second polypeptide that is associated with a positive signal. In one embodiment, the first polypeptide that is associated with a negative signal is selected from the group consisting of CTLA4, PD-1, BTLA, TIM-3, and a TGFβR. In one embodiment, the second polypeptide that is associated with a positive signal is selected from the group consisting of CD28, ICOS, 4-1BB, and a IL-12R.

In one embodiment, the switch receptor comprises: a first domain comprising at least a portion of the extracellular domain of PD1; a switch receptor transmembrane domain comprising at least a portion of the transmembrane domain of CD28; and a second domain comprising at least a portion of the intracellular domain of CD28. In one embodiment, the switch receptor comprises the amino acid sequence set forth in SEQ ID NO: 78. In one embodiment, the switch receptor comprises: a first domain comprising at least a portion of the extracellular domain of PD1; a switch receptor transmembrane domain comprising at least a portion of the transmembrane domain of PD1; and a second domain comprising at least a portion of the intracellular domain of CD28.

In one embodiment, the switch receptor comprises the amino acid sequence set forth in SEQ ID NO: 80.

In one embodiment, the first domain comprises at least a portion of the extracellular domain of PD1 comprises an alanine (A) to leucine (L) substitution at amino acid position 132.

In one embodiment, the switch receptor comprises the amino acid sequence set forth in SEQ ID NO: 82.

In one embodiment, the switch receptor comprises: a first domain comprising at least a portion of the extracellular domain of PD1 comprising an alanine (A) to leucine (L) substitution at amino acid position 132; and a second domain comprising at least a portion of the intracellular domain of CD28.

In one embodiment, the switch receptor comprises: a first domain comprising at least a portion of the extracellular domain of PD1 comprising an alanine (A) to leucine (L) substitution at amino acid position 132; and a second domain comprising at least a portion of the intracellular domain of 4-1BB.

In one embodiment, the switch receptor comprises the amino acid sequence set forth in SEQ ID NO: 86.

In one embodiment, the switch receptor comprises: a first domain comprising at least a portion of the extracellular domain of TIM-3; and a second domain comprising at least a portion of the intracellular domain of CD28.

In one embodiment, the switch receptor comprises the amino acid sequence set forth in SEQ ID NO: 92.

In one embodiment, the switch receptor comprises: a first domain comprising at least a portion of the extracellular domain of a TGFβR; and a second domain comprising at least a portion of the intracellular domain of IL12Rα1.

In one embodiment, the switch receptor comprises the amino acid sequence set forth in SEQ ID NO: 88.

In one embodiment, the switch receptor comprises: a first domain comprising at least a portion of the extracellular domain of a TGFβR; and a second domain comprising at least a portion of the intracellular domain of IL12Rβ1.

In one embodiment, the switch receptor comprises the amino acid sequence set forth in SEQ ID NO: 90.

In certain exemplary embodiments, the modified cell is a modified natural killer (NK) cell, a modified natural killer T (NKT) cell, or a modified T cell. In certain exemplary embodiments, the modified immune cell is a modified T cell. In certain exemplary embodiments, the modified immune cell is autologous.

In another aspect, a modified T cell comprising a chimeric antigen receptor (CAR) that specifically binds MUC1, wherein the CAR comprises: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a hinge domain; a transmembrane domain; a CD2 costimulatory signaling domain; and an intracellular signaling domain, is provided.

In another aspect, a modified T cell comprising a chimeric antigen receptor (CAR) that specifically binds MUC1, wherein the CAR comprises: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a hinge domain; a transmembrane domain; a CD2 costimulatory signaling domain comprising the amino acid sequence set forth in SEQ ID NO: 28; and an intracellular signaling domain, is provided.

In another aspect, a modified T cell comprising a chimeric antigen receptor (CAR) that specifically binds MUC1, wherein the CAR comprises: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; a CD2 costimulatory signaling domain comprising the amino acid sequence set forth in SEQ ID NO: 28; and a CD3 zeta intracellular signaling domain, is provided.

In another aspect, a modified T cell comprising a chimeric antigen receptor (CAR) that specifically binds MUC1, comprising the amino acid sequence set forth in SEQ ID NOs: 2, 39, 41, 43, 45, or 47, is provided.

In another aspect, an isolated nucleic acid sequence encoding a chimeric antigen receptor comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a transmembrane domain; a costimulatory signaling domain; and an intracellular signaling domain, is provided.

In certain exemplary embodiments, the MUC1-specific antigen binding domain is specific for a glycoepitope of MUC1. In certain exemplary embodiments, the MUC1-specific antigen binding domain is specific for a truncated glycoepitope of MUC1.

In certain exemplary embodiments, the VH domain comprises the amino acid sequence set forth in SEQ ID NO: 5. In certain exemplary embodiments, the VL domain comprises the amino acid sequence set forth in SEQ ID NO: 6. In certain exemplary embodiments, the VH domain comprises the amino acid sequence set forth in SEQ ID NO: 5, and the VL domain comprises the amino acid sequence set forth in SEQ ID NO: 6. In certain exemplary embodiments, the MUC1-specific antigen binding domain comprises the amino acid sequence set forth in SEQ ID NO: 4

In certain exemplary embodiments, the MUC1-specific antigen binding domain is encoded by a nucleic acid sequence comprising the nucleotide sequence set forth in SEQ ID NO: 3.

In certain exemplary embodiments, the transmembrane domain comprises a transmembrane region of a protein selected from the group consisting of a type I transmembrane protein, an alpha, beta, or zeta chain of a T cell receptor, CD28, CD2, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), CD278 (ICOS), CD357 (GITR), Toll-like receptor 1 (TLR1), TLR2, TLR3, TLR4, TLR5, TLR6, TLR7, TLR8, and TLR9. In certain exemplary embodiments, the transmembrane domain comprises a CD8 transmembrane region. In certain exemplary embodiments, the transmembrane domain is encoded by a nucleic acid sequence comprising the nucleotide sequence set forth in SEQ ID NO: 8.

In certain exemplary embodiments, the costimulatory signaling domain comprises a costimulatory domain of a protein selected from the group consisting of a TNFR superfamily member, CD27, CD28, 4-1BB (CD137), OX40 (CD134), CD30, CD40, PD-1, ICOS, lymphocyte function-associated antigen-1 (LFA-1), CD2, CD5, CD7, LIGHT, NKG2C, B7-H3, a ligand that specifically binds with CD83, DAP10, DAP12, Lck, Fas, and any derivative or variant thereof. In certain exemplary embodiments, the costimulatory signaling domain is a CD2 costimulatory signaling domain. In certain exemplary embodiments, the costimulatory signaling domain comprises the amino acid sequence set forth in SEQ ID NO: 28. In certain exemplary embodiments, the costimulatory signaling domain is encoded by a nucleic acid sequence comprising the nucleotide sequence set forth in SEQ ID NO: 29.

In certain exemplary embodiments, the intracellular signaling domain comprises a signaling domain of CD3 zeta. In certain exemplary embodiments, the intracellular signaling domain is encoded by a nucleic acid sequence comprising the nucleotide sequence set forth in SEQ ID NO: 31.

In certain exemplary embodiments, the CAR further comprises a CD8 leader sequence. In certain exemplary embodiments, the leader sequence comprises the amino acid sequence set forth in SEQ ID NO: 48.

In certain exemplary embodiments, the CAR further comprises a CD8 hinge domain. In certain exemplary embodiments, the hinge domain is encoded by a nucleic acid sequence comprising a nucleic acid sequence comprising the nucleotide sequence set forth in SEQ ID NO: 14.

In another aspect, an isolated nucleic acid sequence encoding a chimeric antigen receptor comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a hinge domain; a transmembrane domain; a CD2 costimulatory signaling domain; and an intracellular signaling domain, is provided.

In another aspect, an isolated nucleic acid sequence encoding a chimeric antigen receptor comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a hinge domain; a transmembrane domain; a CD2 costimulatory signaling domain comprising a nucleic acid sequence comprising the nucleotide sequence set forth in SEQ ID NO: 29; and an intracellular signaling domain, is provided.

In another aspect, an isolated nucleic acid sequence encoding a chimeric antigen receptor comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; a CD2 costimulatory signaling domain comprising a nucleic acid sequence comprising the nucleotide sequence set forth in SEQ ID NO: 29; and a CD3 zeta intracellular signaling domain, is provided.

In another aspect, an isolated nucleic acid sequence encoding a chimeric antigen receptor comprising a nucleic acid sequence comprising the nucleotide sequence set forth in SEQ ID NOs: 1, 38, 40, 42, 44, or 46, is provided.

In another aspect, an isolated nucleic acid sequence encoding an ICOS costimulatory signaling domain comprising the nucleotide sequence set forth in SEQ ID NO: 27, is provided.

In another aspect, a chimeric antigen receptor (CAR) that specifically binds MUC1 encoded by the nucleic acid of any one of the preceding embodiments, is provided.

In another aspect, a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a hinge domain; a transmembrane domain; a costimulatory signaling domain; and an intracellular signaling domain, is provided.

In another aspect, a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a hinge domain; a transmembrane domain; a CD2 costimulatory signaling domain comprising the amino acid sequence set forth in SEQ ID NO: 28; and an intracellular signaling domain, is provided.

In another aspect, a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; a CD2 costimulatory signaling domain comprising the amino acid sequence set forth in SEQ ID NO: 28; and a CD3 zeta intracellular signaling domain, is provided.

In another aspect, a chimeric antigen receptor (CAR) that specifically binds MUC1 comprising the amino acid sequence set forth in SEQ ID NO: 47, is provided.

In another aspect, an expression construct comprising the isolated nucleic acid of any one of the preceding embodiments, is provided. In certain exemplary embodiments, the expression construct further comprises an EF-1α promoter. In certain exemplary embodiments, the expression construct further comprises a rev response element (RRE). In certain exemplary embodiments, the expression construct further comprises a woodchuck hepatitis virus posttranscriptional regulatory element (WPRE). In certain exemplary embodiments, the expression construct further comprises a cPPT sequence. In certain exemplary embodiments, the expression construct further comprises an EF-1α promoter, a rev response element (RRE), a woodchuck hepatitis virus posttranscriptional regulatory element (WPRE), and a cPPT sequence.

In certain exemplary embodiments, the expression construct is a viral vector selected from the group consisting of a retroviral vector, a lentiviral vector, an adenoviral vector, and an adeno-associated viral vector. In certain exemplary embodiments, the expression construct is a lentiviral vector. In certain exemplary embodiments, the expression construct is a self-inactivating lentiviral vector.

In another aspect, a method for generating the modified immune cell or precursor cell thereof of any one of the preceding embodiments, comprising introducing into an immune cell or precursor cell thereof the isolated nucleic acid of any one of the preceding embodiments, or the expression construct of any one of the preceding embodiments, is provided.

In another aspect, a method of treating a MUC1-associated cancer in a subject in need thereof, comprising administering to the subject a therapeutically effective composition comprising the modified immune cell of any one of the preceding embodiments, is provided.

In certain exemplary embodiments, the MUC1-associated cancer is selected from the group consisting of multiple myeloma, non-small cell lung cancer, breast cancer, pancreatic adenocarcinoma, and ovarian and fallopian tube cancer.

In certain exemplary embodiments, the MUC1-associated cancer is breast cancer. In certain exemplary embodiments the breast cancer is characterized by abnormal glycosylation of MUC1. In certain exemplary embodiments, the breast cancer is selected from the group consisting of a hormone receptor-positive breast cancer, a hormone receptor-negative breast cancer, an estrogen receptor-negative breast cancer, a progesterone receptor-negative breast cancer, and a Her2 receptor-negative breast cancer. In certain exemplary embodiments, the breast cancer is a metastatic breast cancer. In certain exemplary embodiments, the breast cancer is triple negative breast cancer.

In another aspect, a method of treating a MUC1-associated cancer in a subject in need thereof, comprising: administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In another aspect, a method of treating a MUC1-associated multiple myeloma in a subject in need thereof, comprising: administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In another aspect, a method of treating a MUC1-associated non-small cell lung cancer in a subject in need thereof, comprising: administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In another aspect, a method of treating a MUC1-associated triple negative breast cancer in a subject in need thereof, comprising: administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In another aspect, a method of treating a MUC1-associated pancreatic adenocarcinoma in a subject in need thereof, comprising: administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In another aspect, a method of treating a MUC1-associated ovarian and fallopian tube cancer in a subject in need thereof, comprising: administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In certain exemplary embodiments, the method of any one of the preceding embodiments further comprises administering to the subject a lymphodepleting chemotherapy. In certain exemplary embodiments, the lymphodepleting chemotherapy comprises administering to the subject a therapeutically effective amount of cyclophosphamide. In certain exemplary embodiments, the lymphodepleting chemotherapy comprises administering to the subject a therapeutically effective amount of fludarabine. In certain exemplary embodiments, the lymphodepleting chemotherapy comprises administering to the subject a therapeutically effective amount of cyclophosphamide, and a therapeutically effective amount of fludarabine.

In certain exemplary embodiments, the method of any one of the preceding embodiments further comprises administering to the subject a cytokine release syndrome (CRS) management regimen. In certain exemplary embodiments, the CRS management regimen comprises a therapeutically effective amount of tocilizumab. In certain exemplary embodiments, the CRS management regimen comprises a therapeutically effective amount of tocilizumab and/or corticosteroids.

In certain exemplary embodiments, the modified immune cell or modified T cell is autologous.

In certain exemplary embodiments, the administering of the modified immune cell or modified T cell is performed via intratumoral delivery. In certain exemplary embodiments, the administering of the modified immune cell or modified T cell is performed via intravenous delivery. In certain exemplary embodiments, the administering of the modified immune cell or modified T cell is performed via intraperitoneal delivery. The modified immune cell or precursor cell thereof of any one of the preceding embodiments, for use in the method of any one of the preceding embodiments. The isolated nucleic acid sequence of any one of the preceding embodiments, for use in the method of any one of the preceding embodiments. The chimeric antigen receptor of any one of the preceding embodiments, for use in the method of any one of the preceding embodiments. The expression vector of any one of the preceding embodiments, for use in the method of any one of the preceding embodiments.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 3A illustrates 3+ staining in breast cancer tissue without staining of the surrounding stroma.

FIG. 3B illustrates 2+ staining in breast cancer tissue without staining of the surrounding stroma.

DETAILED DESCRIPTION

Definitions

Figure 1:
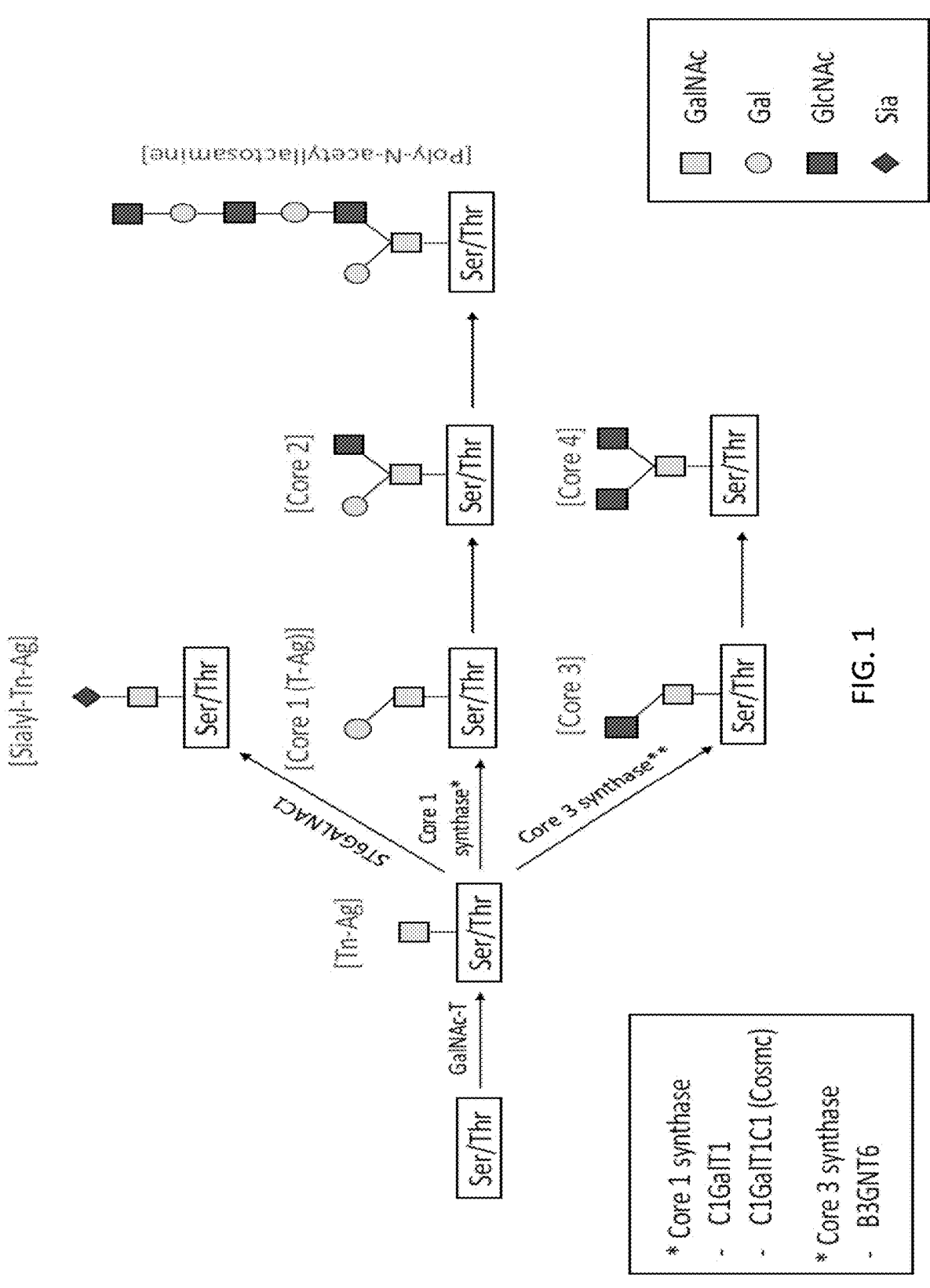
FIG. 1 is a schematic illustrating the initiation of O-glycan biosynthesis highlighting core glycans and associated glycotransferases.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20% or +10%, more preferably +5%, even more preferably +1%, and still more preferably +0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

"Allogeneic" refers to any material derived from a different animal of the same species.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, *Proc. Natl. Acad. Sci. USA* 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CAR has specificity to a selected target, for example MUC1. CARs may also comprise an intracellular activation domain, a transmembrane domain and an extracellular domain comprising an antigen binding region.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Donor antigen" refers to an antigen expressed by the donor tissue to be transplanted into the recipient.

"Recipient antigen" refers to a target for the immune response to the donor antigen.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. In certain exemplary embodiments, the epitope is about 4-18 amino acids, about 5-16 amino acids, about 6-14 amino acids, about 7-12 amino acids, or about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525, 1986; Reichmann et al., *Nature*, 332:323-329, 1988; Presta, *Curr. Op. Struct. Biol.*, 2:593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

The term "immunostimulatory" is used herein to refer to increasing overall immune response.

The term "immunosuppressive" is used herein to refer to reducing overall immune response.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, e.g., a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. In exemplary embodiments, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (a) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai virus vectors, adenovirus vectors, adeno-associated virus vectors, retrovirus vectors, lentivirus vectors, and the like.

"Xenogeneic" refers to any material derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides MUC1 specific chimeric antigen receptors (CARs; e.g., a Tn-MUC1 CAR) and modified cells comprising the same. Also provided are compositions and methods for utilizing MUC1 specific CARs to treat cancer. In particular, a Tn-MUC1 CAR of the present invention may be suitable for treating both liquid (e.g., multiple myeloma and the like) and solid tumors (e.g., breast cancer, non-small cell lung cancer, ovarian and fallopian tube cancer, pancreatic adenocarcinoma and the like).

It was demonstrated herein that Tn-MUC1 is an attractive tumor-specific antigen in various cancers for antibody-directed adoptive immunotherapy. CAR T cells directed against Tn-MUC1 demonstrated potent cytolytic activity against cancer cell lines in vitro and significant tumor eradication in vivo. Strategies to target MUC1 outside of the context of tumor-specific glycosylation may demonstrate on-target, off-tumor toxicities, but Tn-MUC1-targeting CAR T cells surmount the potential toxicities and extend the therapeutic window for solid tumors, such as breast cancer.

Chimeric Antigen Receptor (CAR)

The present invention provides compositions and methods for modified immune cells or precursor cells thereof, e.g., modified T cells, comprising a chimeric antigen receptor (CAR) having affinity for MUC1 or a glycosylated form of MUC1 (e.g. Tn-MUC1). A subject CAR of the invention comprises an antigen binding domain (e.g., Tn-MUC1 binding domain), a transmembrane domain, a costimulatory signaling domain, and an intracellular signaling domain. A subject CAR of the invention may optionally comprise a hinge domain. Accordingly, a subject CAR of the invention comprises an antigen binding domain (e.g., Tn-MUC1 binding domain), a hinge domain, a transmembrane domain, a costimulatory signaling domain, and an intracellular signaling domain. In some embodiments, each of the domains of a subject CAR is separated by a linker.

The antigen binding domain may be operably linked to another domain of the CAR, such as the transmembrane domain, the costimulatory signaling domain or the intracellular signaling domain, each described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding a costimulatory signaling domain.

The antigen binding domains described herein can be combined with any of the transmembrane domains, any of the costimulatory signaling domains, any of the intracellular signaling domains, or any of the other domains described herein that may be included in a CAR of the present invention.

In one aspect, the invention includes a chimeric antigen receptor (CAR) that specifically binds MUC1, comprising: a MUC1-specific antigen binding domain, optionally a hinge domain, a transmembrane domain, a costimulatory signaling domain, and an intracellular signaling domain.

In one aspect, the invention includes a chimeric antigen receptor (CAR) that specifically binds MUC1, comprising: a TnMUC1-specific antigen binding domain, optionally a hinge domain, a transmembrane domain, a costimulatory signaling domain, and an intracellular signaling domain.

In one exemplary embodiment, the invention includes a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; a CD2 costimulatory signaling domain; and a CD3 zeta intracellular signaling domain.

In one exemplary embodiment, the invention includes a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21 a CD8 hinge domain; a CD8 transmembrane domain; a 4-1BB costimulatory signaling domain; and a CD3 zeta intracellular signaling domain.

In one exemplary embodiment, the invention includes a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; an ICOS costimulatory signaling domain; and a CD3 zeta intracellular signaling domain.

In some embodiments, a genetically modified immune cell (e.g., T cell) or precursor cell thereof of the present invention comprises a chimeric antigen receptor (CAR) having affinity for MUC1. In some embodiments, a genetically modified immune cell (e.g., T cell) or precursor cell thereof of the present invention comprises a chimeric antigen receptor (CAR) having affinity for Tn-MUC1.

In certain embodiments, the genetically modified cell is a T cell. In certain embodiments, the genetically modified cell is a natural killer (NK) cell. In certain embodiments, the genetically modified cell is a NKT cell.

Accordingly, in one exemplary embodiment, provided herein is a genetically modified T cell comprising a chimeric antigen receptor (CAR) that specifically binds MUC1, comprising: a MUC1-specific antigen binding domain, an optional hinge domain, a transmembrane domain, a costimulatory signaling domain, and an intracellular signaling domain.

Accordingly, in one exemplary embodiment, provided herein is a genetically modified T cell comprising a chimeric antigen receptor (CAR) that specifically binds MUC1, comprising: a TnMUC1-specific antigen binding domain, an optional hinge domain, a transmembrane domain, a costimulatory signaling domain, and an intracellular signaling domain.

Accordingly, in one exemplary embodiment, provided herein is a genetically modified T cell comprising a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; a CD2 costimulatory signaling domain; and a CD3 zeta intracellular signaling domain.

Accordingly, in one exemplary embodiment, provided herein is a genetically modified T cell comprising a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; a 4-1BB costimulatory signaling domain; and a CD3 zeta intracellular signaling domain.

Accordingly, in one exemplary embodiment, provided herein is a genetically modified T cell comprising a chimeric antigen receptor (CAR) that specifically binds MUC1, comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; a CD8 hinge domain; a CD8 transmembrane domain; an ICOS costimulatory signaling domain; and a CD3 zeta intracellular signaling domain.

In certain embodiments of the invention, the CAR is encoded by a nucleic acid sequence comprising the nucleotide sequence of SEQ ID NOs: 1, 38, 40, 42, 44, or 46. In certain embodiments of the invention, the CAR comprises the amino acid sequence of SEQ ID NOs: 2, 39, 41, 43, 45, or 47.

Sequences of individual domains and the CAR are found in Table 1.

TABLE 1

| SEQ ID NO: | Description | Sequence |
|---|---|---|
| 1 | Tn-MUC1 CAR nucleic acid sequence (5E5BBz) | ATGGCCTTACCAGTGACCGCCTTGCTCCTGCCGCTGGCCTTGCTGCTCCACGC CGCCAGGCCGGGATCCCAGGTGCAGCTGCAGCAGTCTGATGCCGAGCTCGT GAAGCCTGGCAGCAGCGTGAAGATCAGCTGCAAGGCCAGCGGCTACACCTT CACCGACCACGCCATCCACTGGGTCAAGCAGAAGCCTGAGCAGGGCCTGGA GTGGATCGGCCACTTCAGCCCCGGCAACACCGACATCAAGTACAACGACAA GTTCAAGGGCAAGGCCACCCTGACCGTGGACAGAAGCAGCAGCACCGCCTA CATGCAGCTGAACAGCCTGACCAGCGAGGACAGCGCCGTGTACTTCTGCAA GACCAGCACCTTCTTTTTCGACTACTGGGGCCAGGGCACAACCCTGACAGTG TCTAGCGGAGGCGGAGGATCTGGCGGCGGAGGAAGTGGCGGAGGGGGAT CTGAACTCGTGATGACCCAGAGCCCCAGCTCTCTGACAGTGACAGCCGGCGA GAAAGTGACCATGATCTGCAAGTCCTCCCAGAGCCTGCTGAACTCCGGCGAC CAGAAGAACTACCTGACCTGGTATCAGCAGAAACCCGGCCAGCCCCCCAAG CTGCTGATCTTTTGGGCCAGCACCCGGGAAAGCGGCGTGCCCGATAGATTCA CAGGCAGCGGCTCCGGCACCGACTTTACCCTGACCATCAGCTCCGTGCAGGC CGAGGACCTGGCCGTGTATTACTGCCAGAACGACTACAGCTACCCCCTGACC TTCGGAGCCGGCACCAAGCTGGAACTGAAGTCCGGAACCACGACGCCAGCG CCGCGACCACCAACACCGGCGCCCACCATCGCGTCGCAGCCCCTGTCCCTGC GCCCAGAGGCGTGCCGGCCAGCGGCGGGGGGCGCAGTGCACACGAGGGG GCTGGACTTCGCCTGTGATATCTACATCTGGGCGCCCTTGGCCGGGACTTGT GGGGTCCTTCTCCTGTCACTGGTTATCACCCTTTACTGCAAACGGGGCAGAA AGAAACTCCTGTATATATTCAAACAACCATTTATGAGACCAGTACAAACTACT CAAGAGGAAGATGGCTGTAGCTGCCGATTTCCAGAAGAAGAAGAAGGAGG ATGTGAACTGAGAGTGAAGTTCAGCAGGAGCGCAGACGCCCCCGCGTACAA GCAGGGCCAGAACCAGCTCTATAACGAGCTCAATCTAGGACGAAGAGAGGA GTACGATGTTTTGGACAAGAGACGTGGCCGGGACCCTGAGATGGGGGGAA AGCCGAGAAGGAAGAACCCTCAGGAAGGCCTGTACAATGAACTGCAGAAA GATAAGATGGCGGAGGCCTACAGTGAGATTGGGATGAAAGGCGAGCGCCG GAGGGGCAAGGGGCACGATGGCCTTTACCAGGGTCTCAGTACAGCCACCAA GGACACCTACGACGCCCTTCACATGCAGGCCCTGCCCCCTCGC |
| 2 | Tn-MUC1 CAR amino acid sequence (5E5BBz) | MALPVTALLLPLALLLHAARPGSQVQLQQSDAELVKPGSSVKISCKASGYTFTDH AIHWVKQKPEQGLEWIGHFSPGNTDIKYNDKFKGKATLTVDRSSSTAYMQLNS LTSEDSAVYFCKTSTFFFDYWGQGTTLTVSSGGGGSGGGGSGGGGSELVMTQS PSSLTVTAGEKVTMICKSSQSLLNSGDQKNYLTWYQQKPGQPPKLLIFWASTRE |

TABLE 1-continued

| SEQ ID NO: | Description | Sequence |
|---|---|---|
| | | SGVPDRFTGSGSGTDFTLTISSVQAEDLAVYYCQNDYSYPLTFGAGTKLELKSGTT TPAPRPPTPAPTIASQPLSLRPEACRPAAGGAVHTRGLDFACDIYIWAPLAGTCG VLLLSLVITLYCKRGRKKLLYIFKQPFMRPVQTTQEEDGCSCRFPEEEEGGCELRV KFSRSADAPAYKQGQNQLYNELNLGRREEYDVLDKRRGRDPEMGGKPRRKNP QEGLYNELQKDKMAEAYSEIGMKGERRRGKGHDGLYQGLSTATKDTYDALHM QALPPR |
| 3 | 5E5 scFv nucleic acid sequence | CAGGTGCAGCTGCAGCAGTCTGATGCCGAGCTCGTGAAGCCTGGCAGCAGC GTGAAGATCAGCTGCAAGGCCAGCGGCTACACCTTCACCGACCACGCCATCC ACTGGGTCAAGCAGAAGCCTGAGCAGGGCCTGGAGTGGATCGGCCACTTCA GCCCCGGCAACACCGACATCAAGTACAACGACAAGTTCAAGGGCAAGGCCA CCCTGACCGTGGACAGAAGCAGCAGCACCGCCTACATGCAGCTGAACAGCC TGACCAGCGAGGACAGCGCCGTGTACTTCTGCAAGACCAGCACCTTCTTTTT CGACTACTGGGGCCAGGGCACAAACCCTGACAGTGTCTAGCGGAGGCGGAG GATCTGGCGGCGGAGGAAGTGGCGGAGGGGGATCTGAACTCGTGATGACC CAGAGCCCCAGCTCTCTGACAGTGACAGCCGGCGAGAAAGTGACCATGATC TGCAAGTCCTCCCAGAGCCTGCTGAACTCCGGCGACCAGAAGAACTACCTGA CCTGGTATCAGCAGAAACCCGGCCAGCCCCCCAAGCTGCTGATCTTTTGGGC CAGCACCCGGGAAAGCGGCGTGCCCGATAGATTCACAGGCAGCGGCTCCGG CACCGACTTTACCCTGACCATCAGCTCCGTGCAGGCCGAGGACCTGGCCGTG TATTACTGCCAGAACGACTACAGCTACCCCCTGACCTTCGGAGCCGGCACCA AGCTGGAACTGAAG |
| 4 | 5E5 scFv amino acid sequence | QVQLQQSDAELVKPGSSVKISCKASGYTFTDHAIHWVKQKPEQGLEWIGHFSP GNTDIKYNDKFKGKATLTVDRSSSTAYMQLNSLTSEDSAVYFCKTSTFFFDYWG QGTTLTVSSGGGGSGGGGSGGGGSELVMTQSPSSLTVTAGEKVTMICKSSQSL LNSGDQKNYLTWYQQKPGQPPKLLIFWASTRESGVPDRFTGSGSGTDFTLTISS VQAEDLAVYYCQNDYSYPLTFGAGTKLELK |
| 5 | 5E5 scFv heavy chain (VH) variable region amino acid sequence | QVQLQQSDAELVKPGSSVKISCKASGYTFTDHAIHWVKQKPEQGLEWIGHFSP GNTDIKYNDKFKGKATLTVDRSSSTAYMQLNSLTSEDSAVYFCKTSTFFFDYWG QGTTLTVSS |
| 6 | 5E5 scFv light chain (VL) variable region amino acid sequence | ELVMTQSPSSLTVTAGEKVTMICKSSQSLLNSGDQKNYLTWYQQKPGQPPKLLI FWASTRESGVPDRFTGSGSGTDFTLTISSVQAEDLAVYYCQNDYSYPLTFGAGTK LELK |
| 7 | CD8α transmembrane domain amino acid sequence | IYIWAPLAGTCGVLLLSLVITLYC |
| 8 | CD8α transmembrane domain nucleic acid sequence | ATCTACATCTGGGCGCCCTTGGCCGGGACTTGTGGGGTCCTTCTCCTGTCACT GGTTATCACCCTTTACTGC |
| 9 | 4-1BB amino acid sequence | KRGRKKLLYIFKQPFMRPVQTTQEEDGCSCRFPEEEEGGCEL |
| 10 | 4-1BB nucleic acid sequence | AAACGGGGCAGAAAGAAACTCCTGTATATATTCAAACAACCATTTATGAGAC CAGTACAAACTACTCAAGAGGAAGATGGCTGTAGCTGCCGATTTCCAGAAG AAGAAGAAGGAGGATGTGAACTG |
| 11 | CD3 zeta domain amino acid sequence | RVKFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR |
| 12 | CD3 zeta domain nucleic acid sequence | AGAGTGAAGTTCAGCAGGAGCGCAGACGCCCCCGCGTACCAGCAGGGCCA GAACCAGCTCTATAACGAGCTCAATCTAGGACGAAGAGAGGAGTACGATGT TTTGGACAAGAGACGTGGCCGGGACCCTGAGATGGGGGGGAAAGCCGAGAA GGAAGAACCCTCAGGAAGGCCTGTACAATGAACTGCAGAAAGATAAGATGG CGGAGGCCTACAGTGAGATTGGGATGAAAGGCGAGCGCCGGAGGGGCAAG GGGCACGATGGCCTTTACCAGGGTCTCAGTACAGCCACCAAGGACACCTAC GACGCCCTTCACATGCAGGCCCTGCCCCCTCGC |
| 13 | CD8 hinge amino acid sequence | TTTPAPRPPTPAPTIASQPLSLRPEACRPAAGGAVHTRGLDFACD |
| 14 | CD8 hinge nucleic acid sequence | ACCACGACGCCAGCGCCGCGACCACCAACACCGGCGCCCACCATCGCGTCG CAGCCCCTGTCCCTGCGCCCAGAGGCGTGCCGGCCAGCGGCGGGGGGCGCA GTGCACACGAGGGGGCTGGACTTCGCCTGTGAT |

TABLE 1-continued

| SEQ ID NO: | Description | Sequence |
|---|---|---|
| 15 | CD28 transmembrane domain amino acid sequence | FWVLVVVGGVLACYSLLVTVAFIIFWV |
| 16 | CD28 transmembrane domain nucleic acid sequence | TTTTGGGTGCTGGTGGTGGTTGGTGGAGTCCTGGCTTGCTATAGCTTGCTAG TAACAGTGGCCTTTATTATTTTCTGGGTG |
| 17 | CD28 intracellular domain amino acid sequence | RSKRSRLLHSDYMNMTPRRPGPTRKHYQPYAPPRDFAAYRS |
| 18 | CD28 intracellular domain nucleic acid sequence | AGGAGTAAGAGGAGCAGGCTCCTGCACAGTGACTACATGAACATGACTCCC CGCCGCCCCGGGCCCACCCGCAAGCATTACCAGCCCTATGCCCCACCACGCG ACTTCGCAGCCTATCGCTCC |
| 19 | LCCDR1 | QSLLNSGDQKNYLT |
| 20 | LCCDR2 | LLIFWASTRES |
| 21 | LCCDR3 | QNDYSYPL |
| 22 | HCCDR1 | YTFTDHAIH |
| 23 | HCCDR2 | WIGHFSPGNTDIKY |
| 24 | HCCDR3 | KTSTFFFDY |
| 25 | ICOS costimulatory domain amino acid sequence | TKKKYSSSVHDPNGEYMFMRAVNTAKKSRLTDVTL |
| 26 | ICOS costimulatory domain nucleic acid sequence | ACAAAAAAGAAGTATTCATCCAGTGTGCACGACCCTAAC GGTGAATACATGTTCATGAGAGCAGTGAACACAGCCAA AAAATCTAGACTCACAGATGTGACCCTA |
| 27 | ICOS costimulatory domain nucleic acid sequence | ACAAAAAAGAAGTATTCATCCAGTGTGCACGACCCTAACGGT GAATACATGTTCATGAGAGCAGTGAACACAGCCAAAAAATCC AGACTCACAGATGTGACCCTA |
| 28 | CD2 costimulatory domain amino acid sequence | TKRKKQRSRRNDEELETRAHRVATEERGRKPHQIPASTPQNPATS QHPPPPPGHRSQAPSHRPPPPGHRVQHQPQKRPPAPSGTQVHQQ KGPPLPRPRVQPKPPHGAAENSLSPSSN |
| 29 | CD2 costimulatory domain nucleic acid sequence | ACCAAAAGGAAAAAACAGAGGAGTCGGAGAAATGATGAGGA GCTGGAGACAAGAGCCCACAGAGTAGCTACTGAAGAAGGG GCCGGAAGCCCCACCAAATTCCAGCTTCAACCCCTCAGAATC CAGCAACTTCCCAACATCCTCCTCCACCACCTGGTCATCGTTC CCAGGCACCTAGTCATCGTCCCCCGCCTCCTGGACACCGTGTT CAGCACCAGCCTCAGAAGAGGCCTCCTGCTCCGTCGGGCACA CAAGTTCACCAGCAGAAAGGCCCGCCCCTCCCCAGACCTCGA GTTCAGCCAAAACCTCCCCATGGGGCAGCAGAAAACTCATTG TCCCCTTCCTCTAAT |
| 30 | CD3 zeta domain amino acid sequence (Q14K) | RVKFSRSADAPAYKQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR |
| 31 | CD3 zeta domain nucleic acid sequence (Q14K) | AGAGTGAAGTTCAGCAGGAGCGCAGACGCCCCCGCGTACAAGCAGGGCCA GAACCAGCTCTATAACGAGCTCAATCTAGGACGAAGAGAGGAGTACGATGT TTTGGACAAGAGACGTGGCCGGGACCCTGAGATGGGGGGAAAGCCGAGAA GGAAGAACCCTCAGGAAGGCCTGTACAATGAACTGCAGAAAGATAAGATGG CGGAGGCCTACAGTGAGATTGGGATGAAAGGCGAGCGCCGGAGGGGCAAG GGGCACGATGGCCTTTACCAGGGTCTCAGTACAGCCACCAAGGACACCTAC GACGCCCTTCACATGCAGGCCCTGCCCCCTCGC |

TABLE 1-continued

| SEQ ID NO: | Description | Sequence |
|---|---|---|
| 32 | CD28 intracellular domain variant (YMFM) amino acid sequence | RSKRSRLLHSDYMFMTPRRPGPTRKHYQPYAPPRDFAAYRS |
| 33 | CD28 intracellular domain variant (YMFM) nucleic acid sequence | AGGAGTAAGAGGAGCAGGCTCCTGCACAGTGACTACATGTTCATGACTCCCCGCCGC CCCGGGCCCACCCGCAAGCATTACCAGCCCTATGCCCCACCACGCGACTTCGCAGCCT ATCGCTCC |
| 34 | CD27 intracellular domain amino acid sequence | QRRKYRSNKGESPVEPAEPCRYSCPREEEGSTIPIQEDYRKPEPACSP |
| 35 | CD27 intracellular domain nucleic acid sequence | CAACGAAGGAAATATAGATCAAACAAAGGAGAAAGTCCTGTGGAGCCTGCAGAGCC TTGTCGTTACAGCTGCCCCAGGGAGGAGGAGGGCAGCACCATCCCCATCCAGGAGG ATTACCGAAAACCGGAGCCTGCCTGCTCCCCC |
| 36 | OX40 intracellular domain amino acid sequence | ALYLLRRDQRLPPDAHKPPGGGSFRTPIQEEQADAHSTLAKI |
| 37 | OX40 intracellular domain nucleic acid sequence | GCCCTGTACCTGCTCCGCAGGGACCAGAGGCTGCCCCCCGATGCCCACAAGCCCCCT GGGGGAGGCAGTTTCAGGACCCCCATCCAAGAGGAGCAGGCCGACGCCCACTCCAC CCTGGCCAAGATC |
| 38 | Tn-MUC1 CAR nucleic acid sequence (5E528z) | ATGGCCTTACCAGTGACCGCCTTGCTCCTGCCGCTGGCCTTGCTGCTCCACGCCGCCA GGCCGGGATCCCAGGTGCAGCTGCAGCAGTCTGATGCCGAGCTCGTGAAGCCTGGC AGCAGCGTGAAGATCAGCTGCAAGGCCAGCGGCTACACCTTCACCGACCACGCCATC CACTGGGTCAAGCAGAAGCCTGAGCAGGGCCTGGAGTGGATCGGCCACTTCAGCCC CGGCAACACCGACATCAAGTACAACGACAAGTTCAAGGGCAAGGCCACCCTGACCG TGGACAGAAGCAGCAGCACCGCCTACATGCAGCTGAACAGCCTGACCAGCGAGGAC AGCGCCGTGTACTTCTGCAAGACCAGCACCTTCTTTTTCGACTACTGGGGCCAGGGC ACAACCCTGACAGTGTCTAGCGGAGGCGGAGGATCTGGCGGCGGAGGAAGTGGCG GAGGGGGATCTGAACTCGTGATGACCCAGAGCCCCAGCTCTCTGACAGTGACAGCC GG CGAGAAAGTGACCATGATCTGCAAGTCCTCCCAGAGCCTGCTGAACTCCGGCGACCA GAAGAACTACCTGACCTGGTATCAGCAGAAACCCGGCCAGCCCCCCAAGCTGCTGAT CTTTTGGGCCAGCACCCGGGAAAGCGGCGTGCCCGATAGATTCACAGGCAGCGGCT CCGGCACCGACTTTACCCTGACCATCAGCTCCGTGCAGGCCGAGGACCTGGCCGTGT ATTACTGCCAGAACGACTACAGCTACCCCCTGACCTTCGGAGCCGGCACCAAGCTGG AACTGAAGTCCGGAACCACGACGCCAGCGCCGCGACCACCAACACCGGCGCCCACC ATCGCGTCGCAGCCCCTGTCCCTGCGCCCAGAGGCGTGCCGGCCAGCGGCGGGGGG CGCAGTGCACACGAGGGGGCTGGACTTCGCCTGTGATTTTTGGGTGCTGGTGGTGG TTGGTGGAGTCCTGGCTTGCTATAGCTTGCTAGTAACAGTGGCCTTTATTATTTTCTG GGTG AGGAGTAAGAGGAGCAGGCTCCTGCACAGTGACTACATGAACATGACTCCCCGCCG CCCCGGGCCCACCCGCAAGCATTACCAGCCCTATGCCCCACCACGCGACTTCGCAGC CTATCGCTCCAGAGTGAAGTTCAGCAGGAGCGCAGACGCCCCCGCGTACAAGCAGG GCCAGAACCAGCTCTATAACGAGCTCAATCTAGGACGAAGAGAGGAGTACGATGTTT TGGACAAGAGACGTGGCCGGGACCCTGAGATGGGGGGAAAGCCGAGAAG GAAGAACCCTCAGGAAGGCCTGTACAATGAACTGCAGAAAGATAAGATGGCGGAG GCCTACAGTGAGATTGGGATGAAAGGCGAGCGCCGGAGGGGCAAGGGGCACGATG GCCTTTACCAGGGTCTCAGTACAGCCACCAAGGACACCTACGACGCCCTTCACATGC AGGCCCTGCCCCCTCGC |
| 39 | Tn-MUC1 CAR amino acid sequence (5E528z) | MALPVTALLLPLALLLHAARPGSQVQLQQSDAELVKPGSSVKISCKASGYTFTDHAIHWV KQKPEQGLEWIGHFSPGNTDIKYNDKFKGKATLTVDRSSSTAYMQLNSLTSEDSAVYFCK TSTFFFDYWGQGTTLTVSSGGGGSGGGGSGGGGSELVMTQSPSSLTVTAGEKVTMICK SSQSLLNSGDQKNYLTWYQQKPGQPPKLLIFWASTRESGVPDRFTGSGSGTDFTLTISSV QAEDLAVYYCQNDYSYPLTFGAGTKLELKSGTTTPAPRPPTPAPTIASQPLSLRPEACRPA AGGAVHTRGLDFACDFWVLVVVGGVLACYSLLVTVAFIIFWVRSKRSRLLHSDYMNMTP RRPGPTRKHYQPYAPPRDFAAYRSRVKFSRSADAPAYKQGQNQLYNELNLGRREEYDVL DKRRGRDPEMGGKPRRKNPQEGLYNELQKDKMAEAYSEIGMKGERRRGKGHDGLYQ GLSTATKDTYDALHMQALPPR |
| 40 | Tn-MUC1 CAR nucleic acid sequence (5E528z YMFM) | ATGGCCTTACCAGTGACCGCCTTGCTCCTGCCGCTGGCCTTGCTGCTCCACGCCGCCA GGCCGGGATCCCAGGTGCAGCTGCAGCAGTCTGATGCCGAGCTCGTGAAGCCTGGC AGCAGCGTGAAGATCAGCTGCAAGGCCAGCGGCTACACCTTCACCGACCACGCCATC CACTGGGTCAAGCAGAAGCCTGAGCAGGGCCTGGAGTGGATCGGCCACTTCAGCCC |

TABLE 1-continued

| SEQ ID NO: | Description | Sequence |
|---|---|---|

CGGCAACACCGACATCAAGTACAACGACAAGTTCAAGGGCAAGGCCACCCTGACCG
TGGACAGAAGCAGCAGCACCGCCTACATGCAGCTGAACAGCCTGACCAGCGAGGAC
AGCGCCGTGTACTTCTGCAAGACCAGCACCTTCTTTTTCGACTACTGGGGCCAGGGC
ACAACCCTGACAGTGTCTAGCGGAGGCGGAGGATCTGGCGGCGGAGGAAGTGGCG
GAGGGGGATCTGAACTCGTGATGACCCAGAGCCCCAGCTCTCTGACAGTGACAGCC
GG
CGAGAAAGTGACCATGATCTGCAAGTCCTCCCAGAGCCTGCTGAACTCCGGCGACCA
GAAGAACTACCTGACCTGGTATCAGCAGAAACCCGGCCAGCCCCCCAAGCTGCTGAT
CTTTTGGGCCAGCACCCGGGAAAGCGGCGTGCCCGATAGATTCACAGGCAGCGGCT
CCGGCACCGACTTTACCCTGACCATCAGCTCCGTGCAGGCCGAGGACCTGGCCGTGT
ATTACTGCCAGAACGACTACAGCTACCCCCTGACCTTCGGAGCCGGCACCAAGCTGG
AACTGAAGTCCGGAACCACGACGCCAGCGCCGCGACC
ACCAACACCGGCGCCCACCATCGCGTCGCAGCCCCTGTCCCTGCGCCCAGAGGCGTG
CCGGCCAGCGGCGGGGGGCGCAGTGCACACGAGGGGGGCTGGACTTCGCCTGTGAT
TTTTGGGTGCTGGTGGTGGTTGGTG
GAGTCCTGGCTTGCTATAGCTTGCTAGTAACAGTGGCCTTTATTATTTTCTGGGTGAG
GAGTAAGAGGAGCAGGCTCCTGCACAGTGACTACATGTTCATGACTCCCCGCCGCCC
CGGGCCCACCCGCAAGCATTACCAGCCCTATGCCCCACCACGCGACTTCGCAGCCTAT
CGCTCCAGAGTGAAGTTCAGCAGGAGCGCAGACGCCCCCGCGTACAAGCAGGGCCA
GAACCAGCTCTATAACGAGCTCAATCTAGGACGAAGAGAGGAGTACGATGTTTTGG
ACAAGAGACGTGGCCGGGACCCTGAGATGGGGGGGAAAGCCGAGAAGGAAGAACCC
TCAGGAAGGCCTGTACAATGAACTGCAG
AAAGATAAGATGGCGGAGGCCTACAGTGAGATTGGGATGAAAGGCGAGCGCCGGA
GGGGCAAGGGGCACGATGGCCTTTACCAGGGTCTCAGTACAGCCACCAAGGACACC
TACGACGCCCTTCACATGCAGGCCCTGCCCCCTCGC

| 41 | Tn-MUC1 CAR amino acid sequence (5E528z YMFM) | MALPVTALLLPLALLLHAARPGSQVQLQQSDAELVKPGSSVKISCKASGYTFTDHAIHWV KQKPEQGLEWIGHFSPGNTDIKYNDKFKGKATLTVDRSSSTAYMQLNSLTSEDSAVYFCK TSTFFFDYWGQGTTLTVSSGGGGSGGGGSGGGGSELVMTQSPSSLTVTAGEKVTMICK SSQSLLNSGDQKNYLTWYQQKPGQPPKLLIFWASTRESGVPDRFTGSGSGTDFTLTISSV QAEDLAVYYCQNDYSYPLTFGAGTKLELKSGTTTPAPRPPTPAPTIASQPLSLRPEACRPA AGGAVHTRGLDFACDFWVLVVVGGVLACYSLLVTVAFIIFWVRSKRSRLLHSDYMFMTP RRPGPTRKHYQPYAPPRDFAAYRSRVKFSRSADAPAYKQGQNQLYNELNLGRREEYDVL DKRRGRDPEMGGKPRRKNPQEGLYNELQKDKMAEAYSEIGMKGERRRGKGHDGLYQ GLSTATKDTYDALHMQALPPR |
| 42 | Tn-MUC1 CAR nucleic acid sequence (5E527z) | ATGGCCTTACCAGTGACCGCCTTGCTCCTGCCGCTGGCCTTGCTGCTCCACGCCGCCA GGCCGGGATCCCAGGTGCAGCTGCAGCAGTCTGATGCCGAGCTCGTGAAGCCTGGC AGCAGCGTGAAGATCAGCTGCAAGGCCAGCGGCTACACCTTCACCGACCACGCCATC CACTGGGTCAAGCAGAAGCCTGAGCAGGGCCTGGAGTGGATCGGCCACTTCAGCCC CGGCAACACCGACATCAAGTACAACGACAAGTTCAAGGGCAAGGCCACCCTGACCG TGGACAGAAGCAGCAGCACCGCCTACATGCAGCTGAACAGCCTGACCAGCGAGGAC AGCGCCGTGTACTTCTGCAAGACCAGCACCTTCTTTTTCGACTACTGGGGCCAGGGC ACAACCCTGACAGTGTCTAGCGGAGGCGGAGGATCTGGCGGCGGAGGAAGTGGCG GAGGGGGATCTGAACTCGTGATGACCCAGAGCCCCAGCTCTCTGACAGTGACAGCC GG CGAGAAAGTGACCATGATCTGCAAGTCCTCCCAGAGCCTGCTGAACTCCGGCGACCA GAAGAACTACCTGACCTGGTATCAGCAGAAACCCGGCCAGCCCCCCAAGCTGCTGAT CTTTTGGGCCAGCACCCGGGAAAGCGGCGTGCCCGATAGATTCACAGGCAGCGGCT CCGGCACCGACTTTACCCTGACCATCAGCTCCGTGCAGGCCGAGGACCTGGCCGTGT ATTACTGCCAGAACGACTACAGCTACCCCCTGACCTTCGGAGCCGGCACCAAGCTGG AACTGAAGTCCGGAACCACGACGCCAGCGCCGCGACCACCAACACCGGCGCCCACC ATCGCGTCGCAGCCCCTGTCCCTGCGCCCAGAGGCGTGCCGGCCAGCGGCGGGGGG CGCAGTGCACACGAGGGGGGCTGGACTTCGCCTGTGATATCTACATCTGGGCGCCCTT GGCCGGGACTTGTGGGGTCCTTCTCCTGTCACTGGTTATCACCCTTTACTGCCAACGA AGGAAATATAGATCAAACAAAGGAGAAAGTCCTGTGGAGCCTGCAGAGCCTTGTCG TTACAGCTGCCCCAGGGAGGAGGAGGGCAGCACCATCCCCATCCAGGAGGATTACC GAAAACCGGAGCCTGCCTGCTCCCCCAGAGTGAAGTTCAGCAGGAGCGCAGACGCC CCCGCGTACAAGCAGGGCCAGAACCAGCTCTATAACGAGCTCAATCTAGGACGAAGA GAGGAGTACGATGTTTTGGACAAGAGACGTGGCCGGGACCCTGAGATGGGGGGGA AAGCCGAGAAGGAAGAACCCTCAGGAAGGCCTGTACAATGAACTGCAGAAAGATAA GATGGCGGAGGCCTACAGTGAGATTGGGATGAAAGGCGAGCGCCGGAGGGGCAA GGGGCACGATGGCCTTTACCAGGGTCTCAGTACAGCCACCAAGGACACCTACGACG CCCTTCACATGCAGGCCCTGCCCCCTCGC |
| 43 | Tn-MUC1 CAR amino acid sequence (5E527z) | MALPVTALLLPLALLLHAARPGSQVQLQQSDAELVKPGSSVKISCKASGYTFTDH AIHWVKQKPEQGLEWIGHFSPGNTDIKYNDKFKGKATLTVDRSSSTAYMQLNS LTSEDSAVYFCKTSTFFFDYWGQGTTLTVSSGGGGSGGGGSGGGGSELVMTQS PSSLTVTAGEKVTMICKSSQSLLNSGDQKNYLTWYQQKPGQPPKLLIFWASTRE SGVPDRFTGSGSGTDFTLTISSVQAEDLAVYYCQNDYSYPLTFGAGTKLELKSGTT TPAPRPPTPAPTIASQPLSLRPEACRPAAGGAVHTRGLDFACDIYIWAPLAGTCG VLLLSLVITLYCQRRKYRSNKGESPVEPAEPCRYSCPREEEGSTIPIQEDYRKPEPAC SPRVKFSRSADAPAYKQGQNQLYNELNLGRREEYDVLDKRRGRDPEMGGKPRR KNPQEGLYNELQKDKMAEAYSEIGMKGERRRGKGHDGLYQGLSTATKDTYDAL HMQALPPR |

TABLE 1-continued

| SEQ ID NO: | Description | Sequence |
|---|---|---|
| 44 | Tn-MUC1 CAR nucleic acid sequence (5E5Ox40z) | ATGGCCTTACCAGTGACCGCCTTGCTCCTGCCGCTGGCCTTGCTGCTCCACGCCGCCA GGCCGGGATCCCAGGTGCAGCTGCAGCAGTCTGATGCCGAGCTCGTGAAGCCTGGC AGCAGCGTGAAGATCAGCTGCAAGGCCAGCGGCTACACCTTCACCGACCACGCCATC CACTGGGTCAAGCAGAAGCCTGAGCAGGGCCTGGAGTGGATCGGCCACTTCAGCCC CGGCAACACCGACATCAAGTACAACGACAAGTTCAAGGGCAAGGCCACCCTGACCG TGGACAGAAGCAGCAGCACCGCCTACATGCAGCTGAACAGCCTGACCAGCGAGGAC AGCGCCGTGTACTTCTGCAAGACCAGCACCTTCTTTTTCGACTACTGGGGCCAGGGC ACAACCCTGACAGTGTCTAGCGGAGGCGGAGGATCTGGCGGCGGAGGAAGTGGCG GAGGGGGATCTGAACTCGTGATGACCCAGAGCCCCAGCTCTCTGACAGTGACAGCC GG CGAGAAAGTGACCATGATCTGCAAGTCCTCCCAGAGCCTGCTGAACTCCGGCGACCA GAAGAACTACCTGACCTGGTATCAGCAGAAACCCGGCCAGCCCCCCAAGCTGCTGAT CTTTTGGGCCAGCACCCGGGAAAGCGGCGTGCCCGATAGATTCACAGGCAGCGGCT CCGGCACCGACTTTACCCTGACCATCAGCTCCGTGCAGGCCGAGGACCTGGCCGTGT ATTACTGCCAGAACGACTACAGCTACCCCCTGACCTTCGGAGCCGGCACCAAGCTGG AACTGAAGTCCGGAACCACGACGCCAGCGCCGCGACCACCAACACCGGCGCCCACC ATCGCGTCGCAGCCCCTGTCCCTGCGCCCCAGAGGCGTGCCGGCCAGCGGCGGGGGG CGCAGTGCACACGAGGGGGCTGGACTTCGCCTGTGATATCTACATCTGGGCGCCCTT GGCCGGGACTTGTGGGGTCCTTCTCCTGTCACTGGTTATCACCCTTTACTGCGCCCTG TACCTGCTCCGCAGGGACCAGAGGCTGCCCCCCGATGCCCACAAGCCCCCTGGGGG AGGCAGTTTCAGGACCCCCATCCAAGAGGAGCAGGCCGACGCCCACTCCACCCTGGC CAAGATCAGAGTGAAGTTCAGCAGGAGCGCAGACGCCCCCGCGTACAAGCAGGGCC AGAACCAGCTCTATAACGAGCTCAATCTAGGACGAAGAGAGGAGTACGATGTTTTG GACAAGAGACGTGGCCGGGACCCTGAGATGGGGGGAAAGCCGAGAAGGAAGAAC CCTCAGGAAGGCCTGTACAATGAACTGCAGAAAGATAAGATGGCGGAGGCCTACAG TGAGATTGGGATGAAAGGCGAGCGCCGGAGGGGCAAGGGGCACGATGGCCTTTAC CAGGGTCTCAGTACAGCCACCAAGGACACCTACGACGCCCTTCACATGCAGGCCCTG CCCCCTCGC |
| 45 | Tn-MUC1 CAR amino acid sequence (5E5Ox40z) | MALPVTALLLPLALLLLHAARPGSQVQLQQSDAELVKPGSSVKISCKASGYTFTDH AIHWVKQKPEQGLEWIGHFSPGNTDIKYNDKFKGKATLTVDRSSSTAYMQLNS LTSEDSAVYFCKTSTFFFDYWGQGTTLTVSSGGGGSGGGGSGGGGSELVMTQS PSSLTVTAGEKVTMICKSSQSLLNSGDQKNYLTWYQQKPGQPPKLLIFWASTRE SGVPDRFTGSGSGTDFTLTISSVQAEDLAVYYCQNDYSYPLTFGAGTKLELKSGTT TPAPRPPTPAPTIASQPLSLRPEACRPAAGGAVHTRGLDFACDIYIWAPLAGTCG VLLLSLVITLYCALYLLRRDQRLPPDAHKPPGGGSFRTPIQEEQADAHSTLAKIRVK FSRSADAPAYKQGQNQLYNELNLGRREEYDVLDKRRGRDPEMGGKPRRKNPQ EGLYNELQKDKMAEAYSEIGMKGERRRGKGHDGLYQGLSTATKDTYDALHMQ ALPPR |
| 46 | Tn-MUC1 CAR nucleic acid sequence (5E5CD2z) | ATGGCCTTACCAGTGACCGCCTTGCTCCTGCCGCTGGCCTTGCTGCTCCACGC CGCCAGGCCGGGATCCCAGGTGCAGCTGCAGCAGTCTGATGCCGAGCTCGT GAAGCCTGGCAGCAGCGTGAAGATCAGCTGCAAGGCCAGCGGCTACACCTT CACCGACCACGCCATCCACTGGGTCAAGCAGAAGCCTGAGCAGGGCCTGGA GTGGATCGGCCACTTCAGCCCCGGCAACACCGACATCAAGTACAACGACAA GTTCAAGGGCAAGGCCACCCTGACCGTGGACAGAAGCAGCAGCACCGCCTA CATGCAGCTGAACAGCCTGACCAGCGAGGACAGCGCCGTGTACTTCTGCAA GACCAGCACCTTCTTTTTCGACTACTGGGGCCAGGGCACAACCCTGACAGTG TCTAGCGGAGGCGGAGGATCTGGCGGCGGAGGAAGTGGCGGAGGGGGAT CTGAACTCGTGATGACCCAGAGCCCCAGCTCTCTGACAGTGACAGCCGGCGA GAAAGTGACCATGATCTGCAAGTCCTCCCAGAGCCTGCTGAACTCCGGCGAC CAGAAGAACTACCTGACCTGGTATCAGCAGAAACCCGGCCAGCCCCCCAAG CTGCTGATCTTTTGGGCCAGCACCCGGGAAAGCGGCGTGCCCGATAGATTCA CAGGCAGCGGCTCCGGCACCGACTTTACCCTGACCATCAGCTCCGTGCAGGC CGAGGACCTGGCCGTGTATTACTGCCAGAACGACTACAGCTACCCCCTGACC TTCGGAGCCGGCACCAAGCTGGAACTGAAGTCCGGAACCACGACGCCAGCG CCGCGACCACCAACACCGGCGCCCACCATCGCGTCGCAGCCCCTGTCCCTGC GCCCAGAGGCGTGCCGGCCAGCGGCGGGGGGCGCAGTGCACACGAGGGG GCTGGACTTCGCCTGTGATATCTACATCTGGGCGCCCTTGGCCGGGACTTGT GGGGTCCTTCTCCTGTCACTGGTTATCACCCTTTACTGCACCAAAAGGAAAAA ACAGAGGAGTCGGAGAAATGATGAGGAGCTGGAGACAAGAGCCCACAGAG TAGCTACTGAAGAAAGGGGCCGGAAGCCCCACCAAATTCCAGCTTCAACCCC TCAGAATCCAGCAACTTCCCAACATCCTCCTCCACCACCTGGTCATCGTTCCC AGGCACCTAGTCATCGTCCCCCGCCTCCTGGACACCGTGTTCAGCACCAGCCT CAGAAGAGGCCTCCTGCTCCGTCGGGCACACAAGTTCACCAGCAGAAAGGC CCGCCCCTCCCCAGACCTCGAGTTCAGCCAAAACCTCCCCATGGGGCAGCAG AAAACTCATTGTCCCCTTCCTCTAATATCGATAGAGTGAAGTTCAGCAGGAG CGCAGACGCCCCCGCGTACAAGCAGGGCCAGAACCAGCTCTATAACGAGCT CAATCTAGGACGAAGAGAGGAGTACGATGTTTTGGACAAGAGACGTGGCCG GGACCCTGAGATGGGGGGAAAGCCGAGAAGGAAGAACCCTCAGGAAGGC CTGTACAATGAACTGCAGAAAGATAAGATGGCGGAGGCCTACAGTGAGATTG GGATGAAAGGCGAGCGCCGGAGGGGCAAGGGGCACGATGGCCTTTACCAG GGTCTCAGTACAGCCACCAAGGACACCTACGACGCCCTTCACATGCAGGCCC TGCCCCCTCGC |

TABLE 1-continued

| SEQ ID NO: | Description | Sequence |
|---|---|---|
| 47 | Tn-MUC1 CAR amino acid sequence (5E5CD2z) | MALPVTALLLPLALLLHAARPGSQVQLQQSDAELVKPGSSVKISCKASGYTFTDH AIHWVKQKPEQGLEWIGHFSPGNTDIKYNDKFKGKATLTVDRSSSTAYMQLNS LTSEDSAVYFCKTSTFFFDYWGQGTTLTVSSGGGGSGGGGSGGGGSELVMTQS PSSLTVTAGEKVTMICKSSQSLLNSGDQKNYLTWYQQKPGQPPKLLIFWASTRE SGVPDRFTGSGSGTDFTLTISSVQAEDLAVYYCQNDYSYPLTFGAGTKLELKSGTT TPAPRPPTPAPTIASQPLSLRPEACRPAAGGAVHTRGLDFACDIYIWAPLAGTCG VLLLSLVITLYCTKRKKQRSRRNDEELETRAHRVATEERGRKPHQIPASTPQNPAT SQHPPPPPGHRSQAPSHRPPPPGHRVQHQPQKRPPAPSGTQVHQQKGPPLPR PRVQPKPPHGAAENSLSPSSNIDRVKFSRSADAPAYKQGQNQLYNELNLGRREE YDVLDKRRGRDPEMGGKPRRKNPQEGLYNELQKDKMAEAYSEIGMKGERRRG KGHDGLYQGLSTATKDTYDALHMQALPPR |
| 48 | CD8alpha leader amino acid sequence | MALPVTALLLPLALLLHAARP |
| 49 | Tn-MUC1 CAR amino acid sequence (5E5ICOSz) | MALPVTALLLPLALLLHAARPGSQVQLQQSDAELVKPGSSVKISCKASGYTFTDH AIHWVKQKPEQGLEWIGHFSPGNTDIKYNDKFKGKATLTVDRSSSTAYMQLNS LTSEDSAVYFCKTSTFFFDYWGQGTTLTVSSGGGGSGGGGSGGGGSELVMTQS PSSLTVTAGEKVTMICKSSQSLLNSGDQKNYLTWYQQKPGQPPKLLIFWASTRE SGVPDRFTGSGSGTDFTLTISSVQAEDLAVYYCQNDYSYPLTFGAGTKLELKSGTT TPAPRPPTPAPTIASQPLSLRPEACRPAAGGAVHTRGLDFACDFWLPIGCAAFVV VCILGCILICWLTKKKYSSSVHDPNGEYMFMRAVNTAKKSRLTDVTLRVKFSRSA DAPAYKQGQNQLYNELNLGRREEYDVLDKRRGRDPEMGGKPRRKNPQEGLYN ELQKDKMAEAYSEIGMKGERRRGKGHDGLYQGLSTATKDTYDALHMQALPPR |
| 50 | Tn-MUC1 CAR nucleic acid sequence (5E5ICOSz-1) | ATGGCCTTACCAGTGACCGCCTTGCTCCTGCCGCTGGCCTTGCTGCTCCACGCCGCCA GGCCGGGATCCCAGGTGCAGCTGCAGCAGTCTGATGCCGAGCTCGTGAAGCCTGGC AGCAGCGTGAAGATCAGCTGCAAGGCCAGCGGCTACACCTTCACCGACCACGCCATC CACTGGGTCAAGCAGAAGCCTGAGCAGGGCCTGGAGTGGATCGGACACTTCAGCCC CGGCAACACCGACATCAAGTACAACGACAAGTTCAAGGGCAAGGCCACCCTGACCG TGGACAGAAGCAGCAGCACCGCCTACATGCAGCTGAACAGCCTGACCAGCGAGGAC AGCGCCGTGTACTTCTGCAAGACCAGCACCTTCTTTTTCGACTACTGGGGCCAGGGC ACAACCCTGACAGTGTCTAGCGGAGGCGGAGGATCTGGCGGCGGAGGAAGTGGCG GAGGGGGATCTGAACTCGTGATGACCCAGAGCCCCAGCTCTCTGACAGTGACAGCC GGCGAGAAAGTGACCATGATCTGCAAGTCCTCCCAGAGCCTGCTGAACTCCGGCGAC CAGAAGAACTACCTGACCTGGTATCAGCAGAAACCCGGCCAGCCCCCCAAGCTGCTG ATCTTTTGGGCCAGCACCCGGGAAAGCGGCGTGCCCGATAGATTCACAGGCAGCGG CTCCGGCACCGACTTTACCCTGACCATCAGCTCCGTGCAGGCCGAGGACCTGGCCGT GTATTACTGCCAGAACGACTACAGCTACCCCCTGACCTTCGGAGCCGGCACCAAGCT GGAACTGAAGTCCGGAACCACGACGCCAGCGCCGCGACCACCAACACCGGCGCCCA CCATCGCGTCGCAGCCCCTGTCCCTGCGCCCAGAGGCGTGCCGGCCAGCGGCGGGG GGCGCAGTGCACACGAGGGGGCTGGACTTCGCCTGTGATTTCTGGTTACCCATAGGA TGTGCAGCCTTTGTTGTAGTCTGCATTTTGGGATGCATACTTATTTGTTGGCTTACAAA AAAGAAGTATTCATCCAGTGTGCACGACCCTAACGGTGAATACATGTTCATGAGAGC AGTGAACACAGCCAAAAAATCCAGACTCACAGATGTGACCCTAAGAGTGAAGTTCAG CAGGAGCGCAGACGCCCCCGCGTACAAGCAGGGCCAGAACCAGCTCTATAACGAGC TCAATCTAGGACGAAGAGAGGAGTACGATGTTTTGGACAAGAGACGTGGCCGGGAC CCTGAGATGGGGGGAAAGCCGAGAAGGAAGAACCCTCAGGAAGGCCTGTACAATG AACTGCAGAAAGATAAGATGGCGGAGGCCTACAGTGAGATTGGGATGAAAGGCGA GCGCCGGAGGGGCAAGGGGCACGATGGCCTTTACCAGGGTCTCAGTACAGCCACCA AGGACACCTACGACGCCCTTCACATGCAGGCCCTGCCCCCTCGC |
| 51 | Tn-MUC1 CAR nucleic acid sequence (5E5ICOSz-2) | ATGGCCTTACCAGTGACCGCCTTGCTCCTGCCGCTGGCCTTGCTGCTCCACGC CGCCAGGCCGGGATCCCAGGTGCAGCTGCAGCAGTCTGATGCCGAGCTCGT GAAGCCTGGCAGCAGCGTGAAGATCAGCTGCAAGGCCAGCGGCTACACCTT CACCGACCACGCCATCCACTGGGTCAAGCAGAAGCCTGAGCAGGGCCTGGA GTGGATCGGCCACTTCAGCCCCGGCAACACCGACATCAAGTACAACGACAA GTTCAAGGGCAAGGCCACCCTGACCGTGGACAGAAGCAGCAGCACCGCCTA CATGCAGCTGAACAGCCTGACCAGCGAGGACAGCGCCGTGTACTTCTGCAA GACCAGCACCTTCTTTTTCGACTACTGGGGCCAGGGCACAACCCTGACAGTG TCTAGCGGAGGCGGAGGATCTGGCGGCGGAGGAAGTGGCGGAGGGGGAT CTGAACTCGTGATGACCCAGAGCCCCAGCTCTCTGACAGTGACAGCCGGCGA GAAAGTGACCATGATCTGCAAGTCCTCCCAGAGCCTGCTGAACTCCGGCGAC CAGAAGAACTACCTGACCTGGTATTC AGCAGAAACCCGGCCAGCCCCCCAAGCTGCTGATCTTTTGGGCCAGCACCCG GGAAAGCGGCGTGCCCGATAGATTCACAGGCAGCGGCTCCGGCACCGACTT TACCCTGACCATCAGCTCCGTGCAGGCCGAGGACCTGGCCGTGTATTACTGC CAGAACGACTACAGCTACCCCCTGACCTTCGGAGCCGGCACCAAGCTGGAAC TGAAGTCCGGAACCACGACGCCAGCGCCGCGACCACCAACACCGGCGCCCA CCATCGCGTCGCAGCCCCTGTCCCTGCGCCCAGAGGCGTGCCGGCCAGCGCG GCGGGGGGCGCAGTGCACACGAGGGGGCTGGACTTCGCCTGTGATTTCTGGT TACCCATAGGATGTGCAGCCTTTGTTGTAGTCTGCATTTTGGGATGCATACTT ATTTGTTGGCTTACAAAAAAGAAGTATTCATCCAGTGTGCACGACCCTAACG GTGAATACATGTTCATGAGAGCAGTGAACACAGCCAAAAAATCTAGACTCAC AGATGTGACCCTAAGAGTGAAGTTCAGCAGGAGCGCAGACGCCCCCGCGTA |

TABLE 1-continued

| SEQ ID NO: | Description | Sequence |
|---|---|---|
| | | CAAGCAGGGCCAGAACCAGCTCTATAACGAGCTCAATCTAGGACGAAGAGA<br>GGAGTACGATGTTTTGGACAAGAGACGTGGCCGGGACCCTGAGATGGGGG<br>GAAAGCCGAGAAGGAAGAACCCTCAGGAAGGCCTGTACAATGAACTGCAG<br>AAAGATAAGATGGCGGAAGGCCTACAGTGAGATTGGGATGAAAGGCGAGCG<br>CCGGAGGGGCAAGGGGCACGATGGCCTTTACCAGGGTCTCAGTACAGCCAC<br>CAAGGACACCTACGACGCCCTTCACATGCAGGCCCTGCCCCCTCGC |
| 76 | TGFβRII dominant negative receptor amino acid sequence (TGFbRII-DN) | MGRGLLRGLWPLHIVLWTRIASTIPPHVQKSVNNDMIVTDNNGAVKFPQLCKF<br>CDVRFSTCDNQKSCMSNCSITSICEKPQEVCVAVWRKNDENITLETVCHDPKLP<br>YHDFILEDAASPKCIMKEKKKPGETFFMCSCSSDECNDNIIFSEEYNTSNPDLLLVI<br>FQVTGISLLPPLGVAISVIIIFYCYRVNRQQKLSSSG |
| 77 | TGFβRII dominant negative receptor nucleic acid sequence (TGFbRII-DN) | ATGGGTCGGGGGCTGCTCAGGGGCCTGTGGCCGCTGCACATCGTCCTGTGG<br>ACGCGTATCGCCAGCACGATCCCACCGCACGTTCAGAAGTCGGTTAATAACG<br>ACATGATAGTCACTGACAACAACGGTGCAGTCAAGTTTCCACAACTGTGTAA<br>ATTTTGTGATGTGAGATTTTCCACCTGTGACAACCAGAAATCCTGCATGAGCA<br>ACTGCAGCATCACCTCCATCTGTGAGAAGCCACAGGAAGTCTGTGTGGCTGT<br>ATGGAGAAAGAATGACGAGAACATAACACTAGAGACAGTTTGCCATGACCC<br>CAAGCTCCCCTACCATGACTTTATTCTGGAAGATGCTGCTTCTCCAAAGTGCA<br>TTATGAAGGAAAAAAAAAAGCCTGGTGAGACTTTCTTCATGTGTTCCTGTAG<br>CTCTGATGAGTGCAATGACAACATCATCTTCTCAGAAGAATATAACACCAGC<br>AATCCTGACTTGTTGCTAGTCATATTTCAAGTGACAGGCATCAGCCTCCTGCC<br>ACCACTGGGAGTTGCCATATCTGTCATCATCATCTTCTACTGCTACCGCGTTA<br>ACCGGCAGCAGAAGCTGAGTTCATCCGGA |
| 78 | PD1-CTM-CD28 receptor amino acid sequence | MQIPQAPWPVVWAVLQLGWRPGWFLDSPDRPWNPPTFSPALLVVTEGDNA<br>TFTCSFSNTSESFVLNWYRMSPSNQTDKLAAFPEDRSQPGQDCRFRVTQLPNG<br>RDFHMSVVRARRNDSGTYLCGAISLAPKAQIKESLRAELRVTERRAEVPTAHPSP<br>SPRPAGQFQTLVFWVLVVVGGVLACYSLLVTVAFIIFWVRSKRSRLLHSDYMNM<br>TPRRPGPTRKHYQPYAPPRDFAAYRS |
| 79 | PD1-CTM-CD28 receptor nucleic acid sequence | ATGCAGATCCCACAGGCGCCCTGGCCAGTCGTCTGGGCGGTGCTACAACTG<br>GGCTGGCGGCCAGGATGGTTCTTAGACTCCCCAGACAGGCCCTGGAACCCC<br>CCCACCTTCTCCCCAGCCCTGCTCGTGGTGACCGAAGGGGACAACGCCACCT<br>TCACCTGCAGCTTCTCCAACACATCGGAGAGCTTCGTGCTAAACTGGTACCG<br>CATGAGCCCCAGCAACCAGACGGACAAGCTGGCCGCCTTCCCCGAGGACCG<br>CAGCCAGCCCGGCCAGGACTGCCGCTTCCGTGTCACACAACTGCCCAACGGG<br>CGTGACTTCCACATGAGCGTGGTCAGGGCCCGGCGCAATGACAGCGGCACC<br>TACCTCTGTGGGGCCATCTCCCTGGCCCCCAAGGCGCAGATCAAAGAGAGCC<br>TGCGGGCAGAGCTCAGGGTGACAGAGAGAAGGGCAGAAGTGCCCACAGCC<br>CACCCCAGCCCCTCACCCAGGCCCAGCCGGCCAGTTCCAAACCCTGGTGTTTT<br>GGGGTGCTGGTGGTGGTTGGTGGAGTCCTGGCTTGCTATAGCTTGCTAGTAAC<br>AGTGGCCTTTATTATTTTCTGGGTGAGGAGTAAGAGGAGCAGGCTCCTGCAC<br>AGTGACTACATGAACATGACTCCCCGCCGCCCCGGGCCCCACCCGCAAGCATT<br>ACCGCCCTATGCCCCACCACGCGACTTCGCAGCCTATCGCTCC |
| 80 | PD1-PTM-CD28 receptor amino acid sequence | MQIPQAPWPVVWAVLQLGWRPGWFLDSPDRPWNPPTFSPALLVVTEGDNA<br>TFTCSFSNTSESFVLNWYRMSPSNQTDKLAAFPEDRSQPGQDCRFRVTQLPNG<br>RDFHMSVVRARRNDSGTYLCGAISLAPKLQIKESLRAELRVTERRAEVPTAHPSP<br>SPRPAGQFQTLVVGVVGGLLGSLVLLVWVLAVIRSKRSRLLHSDYMNMTPRRP<br>GPTRKHYQPYAPPRDFAAYRS |
| 81 | PD1-PTM-CD28 receptor nucleic acid sequence | ATGCAGATCCCACAGGCGCCCTGGCCAGTCGTCTGGGCGGTGCTACAACTG<br>GGCTGGCGGCCAGGATGGTTCTTAGACTCCCCAGACAGGCCCTGGAACCCC<br>CCCACCTTCTCCCCAGCCCTGCTCGTGGTGACCGAAGGGGACAACGCCACCT<br>TCACCTGCAGCTTCTCCAACACATCGGAGAGCTTCGTGCTAAACTGGTACCG<br>CATGAGCCCCAGCAACCAGACGGACAAGCTGGCCGCCTTCCCCGAGGACCG<br>CAGCCAGCCCGGCCAGGACTGCCGCTTCCGTGTCACACAACTGCCCAACGGG<br>CGTGACTTCCACATGAGCGTGGTCAGGGCCCGGCGCAATGACAGCGGCACC<br>TACCTCTGTGGGGCCATCTCCCTGGCCCCCAAGGCGCAGATCAAAGAGAGCC<br>TGCGGGCAGAGCTCAGGGTGACAGAGAGAAGGGCAGAAGTGCCCACAGCC<br>CACCCCAGCCCCTCACCCAGGCCCAGCCGGCCAGTTCCAAACCCTGGTGGTTG<br>GTGTCGTGGGCGGCCTGCTGGGCAGCCTGGTGCTGCTAGTCTGGGTCCTGG<br>CCGTCATCAGGAGTAAGAGGAGCAGGCTCCTGCACAGTGACTACATGAACA<br>TGACTCCCCGCCGCCCCGGGCCCACCCGCAAGCATTACCAGCCCTATGCCCC<br>ACCACGCGACTTCGCAGCCTATCGCTCC |
| 82 | PD1$^{A132L}$-PTM-CD28 receptor amino acid sequence | MQIPQAPWPVVWAVLQLGWRPGWFLDSPDRPWNPPTFSPALLVVTEGDNA<br>TFTCSFSNTSESFVLNWYRMSPSNQTDKLAAFPEDRSQPGQDCRFRVTQLPNG<br>RDFHMSVVRARRNDSGTYLCGAISLAPKLQIKESLRAELRVTERRAEVPTAHPSP<br>SPRPAGQFQTLVVGVVGGLLGSLVLLVWVLAVIRSKRSRLLHSDYMNMTPRRP<br>GPTRKHYQPYAPPRDFAAYRS |

TABLE 1-continued

| SEQ ID NO: | Description | Sequence |
|---|---|---|
| 83 | PD1$^{A132L}$-PTM-CD28 receptor nucleic acid sequence | ATGCAGATCCCACAGGCGCCCTGGCCAGTCGTCTGGGCGGTGCTACAACTG GGCTGGCGGCCAGGATGGTTCTTAGACTCCCCAGACAGGCCCTGGAACCCC CCCACCTTCTCCCCAGCCCTGCTCGTGGTGACCGAAGGGGACAACGCCACCT TCACCTGCAGCTTCTCCAACACATCGGAGAGCTTCGTGCTAAACTGGTACCG CATGAGCCCCAGCAACCAGACGGACAAGCTGGCCGCCTTCCCCGAGGACCG CAGCCAGCCCGGCCAGGACTGCCGCTTCCGTGTCACACAACTGCCCAACGGG CGTGACTTCCACATGAGCGTGGTCAGGGCCCGGCGCAATGACAGCGGCACC TACCTCTGTGGGGCCATCTCCCTGGCCCCCAAGCTGCAGATCAAAGAGAGCC TGCGGGCAGAGCTCAGGGTGACAGAGAGAAGGGCAGAAGTGCCCACAGCC CACCCCAGCCCCTCACCCAGGCCAGCCGGCCAGTTCCAAACCCTGGTGGTTG GTGTCGTGGGCGGCCTGCTGGGCAGCCTGGTGCTGCTAGTCTGGGTCCTGG CCGTCATCAGGAGTAAGAGGAGCAGGCTCCTGCACAGTGACTACATGAACA TGACTCCCCGCCGCCCCGGGCCCACCCGCAAGCATTACCAGCCCTATGCCCC ACCACGCGACTTCGCAGCCTATCGC |
| 84 | PD-1-4-1BB receptor amino acid sequence (PD1-BB) | MQIPQAPWPVVWAVLQLGWRPGWFLDSPDRPWNPPTFSPALLVVTEGDNA TFTCSFSNTSESFVLNWYRMSPSNQTDKLAAFPEDRSQPGQDCRFRVTQLPNG RDFHMSVVRARRNDSGTYLCGAISLAPKAQIKESLRAELRVTERRAEVPTAHPSP SPRPAGQFQTLVIYIWAPLAGTCGVLLLSLVITLYCKKRGRKKLLYIFKQPFMRPV QTTQEEDGCSCRFPEEEEGGCEL |
| 85 | PD-1-4-1BB receptor nucleic acid sequence (PD1-BB) | ATGCAGATCCCACAGGCGCCCTGGCCAGTCGTCTGGGCGGTGCTACAACTG GGCTGGCGGCCAGGATGGTTCTTAGACTCCCCAGACAGGCCCTGGAACCCC CCCACCTTCTCCCCAGCCCTGCTCGTGGTGACCGAAGGGGACAACGCCACCT TCACCTGCAGCTTCTCCAACACATCGGAGAGCTTCGTGCTAAACTGGTACCG CATGAGCCCCAGCAACCAGACGGACAAGCTGGCCGCCTTCCCCGAGGACCG CAGCCAGCCCGGCCAGGACTGCCGCTTCCGTGTCACACAACTGCCCAACGGG CGTGACTTCCACATGAGCGTGGTCAGGGCCCGGCGCAATGACAGCGGCACC TACCTCTGTGGGGCCATCTCCCTGGCCCCCAAGGCGCAGATCAAAGAGAGCC TGCGGGCAGAGCTCAGGGTGACAGAGAGAAGGGCAGAAGTGCCCACAGCC CACCCCAGCCCCTCACCCAGGCCAGCCGGCCAGTTCCAAACCCTGGTTATCTA CATCTGGGCGCCCTTGGCCGGGACTTGTGGGGTCCTTCTCCTGTCACTGGTT ATCACCCTTTACTGCAAAAAACGGGGCAGAAAGAAACTCCTGTATATATTCA AACAACCATTTATGAGACCAGTACAAACTACTCAAGAGGAAGATGGCTGTA GCTGCCGATTTCCAGAAGAAGAAGAAGGAGGATGTGAACTG |
| 86 | PD1$^{A132L}$-4-1BB receptor amino acid sequence (PD1* BB) | MQIPQAPWPVVWAVLQLGWRPGWFLDSPDRPWNPPTFSPALLVVTEGDNA TFTCSFSNTSESFVLNWYRMSPSNQTDKLAAFPEDRSQPGQDCRFRVTQLPNG RDFHMSVVRARRNDSGTYLCGAISLAPKLQIKESLRAELRVTERRAEVPTAHPSP SPRPAGQFQTLVIYIWAPLAGTCGVLLLSLVITLYCKKRGRKKLLYIFKQPFMRPV QTTQEEDGCSCRFPEEEEGGCEL |
| 87 | PD1$^{A132L}$-4-1BB receptor nucleic acid sequence (PD1*BB) | ATGCAGATCCCACAGGCGCCCTGGCCAGTCGTCTGGGCGGTGCTACAACTG GGCTGGCGGCCAGGATGGTTCTTAGACTCCCCAGACAGGCCCTGGAACCCC CCCACCTTCTCCCCAGCCCTGCTCGTGGTGACCGAAGGGGACAACGCCACCT TCACCTGCAGCTTCTCCAACACATCGGAGAGCTTCGTGCTAAACTGGTACCG CATGAGCCCCAGCAACCAGACGGACAAGCTGGCCGCCTTCCCCGAGGACCG CAGCCAGCCCGGCCAGGACTGCCGCTTCCGTGTCACACAACTGCCCAACGGG CGTGACTTCCACATGAGCGTGGTCAGGGCCCGGCGCAATGACAGCGGCACC TACCTCTGTGGGGCCATCTCCCTGGCCCCCAAGCTGCAGATCAAAGAGAGCC TGCGGGCAGAGCTCAGGGTGACAGAGAGAAGGGCAGAAGTGCCCACAGCC CACCCCAGCCCCTCACCCAGGCCAGCCGGCCAGTTCCAAACCCTGGTTATCTA CATCTGGGCGCCCTTGGCCGGGACTTGTGGGGTCCTTCTCCTGTCACTGGTT ATCACCCTTTACTGCAAAAAACGGGGCAGAAAGAAACTCCTGTATATATTCA AACAACCATTTATGAGACCAGTACAAACTACTCAAGAGGAAGATGGCTGTA GCTGCCGATTTCCAGAAGAAGAAGAAGGAGGATGTGAACTG |
| 88 | TGFβR-IL12Rβ1 receptor amino acid sequence | MEAAVAAPRPRLLLLVLAAAAAAAAALLPGATALQCFCHLCTKDNFTCVTDGLC FVSVTETTDKVIHNSMCIAEIDLIPRDRPFVCAPSSKTGSVTTTYCCNQDHCNKIE LPTTVKSSPGLGPVELAAVIAGPVCFVCISLMLMVYIRAARHLCPPLPTPCASSAIE FPGGKETWQWINPVDFQEEASLQEALVVEMSWDKGERTEPLEKTELPEGAPEL ALDTELSLEDGDRCKAKM |
| 89 | TGFβR-IL12Rβ1 receptor nucleic acid sequence | ATGGAGGCGGCGGTCGCTGCTCCGCGTCCCCGGCTGCTCCTCCTCGTGCTGG CGGCGGCGGCGGCGGCGGCGGCGGCGCTGCTCCCGGGGGCGACGGCGTTA CAGTGTTTCTGCCACCTCTGTACAAAAGACAATTTTACTTGTGTGACAGATGG GCTCTGCTTTGTCTCTGTCACAGAGACCACAGACAAAGTTATACACAACAGC ATGTGTATAGCTGAAATTGACTTAATTCCTCGAGATAGGCCGTTTGTATGTGC ACCCTCTTCAAAAACTGGGTCTGTGACTACAACATATTGCTGCAATCAGGACC ATTGCAATAAAATAGAACTTCCAACTACTGTAAAGTCATCACCTGGCCTTGGT CCTGTGGAACTGGCAGCTGTCATTGCTGGACCAGTGTGCTTCGTCTGCATCT CACTCATGTTGATGGTCTATATCAGGGCCGCACGGCACCTGTGCCCGCCGCT |

TABLE 1-continued

| SEQ ID NO: | Description | Sequence |
|---|---|---|
| | | GCCCACACCCTGTGCCAGCTCCGCCATTGAGTTCCCTGGAGGGAAGGAGACT TGGCAGTGGATCAACCCAGTGGACTTCCAGGAAGAGGCATCCCTGCAGGAG GCCCTGGTGGTAGAGATGTCCTGGGACAAAGGCGAGAGGACTGAGCCTCTC GAGAAGACAGAGCTACCTGAGGGTGCCCCTGAGCTGGCCCTGGATACAGAG TTGTCCTTGGAGGATGGAGACAGGTGCAAGGCCAAGATG |
| 90 | TGFβR-IL12Rβ2 receptor amino acid sequence | MGRGLLRGLWPLHIVLWTRIASTIPPHVQKSVNNDMIVTDNNGAVKFPQLCKF CDVRFSTCDNQKSCMSNCSITSICEKPQEVCVAVWRKNDENITLETVCHDPKLP YHDFILEDAASPKCIMKEKKKPGETFFMCSCSSDECNDNIIFSEEYNTSNPDLLLVI FQVTGISLLPPLGVAISVIIIFYQQKVFVLLAALRPQWCSREIPDDPANSTCAKKYPIA EEKTQLPLDRLLIDWPTPEDPEPLVISEVLHQVTPVFRHPPCSNWPQREKGIQGH QASEKDMMHSASSPPPPRALQAESRQLVDLYKVLESRGSDPKPENPACPWTVL PAGDLPTHDGYLPSNIDDLPSHEAPLADSLEELEPQHISLSVFPSSSLHPLTFSCGD KLTLDQLKMRCDSLML |
| 91 | TGFβR-IL12Rβ2 receptor nucleic acid sequence | ATGGGTCGGGGGCTGCTCAGGGGCCTGTGGCCGCTGCACATCGTCCTGTGG ACGCGTATCGCCAGCACGATCCCACCGCACGTTCAGAAGTCGGTTAATAACG ACATGATAGTCACTGACAACAACGGTGCAGTCAAGTTTCCACAACTGTGTAA ATTTTGTGATGTGAGATTTTCCACCTGTGACAACCAGAAATCCTGCATGAGCA ACTGCAGCATCACCTCCATCTGTGAGAAGCCACAGGAAGTCTGTGTGGCTGT ATGGAGAAAGAATGACGAGAACATAACACTAGAGACAGTTTGCCATGACCC CAAGCTCCCCTACCATGACTTTATTCTGGAAGATGCTGCTTCTCCAAAGTGCA TTATGAAGGAAAAAAAAAAGCCTGGTGAGACTTTCTTCATGTGTTCCTGTAG CTCTGATGAGTGCAATGACAACATCATCTTCTCAGAAGAATATAACACCAGC AATCCTGACTTGTTGCTAGTCATATTTCAAGTGACAGGCATCAGCCTCCTGCC ACCACTGGGAGTTGCCATATCTGTCATCATCATCTTCTACCAGCAAAAGGTGT TTGTTCTCCTAGCAGCCCTCAGACCTCAGTGGTGTAGCAGAGAAATTCCAGA TCCAGCAAATAGCACTTGCGCTAAGAAATATCCCATTGCAGAGGAGAAGAC ACAGCTGCCCTTGGACAGGCTCCTGATAGACTGGCCCACGCCTGAAGATCCT GAACCGCTGGTCATCAGTGAAGTCCTTCATCAAGTGACCCCAGTTTTCAGAC ATCCCCCCTGCTCCAACTGGCCACAAAGGGAAAAAGGAATCCAAGGTCATCA GGCCTCTGAGAAAGACATGATGCACAGTGCCTCAAGCCCACCACCTCCAAGA GCTCTCCAAGCTGAGAGCAGACAACTGGTGGATCTGTACAAGGTGCTGGAG AGCAGGGGCTCCGACCCAAAGCCAGAAAACCCAGCCTGTCCCTGGACGGTG CTCCCAGCAGGTGACCTTCCCACCCATGATGGCTACTTACCCTCCAACATAGA TGACCTCCCCTCACATGAGGCACCTCTCGCTGACTCTCTGGAAGAACTGGAG CCTCAGCACATCTCCCTTTCTGTTTTCCCCTCAAGTTCTCTTCACCCACTCACCT TCTCCTGTGGTGATAAGCTGACTCTGGATCAGTTAAAGATGAGGTGTGACTC CCTCATGCTC |
| 92 | TIM3-CD28 receptor amino acid sequence | MFSHLPFDCVLLLLLLLLTRSSEVEYRAEVGQNAYLPCFYTPAAPGNLVPVCWGK GACPVFECGNVVLRTDERDVNYWTSRYWLNGDFRKGDVSLTIENVTLADSGIY CCRIQIPGIMNDEKFNLKLVIKPAKVTPAPTRQRDFTAAFPRMLTTRGHGPAET QTLGSLPDINLTQISTLANELRDSRLANDLRDSGATIRFWVLVVVGGVLACYSLLV TVAFIIFWVRSKRSRLLHSDYMNMTPRRPGPTRKHYQPYAPPRDFAAYRS |
| 93 | TIM3-CD28 receptor nucleic acid sequence | ATGTTTTCACATCTTCCCTTTGACTGTGTCCTGCTGCTGCTGCTGCTACTACTT ACAAGGTCCTCAGAAGTGGAATACAGAGCGGAGGTCGGTCAGAATGCCTAT CTGCCCTGCTTCTACACCCCAGCCGCCCCAGGGAACCTCGTGCCCGTCTGCTG GGGCAAAGGAGCCTGTCCTGTGTTTGAATGTGGCAACGTGGTGCTCAGGAC TGATGAAAGGGATGTGAATTATTGGACATCCAGATACTGGCTAAATGGGGA TTTCCGCAAAGGAGATGTGTCCCTGACCATAGAGAATGTGACTCTAGCAGAC AGTGGGATCTACTGCTGCCGAATCCAAATCCCAGGCATAATGAATGATGAAA AATTTAACCTGAAGTTGGTCATCAAACCAGCCAAGGTCACCCCTGCACCGAC TCGGCAGAGAGACTTCACTGCAGCCTTTCCAAGGATGCTTACCACCAGGGGA CATGGCCCAGCAGAGACACAGACACTGGGGAGCCTCCCTGACATAAATCTA ACACAAATATCCACATTGGCCAATGAGTTACGGGACTCTAGGTTGGCCAATG ACTTACGGGACTCCGGAGCAACCATCAGATTTTGGGTGCTGGTGGTGGTTG GTGGAGTCCTGGCTTGCTATAGCTTACTAGTAACAGTGGCCTTTATTATTTTC TGGGTGAGGAGTAAGAGGAGCAGGCTCCTGCACAGTGACTACATGAACATG ACTCCCCGCCGCCCCGGGCCCACCCGCAAGCATTACCAGCCCTATGCCCCAC CACGCGACTTCGCAGCCTATCGCTCC |

Accordingly, a subject CAR may be a CAR having affinity for Tn-MUC1, comprising a Tn-MUC1 binding domain comprising the amino acid sequence set forth in SEQ ID NOs: 4, 5, 6, and/or 19-24. A subject Tn-MUC1 CAR may further comprise a leader sequence comprising an amino acid sequence set forth in SEQ ID NO: 48. A subject Tn-MUC1 CAR may further comprise a hinge domain comprising an amino acid sequence set forth in SEQ ID NO: 13. A subject Tn-MUC1 CAR may further comprise a transmembrane domain comprising an amino acid sequence set forth in SEQ ID NOs: 7 and/or 15. A subject Tn-MUC1 CAR may further comprise a costimulatory signaling domain comprising an amino acid sequence set forth in SEQ ID NOs: 9, 17, 25, 28, 32, 34, and/or 36. A subject Tn-MUC1 CAR may further comprise an intracellular signaling domain comprising an amino acid sequence set forth in SEQ ID NOs: 11 and/or 30. A subject Tn-MUC1 CAR may comprise an amino acid sequence set forth in SEQ ID NOs: 2, 39, 41, 43, 45, and/or 47.

Accordingly, a subject CAR may be a CAR having affinity for Tn-MUC1, comprising a Tn-MUC1 binding domain comprising the amino acid sequence set forth in SEQ ID NOs: 4, 5, 6, and/or 19-24. A subject Tn-MUC1 CAR may further comprise a leader sequence comprising an amino acid sequence set forth in SEQ ID NO: 48. A subject Tn-MUC1 CAR may further comprise a hinge domain comprising an amino acid sequence set forth in SEQ ID NO: 13. A subject Tn-MUC1 CAR may further comprise a transmembrane domain comprising an amino acid sequence set forth in SEQ ID NOs: 7 or 15. A subject Tn-MUC1 CAR may further comprise a costimulatory signaling domain comprising an amino acid sequence set forth in SEQ ID NOs: 9, 17, 25, 28, 32, 34, or 36. A subject Tn-MUC1 CAR may further comprise an intracellular signaling domain comprising an amino acid sequence set forth in SEQ ID NOs: 11 or 30. A subject Tn-MUC1 CAR may comprise an amino acid sequence set forth in SEQ ID NOs: 2, 39, 41, 43, 45, or 47.

Antigen Binding Domain

The antigen binding domain of a CAR is an extracellular region of the CAR for binding to a specific target antigen including proteins, carbohydrates, and glycolipids. In some embodiments, the CAR comprises affinity to a target antigen (e.g. a tumor associated antigen) on a target cell (e.g. a cancer cell). The target antigen may include any type of protein, or epitope thereof, associated with the target cell. For example, the CAR may comprise affinity to a target antigen on a target cell that indicates a particular status of the target cell.

In certain embodiments, the CAR of the invention comprises an antigen binding domain that binds to MUC1. In certain embodiments, the antigen binding domain binds to a glycosylated form or glycoepitope of MUC1. In certain embodiments, the antigen binding domain is specific for a truncated glycoepitope of MUC1. In certain embodiments, the antigen binding domain is specific for Tn-MUC1. In certain embodiments, the antigen binding domain of the invention comprises an antibody or fragment thereof, that binds to a MUC1 molecule or glycoepitope of MUC1 (Tn-MUC1). In certain exemplary embodiments, the antigen binding domain is an scFv antibody that binds to Tn-MUC1. The choice of antigen binding domain depends upon the type and number of antigens that are present on the surface of a target cell. For example, the antigen binding domain may be chosen to recognize an antigen that acts as a cell surface marker on a target cell associated with a particular status of the target cell.

As described herein, a CAR of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin. In an exemplary embodiment, a CAR of the present disclosure having affinity for Tn-MUC1 on a target cell may comprise a Tn-MUC1 binding domain. In some embodiments, the Tn-MUC1 binding domain is a murine Tn-MUC1 binding domain, e.g., the Tn-MUC1 binding domain is of murine origin. In some embodiments, the Tn-MUC1 binding domain is a humanized Tn-MUC1 binding domain. In some embodiments, the Tn-MUC1 binding domain is a human Tn-MUC1 binding domain, e.g., the Tn-MUC1 binding domain is of human origin.

In some embodiments, the Tn-MUC1 binding domain is derived from the 5E5 antibody disclosed in PCT Publication No. WO2008/040362, the disclosure of which is incorporated herein by reference in its entirety. Accordingly, a CAR of the present disclosure comprises a Tn-MUC1 binding domain derived from the 5E5 antibody disclosed in PCT Publication No. WO2008/040362. In some embodiments, the Tn-MUC1 binding domain is a humanized Tn-MUC1 binding domain. In some embodiments, the humanized Tn-MUC1 binding domain is derived from any one of the humanized 5E5 heavy and light chain sequences disclosed in PCT Publication No. WO2015/159076, the disclosure of which is incorporated herein by reference in its entirety. Accordingly, a CAR of the present disclosure comprises a humanized Tn-MUC1 binding domain derived from any one of the humanized 5E5 heavy and light chain sequences disclosed in PCT Publication No. WO2015/159076. A CAR of the present disclosure may comprise a humanized Tn-MUC1 binding domain, any transmembrane domain, optionally any hinge domain, any costimulatory domain and any intracellular signaling domain as disclosed herein.

In some embodiments, a CAR of the present disclosure may have affinity for one or more target antigens on one or more target cells. In some embodiments, a CAR may have affinity for one or more target antigens on a single target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through a polypeptide linker, an Fc hinge region, or a membrane hinge region.

The antigen binding domain can include any domain that binds to the antigen and may include, but is not limited to, a monoclonal antibody, a polyclonal antibody, a synthetic antibody, a human antibody, a humanized antibody, a nonhuman antibody, and any fragment thereof. Thus, in one embodiment, the antigen binding domain portion comprises a mammalian antibody or a fragment thereof. In another embodiment, the antigen binding domain of the CAR is selected from the group consisting of an anti-Tn-MUC1 antibody or a fragment thereof. In some embodiments, the antigen binding domain is selected from the group consisting of an antibody, an antigen binding fragment (Fab), and a single-chain variable fragment (scFv). In some embodiments, a Tn-MUC1 binding domain of the present invention is selected from the group consisting of a Tn-MUC1-specific antibody, a Tn-MUC1-specific Fab, and a Tn-MUC1-specific scFv. In one embodiment, a Tn-MUC1 binding domain is a Tn-MUC1-specific antibody. In one embodiment, a Tn-MUC1 binding domain is a Tn-MUC1-specific Fab. In one embodiment, a Tn-MUC1 binding domain is a Tn-MUC1-specific scFv.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker or spacer, which connects the N-terminus of the VH with the C-terminus of the VL, or the C-terminus of the VH with the N-terminus of the VL. The terms "linker" and "spacer" are used interchangeably herein. In some embodiments, the antigen binding domain (e.g., Tn-MUC1 binding domain) comprises an scFv having the configuration from N-terminus to C-terminus, VH-linker-VL. In some embodiments, the antigen binding domain (e.g., Tn-MUC1 binding domain) comprises an scFv having the configuration from N-terminus to C-terminus, VL-linker-VH. Those of skill in the art would be able to select the appropriate configuration for use in the present invention.

The linker is typically rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6): 1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO: 52), $(GGGS)_n$ (SEQ ID NO: 53), and $(GGGGS)_n$ (SEQ ID NO: 54), where n represents an integer of at least 1. Exemplary linker sequences can comprise amino acid sequences including, without limitation, GGSG (SEQ ID NO: 55), GGSGG (SEQ ID NO: 56), GSGSG (SEQ ID NO: 57), GSGGG (SEQ ID NO: 58), GGGSG (SEQ ID NO: 59), GSSSG (SEQ ID NO: 60), GGGGS (SEQ ID NO: 61), GGGGSGGGGSGGGGS (SEQ ID NO: 62) and the like. Those of skill in the art would be able to select the appropriate linker sequence for use in the present invention. In one embodiment, an antigen binding domain (e.g., Tn-MUC1 binding domain) of the present invention comprises a heavy chain variable region (VH) and a light chain variable region (VL), wherein the VH and VL is separated by the linker sequence having the amino acid sequence GGGGSGGGGSGGGGS (SEQ ID NO: 62), which may be encoded by a nucleic acid sequence comprising the nucleotide sequence GGTGGCGGTGGCTCGGGCGG TGGTGGGTCGGGTGGCGGCGGATCT (SEQ ID NO: 63).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 2008 27(6): 455-51; Peter et al., J Cachexia Sarcopenia Muscle 2012 Aug. 12; Shieh et al., J Imunol 2009 183(4): 2277-85; Giomarelli et al., Thromb Haemost 2007 97(6): 955-63; Fife eta., J Clin Invst 2006 116(8): 2252-61; Brocks et al., Immunotechnology 1997 3(3): 173-84; Moosmayer et al., Ther Immunol 1995 2(10:31-40). Agonistic scFvs having stimulatory activity have been described (see, e.g., Peter et al., J Bioi Chem 2003 25278(38): 36740-7; Xie et al., Nat Biotech 1997 15(8): 768-71; Ledbetter et al., Crit Rev Immunol 1997 17(5-6): 427-55; Ho et al., BioChim Biophys Acta 2003 1638(3): 257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')₂" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some instances, the antigen binding domain may be derived from the same species in which the CAR will ultimately be used. For example, for use in humans, the antigen binding domain of the CAR may comprise a human antibody as described elsewhere herein, or a fragment thereof.

In an exemplary embodiment, a Tn-MUC1 CAR of the present invention comprises a Tn-MUC1 binding domain, e.g., a Tn-MUC1-specific scFv. In one embodiment, the Tn-MUC1 binding domain comprises the amino acid sequence set forth in SEQ ID NO: 4. In one embodiment, the Tn-MUC1 binding domain is encoded by a nucleic acid sequence comprising the nucleotide sequence set forth in SEQ ID NO: 3.

In one embodiment, the Tn-MUC1 binding domain comprises a light chain variable region comprising an amino acid sequence set forth in SEQ ID NO: 6. The light chain variable region of the Tn-MUC1 binding domain comprises three light chain complementarity-determining regions (CDRs). As used herein, a "complementarity-determining region" or "CDR" refers to a region of the variable chain of an antigen binding molecule that binds to a specific antigen. Accordingly, a Tn-MUC1 binding domain may comprise a light chain variable region that comprises a CDR1 comprising an amino acid sequence set forth in SEQ ID NO: 19; a CDR2 comprising an amino acid sequence set forth in SEQ ID NO: 20; and a CDR3 comprising an amino acid sequence set forth in SEQ ID NO: 21.

In one embodiment, the Tn-MUC1 binding domain comprises a heavy chain variable region comprising an amino acid sequence set forth in SEQ ID NO: 5. A Tn-MUC1 binding domain may comprise a heavy chain variable region that comprises a CDR1 comprising an amino acid sequence set forth in SEQ ID NO: 22; a CDR2 comprising an amino acid sequence set forth in SEQ ID NO: 23; and a CDR3 comprising an amino acid sequence set forth in SEQ ID NO: 24.

Tolerable variations of the Tn-MUC1 binding domain will be known to those of skill in the art, while maintaining specific binding to Tn-MUC1. For example, in some embodiments the Tn-MUC1 binding domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 4-6 and 19-24.

In some embodiments, the Tn-MUC1 binding domain is encoded by a nucleic acid sequence comprising the nucleotide sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleotide sequence set forth in SEQ ID NO: 3.

The antigen binding domain may be operably linked to another domain of the CAR, such as the transmembrane domain or the costimulatory signaling domain, both described elsewhere herein. In one embodiment, a nucleic acid encoding the antigen binding domain is operably linked to a nucleic acid encoding a transmembrane domain and a nucleic acid encoding a costimulatory signaling domain.

The antigen binding domains described herein, such as the antibody or fragment thereof that binds to Tn-MUC1, can be combined with any of the transmembrane domains described herein, any of the intracellular domains or cytoplasmic domains described herein, or any of the other domains described herein that may be included in the CAR.

Transmembrane Domain

With respect to the transmembrane domain, the CAR of the present invention (e.g., Tn-MUC1 CAR) can be designed to comprise a transmembrane domain that connects the antigen binding domain of the CAR to the intracellular domain. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane regions of particular use in this invention include, without limitation, transmembrane domains derived from (i.e., comprise at least the transmembrane region(s) of) the alpha, beta or zeta chain of the T-cell receptor, CD28, CD2, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), CD278 (ICOS), CD357 (GITR), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. In certain exemplary embodiments, a triplet of phenylalanine, tryptophan and valine will be found at each end of a synthetic transmembrane domain.

The transmembrane domains described herein can be combined with any of the antigen binding domains described herein, any of the costimulatory signaling domains described herein, any of the intracellular signaling domains described herein, or any of the other domains described herein that may be included in a subject CAR.

In some embodiments, the transmembrane domain further comprises a hinge region. A subject CAR of the present invention may also include a hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell. The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, or from about 40 amino acids to about 50 amino acids.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

For example, hinge regions include glycine polymers $(G)_n$, glycine-serine polymers (including, for example, $(GS)_n$, $(GSGGS)_n$ (SEQ ID NO: 52) and $(GGGS)_n$ (SEQ ID NO: 53), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2:73-142). Exemplary hinge regions can comprise amino acid sequences including, but not limited to, GGSG (SEQ ID NO: 55), GGSGG (SEQ ID NO: 56), GSGSG (SEQ ID NO: 57), GSGGG (SEQ ID NO: 58), GGGSG (SEQ ID NO: 59), GSSSG (SEQ ID NO: 60), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1): 162-166; and Huck et al., *Nucleic Acids Res.* (1986) 14(4): 1779-1789. As non-limiting examples, an immunoglobulin hinge region can include one of the following amino acid sequences: DKTHT (SEQ ID NO: 64); CPPC (SEQ ID NO: 65); CPEPKSCDTPPPCPR (SEQ ID NO: 66) (see, e.g., Glaser et al., *J. Biol. Chem.* (2005) 280:41494-41503); ELKTPLGDTTHT (SEQ ID NO: 67); KSCDKTHTCP (SEQ ID NO: 68); KCCVDCP (SEQ ID NO: 69); KYGPPCP (SEQ ID NO: 70); EPKSCDKTHTCPPCP (SEQ ID NO: 71) (human IgG1 hinge); ERKCCVECPPCP (SEQ ID NO: 72) (human IgG2 hinge); ELKTPLGDTTH-TCPRCP (SEQ ID NO: 73) (human IgG3 hinge); SPNMVPHAHHAQ (SEQ ID NO: 74) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO: 75); see, e.g., Yan et al., *J. Biol. Chem.* (2012) 287:5891-5897. In one embodiment, the hinge region can comprise an amino acid sequence derived from human CD8, or a variant thereof.

In one embodiment, the transmembrane domain comprises a CD8α transmembrane domain. In some embodiments, a subject CAR comprises a CD8α transmembrane domain comprising the amino acid sequence set forth in SEQ ID NO: 7, which may be encoded by a nucleic acid sequence comprising the nucleotide sequence set forth in SEQ ID NO: 8.

In another embodiment, a subject CAR comprises a CD8α hinge domain and a CD8α transmembrane domain. In one embodiment, the CD8α hinge domain comprises the amino acid sequence set forth in SEQ ID NO: 13, which may be encoded by a nucleic acid sequence comprising the nucleotide sequence set forth in SEQ ID NO: 14.

In one embodiment, the transmembrane domain comprises a CD28 transmembrane domain. In some embodiments, a subject CAR comprises a CD28 transmembrane domain comprising the amino acid sequence set forth in SEQ ID NO: 15, which may be encoded by a nucleic acid sequence comprising the nucleotide sequence set forth in SEQ ID NO: 16.

Tolerable variations of the transmembrane and/or hinge domain will be known to those of skill in the art, while maintaining its intended function. For example, in some embodiments a transmembrane domain or hinge domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NO: 7, 13, and 15. For example, in some embodiments a transmembrane domain or hinge domain is encoded by a nucleic acid sequence comprising the nucleotide sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the nucleotide sequences set forth in SEQ ID NO: 8, 14, and 16.

The transmembrane domain may be combined with any hinge domain and/or may comprise one or more transmembrane domains described herein.

The transmembrane domains described herein, such as a transmembrane region of alpha, beta or zeta chain of the T-cell receptor, CD28, CD2, CD3 epsilon, CD45, CD4, CD5, CD7, CD8, CD9, CD 16, CD22, CD33, CD37, CD64, CD80, CD86, CD134 (OX-40), CD137 (4-1BB), CD154 (CD40L), CD278 (ICOS), CD357 (GITR), Toll-like receptor 1 (TLR1), TLR2, TLR3, TLR4, TLR5, TLR6, TLR7, TLR8, and TLR9, can be combined with any of the antigen binding domains described herein, any of the costimulatory signaling domains or intracellular domains or cytoplasmic domains described herein, or any of the other domains described herein that may be included in the CAR.

In one embodiment, the transmembrane domain may be synthetic, in which case it will comprise predominantly hydrophobic residues such as leucine and valine. In exemplary embodiments, a triplet of phenylalanine, tryptophan and valine will be found at each end of a synthetic transmembrane domain.

In some embodiments, a subject CAR may further comprise, between the extracellular domain and the transmembrane domain of the CAR, or between the intracellular domain and the transmembrane domain of the CAR, a spacer domain. As used herein, the term "spacer domain" generally means any oligo- or polypeptide that functions to link the transmembrane domain to, either the extracellular domain or, the intracellular domain in the polypeptide chain. A spacer domain may comprise up to 300 amino acids, e.g., 10 to 100 amino acids, or 25 to 50 amino acids. In some embodiments, the spacer domain may be a short oligo- or polypeptide linker, e.g., between 2 and 10 amino acids in length. For example, glycine-serine doublet provides a particularly suitable linker between the transmembrane domain and the intracellular signaling domain of the subject CAR.

Accordingly, a subject CAR of the present disclosure may comprise any of the transmembrane domains, hinge domains, or spacer domains described herein.

Intracellular Domain

A subject CAR of the present invention also includes an intracellular domain. The intracellular domain of the CAR is responsible for activation of at least one of the effector functions of the cell in which the CAR is expressed (e.g., immune cell). The intracellular domain transduces the effector function signal and directs the cell (e.g., immune cell) to perform its specialized function, e.g., harming and/or destroying a target cell.

The intracellular domain or otherwise the cytoplasmic domain of the CAR is responsible for activation of the cell in which the CAR is expressed. Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

In certain embodiments, the intracellular domain comprises a costimulatory signaling domain. In certain embodiments, the intracellular domain comprises an intracellular signaling domain. In certain embodiments, the intracellular domain comprises a costimulatory signaling domain and an intracellular signaling domain. In certain embodiments, the intracellular domain comprises 4-1BB and CD3 zeta. In certain embodiments, the costimulatory signaling domain comprises 4-1BB. In certain embodiments, the intracellular signaling domain comprises CD3 zeta.

In one embodiment, the intracellular domain of the CAR comprises a costimulatory signaling domain which includes any portion of one or more co-stimulatory molecules, such as at least one signaling domain from CD2, CD3, CD8, CD27, CD28, OX40, ICOS, 4-1BB, PD-1, any derivative or variant thereof, any synthetic sequence thereof that has the same functional capability, and any combination thereof.

Examples of the intracellular signaling domain include, without limitation, the ζ chain of the T cell receptor complex or any of its homologs, e.g., η chain, FcεRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcεRI, cytoplasmic tails of Fc receptors, an immunoreceptor tyrosine-based activation motif (ITAM) bearing cytoplasmic receptors, and combinations thereof.

Other examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon Rib), CD79a, CD79b, Fc gamma R11a, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD 1ib, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD 162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs. In some embodiments, intracellular signaling domains includes the signaling domains of human immunoglobulin receptors that contain immunoreceptor tyrosine based activation motifs (ITAMs) such as, but not limited to, Fc gamma RI, Fc gamma RIIA, Fc gamma RIIC, Fc gamma RIIIA, FcRL5 (see, e.g., Gillis et al., Front. (2014) Immunol. 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcR gamma; fceR1 gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; Ig-alpha; membrane-bound immunoglobulin-associated protein; surface IgM-associated protein; etc.). In one embodiment, an intracellular signaling domain suitable for use in a subject CAR of the present disclosure includes a DAP10/CD28 type signaling chain. In one embodiment, an intracellular signaling domain suitable for use in a subject CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the costimulatory signaling domains described herein, any of the antigen binding domains described herein, any of the transmembrane domains described herein, or any of the other domains described herein that may be included in the CAR.

Further, variant intracellular signaling domains suitable for use in a subject CAR are known in the art. The YMFM motif is found in ICOS and is a SH2 binding motif that recruits both p85 and p50alpha subunits of PI3K, resulting in enhanced AKT signaling. See, e.g., Simpson et al. (2010) *Curr. Opin. Immunol.,* 22:326-332. In one embodiment, a CD28 intracellular domain variant may be generated to comprise a YMFM motif.

In one embodiment, the intracellular domain of a subject CAR comprises a 4-1BB costimulatory domain comprising the amino acid sequence set forth in SEQ ID NO: 9, which may be encoded by a nucleic acid sequence comprising the nucleotide sequence set forth in SEQ ID NO: 10. In one embodiment, the intracellular domain of a subject CAR comprises a CD28 costimulatory domain comprising the amino acid sequence set forth in SEQ ID NO: 17, which may be encoded by a nucleic acid sequence comprising the nucleotide sequence set forth in SEQ ID NO: 18. In one embodiment, the intracellular domain of a subject CAR comprises an ICOS costimulatory domain comprising the amino acid sequence set forth in SEQ ID NO: 25, which may be encoded by a nucleic acid sequence comprising the nucleotide sequence set forth in SEQ ID NO: 26 or 27. In one embodiment, the intracellular domain of a subject CAR comprises a CD2 costimulatory domain comprising the amino acid sequence set forth in SEQ ID NO: 28, which may be encoded by a nucleic acid sequence comprising the nucleotide sequence set forth in SEQ ID NO: 29. In one embodiment, the intracellular domain of a subject CAR comprises a CD28 YMFM variant costimulatory domain comprising the amino acid sequence set forth in SEQ ID NO: 32, which may be encoded by a nucleic acid sequence comprising the nucleotide sequence set forth in SEQ ID NO: 33. In one embodiment, the intracellular domain of a subject CAR comprises a CD27 costimulatory domain comprising the amino acid sequence set forth in SEQ ID NO: 34, which may be encoded by a nucleic acid sequence comprising the nucleotide sequence set forth in SEQ ID NO: 35. In one embodiment, the intracellular domain of a subject CAR comprises a OX40 costimulatory domain comprising the amino acid sequence set forth in SEQ ID NO: 36, which may be encoded by a nucleic acid sequence comprising the nucleotide sequence set forth in SEQ ID NO: 37.

In one embodiment, the intracellular domain of a subject CAR comprises a CD3 zeta intracellular signaling domain comprising the amino acid sequence set forth in SEQ ID NO: 11 or 30, which may be encoded by a nucleic acid sequence comprising the nucleotide sequence set forth in SEQ ID NO: 12 or 31.

Tolerable variations of the intracellular domain will be known to those of skill in the art, while maintaining specific activity. For example, in some embodiments the intracellular domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 9, 11, 17, 25, 28, 32, 34, or 36. For example, in some embodiments the intracellular domain is encoded by a nucleic acid sequence comprising a nucleotide sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the nucleotide sequences set forth in SEQ ID NOs: 10, 12, 18, 26, 27, 29, 31, 33, 35, or 37.

In one embodiment, the intracellular domain of a subject CAR comprises an ICOS costimulatory domain and a CD3 zeta intracellular signaling domain. In one embodiment, the intracellular domain of a subject CAR comprises a CD28 costimulatory domain and a CD3 zeta intracellular signaling domain. In one embodiment, the intracellular domain of a subject CAR comprises a CD28 YMFM variant costimulatory domain and a CD3 zeta intracellular signaling domain. In one embodiment, the intracellular domain of a subject CAR comprises a CD27 costimulatory domain and a CD3 zeta intracellular signaling domain. In one embodiment, the intracellular domain of a subject CAR comprises a OX40 costimulatory domain and a CD3 zeta intracellular signaling domain. In one exemplary embodiment, the intracellular domain of a subject CAR comprises a 4-1BB costimulatory domain and a CD3 zeta intracellular signaling domain. In one exemplary embodiment, the intracellular domain of a subject CAR comprises a CD2 costimulatory domain and a CD3 zeta intracellular signaling domain.

CAR Sequences

A subject CAR of the present invention may be a CAR having affinity for MUC1 (e.g. MUC1). In one embodiment, the Tn-MUC1 CAR of the present invention comprises a 4-1BB costimulatory domain and a CD3 zeta intracellular signaling domain comprising the amino acid sequence set forth in SEQ ID NO: 2, which may be encoded by a nucleic acid sequence comprising the nucleotide sequence set forth in SEQ ID NO: 1. In one embodiment, the Tn-MUC1 CAR of the present invention comprises a CD28 costimulatory domain and a CD3 zeta intracellular signaling domain comprising the amino acid sequence set forth in SEQ ID NO: 39, which may be encoded by a nucleic acid sequence comprising the nucleotide sequence set forth in SEQ ID NO: 38. In one embodiment, the Tn-MUC1 CAR of the present invention comprises a CD28 YMFM variant costimulatory domain and a CD3 zeta intracellular signaling domain comprising the amino acid sequence set forth in SEQ ID NO: 41, which may be encoded by a nucleic acid sequence comprising the nucleotide sequence set forth in SEQ ID NO: 40. In one embodiment, the Tn-MUC1 CAR of the present invention comprises a CD27 costimulatory domain and a CD3 zeta intracellular signaling domain comprising the amino acid sequence set forth in SEQ ID NO: 43, which may be encoded by a nucleic acid sequence comprising the nucleotide sequence set forth in SEQ ID NO: 42. In one embodiment, the Tn-MUC1 CAR of the present invention comprises a OX40 costimulatory domain and a CD3 zeta intracellular signaling domain comprising the amino acid sequence set forth in SEQ ID NO: 45, which may be encoded by a nucleic acid sequence comprising the nucleotide sequence set forth in SEQ ID NO: 44. In one embodiment, the Tn-MUC1 CAR of the present invention comprises a CD2 costimulatory domain and a CD3 zeta intracellular signaling domain comprising the amino acid sequence set forth in SEQ ID NO: 47, which may be encoded by a nucleic acid sequence comprising the nucleotide sequence set forth in SEQ ID NO: 46.

Tolerable variations of the CAR will be known to those of skill in the art, while maintaining specific activity. For example, in some embodiments the CAR comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NOs: 2, 39, 41, 43, 45, or 47. For example, in some embodiments the CAR is encoded by a nucleic acid sequence comprising a nucleotide sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleotide sequence set forth in SEQ ID NO: 1, 38, 40, 42, 44, or 46.

In some embodiments, a subject CAR of the present invention comprises a MUC1 binding domain and a transmembrane domain. In one embodiment, the CAR comprises a MUC1 binding domain and a transmembrane domain, wherein the transmembrane domain comprises a CD8 hinge region. In one embodiment, the CAR comprises a MUC1 binding domain and a transmembrane domain, wherein the transmembrane domain comprises a CD8α transmembrane domain. In one embodiment, the CAR comprises a MUC1 binding domain and a transmembrane domain, wherein the transmembrane domain comprises a CD8 hinge region and a CD8α transmembrane domain.

In some embodiments, a subject CAR of the present invention comprises a MUC1 binding domain, a transmembrane domain, and an intracellular domain. In one embodiment, the CAR comprises a Tn-MUC1 binding domain, a transmembrane domain, and an intracellular domain. In one embodiment, the CAR comprises a Tn-MUC1 binding domain, a transmembrane domain, and an intracellular domain comprising a 4-1BB costimulatory domain and a CD3 zeta domain. In one embodiment, the CAR comprises a Tn-MUC1 binding domain, a transmembrane domain, and an intracellular domain comprising a CD28 costimulatory domain and a CD3 zeta domain. In one embodiment, the CAR comprises a Tn-MUC1 binding domain, a transmembrane domain, and an intracellular domain comprising a CD28 YMFM variant costimulatory domain and a CD3 zeta domain. In one embodiment, the CAR comprises a Tn-MUC1 binding domain, a transmembrane domain, and an intracellular domain comprising a CD27 domain and a CD3 zeta domain. In one embodiment, the CAR comprises a Tn-MUC1 binding domain, a transmembrane domain, and an intracellular domain comprising an OX40 domain and a CD3 zeta domain. In one embodiment, the CAR comprises a Tn-MUC1 binding domain, a transmembrane domain, and an intracellular domain comprising a CD2 domain and a CD3 zeta domain.

Accordingly, the present invention provides a modified immune cell or precursor cell thereof, e.g., a modified T cell, a modified NK cell, a modified NKT cell, comprising a chimeric antigen receptor (CAR) having affinity for MUC1 as described herein.

Human Antibodies

It may be preferable that the antigen binding domains of the CAR comprise human antibodies or fragments thereof. Fully human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immuno-globulin transgenes harbored by the transgenic mice rear-range during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lon-berg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633, 425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., *Proc. Natl. Acad. Sci. USA,* 90:2551 (1993); Jakobovits et al., Nature, 362:255-258 (1993); Bruggermann et al., *Year in Immunol.,* 7:33 (1993); and Duchosal et al., *Nature,* 355:258 (1992).

Human antibodies can also be derived from phage-display libraries (Hoogenboom et al., *J. Mol. Biol.,* 227:381 (1991); Marks et al., *J. Mol. Biol.,* 222:581-597 (1991); Vaughan et al., *Nature Biotech.,* 14:309 (1996)). Phage display technol-ogy (McCafferty et al., *Nature,* 348:552-553 (1990)) can be used to produce human antibodies and antibody fragments in vitro, from immunoglobulin variable (V) domain gene rep-ertoires from unimmunized donors. According to this tech-nique, antibody V domain genes are cloned in-frame into either a major or minor coat protein gene of a filamentous bacteriophage, such as M13 or fd, and displayed as func-tional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., *Nature,* 352:624-628 (1991) isolated a diverse array of anti-oxazolone anti-bodies from a small random combinatorial library of V genes derived from the spleens of unimmunized mice. A repertoire of V genes from unimmunized human donors can be constructed and antibodies to a diverse array of antigens (including self-antigens) can be isolated essentially follow-ing the techniques described by Marks et al., *J. Mol. Biol.,* 222:581-597 (1991), or Griffith et al., *EMBO J.,* 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229, 275, each of which is incorporated herein by reference in its entirety). Human antibodies may also be generated in vitro using hybridoma techniques such as, but not limited to, that described by Roder et al. (*Methods Enzymol.,* 121:140-167 (1986)).

Dominant Negative Receptors and Switch Receptors

The present invention provides compositions and meth-ods for modified immune cells or precursors thereof, e.g., modified T cells, comprising a dominant negative receptor and/or a switch receptor. Thus, in some embodiments, the immune cell has been genetically modified to express the dominant negative receptor and/or switch receptor. Sequences of dominant negative receptors and switch recep-tors are found in Table 1. As used herein, the term "dominant negative receptor" refers to a molecule designed to reduce the effect of a negative signal transduction molecule, e.g., the effect of a negative signal transduction molecule on a modified immune cell of the present invention. A dominant negative receptor of the present invention may bind a negative signal transduction molecule, e.g., TGF-β or PD-1, by virtue of an extracellular domain associated with the negative signal, and reduce the effect of the negative signal transduction molecule. Such dominant negative receptors are described herein. For example, a modified immune cell comprising a dominant negative receptor may bind a nega-tive signal transduction molecule in the microenvironment of the modified immune cell, and reduce the effect the negative signal transduction molecule may have on the modified immune cell.

A switch receptor of the present invention may be designed to, in addition to reducing the effects of a negative signal transduction molecule, to convert the negative signal into a positive signal, by virtue of comprising an intracel-lular domain associated with the positive signal. Switch receptors designed to convert a negative signal into a positive signal are described herein. Accordingly, switch receptors comprise an extracellular domain associated with a negative signal and/or an intracellular domain associated with a positive signal.

Tumor cells generate an immunosuppressive microenvi-ronment that serves to protect them from immune recogni-tion and elimination. This immunosuppressive microenvi-ronment can limit the effectiveness of immunosuppressive therapies such as CAR-T cell therapy. The secreted cytokine Transforming Growth Factor β (TGFβ) directly inhibits the function of cytotoxic T cells and additionally induces regu-latory T cell formation to further suppress immune responses. T cell immunosuppression due to TGFβ in the context of prostate cancers has been previously demon-strated (Donkor et al., 2011; Shalapour et al., 2015). To reduce the immunosuppressive effects of TGFβ, immune cells can be modified to express a dominant negative recep-tor that is a dominant negative receptor for TGF-β.

In some embodiments, the dominant negative receptor is a truncated variant of a wild-type protein associated with a negative signal. In some embodiments, the dominant nega-tive receptor is a dominant negative receptor for TGF-β. Accordingly, in some embodiments, the dominant negative receptor for TGF-β is a truncated variant of a wild-type TGF-β receptor. In some embodiments, the dominant nega-tive receptor is a truncated dominant negative variant of the TGF-β receptor type II (TGFβRII-DN). In one embodiment, the TGFβRII-DN comprises the amino acid sequence of SEQ ID NO:76, which may be encoded by the nucleic acid sequence of SEQ ID NO:77.

Tolerable variations of the sequence of TGFβRII-DN will be known to those of skill in the art, while maintaining its intended function. For example, in some embodiments, a dominant negative receptor of the present invention is TGFβRII-DN comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:76 In one embodiment, the dominant negative receptor is TGFβRII-DN comprising the amino acid sequence set forth in SEQ ID NO:76.

In some embodiments, a dominant negative receptor of the present invention is TGFβRII-DN encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO: 77. In one embodiment, the dominant negative receptor is TGFβRII-DN encoded by the nucleic acid sequence set forth in SEQ ID NO:77.

In one embodiment, a switch receptor suitable for use in the present invention is a PD1-CTM-CD28 receptor. The PD1-CTM-CD28 receptor converts a negative PD1 signal into a positive CD28 signal when expressed in a cell. The PD1-CTM-CD28 receptor comprises a variant of the PD1 extracellular domain, a CD28 transmembrane domain, and a CD28 cytoplasmic domain. In one embodiment, the PD1-CTM-CD28 receptor comprises an amino acid sequence of SEQ ID NO: 78, which may be encoded by the nucleic acid sequence of SEQ ID NO:79.

Tolerable variations of the PD1-CTM-CD28 receptor will be known to those of skill in the art, while maintaining its intended biological activity (e.g., converting a negative PD1 signal into a positive CD28 signal when expressed in a cell). Accordingly, a PD1-CTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CTM-CD28 receptor amino acid sequence set forth in SEQ ID NO:78. Accordingly, a PD1-CTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CTM-CD28 receptor nucleic acid sequence set forth in SEQ ID NO:79.

In one embodiment, a switch receptor suitable for use in the present invention is a PD1-PTM-CD28 receptor. The PD1-PTM-CD28 receptor converts a negative PD1 signal into a positive CD28 signal when expressed in a cell. The PD1-PTM-CD28 receptor comprises a variant of the PD1 extracellular domain, a PD1 transmembrane domain, and a CD28 cytoplasmic domain. In one embodiment, the PD1-PTM-CD28 receptor comprises an amino acid sequence of SEQ ID NO:80, which may be encoded by the nucleic acid sequence of SEQ ID NO:81.

Tolerable variations of the PD1-PTM-CD28 receptor will be known to those of skill in the art, while maintaining its intended biological activity (e.g., converting a negative PD1 signal into a positive CD28 signal when expressed in a cell). Accordingly, a PD1-PTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-PTM-CD28 receptor amino acid sequence set forth in SEQ ID NO:80. Accordingly, a PD1-PTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-PTM-CD28 receptor nucleic acid sequence set forth in SEQ ID NO: 81.

In one embodiment, a switch receptor suitable for use in the present invention is a $PD1^{A132L}$-PTM-CD28 receptor. The $PD1^{A132L}$-PTM-CD28 receptor converts a negative PD1 signal into a positive CD28 signal when expressed in a cell. A point mutation at amino acid position 132, substituting alanine with leucine (A132L), of PD1 was found to increase its affinity with PD-L1 by two fold (see, e.g., Zhang et al., Immunity (2004) 20(3), 337-347). The $PD1^{A132L}$-PTM-CD28 receptor comprises a variant of the PD1 extracellular domain that has an amino acid substitution at position 132 (A132L), a PD1 transmembrane domain, and a CD28 cytoplasmic domain. In one embodiment, the $PD1^{A132L}$-PTM-CD28 receptor comprises an amino acid sequence of SEQ ID NO:82, which may be encoded by the nucleic acid sequence of SEQ ID NO:83.

Tolerable variations of the $PD1^{A132L}$-PTM-CD28 receptor will be known to those of skill in the art, while maintaining its intended biological activity (e.g., converting a negative PD1 signal into a positive CD28 signal when expressed in a cell). Accordingly, a $PD1^{A132L}$-PTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the $PD1^{A132L}$-PTM-CD28 receptor amino acid sequence set forth in SEQ ID NO:82. Accordingly, a $PD1^{A132L}$-PTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the $PD1^{A132L}$-PTM-CD28 receptor nucleic acid sequence set forth in SEQ ID NO:83.

In one embodiment, a switch receptor suitable for use in the present invention is a PD1-4-1BB receptor. The PD1-4-1BB receptor (also referred to herein as PD1-BB) converts a negative PD1 signal into a positive 4-1BB signal when expressed in a cell. In one embodiment, the PD1-4-1BB receptor comprises an amino acid of SEQ ID NO:84, which may be encoded by the nucleic acid of SEQ ID NO:85.

Tolerable variations of the PD1-4-1BB receptor will be known to those of skill in the art, while maintaining its intended biological activity (e.g., converting a negative PD1 signal into a positive 4-1BB signal when expressed in a cell). Accordingly, a PD1-4-1BB receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-4-1BB receptor amino acid sequence set forth in SEQ ID NO:84. Accordingly, a PD1-4-1BB receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-4-1BB receptor nucleic acid sequence set forth in SEQ ID NO:85.

In one embodiment, a switch receptor suitable for use in the present invention is a $PD1^{A132L}$-4-1BB receptor. The $PD1^{A132L}$-4-1BB receptor (also referred to herein as PD1*BB) converts a negative PD1 signal into a positive 4-1BB signal when expressed in a cell. In one embodiment, the $PD1^{A132L}$-4-1BB receptor comprises an amino acid sequence of SEQ ID NO:86, which may be encoded by the nucleic acid sequence of SEQ ID NO:87.

Tolerable variations of the $PD1^{A132L}$-4-1BB receptor will be known to those of skill in the art, while maintaining its intended biological activity (e.g., converting a negative PD1 signal into a positive 4-1BB signal when expressed in a cell). Accordingly, a $PD1^{A132L}$-4-1BB receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the $PD1^{A132L}$-4-1BB receptor amino acid sequence set forth in SEQ ID NO:86. Accordingly, a $PD1^{A132L}$-4-1BB receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the $PD1^{A132L}$-4-1BB receptor nucleic acid sequence set forth in SEQ ID NO:87.

In one embodiment, a switch receptor suitable for use in the present invention is a TGFβR-IL12Rβ1 receptor. The TGFβR-IL12Rβ1 receptor converts a negative TGF-β signal into a positive IL-12 signal when expressed in a cell. In one embodiment, the TGFβR-IL12Rβ1 receptor comprises an amino acid sequence of SEQ ID NO:88, which may be encoded by the nucleic acid sequence of SEQ ID NO:89.

Tolerable variations of the TGFβR-IL12Rβ1 receptor will be known to those of skill in the art, while maintaining its intended biological activity (e.g., converting a negative TGF-β signal into a positive IL-12 signal when expressed in a cell). Accordingly, a TGFβR-IL12Rβ1 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ1 receptor amino acid sequence set forth in SEQ ID NO:88. Accordingly, a TGFβR-IL12Rβ1 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ1 receptor nucleic acid sequence set forth in SEQ ID NO:89.

In one embodiment, a switch receptor suitable for use in the present invention is a TGFβR-IL12Rβ2 receptor. The TGFβR-IL12Rβ2 receptor converts a negative TGF-β signal into a positive IL-12 signal when expressed in a cell. In one embodiment, the TGFβR-IL 12Rβ2 receptor comprises an amino acid sequence set forth below of SEQ ID NO: 90, which may be encoded by the nucleic acid sequence of SEQ ID NO:91.

Tolerable variations of the TGFβR-IL12Rβ2 receptor will be known to those of skill in the art, while maintaining its intended biological activity (e.g., converting a negative TGF-β signal into a positive IL-12 signal when expressed in a cell). Accordingly, a TGFβR-IL 12Rβ2 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ2 receptor amino acid sequence set forth in SEQ ID NO:90. Accordingly, a TGFβR-IL 12Rβ2 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ2 receptor nucleic acid sequence set forth in SEQ ID NO:91.

In one embodiment, a switch receptor suitable for use in the present invention is a TIM3-CD28 receptor. The TIM3-CD28 receptor converts a negative TIM-3 signal into a positive CD28 signal when expressed in a cell. In one embodiment, the TIM3-CD28 receptor comprises an amino acid sequence of SEQ ID NO:92, which may be encoded by the nucleic acid sequence of SEQ ID NO:93.

Tolerable variations of the TIM3-CD28 receptor will be known to those of skill in the art, while maintaining its intended biological activity (e.g., converting a negative TIM-3 signal into a positive CD28 signal when expressed in a cell). Accordingly, a TIM3-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TIM3-CD28 receptor amino acid sequence set forth in SEQ ID NO:92. Accordingly, a TIM3-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TIM3-CD28 receptor nucleic acid sequence set forth in SEQ ID NO:93.

Other suitable dominant negative receptors and switch receptors for use in the present invention are described in PCT Publication No. WO2013019615A2, the disclosure of which is incorporated herein by reference.

Modified Immune Cells

The present invention provides a modified immune cell or precursor cell thereof (e.g., a modified T cell, a modified NK cell, a modified NKT cell), comprising a subject CAR. Accordingly, such modified cells possess the specificity directed by the CAR that is expressed therein. For example, a modified cell of the present invention comprising a TnMUC1 CAR possesses specificity for MUC1 on a target cell.

Any modified cell comprising a CAR comprising any antigen binding domain, any hinge, any transmembrane domain, any intracellular costimulatory domain, and any intracellular signaling domain described herein is envisioned, and can readily be understood and made by a person of skill in the art in view of the disclosure herein.

In some embodiments, the modified cell is an immune cell or precursor cell thereof. In an exemplary embodiment, the modified cell is a T cell. In an exemplary embodiment, the modified cell is an autologous cell. In an exemplary embodiment, the modified cell is an autologous immune cell or precursor cell thereof. In an exemplary embodiment, the modified cell is an autologous T cell.

The present invention provides a modified immune cell or precursor cell thereof (e.g., a T cell), comprising a CAR and/or a dominant negative receptor and/or a switch receptor. Accordingly, such modified cells possess the specificity directed by the CAR that is expressed therein. For example, a modified cell of the present invention comprising a TnMUC1-CAR possesses specificity for TnMUC1 on a target cell.

In some embodiments, a modified cell of the present invention comprises a CAR. In one embodiment, a modified cell of the present invention comprises a CAR having affinity for a TnMUC1 on a target cell. In some embodiments, a modified cell of the present invention comprises a dominant negative receptor and/or a switch receptor. In one embodiment, a modified cell of the present invention comprises a dominant negative receptor capable of reducing the effect of a negative signal transduction molecule in the microenvironment. In one embodiment, a modified cell of the present invention comprises a switch receptor capable of reducing the effect of a negative signal transduction molecule in the microenvironment, and converting the negative signal into a positive signal within the modified cell. In some embodiments, a modified cell of the present invention comprises a CAR and a dominant negative receptor and/or a switch receptor. In one embodiment, a modified cell of the present invention comprises a CAR having affinity for TnMUC1 on a target cell, and a dominant negative receptor and/or a switch receptor. Modified cells comprising a dominant negative receptor and/or a switch receptor of the present invention are able to engage negative signal transduction molecules (e.g., inhibitory ligands) in the microenvironment by virtue of their respective extracellular domains. In some embodiments, a modified cell of the present invention comprising a dominant negative receptor is capable of reducing the effect of a negative signal transduction molecule in the microenvironment, wherein the dominant negative receptor comprises an extracellular domain associated with the negative signal. In some embodiments, a modified cell of the present invention comprising a switch receptor is capable of converting the effect of a negative signal transduction molecule in the microenvironment into a positive signal, wherein the switch receptor comprises an extracellular domain associated with the negative signal and an intracellular domain associated with the positive signal.

In an exemplary embodiment, a modified cell of the present invention comprises a dominant negative receptor that is capable of reducing the effect of a negative signal transduction molecule. In one embodiment, a modified cell of the present invention comprises TGFβRII-DN.

In an exemplary embodiment, a modified cell of the present invention comprises a switch receptor that is capable of converting the effect of a negative signal transduction molecule into a positive (e.g., activating) signal within the modified cell. In one embodiment, a modified cell of the present invention comprises PD1-CTM-CD28. In one embodiment, a modified cell of the present invention comprises $PD1^{A132L}$-PTM-CD28. In one embodiment, a modified cell of the present invention comprises TIM3-CD28.

In an exemplary embodiment, a modified cell of the present invention comprises a TnMUC1-CAR and a dominant negative receptor that is capable of reducing the effect of a negative signal transduction molecule. In one embodiment, a modified cell of the present invention comprises a TnMUC1-CAR and TGFβRII-DN. Such modified cells (e.g., modified T cells) in addition to having affinity for TnMUC1 on a target cell, are capable of reducing inhibitory TGF-β signals from the microenvironment they reside in.

In an exemplary embodiment, a modified cell of the present invention comprises a MUC1-CAR and a switch receptor that is capable of converting the inhibitory effect of a negative signal transduction molecule into a positive signal within the modified cell. In one embodiment, a modified cell of the present invention comprises a MUC1-CAR and PD1-CTM-CD28. In one embodiment, a modified cell of the present invention comprises a MUC1-CAR and $PD1^{A132L}$-PTM-CD28. In one embodiment, a modified cell of the present invention comprises a MUC1-CAR and TIM3-CD28. In one embodiment, a modified cell of the present invention comprises a MUC1 CAR and PD1-4-1BB. In one embodiment, a modified cell of the present invention comprises a MUC1-CAR and $PD1^{A132L}$-4-1BB. In one embodiment, a modified cell of the present invention comprises a MUC1-CAR and TGFβR-IL12Rβ1. Such modified cells (e.g., modified T cells) in addition to having affinity for MUC1 on a target cell, are capable of converting inhibitory PD-1, TIM1 or TGFβ signals from the microenvironment into a positive (e.g., activating) signal within the modified cell. Such modified cells (e.g., modified T cells) in addition to having affinity for MUC1 on a target cell, are capable of converting inhibitory PD-1 or TIM-3 signals from the microenvironment into a positive (e.g., activating) CD28 signal within the modified cell.

In an exemplary embodiment, a modified cell of the present invention comprises a MUC1-CAR, TGFβRII-DN, and PD1-CTM-CD28.

Nucleic Acids and Expression Vectors

The present invention provides a nucleic acid encoding a CAR having affinity for MUC1 (e.g. Tn-MUC1). As described herein, a subject CAR comprises an antigen binding domain (e.g., MUC1 binding domain), a transmembrane domain, and an intracellular domain. Accordingly, the present invention provides a nucleic acid encoding an antigen binding domain (e.g., MUC1 binding domain), a transmembrane domain, and an intracellular domain of a subject CAR.

In an exemplary embodiment, a nucleic acid encoding a MUC1 CAR of the present invention is encoded by a nucleic acid sequence comprising the nucleotide sequence set forth in SEQ ID NOs: 1, 38, 40, 42, 44, or 46.

In certain embodiments, the invention provides a nucleic acid encoding a CAR and/or a dominant negative receptor and/or a switch receptor. In one embodiment, a nucleic acid of the present disclosure comprises a nucleic acid sequence encoding a subject CAR of the present invention (e.g., TnMUC1-CAR). In one embodiment, a nucleic acid of the present disclosure comprises a nucleic acid sequence encoding a dominant negative receptor and/or a switch receptor (e.g., a PD1-PTM-CD28 receptor).

In some embodiments, a nucleic acid of the present disclosure provides for the production of a CAR and/or dominant negative receptor and/or a switch receptor as described herein, e.g., in a mammalian cell. In some embodiments, a nucleic acid of the present disclosure provides for amplification of the CAR and/or dominant negative receptor and/or a switch receptor-encoding nucleic acid.

As described herein, a subject CAR comprises an antigen binding domain, a transmembrane domain, and an intracellular domain. Accordingly, the present disclosure provides a nucleic acid encoding an antigen binding domain, a transmembrane domain, and an intracellular domain of a subject CAR. As described herein, various dominant negative receptors and switch receptors are provided. Accordingly, the present invention provides a nucleic acid encoding a dominant negative receptor and/or a switch receptor.

In some embodiments, the nucleic acid encoding a CAR is separate from the nucleic acid encoding a dominant negative receptor and/or a switch receptor. In an exemplary embodiment, the nucleic acid encoding a CAR, and the nucleic acid encoding a dominant negative receptor and/or a switch receptor, resides within the same nucleic acid.

In some embodiments, a nucleic acid of the present invention comprises a nucleic acid comprising a CAR coding sequence and a dominant negative receptor and/or a switch receptor coding sequence. In some embodiments, a nucleic acid of the present invention comprises a nucleic acid comprising a CAR coding sequence and a dominant negative receptor and/or a switch receptor coding sequence that is separated by a linker. A linker for use in the present invention (e.g., in the context of linking a CAR coding sequence and a dominant negative receptor and/or a switch receptor coding sequence) allows for multiple proteins to be encoded by the same nucleic acid sequence (e.g., a multi-cistronic or bicistronic sequence), which are translated as a polyprotein that is dissociated into separate protein components. For example, a linker for use in a nucleic acid of the present disclosure comprising a CAR coding sequence and a dominant negative receptor and/or a switch receptor coding sequence, allows for the CAR and dominant negative receptor and/or switch receptor to be translated as a polyprotein that is dissociated into separate CAR and dominant negative receptor and/or switch receptor components.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunoglobulin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAV0, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a nucleic acid of the present disclosure comprises a nucleic acid sequence comprising a CAR coding sequence and a dominant negative receptor and/or a switch receptor coding sequence that is separated by a linker comprising a T2A peptide sequence. In some embodiments, the T2A peptide sequence comprises the amino acid sequence EGRGSLLTCGDVEENPGP (SEQ ID NO:94), which may be encoded by the nucleic acid sequence GAGGGCAGAGGAAGTCTTCTAA-CATGCGGTGACGTGGAGGAGAATCCCGGCC CT (SEQ ID NO:95). In some embodiments, the linker comprising a T2A peptide sequence may further comprise a spacer sequence as described herein. For example, the linker comprising a T2A peptide sequence may further comprise a spacer sequence comprising the amino acid sequence SGRSGGG (SEQ ID NO:96), which may be encoded by the nucleic acid sequence TCCGGAAGATCTGGCGGCGGA (SEQ ID NO:97.

In some embodiments, a nucleic acid of the present disclosure comprises a nucleic acid sequence comprising a CAR coding sequence and a dominant negative receptor and/or a switch receptor coding sequence that is separated by a linker comprising a F2A peptide sequence. In some embodiments, the F2A peptide sequence comprises the amino acid sequence VKQTLNFDLLKLAGDVESNPGP (SEQ ID NO:98), which may be encoded by the nucleic acid sequence (SEQ ID NO: 99)
GTGAAACAGACTTTGAATTTTGACCTTCTCAAGTTGGCGGGAGACGTGGA

GTCCAACCCAGGGCCG.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH-terminus of its consensus recognition sequence. Various furin consensus recognition sequences (or "furin cleavage sites") are known to those of skill in the art, including, without limitation, Arg-X-Lys-Arg (SEQ ID NO:100) or Arg-X-Arg-Arg (SEQ ID NO: 101), and Arg-X-X-Arg (SEQ ID NO:102), such as an Arg-Gln-Lys-Arg (SEQ ID NO: 103), where X is any naturally occurring amino acid. Another example of a furin cleavage site is X1-Arg-X2-X3-Arg (SEQ ID NO:104), where X1 is Lys or Arg, X2 is any naturally occurring amino acid, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:52) and (GGGS)n (SEQ ID NO:53), where n represents an integer of at least 1. Exemplary spacer sequences can comprise amino acid sequences including, without limitation, GGSG (SEQ ID NO:55), GGSGG (SEQ ID NO:56), GSGSG (SEQ ID NO:57), GSGGG (SEQ ID NO:58), GGGSG (SEQ ID NO:59), GSSSG (SEQ ID NO: 60), and the like. Those of skill in the art would be able to select the appropriate spacer sequence for use in the present invention.

In some embodiments, a nucleic acid of the present disclosure comprises a nucleic acid sequence comprising a CAR coding sequence and a dominant negative receptor and/or a switch receptor coding sequence that is separated by a Furin-(G4S) 2-T2A (F-GS2-T2A) linker. The F-GS2-T2A linker may be encoded by the nucleic acid sequence (SEQ ID NO: 105)
CGTGCGAAGAGGGCGGCGGGGGCTCCGGCGGGGGAGGCAGTGAGGGCC
GCGGCTCCCTGCTGACCTGCGGAGATGTAGAAGAGAACCCAGGCCCC, and may comprise the amino acid sequence RAKRGGGGSGGGGSEGRGSLLTCGDVEENPGP (SEQ ID NO:106). Those of skill in the art would appreciate that linkers of the present invention may include tolerable sequence variations.

In some embodiments, the present invention provides a nucleic acid comprising a nucleic acid sequence encoding a dominant negative receptor and/or a switch receptor as described herein. In some embodiments, a nucleic acid comprises a nucleic acid sequence encoding a dominant negative receptor and/or a switch receptor and a nucleic acid sequence encoding a CAR as described herein (e.g., a TnMUC1-CAR). In one embodiment, the nucleic acid sequence encoding the dominant negative receptor and/or the switch receptor and the nucleic acid sequence encoding the CAR resides on separate nucleic acids. In one embodiment, the nucleic acid sequence encoding the dominant negative receptor and/or the switch receptor and the nucleic acid sequence encoding the CAR resides within the same nucleic acid. In such an embodiment, the nucleic acid sequence encoding the dominant negative receptor and/or the switch receptor and the nucleic acid sequence encoding the CAR is separated by a linker as described herein.

For example, a nucleic acid of the present disclosure may comprise a nucleic acid sequence encoding a dominant receptor, a linker, and a nucleic acid sequence encoding a CAR. In one embodiment, the linker comprises a nucleic acid sequence encoding a 2A peptide (e.g., T2A). In an exemplary embodiment, a nucleic acid of the present disclosure may comprise a nucleic acid sequence encoding a dominant negative receptor and/or a switch receptor and a nucleic acid sequence encoding a CAR separated by a linker sequence comprising a nucleic acid sequence encoding T2A.

Accordingly, in one embodiment, a nucleic acid of the present disclosure comprises from 5' to 3': a nucleic acid sequence encoding a dominant negative receptor and/or a switch receptor, a nucleic acid sequence encoding a linker, and a nucleic acid sequence encoding a CAR. In one embodiment, a nucleic acid of the present disclosure comprises from 5' to 3': a nucleic acid sequence encoding a CAR, a nucleic acid sequence encoding a linker, and a nucleic acid sequence encoding a dominant negative receptor and/or a switch receptor.

Accordingly, in an exemplary embodiment, a nucleic acid of the present invention comprises from 5' to 3': a nucleic acid sequence encoding TGFβRII-DN, a nucleic acid sequence encoding a linker comprising a 2A peptide (e.g., T2A), and a nucleic acid sequence encoding a MUC1 CAR (e.g., SEQ ID NOs: 1, 38, 40, 42, 44, or 46). In one embodiment, a nucleic acid of the present disclosure comprises from 5' to 3': a nucleic acid encoding a MUC1 CAR, a nucleic acid encoding a linker comprising a 2A peptide (e.g., T2A), and a nucleic acid encoding a dominant negative receptor and/or a switch receptor.

In some embodiments, a nucleic acid of the present disclosure may be operably linked to a transcriptional control element, e.g., a promoter, and enhancer, etc. Suitable promoter and enhancer elements are known to those of skill in the art.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. *Proc. Natl. Acad. Sci. USA* (1993) 90:7739; and Marodon et al. (2003) *Blood* 101:3416. As another example, a CD8 gene promoter can be used. NK cell-specific expression can be achieved by use of an NcrI (p46) promoter; see, e.g., Eckelhart et al. *Blood* (2011) 117:1565.

For expression in a yeast cell, a suitable promoter is a constitutive promoter such as an ADHI promoter, a PGK1 promoter, an ENO promoter, a PYK1 promoter and the like; or a regulatable promoter such as a GALI promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADHI promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a tre promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.* (1991) 173(1): 86-93; Alpuche-Aranda et al., *Proc. Natl. Acad. Sci. USA* (1992) 89(21): 10079-83), a nirB promoter (Harborne et al. *Mol. Micro.* (1992) 6:2805-2813), and the like (see, e.g., Dunstan et al., *Infect. Immun.* (1999) 67:5133-5141; Mckelvie et al., *Vaccine* (2004) 22:3243-3255; and Chatfield et al., *Biotechnol.* (1992) 10:888-892); a sigma70 promoter, e.g., a consensus sigma70 promoter (see, e.g., GenBank® Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al., *Infect. Immun.* (2002) 70:1087-1096); an rpsM promoter (see, e.g., Valdivia and Falkow *Mol. Microbiol.* (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., *Nucl. Acids Res.* (1984) 12:7035); and the like. Suitable strong promoters for use in prokaryotes such as *Escherichia coli* include, but are not limited to Trc, Tac, T5, T7, and P Lambda. Non-limiting examples of operators for use in bacterial host cells include a lactose promoter operator (LacI repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., *Proc. Natl. Acad. Sci. U.S.A.* (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the EF-1 alpha promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *Proc. Natl. Acad. Sci. USA* (2000) 28: e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, MA), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released upon CAR signaling. See, e.g., Chmielewski and Abken, Expert Opin. Biol. Ther. (2015) 15(8): 1145-1154; and Abken, Immunotherapy (2015) 7(5): 535-544.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in any way as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., *Invest. Opthalmol. Vis. Sci.* (1994) 35:2543-2549; Borras et al., *Gene Ther.* (1999) 6:515-524; Li and Davidson, *Proc. Natl. Acad. Sci. USA* (1995) 92:7700-7704; Sakamoto et al., H. Gene Ther. (1999) 5:1088-1097; WO 94/12649, WO 93/03769; WO 93/19191; WO 94/28938; WO 95/11984 and WO 95/00655); adeno-associated virus (see, e.g., Ali et al., *Hum. Gene Ther.* (1998) 9:81-86, Flannery et al., *Proc. Natl. Acad. Sci. USA* (1997) 94:6916-6921; Bennett et al., *Invest. Opthalmol. Vis. Sci.* (1997) 38:2857-2863; Jomary et al., *Gene Ther.* (1997) 4:683 690, Rolling et al., *Hum. Gene Ther.* (1999) 10:641-648; Ali et al., *Hum. Mol. Genet.* (1996) 5:591-594; Srivastava in WO 93/09239, Samulski et al., *J. Vir.* (1989) 63:3822-3828; Mendelson et al., *Virol.* (1988) 166:154-165; and Flotte et al., *Proc. Natl. Acad. Sci. USA* (1993) 90:10613-10617); SV40; herpes simplex virus; human immunodeficiency virus (see, e.g., Miyoshi et al., *Proc. Natl. Acad. Sci. USA* (1997) 94:10319-23; Takahashi et al., *J. Virol.* (1999) 73:7812-7816); a retroviral vector (e.g., murine leukemia virus, spleen necrosis virus, and vectors derived from retroviruses such as Rous sarcoma virus, Harvey sarcoma virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the CAR into an immune cell or precursor thereof (e.g., a T cell). Accordingly, an expression vector (e.g., a lentiviral vector) of the present invention may comprise a nucleic acid encoding a CAR. In some embodiments, the expression vector (e.g., lentiviral vector) will comprise additional elements that will aid in the functional expression of the CAR encoded therein. In some embodiments, an expression vector comprising a nucleic acid encoding a CAR further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a CAR encoding nucleic acid sequence). Physiologic promoters (e.g., an EF-1α promoter) may be less likely to induce integration mediated genotoxicity, and may abrogate the ability of the retroviral vector to transform stem cells Other physiological promoters suitable for use in a vector (e.g., a lentiviral vector) are known to those of skill in the art and may be incorporated into a vector of the present invention. In some embodiments, the vector (e.g., a lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., a lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a CAR of the present disclosure. Methods for introducing RNA into a host cell are known in the art. See, e.g., Zhao et al. *Cancer Res*. (2010) 15:9053. Introducing RNA comprising a nucleotide sequence encoding a CAR of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 *FEBS Letters* 479:79-82).

Methods of Generating Modified Immune Cells

The present invention provides methods for producing/generating a modified immune cell or precursor cell thereof (e.g., a T cell/NK cell/NKT cell). The cells are generally engineered by introducing a nucleic acid encoding a subject CAR (e.g., MUC1 CAR).

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, MA) or the Gene Pulser II (BioRad, Denver, CO), Multiporator (Eppendorf, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. *Hum Gene Ther.*, 12(8): 861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

In some embodiments, a nucleic acid encoding a subject CAR of the invention is introduced into a cell by an expression vector. Expression vectors comprising a nucleic acid encoding a subject CAR (e.g., MUC1 CAR) are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggyback, and Integrases such as Phi31. Some other suitable expression vectors include herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the subject CAR in the host cell. In some embodiments, the adenovirus genome is a 36 kb, linear, double stranded DNA, where a foreign DNA sequence (e.g., a nucleic acid encoding a subject CAR) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus, which takes advantage of the adenovirus coupled systems. This AAV expression vector has a high frequency of integration into the host genome. It can infect non-dividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., a nucleic acid encoding a subject CAR) into the viral genome at certain locations to produce a virus that is replication defective. Though the retrovirus vectors are able to infect a broad variety of cell types, integration and stable expression of the subject CAR, requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the human immunodeficiency viruses (HIV-1, HIV-2) and the simian immunodeficiency virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression, e.g., of a nucleic acid encoding a subject CAR (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell is an immune cell or precursor thereof, e.g., a T cell, an NK cell, or an NKT cell.

The present invention also provides genetically engineered cells which include and stably express a subject CAR of the present disclosure. In some embodiments, the genetically engineered cells are genetically engineered T-lymphocytes (T cells), regulatory T cells (Tregs), naive T cells (TN), memory T cells (for example, central memory T cells (TCM), effector memory cells (TEM)), natural killer cells (NK cells), natural killer T cells (NKT cells) and macrophages capable of giving rise to therapeutically relevant progeny. In one embodiment, the genetically engineered cells are autologous cells.

Modified cells (e.g., comprising a subject CAR) may be produced by stably transfecting host cells with an expression vector including a nucleic acid of the present disclosure. Additional methods to generate a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a subject CAR of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 *Glycobiology* 5:505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the host cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However, polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The poly A/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* poly A polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In certain exemplary embodiments, RNAs produced by the methods disclosed herein include a 5' cap. The 5' cap is provided using techniques known in the art and described herein (Cougot, et al., *Trends in Biochem. Sci.,* 29:436-444 (2001); Stepinski, et al., *RNA,* 7:1468-95 (2001); Elango, et al., *Biochim. Biophys. Res. Commun.,* 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of host cell activity in basic research and therapy, in the fields of cancer, stem cells, acute and chronic infections, and autoimmune diseases, including the assessment of the ability of the genetically modified host cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of host cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this non-physiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatuses for therapeutic application of electroporation are available commercially, e.g., the MedPulser™ DNA Electroporation Therapy System (Inovio/Genetronics, San Diego, CA), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Accordingly, the present invention provides a method for generating a modified immune cell or precursor cell thereof comprising introducing into the cell an isolated nucleic acid (e.g., an expression construct) encoding for a subject CAR as described herein, using any of the delivery methods described herein or are known to those of skill in the art.

Sources of Immune Cells

Prior to expansion, a source of immune cells is obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. In certain exemplary embodiments, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells and/or NKT cells. Other exemplary cells include stem cells, such as multipotent and pluripotent stem cells, including induced pluripotent stem cells (iPSCs). In certain aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell, a hematopoietic stem cell, a natural killer cell (NK cell), a natural killer T cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g., transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In certain aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in certain aspects, contain lymphocytes, including T cells, monocytes, granulocytes, B cells, other nucleated white blood cells, red blood cells, and/or platelets, and in certain aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some certain, a washing step is accomplished by tangential flow filtration (TFF) according to the manufacturer's instructions. In certain embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune cells are obtained from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or another saline solution with or without buffer. In some embodiments, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in certain aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. Such separation steps can be based on positive selection, in which the cells having bound the reagents are retained for further use, and/or negative selection, in which the cells having not bound to the antibody or binding partner are retained. In some examples, both fractions are retained for further use. In certain aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In certain exemplary embodiments, multiple rounds of separation steps are carried out, where the positively or negatively selected fraction from one step is subjected to another separation step, such as a subsequent positive or negative selection. In certain exemplary embodiments, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker$^-$) or express relatively low levels (marker$^{low}$) of one or more markers. For example, in certain aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD127). In certain exemplary embodiments, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In certain aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in certain aspects is particularly robust in such sub-populations. In some embodiments, combining TCM-enriched CD8+ T cells and CD4+ T cells further enhances efficacy.

In some embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and/or a CD8+ T population is enriched for central memory (TCM) cells. In some embodiments, the enrichment for central memory T (TCM) cells is based on positive or high surface expression of CD45RO, CD62L, CCR7, CD28, CD3, and/or CD 127; in certain aspects, it is based on negative selection for cells expressing or highly expressing CD45RA and/or granzyme B. In certain aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in certain aspects are carried out simultaneously and in other aspects are carried out sequentially, in either order. In some certain, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In certain aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. An exemplary method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of Immune Cells

Whether prior to or after modification of cells to express a subject CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the immune cells of the invention may be expanded by contact with a surface having attached thereto an agent that stimulates a CD3/TCR complex associated signal and a ligand that stimulates a co-stimulatory molecule on the surface of the immune cells. In particular, immune cell populations may be stimulated by contact with an anti-CD3 antibody, or an antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the immune cells, a ligand that binds the accessory molecule is used. For example, immune cells can be contacted with an anti-CD3 antibody and an anti-CD28 antibody, under conditions appropriate for stimulating proliferation of the immune cells. Examples of an anti-CD28 antibody include 9.3, B-T3, XR-CD28 (Diaclone, Besancon, France) and these can be used in the invention, as can other methods and reagents known in the art (see, e.g., ten Berge et al., *Transplant Proc.* (1998) 30(8): 3975-3977; Haanen et al., *J. Exp. Med.* (1999) 190(9): 1319-1328; and Garland et al., *J. Immunol. Methods* (1999) 227(1-2): 53-63).

Expanding the immune cells by the methods disclosed herein can be multiplied by about 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700 fold, 800-fold, 900-fold, 1000-fold, 2000-fold, 3000-fold, 4000-fold, 5000-fold, 6000-fold, 7000-fold, 8000-fold, 9000-fold, 10,000-fold, 100,000-fold, 1,000,000-fold, 10,000,000-fold, or greater, and any and all whole or partial integers therebetween. In one embodiment, the immune cells expand in the range of about 20-fold to about 50-fold.

Following culturing, the immune cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. In certain exemplary embodiments, the level of confluence is 70% or greater before passing the cells to another culture apparatus. In particularly exemplary embodiments, the level of confluence is 90% or greater. A period of time can be any time suitable for the culture of cells in vitro. The immune cell medium may be replaced during the culture of the immune cells at any time. In certain exemplary embodiments, the immune cell medium is replaced about every 2 to 3 days. The immune cells are then harvested from the culture apparatus whereupon the immune cells can be used immediately or cryopreserved to be stored for use at a later time. In one embodiment, the invention includes cryopreserving the expanded immune cells. The cryopreserved immune cells are thawed prior to introducing nucleic acids into the immune cell.

In another embodiment, the method comprises isolating immune cells and expanding the immune cells. In another embodiment, the invention further comprises cryopreserving the immune cells prior to expansion. In yet another embodiment, the cryopreserved immune cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of immune cells comprises the addition to the cellular growth factors, such as those described in U.S. Pat. No. 5,199,942, or other factors, such as flt3-L, IL-1, IL-3 and c-kit ligand. In one embodiment, expanding the immune cells comprises culturing the immune cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated PO. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging. Therefore the number of population doublings of a culture is greater than the passage number.

The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for immune cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the immune cells may include an agent that can co-stimulate the immune cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10,000-fold, 100,000-fold, 1,000,000-fold, 10,000,000-fold, or greater. In one embodiment, the immune cells expand in the range of about 2-fold to about 50-fold, or more by culturing the electroporated population. In one embodiment, human T regulatory cells are expanded via anti-CD3 antibody coated KT64.86 artificial antigen presenting cells (aAPCs). Methods for expanding and activating immune cells can be found in U.S. Pat. Nos. 7,754,482, 8,722,400, and 9,555,105, the contents of which are incorporated herein in their entirety.

In one embodiment, the method of expanding the immune cells can further comprise isolating the expanded immune cells for further applications. In another embodiment, the method of expanding can further comprise a subsequent electroporation of the expanded immune cells followed by culturing. The subsequent electroporation may include introducing a nucleic acid encoding an agent, such as a transducing the expanded immune cells, transfecting the expanded immune cells, or electroporating the expanded immune cells with a nucleic acid, into the expanded population of immune cells, wherein the agent further stimulates the immune cell. The agent may stimulate the immune cells, such as by stimulating further expansion, effector function, or another immune cell function.

Methods of Treatment

Mucins are high molecular weight glycosylated proteins that function in normal, healthy cells as a physicochemical protection from toxins and mutagens when overexpressed in epithelial cells. Expression is noted in other healthy cell types where mucins can function as adhesion modulators or play a role in signal transduction and regulation of cell growth (Winterford et al. (1999) *J Histochem Cytochem*, 47(8): 1063-1074). Tumorigenesis and metastasis have been shown to increase with changes in cell surface glycosylation of mucins (protein modifications after additions of sugar moieties to specific amino acids) of various proteins (Ren et al. (2014) *Tumour Biol*, 35(10): 9603-9612; Tarp et al. (2008) *Glycobiology*, 17(2): 197-209; Taylor-Papadimitriou et al. (1999) 1455(2-3): 301-313). At least nine of the 20 amino acids can be modified by a variety of carbohydrates (Stowell et al. (2015) *Annu Rev Pathol*, 10:473-510). Tn (GalNAcal-O-Ser/Thr) and sialyl-Tn (STn) (NeuAca2-6-GalNAcal-O-Ser/Thr) are among the most prevalent aberrant glycoforms found in cancer (Springer (1984) *Science*, 224(4654): 1198-1206). This aberrant glycosylation also leads to a tumor-specific form of the full-length Mucin1 glycoprotein referred to as TnMUC1, thought to play a key role in carcinogenesis (Ju et al. (2005) *Nature*, 437(7063): 1252; Ju et al. (2008) *Cancer Res*, 68(6): 1636-1646; Ju et al. (2014) *Cancer Biomark*, 14(1): 63-81; Varki et al. (2017) *Essentials of Glycobiology* [Internet]. 3rd edition. Cold Spring Harbor (NY): Cold Spring Harbor Laboratory Press; 2015-2017). Aberrant expression of Tn/sTn glycoforms have in particular been found on the cell membrane-bound mucin (MUC1), which is a large protein with tandem repeated sequences carrying O-glycans overexpressed in most adenocarcinomas (Cascio et al. (2017) *Oncotarget*, 8(62): 105284-98; Finn et al. (2011) *Immunol Research*, 50(2-3): 261-268). Some healthy tissues of an epithelial origin express MUC1 on the cell surface (Winterford et al. (1999) *J Histochem Cytochem*, 47(8): 1063-1074); the aberrantly glycosylated version (TnMUC1) is expressed in the Golgi apparatus and is a precursor to the full length MUC1 observed on the cell surface (Posey et al. (2016) *Immunity*, 44(6): 1444-1454). Tumor-associated TnMUC1 is overexpressed in a proportion of multiple myeloma cases (Andrulis et al. (2014) *Histopathology*, 64:799-806; Cloosen et al. (2006) *British Journal of Haematology*, 135:513-516) and in a variety of solid tumors including those of the: breast, colon, lung, stomach, ovary, and pancreas, where a loss of membrane polarity and abnormal O-glycosylation results in expression of Tn and STn glycoforms on the tumor cell surface (Lavrsen et al. (2013) *Glycoconjugates*, 30(3): 227-236; Pinto et al. (2012) *J Cellular Mol Medicine*, 16:1474-1484; Sørensen et al. (2006) *Glycobiology*, 16:96-107).

In one aspect, the invention includes a method of treating a MUC1-associated cancer in a subject in need thereof. In another aspect, the invention includes a method of treating a MUC1-associated cancer in a subject comprising administering to a subject in need thereof a therapeutically effective population of modified immune cells of the present invention. In some embodiments, the MUC1-associated cancer is selected from the group consisting of multiple myeloma, breast cancer, colon cancer, lung cancer, stomach cancer, cancer of the ovary, and cancer of the pancreas. In some embodiments, the MUC1-associated cancer is selected from the group consisting of a MUC1-associated breast cancer, a MUC1-associated multiple myeloma, a MUC1-associated non-small cell lung cancer, a MUC1-associated pancreatic adenocarcinoma, a MUC1-associated ovarian and fallopian tube cancers.

The method comprises administering to the subject a modified immune cell (e.g., MUC1 CAR T cell) of the present invention.

As used herein, the terms "subject" and "patient" refer to organisms to be treated by the methods of the present invention. The terms "subject" and "patient" may be used interchangeably herein. Such organisms include, but are not limited to, mammals (e.g., murines, simians, equines, bovines, porcines, canines, felines, and the like), and in an exemplary embodiment includes humans. As used herein, the terms "treat," "treatment" and "treating" include any effect, e.g., lessening, reducing, modulating, ameliorating or eliminating, that results in the improvement of the condition, disease, disorder, and the like, or ameliorating a symptom thereof, such as for example, reduced number of cancer cells, reduced tumor size, reduced tumor burden, reduced rate of cancer cell infiltration into peripheral organs, or reduced rate of tumor metastasis or tumor growth.

Positive therapeutic effects in cancer can be measured in a number of ways (See, W. A. Weber, J. Null. Med. 50:1S-10S (2009); Eisenhauer et al., Eur. J. Cancer 45:228-247 (2009)). In some embodiments, response to a subject CAR T cell therapy (e.g., TN-MUC1 CAR T cell therapy) is assessed using RECIST 1.1 criteria (see, Eisenhauer et al., supra). In some embodiments, the treatment achieved by a therapeutically effective amount (e.g., of a TN-MUC1 CAR T cell therapy) is any of a partial response (PR), a complete response (CR), progression free survival (PFS), disease free survival (DFS), objective response (OR), a change in the duration of response (e.g., an increase in the duration of response), a change in the time to response (e.g., a shortened time to response), or overall survival (OS). The therapeutically effective amount described herein that is effective to treat breast cancer in a patient may vary according to various factors such as the disease state, age, and weight of the patient, and the ability of the therapy to elicit an anti-cancer response in the subject.

"RECIST 1.1 Response Criteria" as used herein means the definitions set forth in Eisenhauer et al. (2009) *Eur J Cancer*, 45(2): 228-247 for target lesions or non-target lesions, as appropriate, based on the context in which response is being measured.

"Tumor" as it applies to a subject diagnosed with, or suspected of having, cancer (e.g., MUC1-associated breast cancer, MUC1-associated multiple myeloma, MUC1-associated non-small cell lung cancer, MUC1-associated pancreatic adenocarcinoma, MUC1-associated ovarian and fallopian tube cancers), refers to a malignant or potentially malignant neoplasm or tissue mass of any size.

"Tumor burden" also referred to as "tumor load," refers to the total amount of tumor material distributed throughout the body. Tumor burden refers to the total number of cancer cells or the total size of tumor(s) throughout the body, including lymph nodes and bone narrow. Tumor burden can be determined by a variety of methods known in the art, such as, e.g., by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CT or MRI scans.

In one aspect, the invention includes a method of treating a MUC1-associated breast cancer in a subject in need thereof, comprising administering to the subject a therapeutically effective population of modified immune cells, wherein the modified immune cells comprise a chimeric antigen receptor (CAR). In certain embodiments, the CAR comprises a MUC1-specific antigen binding domain, a transmembrane domain, a costimulatory signaling domain, and an intracellular signaling domain.

In one aspect, the invention includes a method of treating a MUC1-associated multiple myeloma in a subject in need thereof, comprising administering to the subject a therapeutically effective population of modified immune cells, wherein the modified immune cells comprise a chimeric antigen receptor (CAR). In certain embodiments, the CAR comprises a MUC1-specific antigen binding domain, a transmembrane domain, a costimulatory signaling domain, and an intracellular signaling domain. In other embodiments, the modified cell further comprises a dominant negative receptor and/or switch receptor.

In one aspect, the invention includes a method of treating a MUC1-associated non-small cell lung cancer in a subject in need thereof, comprising administering to the subject a therapeutically effective population of modified immune cells, wherein the modified immune cells comprise a chimeric antigen receptor (CAR). In certain embodiments, the CAR comprises a MUC1-specific antigen binding domain, a transmembrane domain, a costimulatory signaling domain, and an intracellular signaling domain. In other embodiments, the modified cell further comprises a dominant negative receptor and/or switch receptor.

In one aspect, the invention includes a method of treating a MUC1-associated pancreatic adenocarcinoma in a subject in need thereof, comprising administering to the subject a therapeutically effective population of modified immune cells, wherein the modified immune cells comprise a chimeric antigen receptor (CAR). In certain embodiments, the CAR comprises a MUC1-specific antigen binding domain, a transmembrane domain, a costimulatory signaling domain, and an intracellular signaling domain. In other embodiments, the modified cell further comprises a dominant negative receptor and/or switch receptor.

In one aspect, the invention includes a method of treating a MUC1-associated ovarian and/or fallopian tube cancer in a subject in need thereof, comprising administering to the subject a therapeutically effective population of modified immune cells, wherein the modified immune cells comprise a chimeric antigen receptor (CAR). In certain embodiments, the CAR comprises a MUC1-specific antigen binding domain, a transmembrane domain, a costimulatory signaling domain, and an intracellular signaling domain. In other embodiments, the modified cell further comprises a dominant negative receptor and/or switch receptor.

In certain embodiments, the MUC1-specific antigen binding domain binds to a glycosylated form of MUC1, i.e. is specific for a glycoepitope of MUC1. In certain embodiments, the MUC1-specific antigen binding domain is specific for a truncated glycoepitope of MUC1. In certain embodiments, the MUC1-specific antigen binding domain is specific for TnMUC1. In certain embodiments, the MUC1-specific antigen binding domain may comprise the heavy chain complementarity determining region (CDR) sequences of SEQ ID NOs: 22, 23 and 24 and/or the light chain complementarity determining region (CDR) sequences of SEQ ID NOs: 19, 20 and 21. In certain embodiments, the MUC1-specific antigen binding domain may comprise all six complementarity determining region (CDR) sequences of SEQ ID NOs: 19-24. In certain embodiments, the MUC1-specific antigen binding domain may comprise the heavy chain variable domain (VH) sequence of SEQ ID NO: 5 and/or the light chain variable domain (VL) sequence of SEQ ID NO: 6. In certain embodiments, the MUC1-specific antigen binding domain comprises the amino acid sequence of SEQ ID NO: 2.

The CAR used in the methods of the invention may comprise a transmembrane domain selected from the group consisting of an artificial hydrophobic sequence, a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In certain exemplary embodiments, the transmembrane domain comprises a CD8a transmembrane domain.

The CAR may comprise a costimulatory signaling domain comprising a costimulatory domain of a protein selected from the group consisting of a TNFR superfamily member, CD27, CD28, 4-1BB (CD137), OX40 (CD134), CD30, CD40, PD-1, ICOS, lymphocyte function-associated antigen-1 (LFA-1), CD2, CD5, CD7, LIGHT, NKG2C, B7-H3, a ligand that specifically binds with CD83, DAP10, DAP12, Lck, Fas, and any combination thereof. In certain exemplary embodiments, the costimulatory signaling domain comprises a 4-1BB costimulatory domain.

The intracellular signaling domain may comprise a signaling domain of a protein selected from the group consisting of CD3 zeta, FcyRIII, FcsRI, a cytoplasmic tail of an Fc receptor, an immunoreceptor tyrosine-based activation motif (ITAM) bearing cytoplasmic receptor, TCR zeta, FcR gamma, FcR beta, CD3 gamma, CD3 delta, CD3 epsilon, CD5, CD22, CD79a, CD79b, and CD66d. In certain exemplary embodiments, the intracellular signaling domain comprises a CD3 zeta signaling domain.

The CAR may further comprise a CD8a leader sequence and/or an extracellular hinge domain selected from the group consisting of an Fc fragment of an antibody, a hinge region of an antibody, a CH2 region of an antibody, a CH3 region of an antibody, an artificial spacer sequence, a hinge comprising an amino acid sequence of CD8, and any combination thereof. In certain exemplary embodiments, the extracellular hinge domain comprises a CD8a extracellular hinge domain.

In certain embodiments, the CAR is encoded by a nucleic acid sequence comprising the nucleotide sequence of SEQ ID NOs: 1, 38, 40, 42, 44, or 46. In certain embodiments, the CAR comprises the amino acid sequence of SEQ ID NOs: 2, 39, 41, 43, 45, or 47.

In certain exemplary embodiments, the CAR is encoded by a nucleic acid sequence comprising the nucleotide sequence of SEQ ID NO: 46. In certain exemplary embodiments, the CAR comprises the amino acid sequence of SEQ ID NO: 47.

A CAR of the present disclosure, when present in a T lymphocyte or an NK cell, can mediate cytotoxicity toward a target cell. A CAR of the present disclosure binds to an antigen present on a target cell, thereby mediating killing of a target cell by a T lymphocyte or an NK cell genetically modified to produce the CAR. The antigen-binding domain of the CAR (e.g., anti-TN-MUC1 scFv) binds to an antigen present on the surface of a target cell (e.g., TN-MUC1 antigen). Target cells include, but are not limited to, cancer cells, e.g., breast cancer cells. Thus, the present disclosure provides methods of killing, or inhibiting the growth of, a target cancer cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cancer cell, and mediates killing of the target cell.

The present disclosure provides a method of treating cancer in a subject having a cancer, the method comprising: i) introducing a chimeric antigen receptor of the present disclosure, or introducing an expression vector of the present disclosure, into a cell, to produce a modified cell; and ii) administering the modified cell to the subject. In some embodiments, the cell is obtained from the subject (i.e., the cell is autologous), engineered ex vivo, and administered to the same subject. In some embodiments, the cell is obtained from one subject, engineered ex vivo, and administered to a second suitable subject (i.e., the cell is allogeneic).

In some embodiments, a method is provided including retrieving cytotoxic cells from a subject, genetically modifying the cytotoxic cells by introducing a CAR gene of the present invention into the cytotoxic cells, and administering the modified cytotoxic cells to the subject. In some embodiments, the cytotoxic cells are selected from T cells, naive T cells, memory T cells, effector T cells, natural killer cells, and macrophages. In one embodiment, the cytotoxic cells are T cells.

In one embodiment, the T cells are obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art, may be used. In some embodiments of the present invention, T cells can be obtained from blood collected from a subject using any number of techniques known to the skilled artisan, such as Ficoll™ separation.

For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In one embodiment, the time period ranges from 30 minutes to 36 hours or longer and all integer values there between. In one embodiment, the time period is at least 1, 2, 3, 4, 5, or 6 hours. In one embodiment, the time period is 10 to 24 hours. In one embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled person would recognize that multiple rounds of selection can also be used in the context of this invention. In some embodiments, it may be desirable to perform the selection procedure and use the "unselected" cells in the activation and expansion process. "Unselected" cells can also be subjected to further rounds of selection.

The obtained cells are then modified as described herein. A polynucleotide encoding the subject CAR (e.g., a TN-MUC1 CAR), typically located in an expression vector, is introduced into the cytotoxic cells such that the cytotoxic cells will express, preferably stably, the CAR. In some embodiments, the polynucleotide encoding the CAR also encodes a CAR inducible expression cassette for a transgenic polypeptide product that is produced and released upon CAR signaling. In some embodiments, the polynucleotide encoding the CAR also encodes a cytokine (e.g., IL-12) operably linked to a T-cell activation responsive promoter. In some embodiments, the expression vector comprises both the polynucleotide encoding the CAR and the polynucleotide encoding the cytokine operably linked to the T-cell activation responsive promoter. See, e.g., Chmielewski and Abken, *Expert Opin. Biol. Ther.* (2015) 15(8): 1145-1154; and Abken, *Immunotherapy* (2015) 7(5): 535-544. In some embodiments the cells are genetically engineered with an expression vector comprising the polynucleotide encoding the CAR and an expression vector comprising the polynucleotide encoding the cytokine (e.g., IL-12) operably linked to the T-cell activation responsive promoter. In some embodiments, the polynucleotide introduction need not result in integration but rather only transient maintenance of the polynucleotide introduced may be sufficient. In this way, one could have a short term effect, where cytotoxic cells could be introduced into the host and then turned on after a predetermined time, for example, after the cells have been able to migrate to a particular site for treatment.

Depending upon the nature of the cytotoxic cells and the diseases to be treated, the modified cytotoxic cells (e.g., modified T cells) may be introduced into the subject, e.g. a mammal, in a wide variety of ways. The genetically engineered cytotoxic cells may be introduced at the site of the tumor. In one embodiment, the genetically engineered cytotoxic cells navigate to the cancer or are modified to navigate to the cancer. The number of modified cytotoxic cells that are employed will depend upon a number of factors such as the circumstances, the purpose for the introduction, the lifetime of the cells, the protocol to be used. For example, the number of modified cytotoxic cells that are employed may depend upon the number of administrations, the ability of the cells to multiply, and the stability of the recombinant construct. The modified cytotoxic cells may be applied as a dispersion injected at or near the site of interest. In one embodiment, the cells may be in a physiologically-acceptable medium.

It should be appreciated that the treatment method is subject to many variables, such as the cellular response to the CAR (e.g., a TN-MUC1 CAR), the efficiency of expression of the CAR by the cytotoxic cells and, as appropriate, the level of secretion, the activity of the expressed CAR, the particular need of the subject, which may vary with time and circumstances, the rate of loss of the cellular activity as a result of loss of modified cytotoxic cells or the expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

Accordingly, in an exemplary embodiment, the present invention provides a method of treating a MUC1 associated cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain.

In an exemplary embodiment, provided is a method of treating a MUC1 associated cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a CD8α hinge domain; a CD8α transmembrane domain; a CD2 costimulatory signaling domain; and a CD3 zeta intracellular signaling domain.

An exemplary type of cancer to be treated with the modified cytotoxic cells (e.g., modified T cells comprising a TN-MUC1 CAR) or pharmaceutical compositions of the invention include cancers of the breast. In certain embodiments, the breast cancer treated by any of the methods of the invention is characterized by abnormal glycosylation of MUC1.

Breast cancer that is diagnosed histologically as Hormone Receptor (HR, estrogen receptor, ER or progesterone receptor, PR) negative and Human Epidermal Growth Factor receptor 2 (HER2) negative is known as triple negative breast cancer (TNBC) and comprises approximately 15% of all breast cancer. TNBC in general have poor outcomes due to the aggressive nature of the disease associated with a high proliferation index; the standards of care in this subset of breast cancer are generally unlike other subsets (Gradishar et al. (2018) NCCN Guidelines v.2018 Breast Cancer. website: www.nccn.org/professionals/physician_gls/pdf/breast.pdf (accessed February 2019)). As with all breast cancer, local therapy utilizes both surgery and radiotherapy, however despite adequate local therapy, many patients with TNBC go on to develop distant metastatic disease. A majority of these patients do not respond well to conventional chemotherapy and to date, there have been few clear, druggable targets identified for effective treatment of TNBC (Gerratana et al. (2018) Cancer Treat Rev, 68:102-110).

Metastatic TNBC represents a high unmet need, with the median OS of 6 months from the time of initial diagnosis with metastatic disease versus 20 months for those patients with hormone receptor-positive and/or Her2-positive metastatic breast cancer. With different biology and targets, the outcomes of metastatic HER2-positive and hormone receptor-positive breast cancer continue to improve, however TNBC remains an unmet need (Ganesan et al. (2014) Mol Cancer Ther, 12:3175-3184). Immunotherapy with PD-1/PD-L1 inhibition have demonstrated promising results in advanced TNBC in clinical studies. A combination of atezolizumab with a standard chemotherapy agent (nab-paclitaxel) in advanced TNBC demonstrated significant improvement in PFS (all patients) and OS (PD-L1 positive, Schmid et al. (2018) New England J Med, 379(22): 2108-2121).

In some embodiments, the breast cancer is hormone receptor-positive (HR-positive). In some embodiments, the breast cancer is hormone receptor-negative. In some embodiments, the breast cancer is estrogen receptor-negative. In some embodiments, the breast cancer is progesterone receptor-negative. In some embodiments, the breast cancer is Her2 receptor-negative. In some embodiments, the breast cancer is a metastatic breast cancer. In some embodiments, the breast cancer is triple negative breast cancer (ER-negative, PR-negative, and HER2-negative). In some embodiments, the breast cancer is triple positive breast cancer (ER-positive, PR-positive, and HER2-positive). In some embodiments, the breast cancer is triple negative, metastatic breast cancer. In some embodiments, the breast cancer is an incurable, unresectable, locally advanced or metastatic breast cancer (LA/MBC). In some embodiments, the breast cancer is ER-negative and/or PR-positive and HER2-negative breast cancer. In some embodiments, the breast cancer is HER2-positive and LA/MBC. In some embodiments, the breast cancer is triple negative breast cancer and LA/MBC.

Exemplary breast cancers are those that express abnormally glycosylated MUC1 (e.g., TnMUC1) in a cell expressing the cancer (i.e., TnMUC1-expressing cancers). In certain exemplary embodiments, a breast cancer is selected from the group consisting of carcinomas, sarcomas, phyllodes, Paget disease, and angiosarcomas. In certain exemplary embodiments, a breast cancer is selected from the group consisting of ductal carcinoma in situ, invasive ductal carcinoma or subtype thereof (e.g., tubular carcinoma of the breast, medullary carcinoma of the breast, mucinous carcinoma of the breast, papillary carcinoma of the breast, cribriform carcinoma of the breast, and the like), invasive lobular carcinoma, inflammatory breast cancer, lobular carcinoma in situ, male breast cancer, Paget's disease of the nipple, phyllodes tumors of the breast, metastatic breast cancer, and certain molecular subtypes (e.g., luminal A breast cancer, luminal B breast cancer, triple-negative/basal-like breast cancer, HER2-enriched breast cancer, normal-like breast cancer).

A breast cancer may be characterized by the expression of several markers. For example, breast cancer may be an estrogen receptor positive (ER+) breast cancer, a progesterone receptor positive (PR+) breast cancer, a hormone receptor negative (HR−) breast cancer, a HER2 gene overexpressing (HER2+) breast cancer, a HER2 gene wild-type or under-expressing (HER2−) breast cancer. Breast cancer may be a group 1 (luminal A) breast cancer, i.e., ER+/PR+/HER2−, a group 2 (luminal B) breast cancer, i.e., ER+/PR−/HER2+, a group 3 (HER2+) breast cancer, i.e., ER−/PR−/HER2+, or a group 4 (basal-like or triple negative (TN)) breast cancer, i.e., ER−/PR−/HER2−.

A breast cancer can be categorized as grade 1, 2 or 3. Grade 1 or well-differentiated (score 3, 4, or 5) breast cancer comprises cells that are slower-growing, and look more like normal breast tissue than the higher grades of breast cancer. Grade 2 or moderately differentiated (score 6, 7) breast cancer comprises cells that grow at a speed of and look like cells somewhere between grades 1 and 3. Grade 3 or poorly differentiated (score 8, 9) breast cancer comprises cells that look very different from normal cells and typically grow and spread faster than grades 1 or 2.

Accordingly, in an exemplary embodiment, the present invention provides a method of treating a MUC1 associated triple negative breast cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain.

In an exemplary embodiment, provided is a method of treating a MUC1 associated triple negative breast cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a CD8α hinge domain; a CD8α transmembrane domain; a 4-1BB costimulatory signaling domain; and a CD3 zeta intracellular signaling domain.

In an exemplary embodiment, provided is a method of treating a MUC1 associated triple negative breast cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a CD8α hinge domain; a CD8α transmembrane domain; a CD2 costimulatory signaling domain; and a CD3 zeta intracellular signaling domain.

An exemplary type of cancer to be treated with the modified cytotoxic cells (e.g., modified T cells comprising a TN-MUC1 CAR) or pharmaceutical compositions of the invention include multiple myeloma. Multiple myeloma (MM) is a disease defined by the accumulation of clonal bone marrow plasma cells and development of clinical complications including hypercalcemia, renal insufficiency, symptomatic anemia, destructive lytic bone lesions, and susceptibility to infections. According to the National Cancer Institute Surveillance, Epidemiology, and End Results (NCI SEER) database, in the United States (US), over 30,000 patients were estimated to be diagnosed with multiple myeloma, with a mortality of over 12,000 (Siegel (2016) *CA Cancer J Clin,* 66:7-30). Treatment of multiple myeloma has advanced significantly over the past decade, and an expanding palette of drugs targeting multiple myeloma plasma cells, including proteasome inhibitors, immunomodulatory drugs (IMiDs), steroids, and alkylators, is now clinically available, such that the vast majority of newly diagnosed patients respond to initial therapy. When induction therapy is followed by high-dose chemotherapy and autologous stem cell transplantation (ASCT), approximately one-third of patients achieve complete remissions, and many more experience clinically meaningful responses (San Miguel et al. (2013) *Lancet Oncol,* 14:1055-1066). Despite these advances, and even in patients who achieve deep remissions by sensitive molecular or flow cytometric detection methods, nearly all patients relapse with disease that becomes progressively more refractory to successive lines of therapy (Martinez-Sanchez et al. (2008) *Br J Haematology,* 142:766-774; Paiva et al. (2012) *Blood,* 119:687-691).

In patients with resistant disease with both bortezomib and IMiDs, median progression-free and overall survival (OS) are reported generally 6 to 9 months (Kumar et al. (2012) *Leukemia,* 26:149-157). Second-generation proteasome inhibitors (e.g., carfilzomib), IMiDs (e.g., pomalidomide), and monoclonal antibodies (e.g., daratumumab) are useful additions but only incrementally improve outcomes (median progression free survival [PFS] 3 to 4 months) (Siegel (2016) *CA Cancer J Clin,* 66:7-30; San Miguel et al. (2013) *Lancet Oncol,* 14:1055-1066; Lonial et al. (2016) *Lancet,* 387(10027): 1551-1560). Immunotherapy using inhibition of the PD-1/PD-L1 checkpoint has been evaluated in many myeloma trials. Combination of PD-1 targeted agents with IMiDs led to promising clinical activity and continued studies evaluate the possible safety signal with IMID-PD1 combination (Costa et al. (2018) *Frontiers Immunol,* 9:2204). Trials with CAR-T therapy are ongoing with promising preliminary activity. The primary antigen targeted being the B cell maturation antigen or BCMA in ongoing studies (Costa et al. (2018) *Frontiers Immunol,* 9:2204). Despite recent advances, relapsed/refractory multiple myeloma remains a disease setting with high unmet need.

Multiple myeloma (MM) may be characterized by various methods including laboratory tests, imaging and biopsies. Laboratory tests include: a complete blood count to measure the level of red cells, white cells, and platelets in the blood; a blood chemistry test to measure the level of blood creatinine, albumin, calcium, lactic dehydrogenase, and other electrolytes; a urine test to measure the presence of myeloma protein, e.g., Bence Jones protein (e.g., urine protein electrophoresis, urine immunofixation); a quantitative immunoglobulin test to measure the blood levels of different antibodies, where the level of a certain type of antibody may be higher than others in subjects having MM; blood test to assess the presence and level of abnormal protein produced by myeloma cells, e.g., monoclonal immunoglobulin, monoclonal protein (M protein), M spike, paraprotein; blood test to measure light chain levels in the blood; blood test to assess presence and levels of beta-2 microglobulin.

A diagnosis of multiple myeloma often requires: (1) a plasma cell tumor (proven by biopsy) or at least 10% plasma cells in the bone marrow; and (2) at least one of high blood calcium level, poor kidney function, low red blood cell counts (anemia), holes in the bones from tumor found on imaging studies (CT, MRI, PET scan), increase in one type of light chain in the blood so that one type is 100 times more common than the other, and 60% or more plasma cells in the bone marrow.

Multiple myeloma can be staged according to the Revised International Staging System (RISS) based on four factors: the amount of albumin in the blood, the amount of beta-2-microglobulin in the blood, the amount of lactate dehydrogenase (LDH) in the blood, and the specific gene abnormalities (cytogenetics) of the cancer. RISS stage group I is characterized by serum beta-2-microglobulin less than 3.5 mg/L, albumin level at 3.5 g/dL or greater, cytogenetics considered not high risk, and LDH levels are normal. RISS stage group II is characterized as not belonging in stage group I or stage group III. RISS stage group III is characterized by serum beta-2-microglobulin at 5.5 mg/L or greater, cytogenetics considered high risk, and/or LDH levels are high.

Accordingly, in an exemplary embodiment, a method of treating a MUC1 associated multiple myeloma in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In an exemplary embodiment, a method of treating a MUC1 associated multiple myeloma in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a CD8α hinge domain; a CD8α transmembrane domain; a CD2 costimulatory signaling domain; and a CD3 zeta intracellular signaling domain, is provided.

An exemplary type of cancer to be treated with the modified cytotoxic cells (e.g., modified T cells comprising a TN-MUC1 CAR) or pharmaceutical compositions of the invention include non-small cell lung cancer. Lung cancer is a leading cause of cancer-related mortality around the world and remains a significant unmet need despite advances in therapy. Non-small cell lung cancer (NSCLC) accounts for 85% of all lung cancer cases in the US, with a significant proportion of the remaining 15% being small cell lung cancers (SCLC) (Zappa et al. (2016) *Transl Lung Cancer Res*, 5(3): 288-300; Alvarado-Luna et al. (2016) *Transl Lung Cancer Res*, 5(1): 26-38). Surgical resection remains the single most consistent and successful option for localized NSCLC; however, close to 70% of patients with lung cancer present with locally advanced or metastatic disease at the time of diagnosis (Molina et al. (2008) *Mayo Clin Proc*, 83(5): 584-594). Overall, the prognosis for lung cancer patients is poor, with 5-year relative survival less than 18%. The median OS time for patients with stage IV NSCLC is 4 months, while 1- and 5-year survival is less than 16% and 2%, respectively (Cetin et al. (2011) *Clin Epidemiol*, 3:139-148).

Platinum-based regimens (doublet chemotherapy; e.g., cisplatin with gemcitabine or carboplatin with paclitaxel/gemcitabine) continues to remain one of the mainstays of treatment for non-resectable NSCLC, in addition to radiation for stage III or IV lung cancer (Ettinger et al. (2019) website: nccn.org/professionals/physician_gls/pdf/nscl.pdf (accessed February 2019)). Single-agent targeted therapy is added to the doublet for patients with anaplastic lymphoma kinase (ALK) or sensitizing epidermal growth factor receptor (EGFR) mutations or other driver mutations/alterations (Ettinger et al, supra; Yoon et al. (2017) *World J Clin Oncol*, 8(1): 1-20). These targeted therapies have had a major impact on the treatment of NSCLC in patients with genetic alterations, and have resulted in vastly improved outcomes (Ettinger et al, supra). However, resistance to TKIs has emerged as a significant unmet medical need with recent evidence positing unique mechanisms of TKI-resistance (Lin et al. (2014) *J Cancer Res*, 4(5): 411-435). Inhibition of the immune checkpoint PD-1/PD-L1 is utilized in both the first-line and second line setting in patients with locally advanced or metastatic NSCLC. PD-1/PD-L1 pathway inhibition has demonstrated improved overall survival, with longer duration of response and fewer adverse events compared to chemotherapy alone. Currently, the NCCN guidelines recommend PD-1 inhibition in both the first line setting (associated with strong expression of PD-L1 in the tumor) and for second line setting (irrespective of PD-L1 expression; Ettinger et al, supra). Despite recent advances with both targeted agents and checkpoint inhibition, NSCLC remains a significant area of unmet need.

NSCLCs include adenocarcinomas, squamous cell carcinomas, and large cell carcinomas. NSCLC may be characterized by various methods including laboratory tests, imaging and biopsies. For example, diagnosis of NSCLC may require tests including bone scans, imaging tests (MRI, CT scan, PET scan), microscopic examination of sputum to check for cancer cells, and biopsy of lung.

NSCLC can be staged according to the American Joint Committee on Cancer (AJCC) Tumor, Node, Metastasis (TNM) system, which is based on three main factors: (1) the size and extent of the main tumor; (2) the spread to nearby lymph nodes; and (3) the spread to distant sites. The earliest stage of NSCLC is stage 0 (also called carcinoma in situ). Other stages range from stage I to stage IV, with a higher numbered stage meaning that the cancer has spread more.

Accordingly, in an exemplary embodiment, a method of treating a MUC1 associated non-small cell lung cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In an exemplary embodiment, provided is a method of treating a MUC1 associated non-small cell lung cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a CD8α hinge domain; a CD8α transmembrane domain; a CD2 costimulatory signaling domain; and a CD3 zeta intracellular signaling domain.

An exemplary type of cancer to be treated with the modified cytotoxic cells (e.g., modified T cells comprising a TN-MUC1 CAR) or pharmaceutical compositions of the invention include pancreatic adenocarcinoma. Pancreatic ductal adenocarcinoma is a highly lethal malignancy. It is the fourth leading cause of cancer-related death in the United States with approximately 45,000 new cases per year. Surgical resection is the only potentially curative treatment, however with the majority of patients presenting with advanced disease only 15-20% of patients are candidates for surgical intervention (Fogel et al. (2017) *Am J Gastroenterology*, 112(4): 537-555). Overall, prognosis is poor even with surgical intervention: the five-year survival with surgery is approximately 25% for node-negative and 10% for node-positive disease. With the majority of patients presenting with unresectable disease, chemotherapy is the mainstay of treatment. Modest gains in efficacy have been observed previous to recent development with combination chemotherapy. FOLFIRINOX treatment demonstrated increased median OS and PFS when compared to gemcitabine alone, although increased toxicity is observed with combination therapy. Alternate combination therapy includes gemcitabine and nab-paclitaxel, which is used more widely than FOLFIRINOX due to its favorable toxicity profile even though median OS was inferior.

Despite successes with targeted therapy and immunotherapy approaches in other solid tumors, similar improvements in efficacy are not evident with pancreatic cancer (Amanam et al. (2018) *Cancers*, 10(2). pii: E36). Interestingly, immune-checkpoint inhibitors have had more success in pancreatic adenocarcinoma. Overall, pancreatic adenocarcinoma remains an area of high unmet need and clinical trials are considered part of the standard of care in this disease setting (Tempero et al. (2019) website: nccn.org/professionals/physician_gls/pdf/pancreatic.pdf. (Accessed February 2019)).

Pancreatic adenocarcinoma can be characterized using imaging tests (CT scan, MRI, ultrasound, cholangiopancreatography, PET scan, angiography), blood tests, and biopsies. Blood tests to detect pancreatic adenocarcinoma include liver function tests, and assessing the presence of tumor markers such as CA 19-9 and carcinoembryonic antigen (CEA).

Pancreatic adenocarcinoma can be staged according to the American Joint Committee on Cancer (AJCC) Tumor, Node, Metastasis (TNM) system, which is based on three main factors: (1) the size and extent of the main tumor; (2) the spread to nearby lymph nodes; and (3) the spread to distant sites. The earliest stage of pancreatic adenocarcinoma is stage 0 (also called carcinoma in situ). Other stages range from stage I to stage IV, with a higher numbered stage meaning that the cancer has spread more.

Accordingly, in an exemplary embodiment, a method of treating a MUC1 associated pancreatic adenocarcinoma in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In an exemplary embodiment, provided is a method of treating a MUC1 associated pancreatic adenocarcinoma in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a CD8α hinge domain; a CD8α transmembrane domain; a CD2 costimulatory signaling domain; and a CD3 zeta intracellular signaling domain.

An exemplary type of cancer to be treated with the modified cytotoxic cells (e.g., modified T cells comprising a TN-MUC1 CAR) or pharmaceutical compositions of the invention include epithelial ovarian cancer. Epithelial ovarian cancers generally include fallopian tube malignancies as well as primary peritoneal cancers. More than 70% of women with epithelial ovarian cancer present with advanced disease at the time of first diagnosis. Although patients with advanced disease can achieve complete remission after surgical cytoreduction and platinum- and taxane-based chemotherapy, up to 80% eventually experience recurrence (Herzog et al. (2017) *Gynecol Oncol Res Pract,* 4:13).

Selection of treatment for recurrence of advanced epithelial ovarian cancer is generally guided by the progression-free interval. Though platinum-containing induction chemotherapy remains a standard first-line treatment, most patients eventually become resistant, generally defined as progression on or within 6 months of completion of the platinum-containing regimen (Armstrong et al. (2018) website: nccn.org/professionals/physician_gls/pdf/ovarian.pdf (accessed February 2019)). Platinum-resistance in the setting of advanced ovarian cancer remains an area of high unmet need (Oronsky et al. (2017) *Medical Oncology,* 34(6): 103). In addition to platinum-based therapies, molecularly targeted inhibitors of vascular endothelial growth factor (VEGF; i.e. bevacizumab) and poly ADP ribose polymerase (PARP, i.e., olaparib, rucaparib, and niraparib) have emerged as treatment options in patients following prior lines of chemotherapy. Among the immunotherapy options, pembrolizumab is considered acceptable for recurrent disease in patients with MSI-H or dMMR solid tumors as per standard oncology guidelines (Armstrong et al., supra; Fan et al. (2018) *Curr Treat Options Oncol,* 19(12): 74). The standard of care for patients with advanced epithelial ovarian cancers remains platinum-based therapy and once patients develop resistant disease, the unmet need is high and new therapy options are needed.

Epithelial ovarian cancers can be characterized using imaging tests, blood tests, and biopsies. Blood tests to detect epithelial ovarian cancers include measuring the level of CA-125, human chorionic gonadotropin (HCG), alpha-fetoprotein (AFP), and/or lactate dehydrogenase (LDH). Some epithelial ovarian cancers may be characterized by an elevated level of inhibin and hormones such as estrogen and testosterone.

Ovarian epithelial cancer can be staged according to the International Federation of Gynecology and Obstetrics (FIGO) or American Joint Committee on Cancer (AJCC) Tumor, Node, Metastasis (TNM) system, which are based on three main factors: (1) the size and extent of the main tumor; (2) the spread to nearby lymph nodes; and (3) the spread to distant sites. The earliest stage of ovarian epithelial cancer is stage 0 (also called carcinoma in situ). Other stages range from stage I to stage IV, with a higher numbered stage meaning that the cancer has spread more.

Accordingly, in an exemplary embodiment, a method of treating a MUC1 associated ovarian and/or fallopian tube cancer in a subject in need thereof, comprising administering to the subject a therapeutically effective composition comprising a modified T cell comprising: a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a hinge domain; a transmembrane domain; a costimulatory signaling domain; and an intracellular signaling domain, is provided.

In an exemplary embodiment, provided is a method of treating a MUC1 associated ovarian and/or fallopian tube cancer in a subject in need thereof, comprising: administering to the subject a therapeutically effective composition comprising a modified T cell comprising a MUC1-specific antigen binding domain comprising a heavy chain variable (VH) domain and a light chain variable (VL) domain, wherein the VH domain comprises the heavy chain complementarity determining region (CDR) sequences set forth in SEQ ID NOs: 22, 23, and 24, and wherein the VL domain comprises the light chain complementarity determining region (CDR) sequences set forth in SEQ ID NOs: 19, 20, and 21; optionally a CD8α hinge domain; a CD8α transmembrane domain; a CD2 costimulatory signaling domain; and a CD3 zeta intracellular signaling domain.

In certain embodiments, the population of modified immune cells administered to the subject comprises immune cells selected from the group consisting of natural killer (NK) cells, NKT cells, and T cells. In certain exemplary embodiments, the population of modified immune cells comprises modified T cells. In certain embodiments, the modified T cells are autologous.

The cells of the invention may be administered by any means known to one of ordinary skill in the art. For example, in certain embodiments, the administering may be performed via intratumoral delivery, via intravenous delivery, or via intraperitoneal delivery.

The amount of modified immune cells (e.g., modified T cells) to be administered to a subject in need is, generally, a therapeutically effective amount. As used herein, a "therapeutically effective amount" refers to a dose of modified immune cells that results in the cytotoxic killing of cancer cells (e.g., breast cancer cells) in the subject. In some embodiments, a suitable dose of modified immune cells when administered to the subject, results in a reduction of the cancer. Reduction of the cancer can be in the form of an output of one or more parameters indicative of the cancer, and be performed by various methods known in the art, for example, by detection of circulating tumor cells, detection of certain cancer-specific markers in the blood, detection of markers in a biopsy, tumor imaging, and the like. Generally, a suitable dose of modified immune cells when administered to the subject, results in a reduction of one or more parameters at least about 5%, 10%, 15%, 20%, 25%, 30%, 35%, 40%, 45%, 50%, 55%, 60%, 65%, 70%, 75%, or more from baseline.

As used herein, the term "effective amount" or "therapeutically effective amount" refers to the amount of an agent (e.g., a TN-MUC1 CAR T cell composition) sufficient to effect beneficial or desired results. An effective amount can be administered in one or more administrations, applications or dosages and is not intended to be limited to a particular formulation or administration route. A therapeutically effective amount can vary depending upon known factors, such as the mode and route of administration; the age, health, and weight of the recipient; the type and extent of disease or indication to be treated, the nature and extent of symptoms, kind of concurrent treatment, frequency of treatment, and the effect desired.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in certain aspects include a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In certain aspects, the desired dose is a desired number of cells or a desired number of cells per unit of body weight of the subject to whom the cells are administered, e.g., cells/kg. In certain aspects, the desired dose is at or above a minimum number of cells or minimum number of cells per unit of body weight. In certain aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In certain aspects, the desired dose is a desired number of cells of the sub-type or population, or a desired number of such cells per unit of body weight of the subject to whom the cells are administered, e.g., cells/kg. In certain aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg, $10^4$, and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells. In an exemplary embodiment, a suitable dosage is from about $1\times10^7$ total cells to about $3\times10^7$ total cells.

In some embodiments, the dose of total cells and/or dose of individual sub-populations of cells is within a range of between at or about $1\times10^5$ cells/m² to about $1\times10^{11}$ cells/m². In an exemplary embodiment, the dose of total cells and/or dose of individual sub-populations of cells is within a range of between at or about $1\times10^7$/m² to at or about $3\times10^7$/m². In an exemplary embodiment, the dose of total cells and/or dose of individual sub-populations of cells is within a range of between at or about $1\times10^8$/m² to at or about $3\times10^8$/m². In some embodiments, the dose of total cells and/or dose of individual sub-populations of cells is the maximum tolerated dose by a given patient.

In some embodiments, the cells are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1\times10^5$ $CD4^+$ and/or $CD8^+$ cells/kg, $1.5\times10^5$ $CD4^+$ and/or $CD8^+$ cells/kg, $2\times10^5$ $CD4^+$ and/or $CD8^+$ cells/kg, or $1\times10^6$ $CD4^+$ and/or $CD8^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ $CD4^+$ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion. In some embodiments, a dose of modified cells is administered to a subject in need thereof, in a fractionated dose or split dose. In such embodiments, the first dose is administered, and a subsequent dose is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, 2 or more weeks, 3 or more weeks, 4 or more weeks, 5 or more weeks, or any period in between, after the first dose.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In certain aspects, the biological activity is measured by assessing clinical outcome, such as reduction in tumor burden or load.

In certain embodiments, the subject can be administered, in addition to the CAR, a secondary treatment.

In some embodiments, the subject can be administered conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In certain exemplary embodiments, the conditioning therapy comprises administering an effective amount of a combination of cyclophosphamide and fludarabine to the subject. Accordingly, the present disclosure provides a method of treatment comprising administering a conditioning therapy comprising an effective amount of a combination of cyclophosphamide and fludarabine to the subject, prior to administering CAR T therapy (e.g., modified T cells comprising a TN-MUC1 CAR of the present disclosure). Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In certain embodiments, the subject is provided a secondary treatment. Secondary treatments include but are not limited to chemotherapy, radiation, surgery, and medications.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days, Dosing of lymphodepletion chemotherapy may be scheduled on Days −6 to −4 (with a −1 day window, i.e., dosing on Days −7 to −5) relative to TnMUC1 CAR-T infusion on day 0.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS) (grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology*, 15:47; Teachey et al. (2016) *Cancer Discov*, 6(6): 664-679).

Features consistent with macrophage activation syndrome (MAS) or hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

Patient Selection

Methods provided herein involve selecting and treating a subject suitable for treatment. Accordingly, the present disclosure provides inclusion and exclusion criteria for subjects suitable for treatment using a method described herein.

In an exemplary embodiment, a suitable subject must have a confirmed diagnosis of metastatic treatment-resistant ovarian cancer (including cancers of the fallopian tube), pancreatic adenocarcinoma, hormone receptor (HR)-negative and HER2-negative (triple negative) breast cancer (TNBC) or non-small cell lung cancer (NSCLC), or relapsed/refractory multiple myeloma.

In some embodiments, a suitable subject has an ECOG score of 0 or 1.

In some embodiments, a suitable subject has received prior therapy for multiple myeloma: relapsed or refractory disease after either one of the following (i) at least 3 prior regimens, which must have contained an alkylating agent, proteasome inhibitor, and thalidomide analog (lenalidomide or pomalidomide), (ii) at least 2 prior regimens if 'double-refractory' to a proteasome inhibitor and thalidomide analog, defined as progression on or within 60 days of treatment with these agents, and/or (iii) patients must be at least 90 days since autologous stem cell transplant (ASCT), if performed.

In some embodiments, induction therapy, autologous stem cell transplant (ASCT), and maintenance therapy if given sequentially without intervening progression are considered 1 'regimen.'

In some embodiments, a suitable subject has received prior therapy for non-small cell lung cancer (NSCLC). In one embodiment, a suitable subject having had prior therapy for NSCLC has received standard therapy, including both checkpoint inhibition (PD-1/PD-L1 directed therapy) and platinum-based chemotherapy or be intolerant of these standard therapies. In one embodiment, a suitable subject having had prior therapy for NSCLC with EGFR or ALK alterations has received prior targeted therapy directed at the specific identified mutations in addition to the standard therapy classes described above.

In some embodiments, a suitable subject has received prior therapy for pancreatic adenocarcinoma. In one embodiment, a suitable subject having had prior therapy for pancreatic adenocarcinoma has experienced disease progression following at least one standard of care systemic chemotherapy for metastatic or unresectable disease.

In some embodiments, a suitable subject has received prior therapy for triple-negative breast cancer (TNBC). In one embodiment, a suitable subject having had prior therapy for TNBC has experienced disease progression following at least one prior systemic anti-cancer therapy regimen as part of their treatment for management of metastatic breast cancer.

In some embodiments, a suitable subject has received prior therapy for ovarian cancer. In one embodiment, a suitable subject having had prior therapy for ovarian cancer is suitable if considered platinum-resistant (initially sensitive to platinum therapy) and has received at least two prior lines of therapy for metastatic ovarian cancer, including at least one prior line of therapy including a platinum-containing regimen.

In some embodiments, a suitable subject has an evaluable disease.

In one embodiment, a suitable subject having multiple myeloma is suitable if: the subject has measurable disease on treatment (study) entry, which includes at least one of the following: (1) Serum M spike ≥0.5 g/dL; (2) 24-hour urine M-spike ≥200 mg; (3) Involved serum free light chain (FLC) ≥50 mg/L with abnormal ratio; (4) Measurable plasmacytoma on examination or imaging; (5) Bone marrow plasma cells ≥20%.

In some embodiments, subjects with IgA myeloma in whom serum protein electrophoresis is deemed unreliable, due to co-migration of normal serum proteins with the paraprotein in the beta region, may be suitable as long as total serum IgA level is elevated above normal range.

In one embodiment, a suitable subject having a solid tumor will have their disease status assessed as per Response Evaluation Criteria In Solid Tumors Criteria (RECIST v.1.1; see, Eisenhauer et al. (2009) *Eur J Cancer,* 45(2): 228-247). Tumor imaging may be performed at least within 28 days before apheresis. Phase-specific criteria include: Phase 1: subjects must have evaluable disease in Phase 1 per RECIST v.1.1; Phase 1a expansion: subjects must have measurable disease in Phase 1a expansion per RECISTv.1.1.

In some embodiments, suitable subjects have a TnMUC1+ disease, determined by centrally tested TnMUC1 expression in a prior or archival tumor biopsy. If an archival tumor biopsy sample is not available, then the subject may undergo an optional biopsy for the purposes of screening eligibility with only non-significant risk biopsy procedures.

In some embodiments, suitable subjects have completed prior anti-cancer therapy at least 2 weeks prior to Screening and toxicities from any previous therapy must have recovered to grade 1 or 0 (with the exception of alopecia, well controlled electrolyte or endocrine abnormalities, well-controlled peripheral neuropathy, and vitiligo).

In some embodiments, suitable subjects have a life expectancy greater than 3 months.

In some embodiments, suitable subjects have adequate vital organ function as defined by:

(1) Serum creatinine ≤1.5 mg/dL or estimated creatinine clearance ≥30 ml/min (per Institutional standard calculation);

(2) Alanine aminotransferase (ALT) and aspartate aminotransferase (AST)≤3× the upper limit of normal (ULN) and total bilirubin≤2.0 mg/dL. No specific exclusions are made for patients with hepatic disease;

(3) Serum total bilirubin <1.5×ULN;

(4) Serum albumin ≥3.0 g/dL (solid tumor patients in Arm 1 and Phase 1a only, not applicable to patients with multiple myeloma);

(5) Left ventricular ejection fraction (LVEF) ≥45%. LVEF assessment must have been performed within 8 weeks of screening.

In some embodiments, suitable subjects have adequate hematologic reserve (without the use of supportive transfusion or hematopoietic growth factors within 4 weeks of apheresis), as defined by:

(1) Hemoglobin ≥9 g/dL;

(2) Absolute neutrophil count ≥1000/μL;

(3) Platelet count ≥50,000/μL (≥30,000/μL if bone marrow plasma cells are ≥50% of cellularity for myeloma patients);

(4) Absolute lymphocyte count of >500/μL. In one embodiment, suitable subjects must not be transfusion-dependent to maintain hematologic parameters.

In some embodiments, suitable subjects of reproductive potential agree to use approved contraceptive methods per protocol.

In some embodiments, suitable subjects considered for treatment using a method described herein must not meet any of the following criteria:

(1) Active invasive cancer other than the proposed cancers included in the treatment (study);

(2) Current treatment with systemic high-dose corticosteroids (defined as a dose greater than the equivalent of prednisone 20 mg/day). Subjects with multiple myeloma at the time of treatment (study) entry must complete prior active high-dose corticosteroid therapy prior to apheresis and be maintained on low-dose corticosteroid therapy or no corticosteroid therapy. Low-dose physiologic replacement therapy with corticosteroids equivalent to prednisone 20 mg/day or lower is acceptable;

(3) Active autoimmune disease (including connective tissue disease, uveitis, sarcoidosis, inflammatory bowel disease or multiple sclerosis) or have a history of severe autoimmune disease requiring prolonged immunosuppressive therapy (any immunosuppressive therapy should have been stopped within 6 weeks prior to screening visit);

(4) Current, active HIV, HCV, HBV infections. Viral testing at Screening is required in all subjects to rule out subclinical infections;

(5) Other active or uncontrolled medical or psychiatric condition that would preclude participation the treatment regimen;

(6) Prior allogeneic stem cell transplant;

(7) Active and untreated central nervous system (CNS) malignancy. Treated lesions may be considered inactive if they are stable for at least 1 month following definitive treatment. Subject must not require corticosteroid therapy or anti-epileptic medications for the management of brain metastases;

(8) History of severe infusion reaction to monoclonal antibodies or biological therapies, or to study product excipients (e.g., human serum albumin, DMSO, dextran 40) that would preclude the patient safely receiving CART-TnMUC1 cells;

(9) Active or recent (within the past 6 months prior to apheresis) cardiac disease, defined as (i) New York Heart Association (NYHA) Class III or IV heart failure, (ii) unstable angina or (iii) a history of recent (within 6 months) myocardial infarction or sustained (>30 second) ventricular tachyarrhythmias;

(10) Have inadequate venous access for or contraindications for the apheresis procedure;

(11) Pregnant or breastfeeding women.

In another exemplary embodiment, a suitable subject must have a confirmed diagnosis of metastatic treatment-resistant ovarian cancer (including cancers of the fallopian tube), pancreatic adenocarcinoma, hormone receptor (HR)-negative and HER2-negative (triple negative) breast cancer (TNBC) or non-small cell lung cancer (NSCLC), or relapsed/refractory multiple myeloma.

In some embodiments, a suitable subject has an Eastern Cooperative Oncology Group (ECOG) score of 0 or 1.

In some embodiments, a suitable subject has had prior therapies as defined by tumor type, as described herein.

In some embodiments, a suitable subject has an evaluable disease as defined by tumor type, as described herein.

In some embodiments, a suitable subject has TnMUC1+ disease, determined by centrally tested TnMUC1 expression in a prior or archival tumor biopsy.

In some embodiments, a suitable subject has completed prior anti-cancer therapy at least 2 weeks prior to Screening and toxicities.

In some embodiments, a suitable subject has a life expectancy greater than 3 months.

In some embodiments, a suitable subject has a level of serum creatinine ≤1.2 mg/dL or calculated creatinine clearance >60 ml/min (using the Cockroft & Gault formula).

In some embodiments, a suitable subject has a level of asparatate aminotransferase (AST) or alinine aminotransferase (ALT)≤2.5× upper institutional limit of normal with the following exception: Patients with known hepatic metastases, AST or ALT ≤3× upper institutional limit of normal.

In some embodiments, a suitable subject has a level of serum total bilirubin <1.5 mg/dL with the following exception: patients with known Gilbert's disease, serum total bilirubin <3 mg/dL.

In some embodiments, a suitable subject has a level of serum albumin ≥3.0 g/dL (solid tumor patients in Arm 1 and Phase 1a only, not applicable to patients with multiple myeloma).

In some embodiments, a suitable subject has been assessed with left ventricular ejection fraction (LVEF) ≥50%. LVEF assessment must have been performed within 8 weeks of screening.

In some embodiments, a suitable subject has a level of hemoglobin ≥9 g/dL.

In some embodiments, a suitable subject has a level of absolute neutrophil count ≥ 1500/µL.

In some embodiments, a suitable subject has a level of platelet count ≥100,000/µL (>30,000/µL if bone marrow plasma cells are ≥50% of cellularity for myeloma patients).

In some embodiments, a suitable subject has a level of absolute lymphocyte count of >500/µL.

In some embodiments, suitable subjects considered for treatment using a method described herein must not have or be any of the following:

(1) Active invasive cancer other than the proposed cancers included in the treatment (study);

(2) Current treatment with systemic high-dose corticosteroids (defined as a dose greater than the equivalent of prednisone 20 mg/day);

(3) Active autoimmune disease (including connective tissue disease, uveitis, sarcoidosis, inflammatory bowel disease or multiple sclerosis) or have a history of severe autoimmune disease requiring prolonged immunosuppressive therapy (any immunosuppressive therapy should have been stopped within 6 weeks prior to screening visit);

(4) Current, active human immunodfifficiency virus (HIV), hepatitis C virus (HCV), hepatitis B virus (HBV) infections;

(5) Prior allogeneic stem cell transplant;

(6) Active and untreated central nervous system (CNS) malignancy;

(7) History of severe infusion reaction to monoclonal antibodies or biological therapies, or to treatment (study) product excipients (e.g., human serum albumin, dimethyl sulfoxide [DMSO], dextran 40) that would preclude the patient safely receiving CART-TnMUC1 cells;

(8) Active or recent (within the past 6 months prior to apheresis) cardiac disease, defined as (1) New York Heart Association (NYHA) Class III or IV heart failure, (2) unstable angina or (3) a history of recent (within 6 months) myocardial infarction or sustained (>30 second) ventricular tachyarrhythmias;

(9) Have inadequate venous access for or contraindications for the apheresis procedure; and/or

(10) Pregnant or breastfeeding women.

Clinical Trial Assay

In some embodiments, a clinical trial assay will be used in patient screening and selection for participation into a clinical trial. In an exemplary embodiment, the clinical trial assay is a TnMUC1 clinical trial assay (CTA). The TnMUC1 CTA may be an immunohistochemistry assay (see, Experimental Example 8 herein), and may be incorporated into an in vitro companion diagnostic device (CDx).

Pharmaceutical Compositions

The modified immune cell (e.g., a Tn-MUC1 CAR T cell) described herein may be included in a composition for immunotherapy, in particular for treating a MUC1-associated cancer. The composition may include a pharmaceutical composition and further include a pharmaceutically acceptable carrier. A therapeutically effective amount of the pharmaceutical composition comprising the modified immune cells may be administered.

Pharmaceutical compositions of the present invention may comprise the modified immune cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In certain exemplary embodiments, compositions described herein are formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

Also provided are populations of immune cells described herein, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as regulatory T cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In certain aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In certain aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in certain aspects are included in the compositions. Suitable buffering agents include, for example, citric acid, sodium citrate, phosphoric acid, potassium phosphate, and various other acids and salts. In certain aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Formulations described herein can include aqueous solutions. The formulation or composition may also contain more than one active ingredient useful for the particular indication, disease, or condition being treated with the cells, e.g., those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in certain aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in certain aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

It can generally be stated that a pharmaceutical composition comprising the modified immune cells described herein may be administered at a dosage of $10^4$ to $10^9$ cells/kg body weight, in some instances $10^5$ to $10^6$ cells/kg body weight, including all integer values within those ranges. Immune cell compositions may also be administered multiple times at these dosages. The cells can be administered by using infusion techniques that are commonly known in immunotherapy (see, e.g., Rosenberg et al., *New Eng. J. of Med.* 319:1676, 1988). The optimal dosage and treatment regime for a particular patient can readily be determined by one skilled in the art of medicine by monitoring the patient for signs of disease and adjusting the treatment accordingly.

The administration of the modified immune cells of the invention may be administered by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. In some embodiments, the administration of the modified immune cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Analysis of The Cancer Genome Atlas: The 956-patient breast cancer cohort of The Cancer Genome Atlas (TCGA) was queried for normalized gene expression of MUC1 and of glycosylation enzymes of interest: C1GalT1, C1GalT1C1, ST6GalNAc1 and B3GNT6. Clinical and tumor characteristics were compared. Tumors were stratified by their Her-2/neu (Her2) receptor expression status as Her2+ or Her2− and hormone receptor (HR), i.e. estrogen or progesterone receptor, expression status as either HR+ or HR−. Gene expression was analyzed according to subtype using one-way ANOVA.

Quantitative polymerase chain reaction (qPCR): Several commercially available breast cancer cell lines, MCF10A (cat. no), MCF7 (cat. no), BT20 (cat. no), MDA-MB-231 (cat. no) and MDA-MB-453 (cat no) were purchased from ATCC, expanded and maintained according to manufacturer's instructions. All cell lines were expanded at the lowest possible passage number for our assays and were all tested negative for mycoplasma. Gene expression of each breast cancer cell line was compared to expression of MCF10A, a non-tumorigenic breast epithelium cell line.

A prospective breast cancer tissue bank was maintained with samples collected from patients who present with an operable, palpable breast cancer. Samples of the tumor and normal breast tissue are collected at the time of preparation for pathologic analysis and snap frozen in liquid nitrogen. Samples were stored at −80° C. until use.

A cohort of 50 breast tumors and 10 matched normal breast tissue samples was selected from the prospectively procured tissue bank. Samples were thawed, mechanically dissociated and homogenized using Lysing Matrix D tubes (MP Biomedicals, Santa Ana, CA). Frozen stocks of five cell lines (MCF10A-non-tumorigenic breast epithelium, MCF7-HR+ Her2−, BT20-TNBC, MDA-MB-231-TNBC and MDA-MB-453-TNBC) were thawed. RNA was purified from all samples using the RNeasy Mini Kit (Qiagen, Germantown, MD) and cDNA was prepared via RT-PCR using the SuperScript III First-Strand Synthesis System (Invitrogen, Carlsbad, CA).

Samples were analyzed for gene expression of GAPDH, MUC1, C1GalT1, C1GalT1C1, ST6GalNAc1 and B3GNT6 using TaqMan probes and the Viia7 Real-Time PCR system (Applied Biosystems, Carlsbad, CA). Expression of all genes was normalized to GAPDH expression. The relative RNA expression levels of each gene was compared between tumor (n=50) and matched normal tissues (when available, n=10). The double delta method for analysis was used to calculate-fold change and mean fold change (MFC) was calculated for each gene.

Immunohistochemistry: Estrogen (ER), progesterone (PR) and Her-2/neu (Her2) receptor expression were evaluated by standard immunohistochemistry (IHC) staining techniques on formalin-fixed paraffin-embedded (FFPE) breast cancer tissue samples for all participants as part of standard pathology evaluation.

Archival formalin fixed paraffin-embedded (FFPE) tumor samples from the cohort described above were also available for immunohistochemistry (IHC) staining analyses to evaluate expression of Tn-MUC1 using 5E5 mAb and HRP-conjugated anti-mouse Ig. Results of IHC staining were evaluated by a blinded board-certified pathologist and recorded as H-score defined as the product of the intensity and proportion of tumor cells staining positive for Tn-MUC1 using the following formula: [1×(% cells 1+)+2×(% cells 2+)+3×(% cells 3+)]. The distribution of H-scores (0-300) was assessed and found to be non-normal with a bimodal distribution centering at H-score value of 142. This value (142) was then used as the cut-off value to dichotomize the results as either positive or negative. Comparisons of H-scores were made between breast cancer subtypes using independent t-tests, and comparisons of clinical characteristics and survival were made between the H-score groups using chi-square and Kaplan-Meier survival tests.

Human CAR T cell generation and cytotoxicity assays: Normal donor human T cells were activated and transduced to produce control CD19-BBz CAR and 5E5-BBz CAR T cells as previously described (Posey et al., (2016) *Immunity* 44, 1444-1454). Cytotoxicity assays were performed using the xCELLigence (ACEA Biosciences) real-time cellular impedance assay as previously described (Watanabe et al., (2018) *JCI Insight* 3). In brief, tumor cells were seeded in e-plates at low density and T cells were co-incubated with tumor cell lines ~24 hours after seeding at an effector-target ratio of 10:1 for 100 hours and cell index was recorded every 15 minutes.

Xenograft mouse model of CAR T cell delivery: Breast cancer xenograft models were established by injecting 1 million luciferase-expressing MDA-MB-453 cells in 100 μL of PBS into the mammary fat pad or in 200 μL of 50:50 PBS:matrigel subcutaneously on the right flank of the mice. One week post tumor inoculation, when the mean total flux of the tumor was ~$10^9$ for the fat pad model and $10^8$ for the subcutaneous model, mice were treated with 5 million NTD, CD19 CAR, or 5E5 CAR T cells injected intravenously in the lateral tail vein, intratumorally into the fat pad or subcutaneous tumor, or intraperitoneally. Mice were serially imaged for tumor bioluminescence using a Xenogen IVIS-200 Spectrum.

Murine CAR T cell generation, in vitro cytotoxicity assays, and syngeneic mouse model: Murine CAR backbone constructs were synthesized with murine elements of homology to human CAR backbones (CD8a leader, CD8a extracellular hinge and transmembrane domain, 4-1BB costimulatory domain and CD3zeta) and cloned into the MSGV retroviral vector, as previously described (Watanabe et al., (2018) *JCI Insight* 3). 5E5 scFv and HMFG1 scFv were subcloned into the murine CAR backbone through the restriction sites BamHI and BspEI and retrovirus was packaged using the Plat E cell line to produce ecotropic retrovirus. For murine T cell transductions, spleens were harvested from hMUC1.tg donor mice and T cells were activated with anti-mouse CD3 and anti-mouse CD28 antibody-coated beads (Dynabeads, Thermo Fisher Scientific). Transduction of T cells with CAR-encoding retrovirus occurred on retronectin-coated plates one day after bead stimulation. Mouse CAR T cells were expanded for 4 days after transduction in the presence of 50 U/mL human IL-2 and injected into hMUC1.tg mice on day 5 after T cell activation.

On the day of mouse injection, mouse CAR T cells were co-cultured with Jurkat luciferase-expressing cell line at an effector to target ratio of 20:1 for 16 hours. Cells were then washed once in PBS, lysed in luciferase cell culture lysis reagent (Promega), and subsequently mixed with luciferase assay reagent (Promega). Luminescence of the lysates was analyzed using a plate spectrophotometer. Specific lysis of each sample was calculated using the luminescence of target cells alone, and Triton™-X lysed target cells, corresponding to 0% lysis and 100% lysis respectively.

Statistical analyses: Statistical analyses were performed using SPSS 24 (IBM, Armonk, NY) and Prism (GraphPad). P values were taken to be significant if <0.05.

The results of the experiments are now described.

Example 1: Gene Expression Analyses of MUC1 and Relevant Glycotransferases in Breast Cancer—a TCGA Gene Expression Analysis of Breast Cancer Samples One known mechanism of abnormal O-glycosylation on surface glycoproteins in tumors is the mutation or epigenetic silencing of the involved glycotransferases, but another mechanism of overexpressed glycoproteins, such as MUC1, and thereby saturation of the cellular glycomachinery, has also been proposed. Studies of Tn-MUC1 expression analysis in breast cancer were initiated by interrogating whether MUC1 or any of the immediate O-glycotransferases (and the chaperone protein C1GalT1C1) had differential gene expression in the 956-patient breast cancer cohort samples of TCGA. There were no differences in gene expression when patients were stratified by race, nodal stage, metastatic status or overall cancer stage (all p >0.05). MUC1 expression differed by tumor stage with T1 and T2 tumors exhibiting lower expression than T3 and T4 tumors (p<0.001). MUC1 and all O-glycotransferases assayed exhibited differential expression when the cohort was stratified by tumor subtype except the T synthase chaperone, C1GalT1C1. When compared with HR− cancers, HR+ cancers had higher expression of MUC1 (p<0.001) and lower expression of C1GalT1 (p<0.001). Expression of ST6GalNAc1 and B3GNT6 were highest in HR−, Her2+ cancers (both p<0.001). Results suggested that all tumor subtypes regardless of Her2 or HR expression status have aberrant glycosylation of MUC1.

Figure 2A:
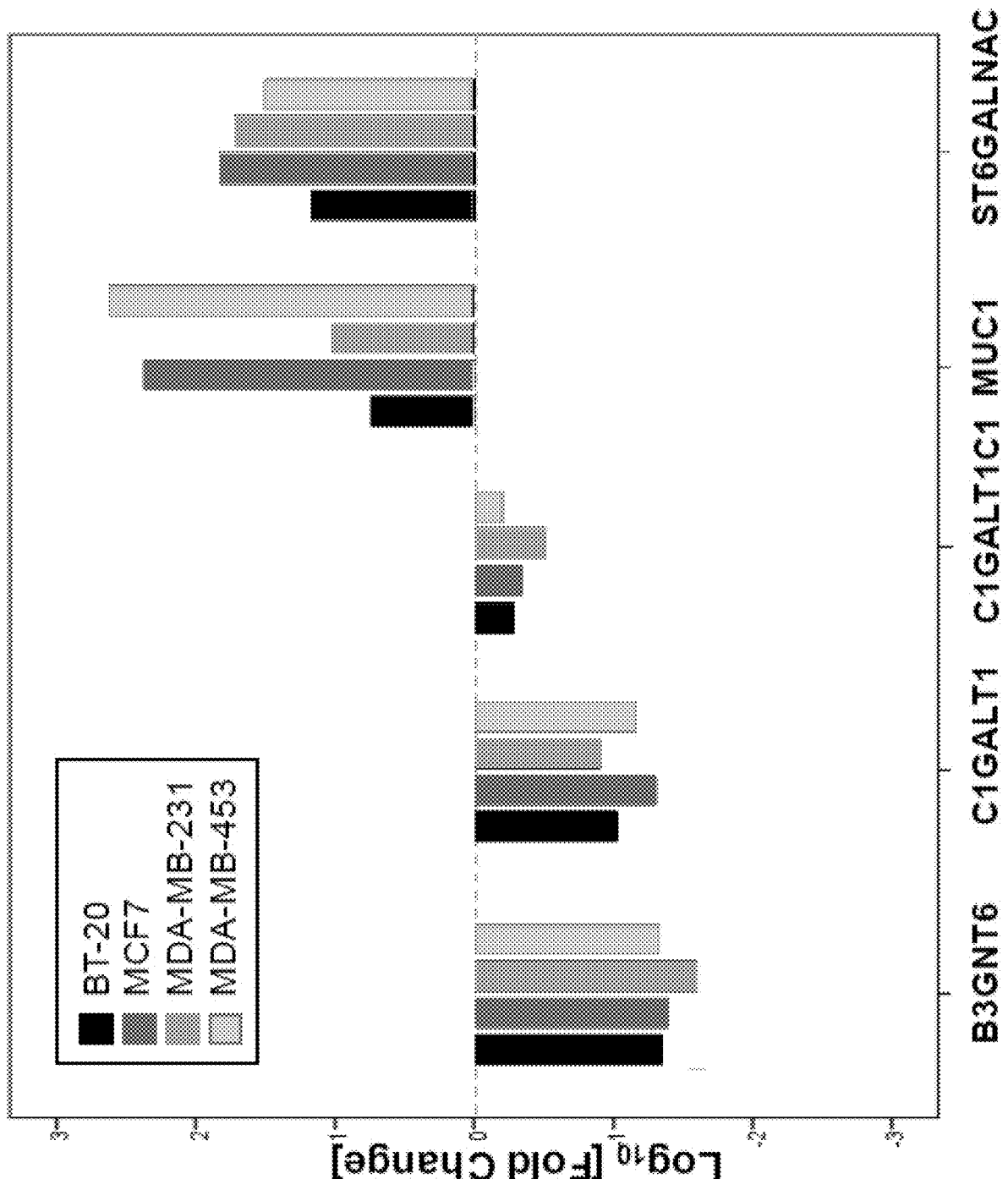
FIGS. 2A and 2B are a set of plots illustrating gene expression analysis of MUC1 and glycosylation enzymes by qPCR. Gene expression was measured in 4 breast cancer cell lines (BT-20, MCF7, MDA-MB-231, and MDA-MB-453) and compared to that of MCF10A, a non-tumorigenic breast epithelium cell line.
Figure 2B:
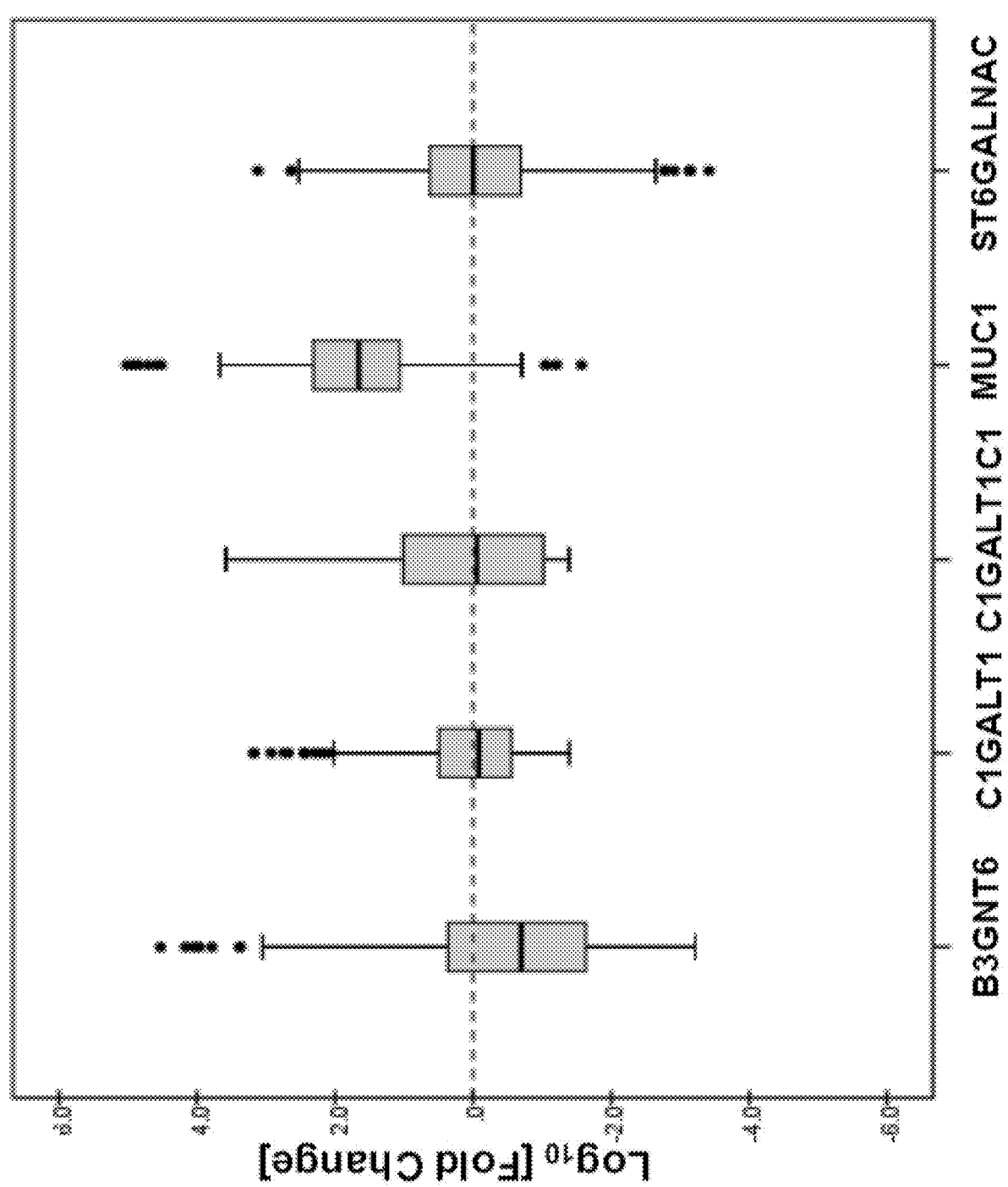
Figure 7A:
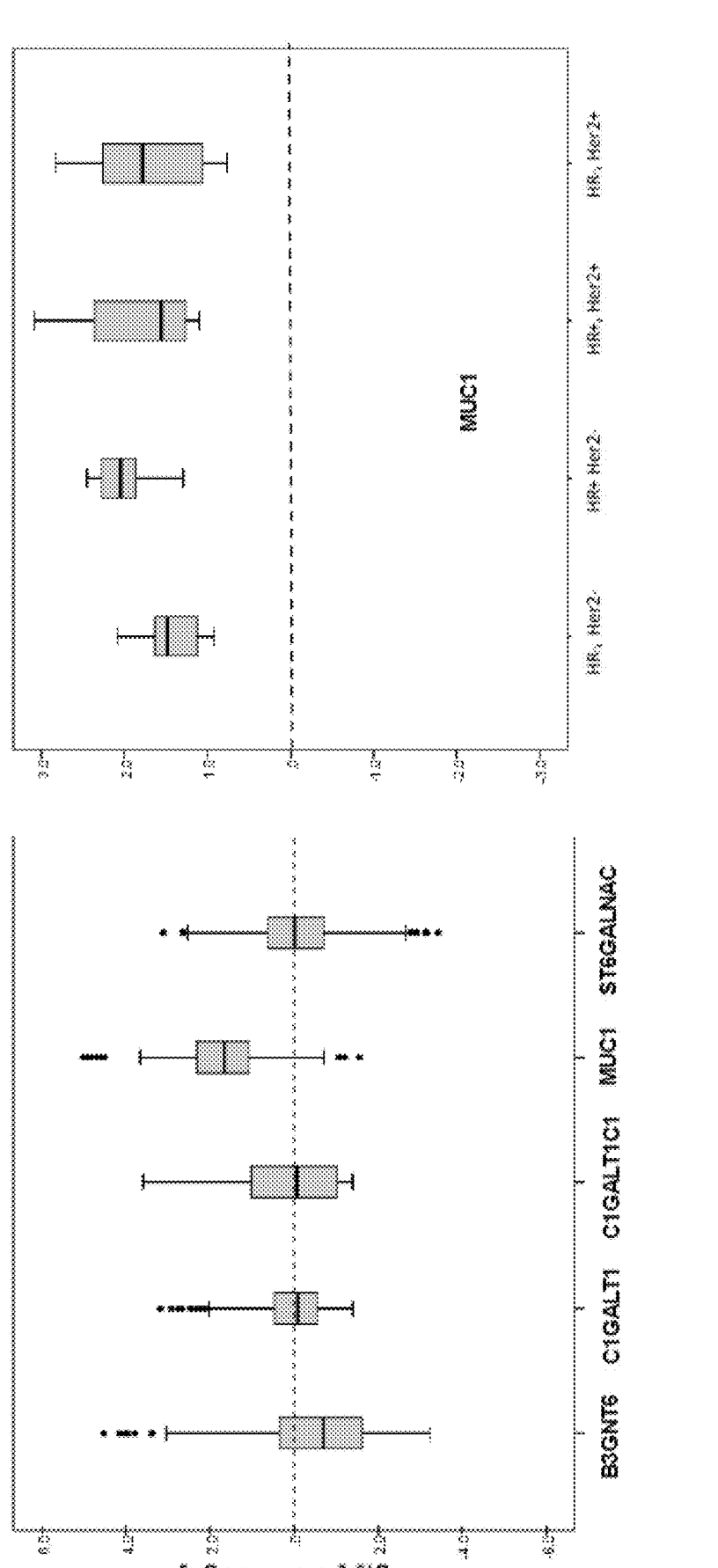
FIGS. 7A-7C are a series of plots illustrating gene expression of MUC1, ST6GALNAC1, B3GNT6, C1GALT1, and C1GALT1C1 in 50 patient-derived breast cancer samples compared to mean gene expression of 10 matched patient-derived normal breast tissue samples.
Figure 7B:
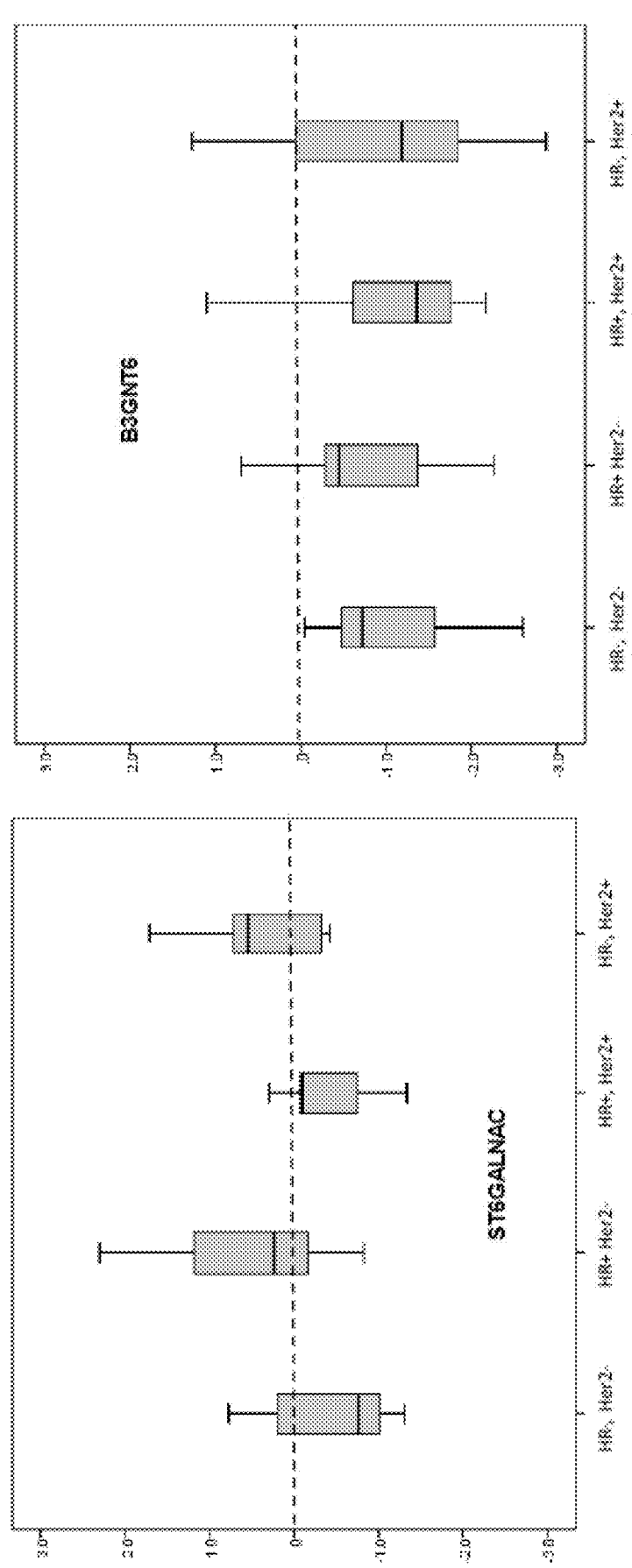
Figure 7C:
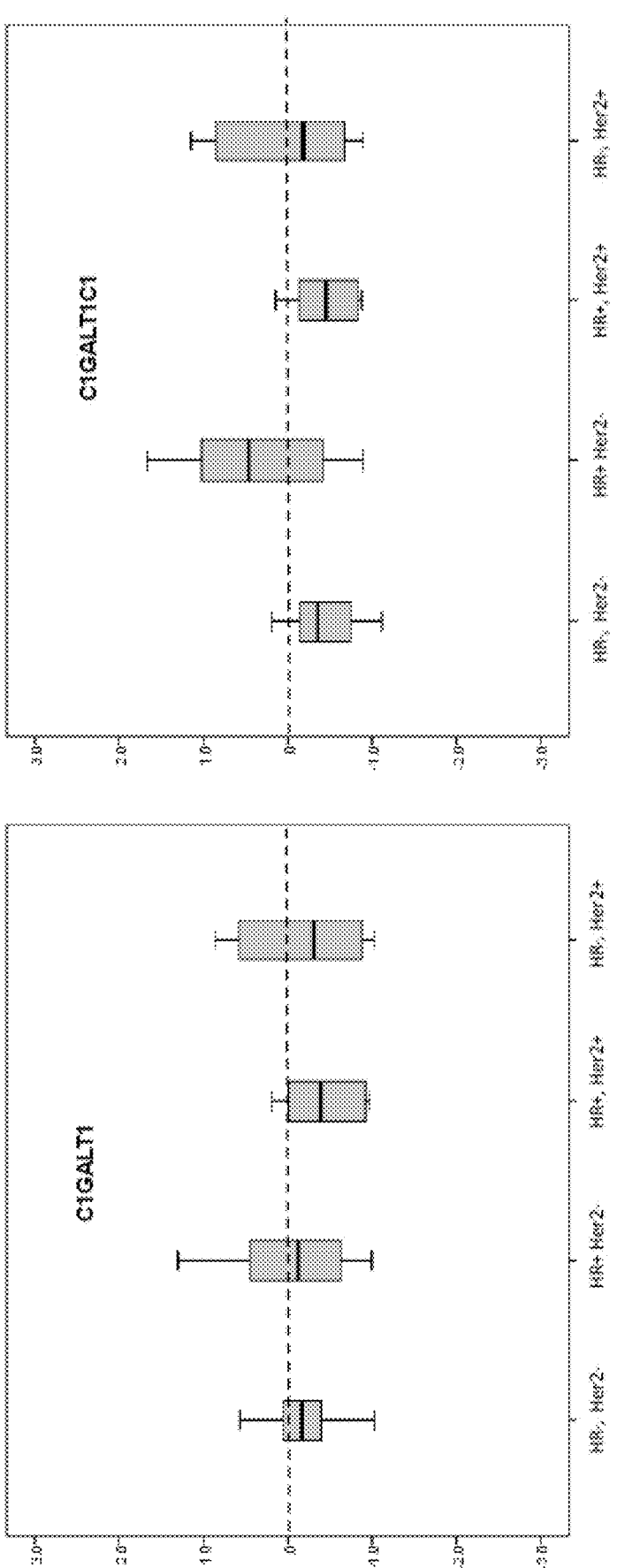

Example 2: Gene Expression Analyses of MUC1 and Relevant Glycotransferases in Breast Cancer Cell Lines and in Matched Normal and Breast Cancer Tissue Samples Gene expression of MUC1 and the related O-glycotransferases were analyzed in several commercially available breast cancer cell lines with varying HR or Her2 expression status. MCF10A is a HR− non-invasive breast epithelial cell line. MCF7 is a HR⁺ Her2⁻ breast cancer cell line. BT20, MDA-MB-231, and MDA-MB-453 are HR− Her2− breast cancer cell lines. All breast cancer cell lines had lower expression of B3GNT6 (MFC 0.04), C1GALT1 (MFC 0.07), and C1GALT1C1 (0.44), and higher expression of MUC1 (142.85) and ST6GALNAC1 (61.06) (FIG. 2A), consistent with the two mechanisms of abnormal O-glycan expression. Similarly, when compared to matched normal breast tissue, breast tumor samples had lower expression of B3GNT6 (MFC 0.16) and higher expression of MUC1 (MFC 31.62) (FIGS. 7A-7C). Expression was essentially equivalent for C1GALT1 (MFC 0.93), C1GALT1C1 (MFC 0.95), and ST6GALNAC1 (MFC 1.02). There were no differences in MFC between breast cancer subtypes for expression of all 5 genes in the patient-derived cohort (all p>0.05). These results suggest that overexpression of MUC1 and loss of core 3 O-glycans are common features of breast cancers. Blockade of core 3 synthesis is one route to truncated Tn antigen expression.

Figure 3B:
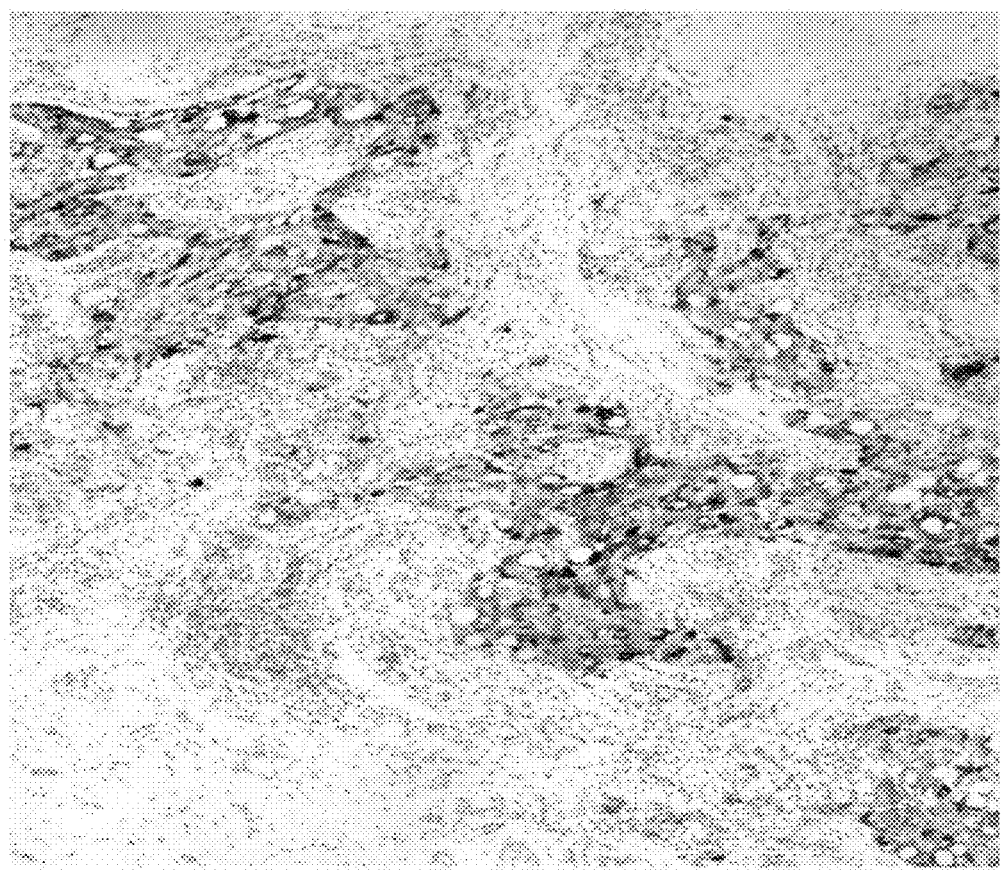
FIGS. 3A and 3B are a set of images depicting expression of Tn-MUC1 in breast cancer tissue as assessed by immunohistochemistry with anti-5E5 antibody.
Figure 3A:

Example 3: Tn-MUC1 Glycoepitope is Specifically Expressed in Breast Cancer and not in Adjacent Normal Breast Tissues—an Immunohistochemistry (IHC) Analyses in Normal and Malignant Breast Tissues Tn-MUC1 glycoepitope expression was quantified by IHC using the 5E5 anti-Tn-MUC1 antibody (FIGS. 3A and 3B). Normal adjacent breast tissues were present in 7 of the 52 breast tumor tissue sections. Tumor epithelial cells stained intensely for TN-MUC1 while staining of adjacent normal breast epithelial cells for TN-MUC1 was lacking or at a significantly lower H-score. The mean H-score for tumor tissue was 183.8±95.7 and for normal breast tissue was 34.9±32.8 (p<0.001). When stratified by breast cancer subtypes according to HR or Her2 receptor expression status, HR−/Her2− (or commonly referred to as triple negative) breast tumor samples had the lowest mean H-score (157.7±96.9) when compared to HR+/Her2− (228.0±86.5) and HR+ or HR−/Her2+ (220.5±65.4) samples (p=0.04). The tumor tissue of half of the samples (n=26) exhibited both cytoplasmic and membranous staining while 18 (34.6%) had pure cytoplasmic staining and 8 (15.4%) had pure membranous staining. Of note, cytoplasmic staining of Tn-MUC1 is commonly found in MUC1-producing tissues, as the Tn antigen is a naturally occurring biochemical step to full O-glycosylation in the Golgi; membranous staining of Tn-MUC1 is considered abnormal and cancer-specific. There was no difference in the distribution of staining location between breast cancer subtypes (p=0.72). When analyzed by H-score group (positive or negative), there were no differences in age, race, tumor size, tumor grade, nodal stage, lympho-vascular invasion, extracapsular extension, current disease status, disease-free survival or overall survival between the groups (all p>0.05).

Figure 4:
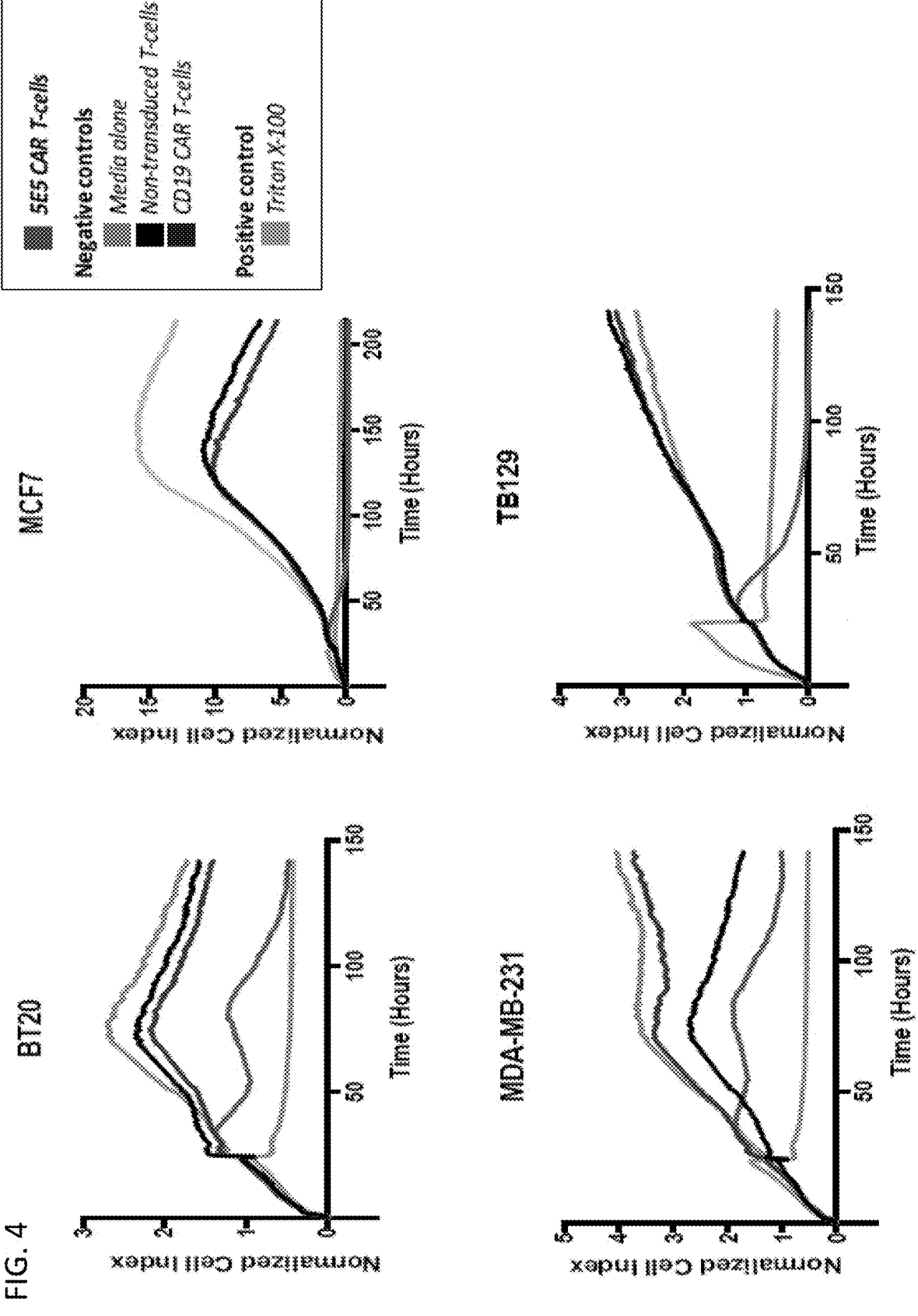
FIG. 4 is a series of plots illustrating results from cytotoxicity assays using anti-Tn-MUC1 CAR T cells and four breast cancer cell lines. 5E5-CAR, CD19-specific CAR, or NTD T cells were co-cultured with breast cancer cell lines at an effector:target ratio of 10:1. Cytolysis was measured through real-time impedance measurements every 15 minutes for 100 hours post-T cell addition.

Example 4: Tn-MUC1-Specific CAR T Cells are Efficacious In Vitro and in Xenograft Models Anti-Tn-MUC1 CAR T cells, which were developed utilizing the scFv of the 5E5 mAb, exhibited potent cytotoxicity against breast cancer cell lines BT20, MDA-MB-231, MCF7, and TB129, a patient-derived TNBC cell line developed at the University of Pennsylvania. In all cases, tumor growth was impeded after anti-Tn-MUC1 CAR T cell co-culture when compared with negative controls (media alone, non-transduced (NTD) T cells, and anti-CD19 CAR T cells). The reduction in tumor growth also reached or approached that of the negative control, cells treated with Triton™-X-100, in under 100 hours of co-culture (FIG. 4).

Figure 5A:
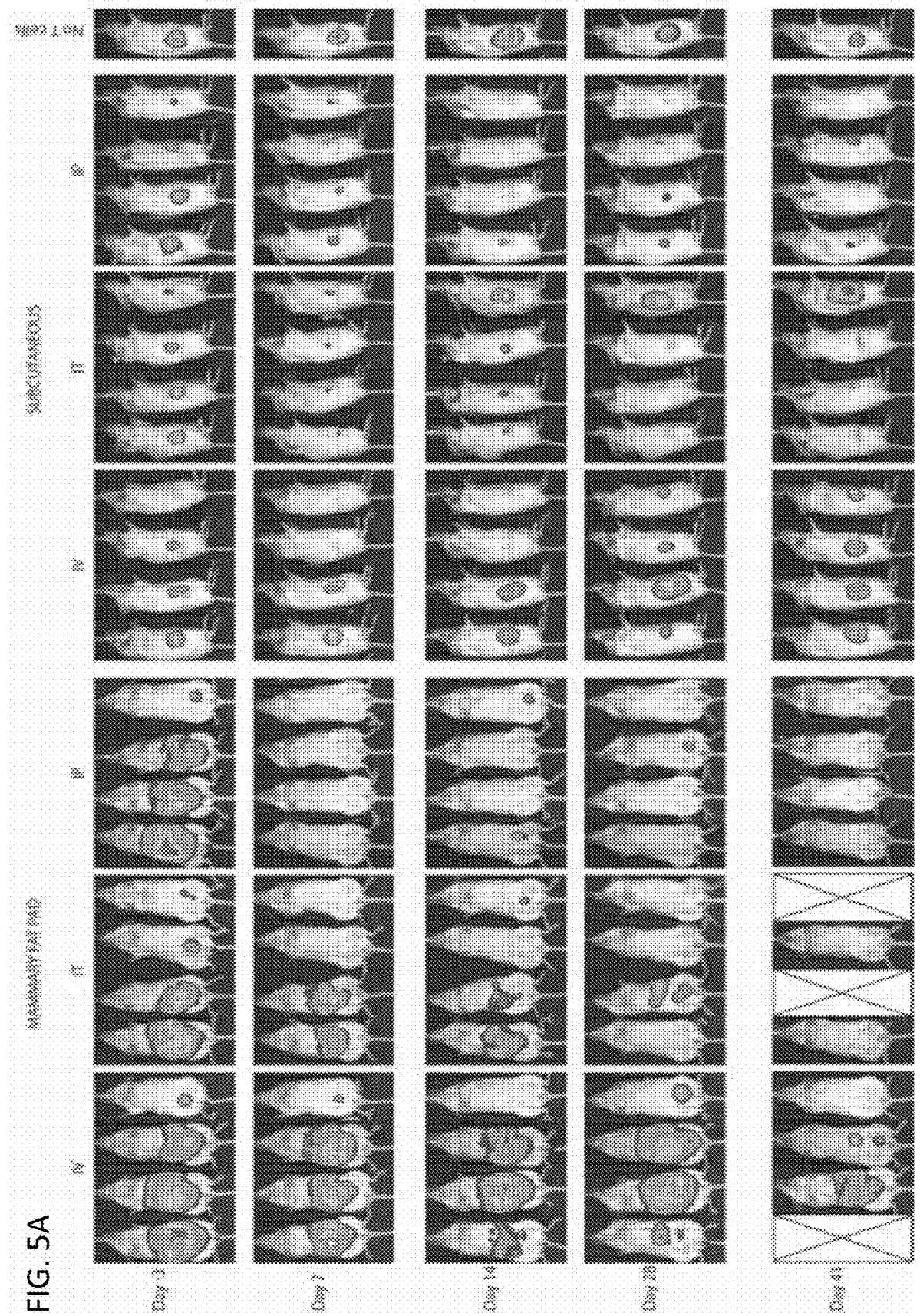
FIGS. 5A-5C are a series of plots and images illustrating the finding that intraperitoneal and intratumoral delivery of 5E5-CAR T cells enhances anti-tumor efficacy.
Figure 5B:
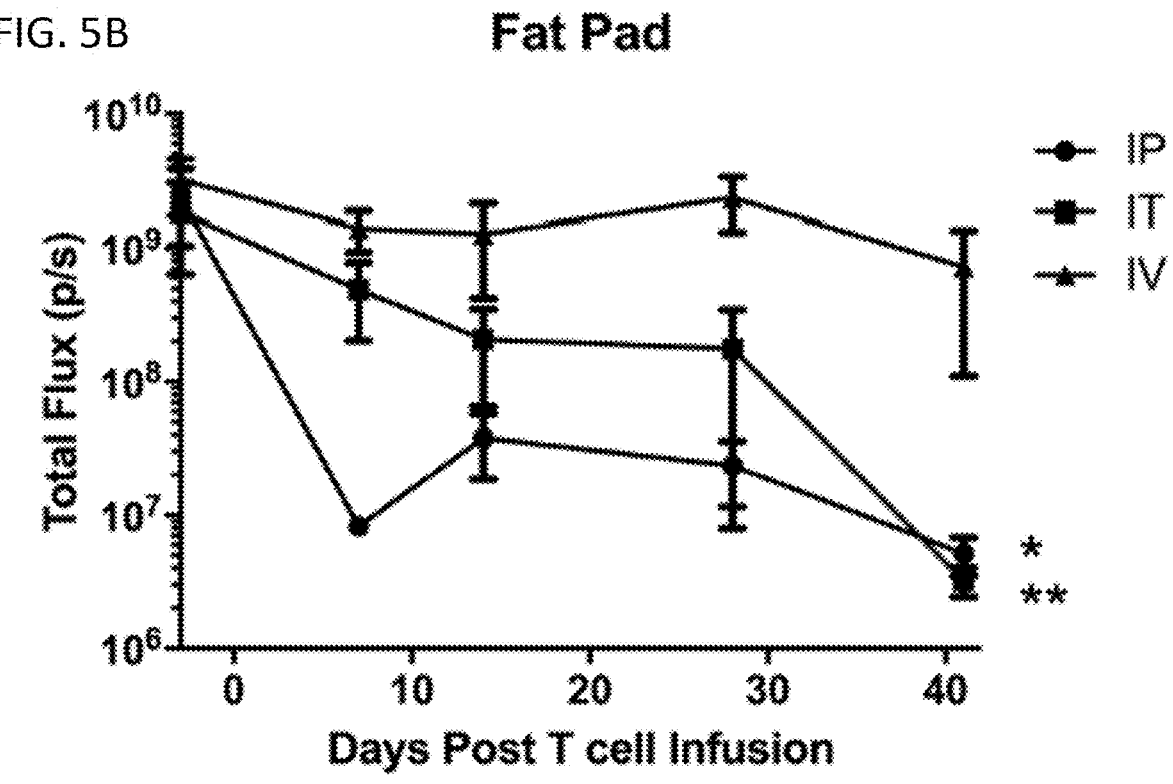
Figure 5B:
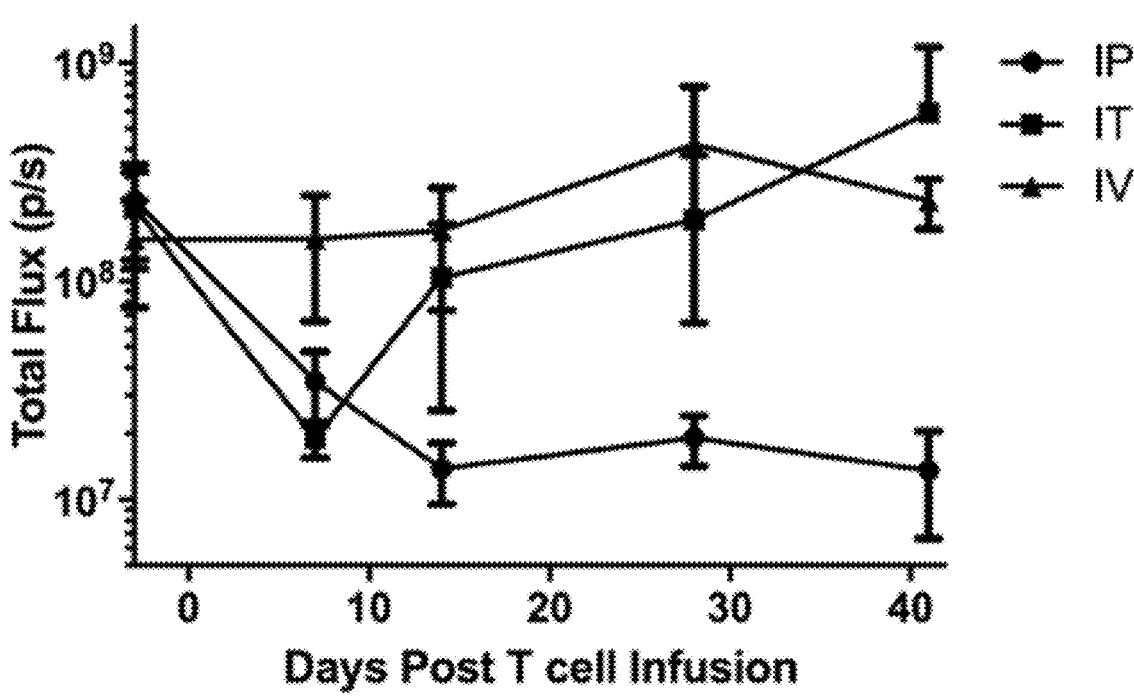
Figure 5C:
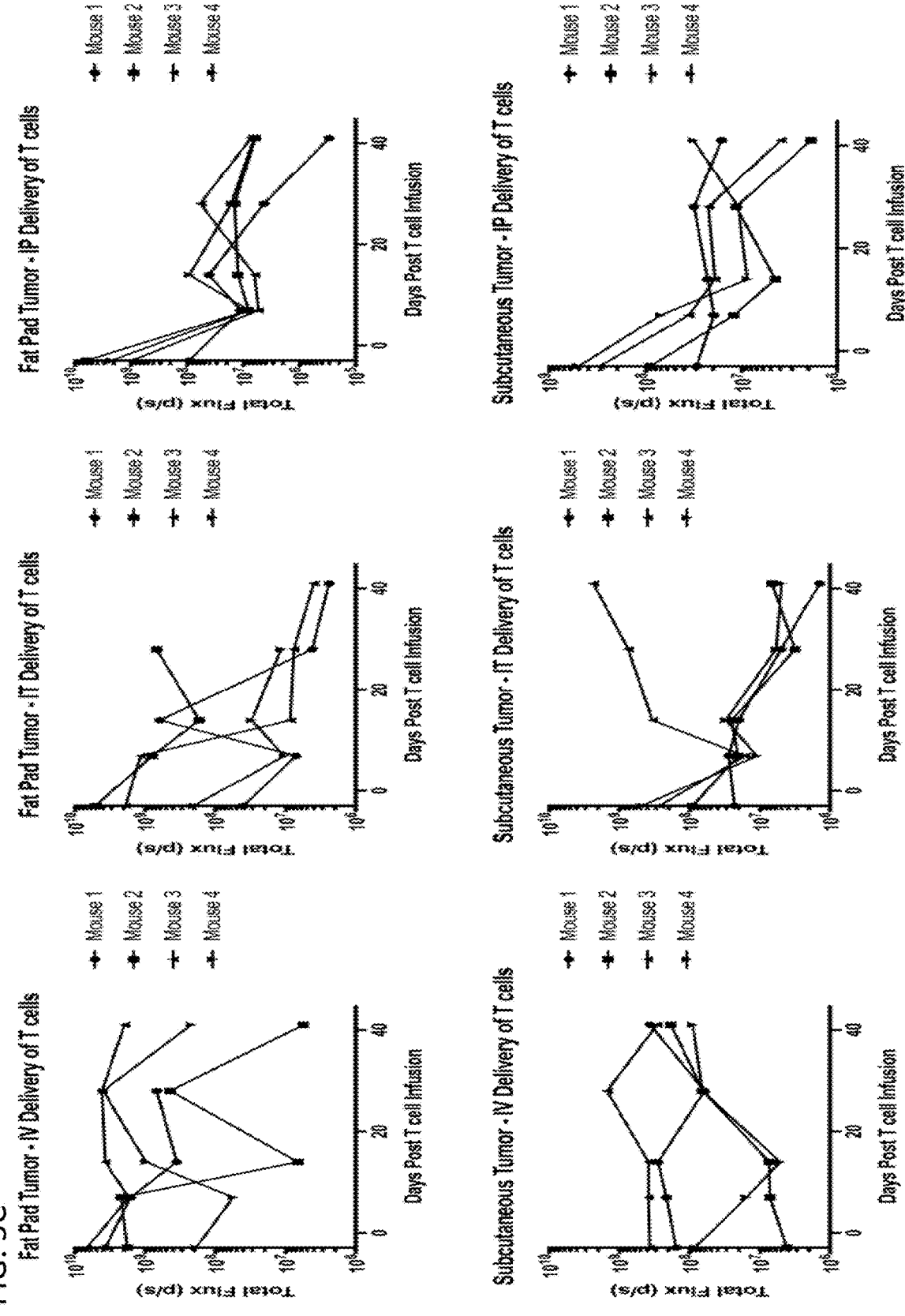

Given this in vitro cytotoxicity and prior clinical studies that evaluated intratumoral injection of transiently-expressed cMet-specific CAR T cells in patients with TNBC (Tchou et al., (2017) *Cancer Immunol* Res 5, 1152-1161), the efficacy and best route of delivery of CAR T cells in a xenograft mouse model of TNBC was determined. Mice were inoculated with luciferase-expressing MDA-MB-453 cells either in the mammary fat pad or subcutaneously on the right flank. One week after tumor inoculation, mice were treated with 5 million NTD, anti-CD19 CAR, or anti-Tn-MUC1 (5E5) CAR T cells through intravenous (tail vein), intratumoral, or intraperitoneal delivery, where the CAR was expressed in 50% of cells. Mice were serially imaged for tumor bioluminescence and a sharp decrease in tumor burden was observed for mice bearing mammary fat pad tumors that were treated with CAR T cells intraperitoneally (p-0.0115) or intratumorally (p=0.0076), when compared to intravenous delivery). Similarly, trends in anti-tumor efficacy were observed for intraperitoneal and intratumoral delivery of 5E5 CAR T cells for mice bearing subcutaneous tumors as well (FIGS. 5A-5C). These data support preclinical work demonstrating that the route of CAR T cell delivery can enhance anti-tumor efficacy.

Example 5: Off-Tumor, On-Target Evaluation of Tn-MUC1 in Transgenic Mice Expressing Human MUC1

The tumor-specificity of a CAR T cell target is important in order to avoid dose-limiting toxicities, which will allow clinicians to reach therapeutic doses where anti-tumor efficacy is expected. A history of off-tumor, on-target toxicities have been reported for CAR T cells targeting Her2 and carbonic anhydrase IX in clinical studies, and EGFR and GD2, among others in preclinical studies.

Figures 6A, 6B:
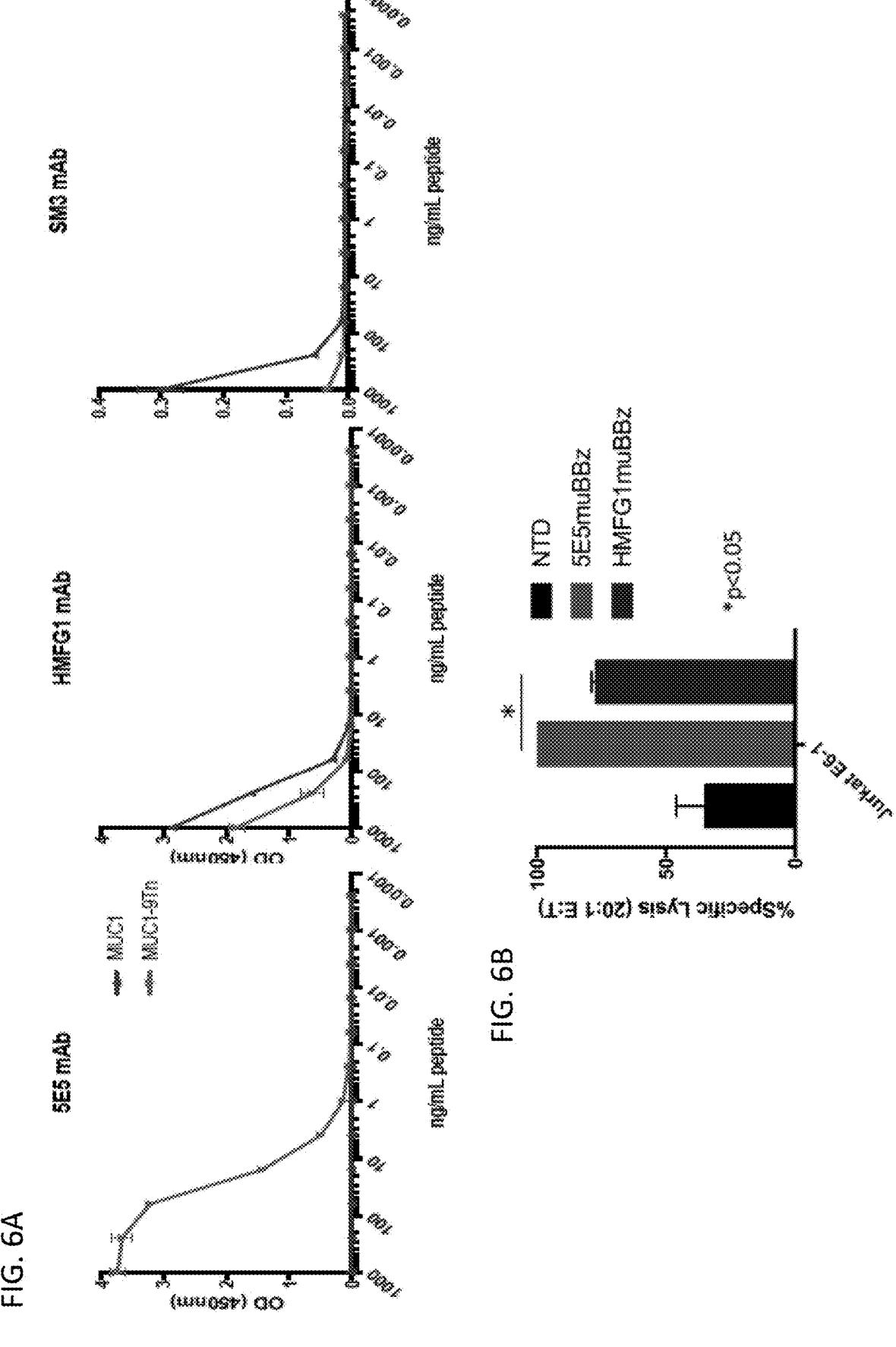
FIGS. 6A and 6B are a series of plots and images illustrating the finding that intraperitoneal delivery of murine HMFG1-CAR T cells in human MUC1 transgenic mice causes off-tumor, on-target toxicity not observed from murine 5E5-CAR T cells.

In order to evaluate potential off-tumor, on-target toxicity of Tn-MUC1, fully murine CARs were developed that utilized murine domains of CD8α leader, extracellular hinge and transmembrane, 4-1BB co-stimulatory domain, and CD3ζ, consistent with prior work (Watanabe et al., (2018) *JCI Insight* 3). The reactivity of 5E5 mAb and two commercially available anti-MUC1 mAbs with public scFv sequences (HMFG1 and SM3) were evaluated for reactivity to MUC1 60mer peptide and MUC1-Tn 60mer peptide. Specificity and high affinity of 5E5 mAb for MUC1-Tn but low affinity of HMFG1 and SM3 mAbs for MUC1 60mer peptide, in the presence and absence of glycosylation, were observed. Given that HMFG1 exhibited stronger reactivity for MUC1 than SM3, murine 5E5-based and HMFG1-based CARs were generated and mouse T cells expressing each CAR were expanded. Murine 5E5-CAR T cells exhibited greater lysis of Jurkat cells in vitro than HMFG1-CAR T cells and NTD T cells, likely due to C1GalT1C1 truncation in Jurkat cells (FIGS. 6A and 6B). In non-tumor bearing human MUC1 transgenic (hMuc1.tg) mice, 5 million T cells (NTD, 5E5-CAR, or HMFG1-CAR) were injected n the peritoneal cavity. Three days after injection, mice in the HMFG1-CAR group expectantly died, so necropsy was performed on remaining mice. Destructed glomeruli and hemorrhaging in the kidneys and lungs of mice treated with HMFG1-CARs was observed, but histological toxicities in the tissues from mice treated with NTD or 5E5-CARs was not. These data indicate that strategies to target normal MUC1 may cause off-tumor, on-target toxicities, as observed after intratumoral injection of pSM3-CAR T cells in a patient with seminal vesicle cancer (You et al., (2016)

*Sci China Life Sci* 59, 386-397), while anti-Tn-MUC1-CARs can increase the therapeutic window for targeting MUC1-expressing tumors.

Example 6: Discussion

In this study, since gene expression analyses are unable to determine the expression of the aberrantly glycosylated form of MUC1, the expression of MUC1 and the enzymes involved in its glycosylation were investigated to determine if the pattern of gene expression supports accumulation of Tn-MUC1 or STn-MUC1.

In the TCGA, MUC1 was highly expressed by all breast cancer subtypes. As expected, HR+ breast cancers had the highest expression since MUC1 is under transcriptional control by steroid hormones. qPCR studies demonstrated that tumor cells have higher expression of MUC1 than normal breast tissue. Without wishing to be bound by specific theory, accumulation of MUC1 may overwhelm the glycosylation pathway, resulting in aberrantly glycosylated mucins being expressed on the cell surface, supporting Tn-MUC1 and STn-MUC1 expression by tumor cells.

Core 1 synthase enzymes C1GalT1 and its chaperone C1GalT1C1 (Cosmc) expression were lower in breast tumor tissue than normal breast tissue. Similarly, expression of Core 3 synthase (B3GNT6) was decreased in breast tumor tissue. Breast tumor tissues also had higher expression of sialyl transferase, ST6GALNac. This suppression both Core 1 and Core 3 synthase enzymes and increased expression of sialyl transferase would prevent progression along the MUC1 glycosylation pathway, resulting in accumulation of Tn-MUC1 and increased synthesis of STn-MUC1 (FIGS. 7A-7C).

An important characteristic of an antigen target for immunotherapy is that it is expressed by tumor tissue and not normal tissue order to limit the on-target off-tumor recognition by CAR T cells. It was demonstrated utilizing an anti-Tn-MUC1 antibody that, while there was very limited expression of abnormally glycosylated MUC1 by normal breast tissue, all breast tumor samples expressed them and to a much higher degree. This expression was irrespective of breast cancer subtype, indicating that this targeted therapy, unlike those that currently exist for breast cancer, may not be subtype dependent.

The anti-Tn-MUC1 CAR most notably resulted in target-specific cytotoxicity in in vitro studies using breast cancer cell lines of various subtype. Tn-MUC1 was expressed in all breast cancer subtypes regardless of their HR or Her2 expression status, rendering it a versatile breast cancer specific antigen and a viable target for CAR T cell therapy in breast cancer.

Example 7: TnMUC1 CAR Preclinical Studies

TnMUC1(5E5)-based chimeric antigen receptors (CARs) containing various costimulatory domains were generated and tested for transgene expression in human T cells. Transgene expression was measured by flow cytometry using biotinylated protein L and streptavidin-PE or Biotin-Goat Anti-Mouse and streptavidin-PE. Expression of the various CARs are shown in FIG. 8.

Figure 8:
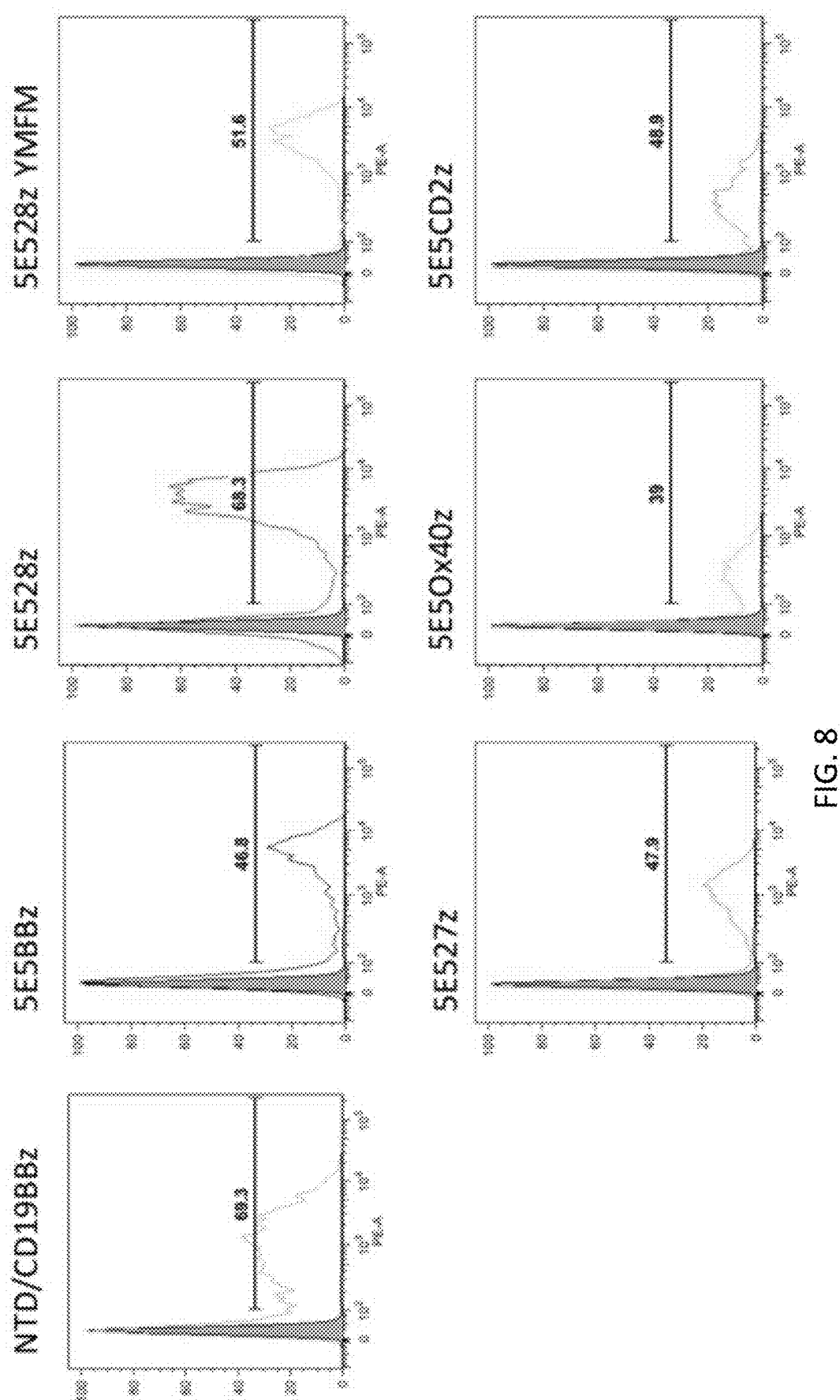
FIG. 8 is a set of flow cytometry plots showing the expression of the various TnMUC1 CAR transgenes as indicated.

As shown in FIG. 8, transduction efficiencies for the TnMUC1 CARs were 69.3% for CD19BBz (CD19 directed CAR comprising 4-1BB and CD3zeta intracellular signaling domains); 46.8% for 5E5BBz (5E5 scFv based CAR comprising 4-1BB and CD3zeta intracellular signaling domains); 68.3% for 5E528z (5E5 scFv based CAR comprising CD28 and CD3zeta intracellular signaling domains); 51.6% for 5E528z YMFM (5E5 scFv based CAR comprising a CD28 variant (YMFM) domain and CD3zeta intracellular signaling domains); 47.9% for 5E527z (5E5 scFv based CAR comprising CD27 and CD3zeta intracellular signaling domains); 39% for 5E5Ox40z (5E5 scFv based CAR comprising OX40 and CD3zeta intracellular signaling domains); and 48.9% for 5E5CD2z (5E5 scFv based CAR comprising CD2 and CD3zeta intracellular signaling domains).

Proliferation and cytokine secretion studies were performed on the various TnMUC1 CARs using the MCF7 breast cancer cell line.

Various TnMUC1 CARs were assessed in a carboxyfluorescein succinimidyl ester (CFSE) assay that measures the dilution of a dye between daughter cells. In the CFSE assay, TnMUC1 positive MCF7 cells were co-cultured with the various TnMUC1 CAR transduced T cells. MCF7 cells were prepared in D10 media at $0.5\times10^6$/mL, and 100 μL was added in each well (approximately 50,000 tumor cells/well). T cells were counted and resuspended at $1\times10^6$ cells/mL in R10 media. Transduction efficiency of CAR T cells was normalized to 30% using NTD cells. CFSE staining solution was diluted 1:1000 in PBS (5 μM), and $1\times10^6$ total T cells (normalized to 30% scFv) were resuspended in 1 mL CFSE/PBS staining solution. Cells were incubated for 5 minutes at room temperature, protected from light. After incubation, 10 mL of R10 media was used to wash cells, after which they were resuspended in 1 mL R10 culture media, and 100 μL cells were added to into the wells with tumor cells for a final E: T ratio of 2:1 (100,000 T cells: 50,000 tumor cells). For flow cytometry, cells were transferred to a 96-well round-bottomed plate and washed with 100 μL fluorescence activated cell sorter (FACS) buffer, centrifuging at 2000 rpm for 5 minutes. Cells were resuspended in 100 μL FACS buffer per well, and stained for 20 minutes on ice with 5 μL/100 μL biotinylated goat anti-mouse antibody. Cells were washed 2× with FACS buffer and stained with 1 μL/100 μL of each streptavidin-PE and CD3-BV605 for 20 minutes on ice. Cells were then washed in PBS and stained with L/D violet 0.1 μL/100 μL in PBS for 20 minutes at room temperature. After staining, cells were washed with FACS buffer, resuspended in 350 μL of FACS buffer+50 μL (0.54×105 beads/mL) of CountBright absolute counting beads per well, and acquired using a BD LSR-Fortessa. T cells were measured by flow cytometry relative to CountBright absolute counting beads to determine relative cell counts.

Figure 9:
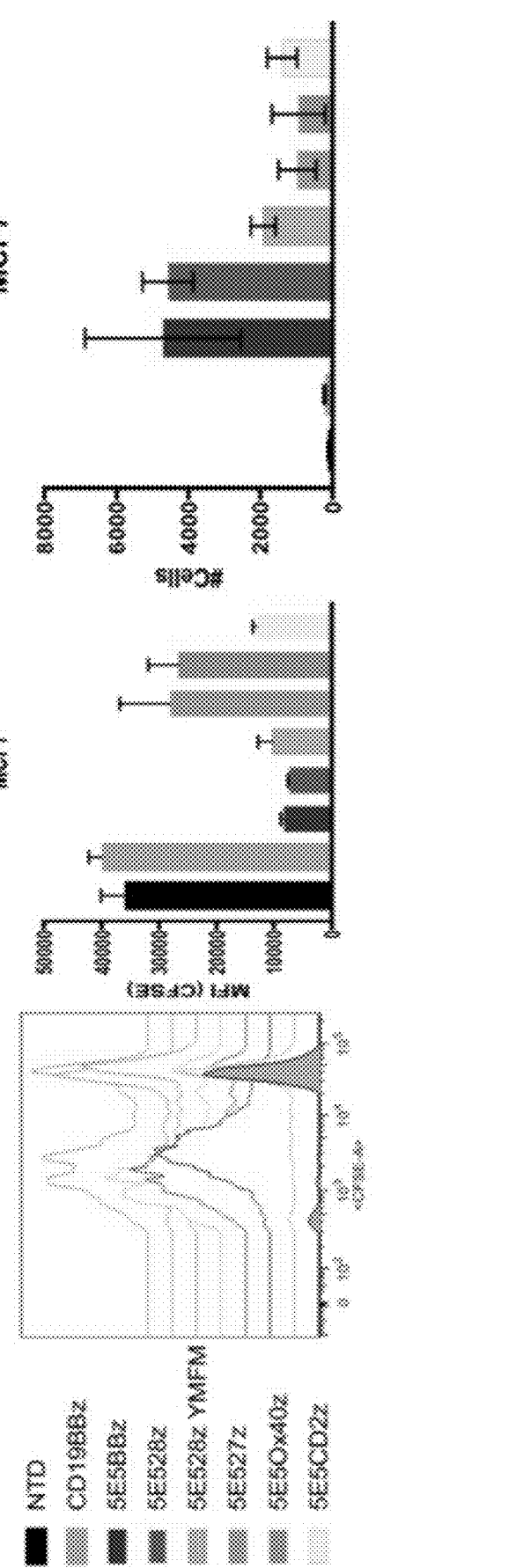
FIG. 9 shows the results of a CFSE assay, demonstrating that the various TnMUC1 CAR-T cells as indicated proliferate in response to MCF7 cells.

FIG. 9 shows the results of the CFSE assay, demonstrating that the various TnMUC1 CAR-T cells proliferate in response to MCF7 cells. Neither CD19BBz-T cells nor non-transduced cells (NTD) proliferated in response to MCF7 cells.

Figure 10:
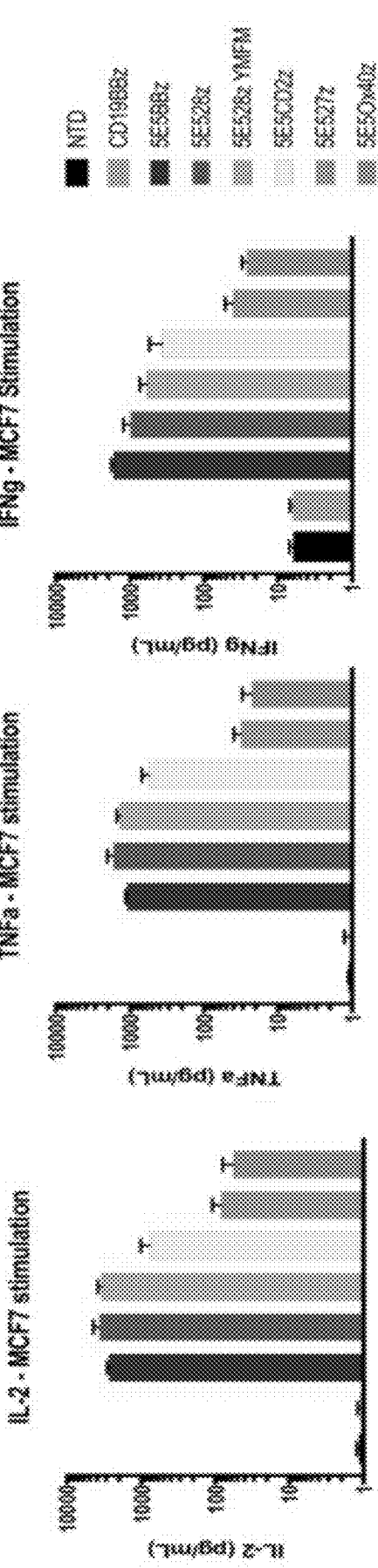
FIG. 10 is a set of three charts showing, from left to right, the level of IL-2, TNFa, and IFNg secretion of the various TnMUC1 CAR-T cells as indicated.

Cytokine secretion of the various TnMUC1 CAR-T cells were tested in response to stimulation by co-culturing with MCF7 cells. FIG. 10 shows the level of IL-2, TNFa, and IFNg secretion of the various TnMUC1 CAR-T cells as indicated.

Figure 11:
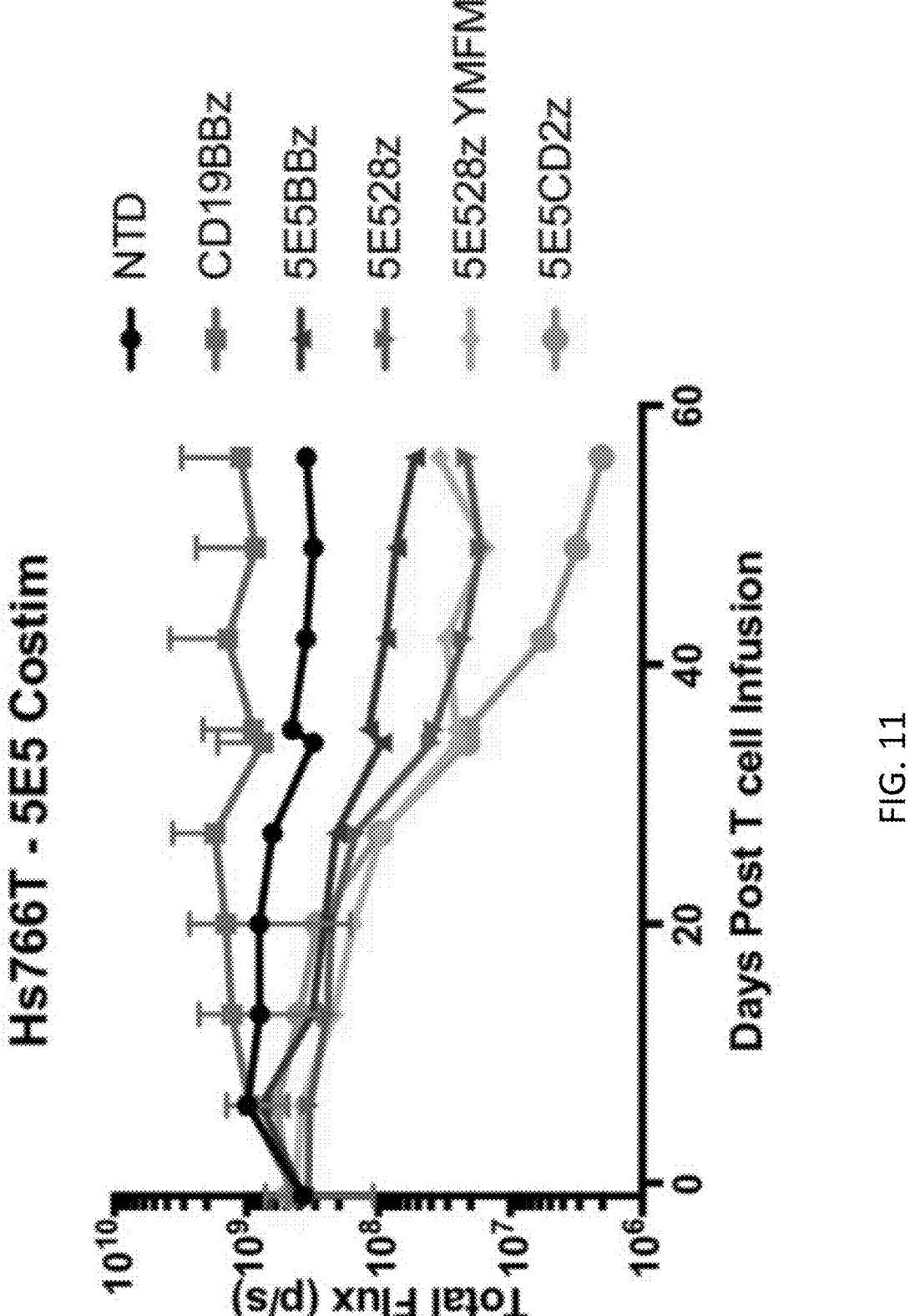
FIG. 11 is a graph showing the total flux in photons per second measured in mice post-intravenous administration of the various TnMUC1 CAR-T cells as indicated, over time.
Figure 12B:
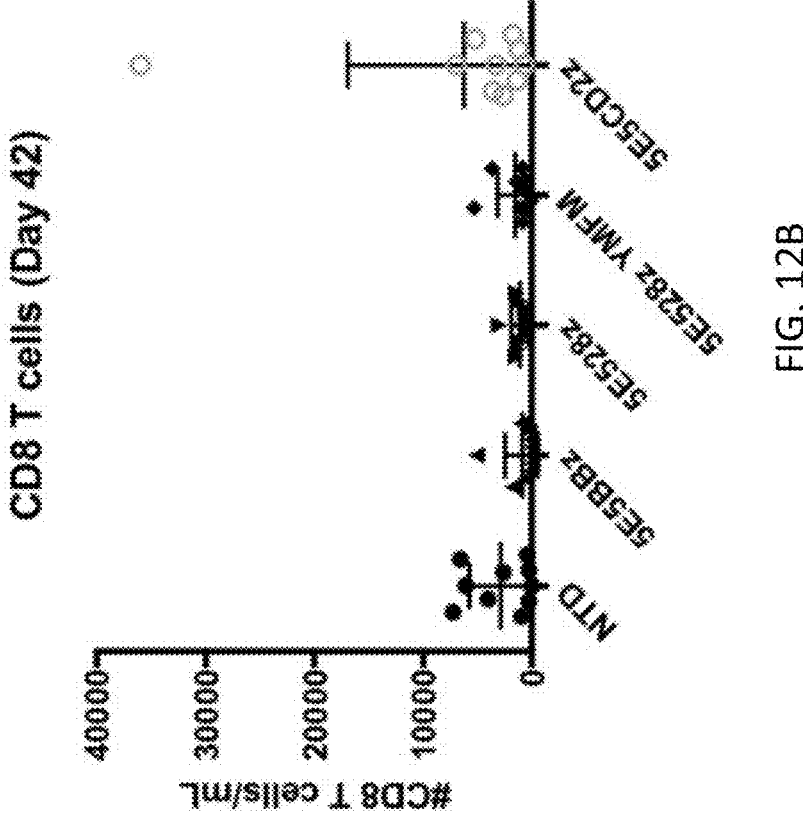
FIGS. 12A and 12B are plots showing the level of various TnMUC1 CAR-T cells measured in the peripheral blood of infused mice at day 42 post infusion.
Figure 12A:
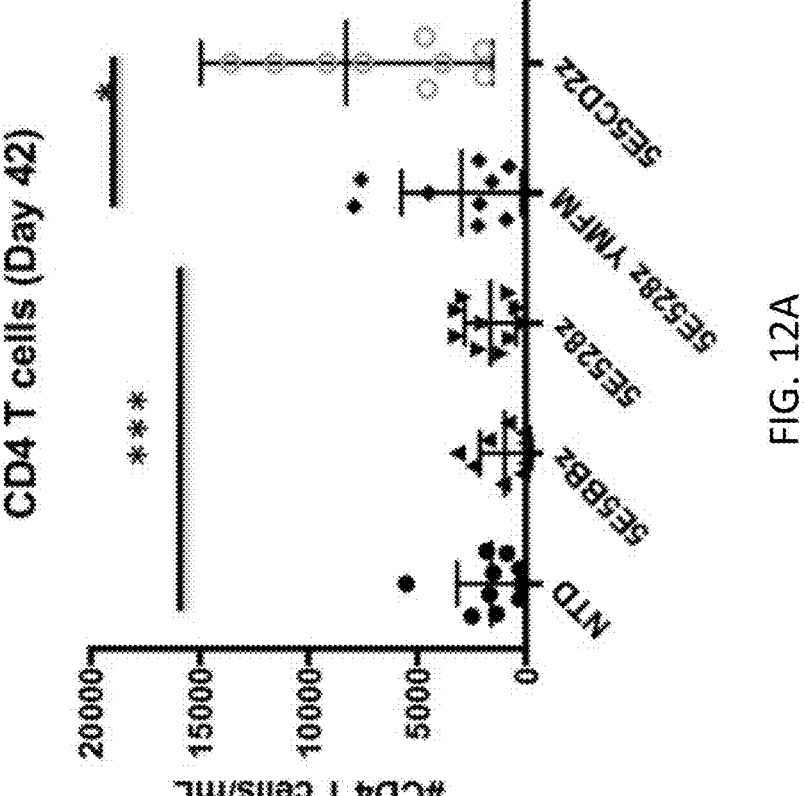

The in vivo efficacy of various TnMUC1 CAR-T cells were tested in the TnMUC1+hs766T pancreatic tumor NSG immunodeficient mouse model. Since the murine MUC1 lacks the epitope for 5E5 scFv, the efficacy of the various TnMUC1 CARS reflects the background seen with non-transduced (NTD) cells plus any specific efficacy derived from interaction of the TnMUC1 CAR with the TnMUC1+ tumor. Hs766T tumors were established via the IP route in mice using $5\times10^5$ Hs766T pancreatic cancer cell line labelled with Click Beetle Green (CBG). After 1 month when tumor burdens were at a mean total flux of $4.5 \times 10^8$ p/s, the mice were dosed IV with the various TnMUC1 CAR-T cells as indicated in FIG. 11, which shows the total flux measured in mice post-IV administration of TnMUC1 CAR-T cells as a function of the number of days post T cell infusion.

The levels of the various TnMUC1 CAR-T cells in the peripheral blood of the infused mice were measured by retroorbital bleed at day 42 post infusion. As shown in FIGS. 12A and 12B, 5E5CD2z CAR-T infused mice had higher average numbers of human CD4+ T cells (FIG. 12A) and CD8+ T cells (FIG. 12B) in the peripheral blood.

Nonclinical Studies with CART-ThMUC1

To create T cells that will recognize and kill cells expressing the TnMUC1 antigen, a CD2ζ-based CAR was created. This CAR based on a monoclonal antibody (5E5) specific to a Tn-MUC1 glycopeptide epitope is described herein. This CAR is composed of the extracellular targeting region (based on the 5E5 monoclonal Ab), the CD8a hinge and transmembrane domain and two intracellular signaling domains of CD2ζ and CD3ζ. The CD2 signal was observed to be associated with strong persistence of T cells in the setting of autoimmune disease and may lead to better persistence of the CART cell product within a patient (Mckinney et al. (2015) *Nature*, 523:612; Bridgman et al. (2014) *Clin Exp Immunol*, 175(2): 258-267; Zhao et al. (2015) *Cancer Cell*, 28(4): 415-428). A lentivirus vector containing the 5E5-based CAR was constructed to transduce autologous T cells obtained by leukapheresis to create the CART product. In a clinical trial, a self-inactivating lentiviral vector (LV) will be used to transfer the CAR constructs into autologous T lymphocytes by ex vivo transduction. Lymphocytes will be enriched from leukapheresis product and transduced with the LV. LV-mediated transduction of T lymphocytes isolated from the peripheral blood has been previously tested in other clinical trials.

To demonstrate the activity and safety of these CART cells engineered to recognize the TnMUC1 antigen (CART-TnMUC1), nonclinical pharmacology studies and nonclinical toxicology studies have been performed.

Nonclincal studies have been conducted with CART-TnMUC1 (5E5 scFv based CAR comprising a CD2 and CD3zeta intracellular signaling domain) to demonstrate the potential mechanism of action of this approach against multiple tumor models as well as studies to investigate the potential for the CART-TnMUC1 cells to target normal human tissues. Data described here are presented to demonstrate the potential for anti-tumor activity with CART-TnMUC1 and limited potential to target normal human tissues. The description and composition of T cells used in these studies are described in Table 2.

TABLE 2

Description and Composition of T cells Used in Nonclinical Studies

| | Chimeric Antigen Receptor Components | | | |
|---|---|---|---|---|
| Nomenclature | Murine scFv | Hinge & Transmembrane | Signaling | T Cell Species |
| CART-TnMUC1 | anti-TnMUC1 5E5 | Human CD8α | Human CD2 and CD3ζ | Human |
| CART-TnMUC1-BBz | anti-TnMUC1 5E5 | Human CD8α | Human 4-1BB and CD3ζ | Human |
| mCART-TnMUC1-BBz | anti-TnMUC1 5E5 | Murine CD8α | Murine 4-1BB and CD3ζ | Mouse |
| CART-19 | anti-CD19 FMC63 | Human CD8α | Human 4-1BB and CD3ζ | Human |
| NTD cells | — | — | — | Human |
| Murine NTD (mNTD) cells | — | — | — | Mouse |

CART = chimeric antigen receptor T-cell;
CD = cluster of differentiation;
NTD = non-transduced T (cells);
scFV = single chain Fy fragment Target Cells Used in Nonclinical Studies Since CART cells act in an antigen dependent fashion determined by the specificity of the scFv portion of the CAR, activity can be seen against antigen positive targets regardless of the type of cell expressing the antigen. Target cell lines (Table 3) were selected to represent both solid and hematological malignancies, and to assess the pharmacology towards target cells with both low and high antigen expression levels as determined by polymerase chain reaction (PCR) and flow cytometry assays (see, Posey et al. (2016) *Immunity*, 44:1444-1454).

TABLE 3

Target Tumor Cell Lines Used in Nonclinical Studies

| Cell Line[a] | Description | MUC1 RNA[b] | TnMUC1 Status[c] | Source |
|---|---|---|---|---|
| Capan-2 | Pancreatic ductal adenocarcinoma cell line derived from human pancreas, isolated from a 56-year-old Caucasian male. | 11 | ++ | ATCC |
| Hs766T | Pancreatic cancer epithelial cell line derived from metastatic site (lymph node), isolated from a 64-year-old Caucasian male | 0.18 | + | ATCC |
| Jurkat E6-1 | Acute T cell leukemia lymphoblastic cell line derived from peripheral blood. | 0.03 | +++ | ATCC |
| Jurkat CD19t-P2A-COSMC | Jurkat E6-1 cells transduced with a lentiviral vector encoding COSMC and CD19 lacking the intracellular domain (CD19t), as a selection marker, | NT | – | UPenn Posey lab (derived from Jurkat E6-1 cells) |

US 12,624,081 B2

127

TABLE 3-continued

Target Tumor Cell Lines Used in Nonclinical Studies

| Cell Line[a] | Description | MUC1 RNA[b] | TnMUC 1 Status[c] | Source |
|---|---|---|---|---|
| (Jurkat COSMC) | separated by P2A signaling peptide (CD19t-P2A-COSMC). COSMC is a chaperone necessary for T synthase expression which is capable of converting Tn glycans into Core 1 glycans for normal glycosylation. Restoration of COSMC provides a control cell line due to loss of Tn antigen. | | | |
| MCF7 | Breast cancer cell line derived from metastatic site (pleural effusion), isolated from a 69-year-old Caucasian female | 1.6 | ++ | ATCC |

ATCC = American Type Culture Collection;
CD = cluster of differentiation;
MUC1 = mucin, cell surface associated;
NT—not tested;
RNA = ribonucleic acid;
UPenn = University of Pennsylvania
[a]Each cell type listed was engineered to express Green Fluorescent Protein and Click Beetle Green luciferase for use in flow cytometry and bioluminescent assays, unless expressly stated that the unmodified parent was used
[b]% GADPH housekeeping reference gene
[c]As determined by flow cytometry (Posey et al. 2016): '−' no signal, '+' <10-fold, '++' <100-fold, and '+++' <1000-fold isotype control Nonclinical Pharmacology The nonclinical pharmacology studies have been designed to demonstrate the ability of CART-TnMUC1 cells to specifically recognize TnMUC1+ tumor target cells, while not being activated by antigen negative targets.

CART-TnMUC1, CART-TnMUC1-BBz and control T cells were stimulated with TnMUC1 positive and negative target cells, and investigated for primary and secondary pharmacological properties. The primary pharmacology of CART cells measures their direct anti-tumor activity and was assessed in vitro as the ability to lyse TnMUC1 positive target cells, and in vivo as the ability to control disseminated TnMUC1 positive tumors in NSG mice. The secondary pharmacology of CART cells is their ability to proliferate, secrete cytokines and chemokines, and for the CD4 subset to express CD40L in response to TnMUC1 positive target cells. The proliferative properties of CART cells result in an antigen-specific increase in the CART population, which facilitates tumor control. The ability to secrete cytokines and chemokines can have direct effects on tumors as well as orchestrating integrated immune responses. Likewise CD40L expression by activated CD4 T cells is a key mechanism via which CD4 T cells provide 'help' to integrated immune responses, in which the endogenous immune cells of the host may contribute to tumor control.

Figure 13:
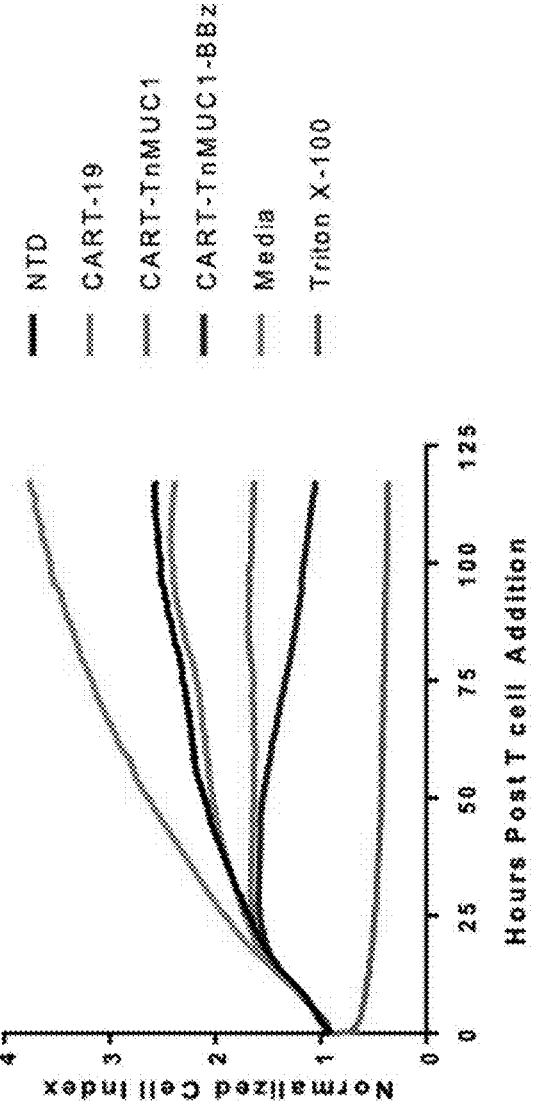
FIG. 13 is a graph demonstrating the cytotoxicity of CART-TnMUC1, CART-TnMUC1-BBz, and negative control cells (CART-19 and NTD) towards the Hs766T pancreatic cancer cell line.

In Vitro Cytotoxic Activity of CART-TnMUC1 to ThMUC1 Positive Tumor Cells:

CART-TnMUC1 cell killing of the TnMUC1+MCF7 breast cancer cell line and pancreatic cancer cell lines Hs766T and Capan-2 was evaluated using the xCELLigence (ACEA Biosciences) real-time cellular impedance assay as previously described (Watanabe et al. (2018) JCI Insight, 3). CART cells were cultured with tumor cells (MCF7, Hs766T, Capan2) for 24 hours and then cell impedance tested. Tumor growth was impeded by co-culture with CART-TnMUC1 cells when compared with negative controls (media alone, NTD cells, CART-19 T cells). CART-TnMUC1 cells and CART-TnMUC1-BBz cells showed similar kinetics of cyto-toxicity against Hs766T cells (FIG. 13). CART-TnMUC1 also showed cytotoxicity against MCF7 (in both assays) and Capan2 cells; however, where directly compared, the kinetics of cytotoxicity for CART-TnMUC1 were slower and less potent than CART-TnMUC1-BBz cells. Without being bound to any theory, this may be due to differential CAR expression levels and/or the result of differential signaling pathway activation.

FIG. 13 is a graph demonstrating the cytotoxicity of CART-TnMUC1, CART-TnMUC1-BBz, and negative control cells (CART-19 and NTD) towards Hs766T pancreatic cancer cell line. Additional controls were media alone, and Triton™-X-100, a nonionic surfactant that rapidly lyses membranes leading to cell death.

Figures 14A, 14B, 14C:
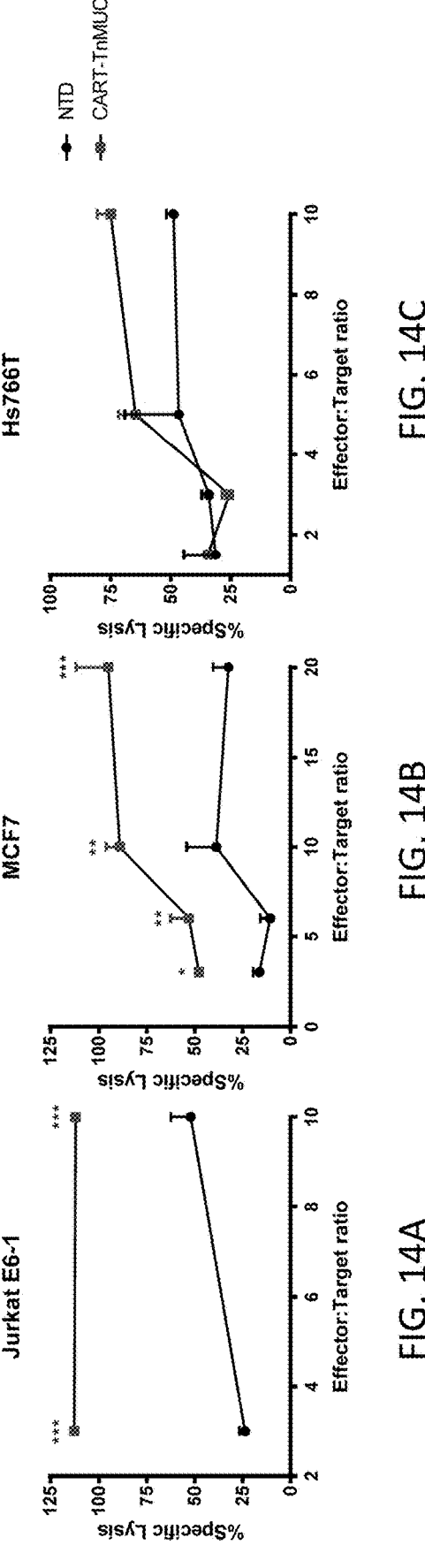
FIGS. 14A-14C are a series of graphs showing targeted cell killing by CART-TnMUC1 cells of various cell lines as indicated.

The cytotoxicity of CART-TnMUC1 cells was further investigated in a luciferase-based assay against labelled Jurkat E6-1, MCF7, and Hs766T cells using NTD cells as a control (FIGS. 14A-14C). In this assay format CART-TnMUC1 cells demonstrated potent killing of Jurkat E6-1 cells at 3:1 and 10:1 E:T ratios (FIG. 14A). Potent killing of MCF7 breast cancer cells was also detected, which increased with E: T ratio (FIG. 14B). There was also a trend to killing of the Hs766T cells although this did not reach significance (FIG. 14C).

FIGS. 14A-14C demonstrate targeted cell killing by CART-TnMUC1 cells. CART-TnMUC1 or NTD cells were cultured with Jurkat E6-1 cells (left), MCF7 breast cancer cells (center), or Hs766T pancreatic cancer cells (right) at the indicated effector-to-target ratios. For MCF7, the total number of tumor cells utilized for the 3:1 and 10:1 E:T ratios was reduced by half in order to achieve 6:1 and 20:1 E:T ratios, respectively. For Hs766T, the total number of tumor cells utilized for the 3:1 and 10:1 E:T ratios was doubled in order to achieve 1.5:1 and 5:1 E:T ratios, respectively. Statistical comparisons were between CART-TnMUC1 and NTD cells using multiple t-tests. *=p<0.05, =p<0.01, *=p<0.001, ****=p<0.0001.

The specificity of CART-TnMUC1 cytotoxicity was also established in the luciferase-based assay system against wild-type TnMUC1+ Jurkat E6-1 cells and TnMUC1-Jurkat CD19t-P2A-COSMC cells, (these cells express the chaperone COSMC and thus carry out full glycosylation rendering it TnMUC1-on the cell surface). Significant cytotoxicity was observed at two E: T ratio: 3:1 and 10:1, meanwhile there was no cytotoxicity against the Jurkat CD19t-P2A-COSMC cells (FIG. 15A for Jurkat E6-1; and FIG. 15B for Jurkat CD19t-P2A-COSMC).

Figures 15A, 15B:
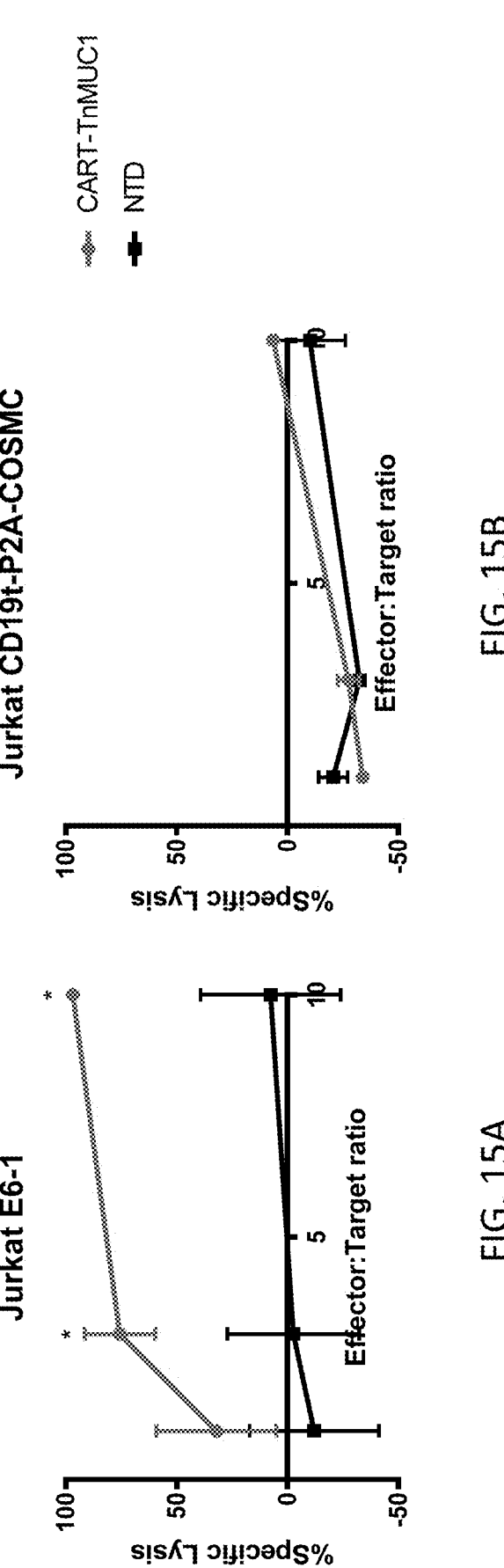
FIGS. 15A and 15B are a series of graphs showing targeted cell killing by CART-TnMUC1 cells in response to Tn antigen of various cell lines as indicated.

FIGS. 15A and 15B show targeted cell killing by CART-TnMUC1 cells in response to Tn antigen. In vitro cytotoxicity assay of T cells, CART-TnMUC1 or NTD cells were cultured with Jurkat E6-1 (FIG. 15A) or Jurkat CD19t-P2A-COSMC (FIG. 15B) cell lines at the indicated effector-to-target ratios. *=p<0.05. 5E5-CD2z CAR T cells exhibited potent cytotoxicity against Jurkat cells. NTD cells did not exhibit cytotoxicity against the same target cell lines.

In vivo Anti-Tumor Activity of CART-TnMUC1: CART-TnMUC1 cells were studied in an animal model of intraperitoneal (IP) TnMUC1+Hs766T tumors in the immunodeficient NSG mouse. The NSG model is a widely used xenotransplantation model for engraftment of human tumor and T cells (Barrett et al. (2011) *Hum Gene Ther*, 22:1575-1586). Table 4 and Table 5 describe the conditions tested in this tumor challenge model. Hs766T tumors were established via the intraperitoneal (IP) route in mice using $5 \times 10^5$ Hs766T pancreatic cancer cell line labelled with Click Beetle Green (CBG). After 1 month when tumor burdens were at a mean total flux of $4.5 \times 10^8$ p/s, the mice were randomized between the treatment groups and dosed IV with CART-TnMUC1 cells, or CART-TnMUC1-BBz, or two negative controls: CART-19 and NTD cells.

TABLE 4

Summary of Study Parameters for in vivo Pharmacology Experiments

| Study | Study Duration[a] | T cell Normal Donor ID | T cell Treatment Groups | Total Cell Dose | Number of Mice per Group[b] |
|---|---|---|---|---|---|
| Hs766T: Pancreatic cancer xenograft study in NSG mice | 63 days | ND473 | CART-TnMUC1 | $5 \times 10^6$ | 10 (1F9M) |
| | | | CART-TnMUC1-BBz | $5 \times 10^6$ | 10 (6F4M) |
| | | | CART-19 | $5 \times 10^6$ | 9 (3F6M)[c] |
| | | | NTD cells | $5 \times 10^6$ | 10 (7F3M) |

CART = chimeric antigen receptor T cell;
F = female;
M = male;
NSG = NOD scid gamma;
NTD = non transduced T (cells)
[a]Defined by the time from T cell infusion to terminal sacrifice.
[b]F/M: animals randomized based on tumor burden.
[c]One mouse died during T cell administration.

The CART expression in these mice and the total number of CAR+ T cells injected are summarized in Table 5. A staining level of 2.89% was seen in the nontransduced controls which reflects the background of the assay and not CAR expression as these cells were not exposed to CAR-encoding lentivectors.

TABLE 5

Treatment Group Definitions

| Group | T cell treatment Group | Number of CAR + T cells Injected | Number of Total T cells Injected |
|---|---|---|---|
| 1 | Unmodified (NTD) | N/A | $5 \times 10^6$ |
| 2 | CART-19 cells | $1.5 \times 10^6$ | $5 \times 10^6$ |

TABLE 5-continued

Treatment Group Definitions

| Group | T cell treatment Group | Number of CAR + T cells Injected | Number of Total T cells Injected |
|---|---|---|---|
| 3 | CART-TnMUC1 cells | $1.5 \times 10^6$ | $5 \times 10^6$ |
| 4 | CART-TnMUC1-BBz cells | $1.5 \times 10^6$ | $5 \times 10^6$ |

CART = chimeric antigen receptor T cell;
N/A = not applicable;
NTD = non transduced T (cells)

Engraftment and progression of CBG+Hs766T tumors were measured by bioluminescence imaging. Bioluminescence imaging in live mice started on Day −1 and continued weekly through study; a final bioluminescence measurement was obtained on Day 60. These results are shown in FIG. 16.

Figure 16:
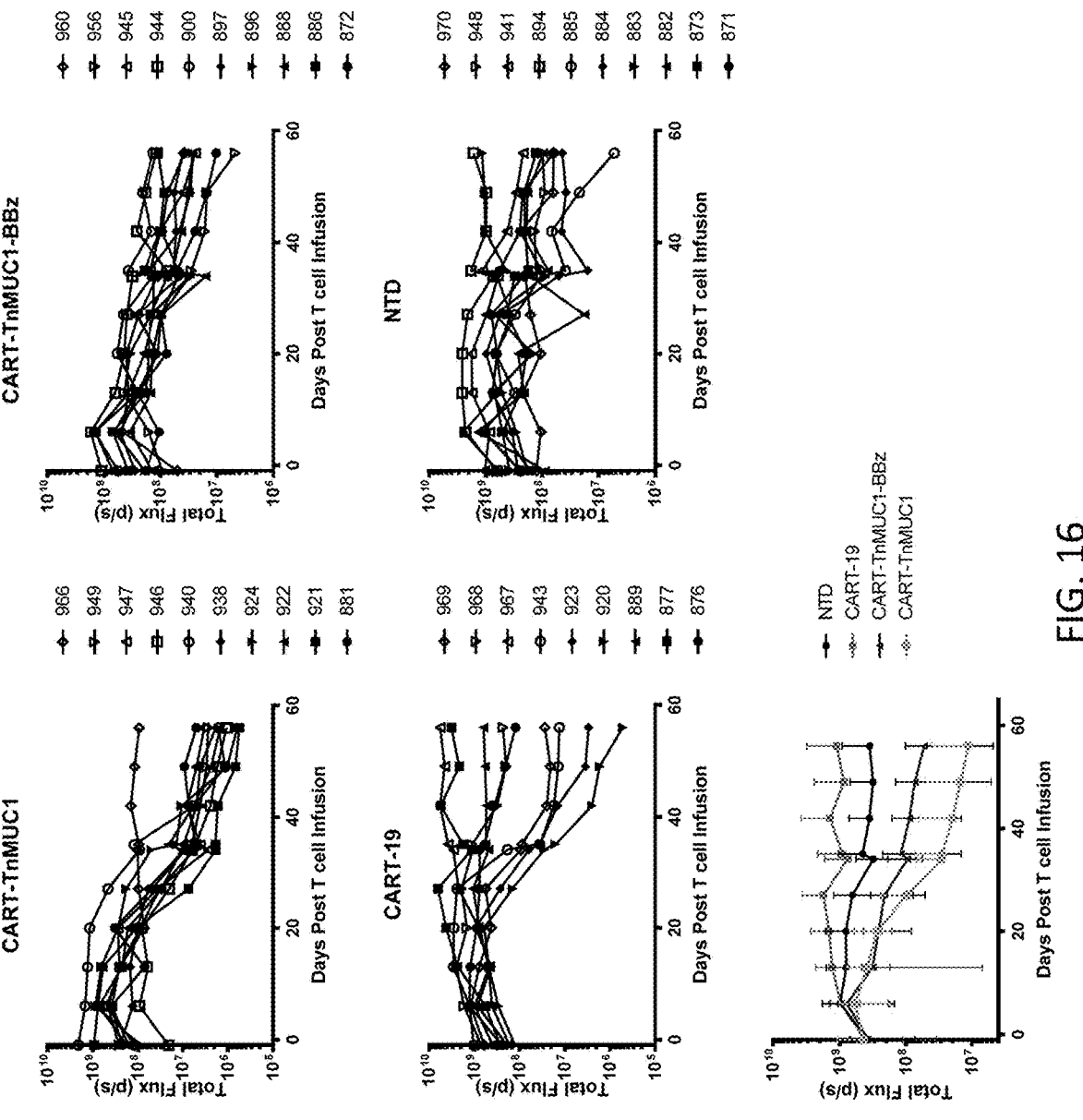
FIG. 16 shows a series of graphs plotting the bioluminescent imaging of tumor burden in a mouse model of pancreatic cancer.

FIG. 16 shows graphs plotting the bioluminescent imaging of tumor burden in a mouse model of pancreatic cancer. NSG mice were injected with CBG+Hs766T cells and treated with $5 \times 10^6$ total T cells ($1.5 \times 10^6$ CAR+ cells in CART-treated groups) with CART-TnMUC1, CART-TnMUC1-BBz, CART-19, or NTD cells. Bioluminescent imaging of tumor burden was measured at multiple time-points as indicated, displayed as photons per second (p/s). Panels represent the results for individual mice, and the mean±SD. Statistics were determined by unpaired, two-tailed T tests and one-way ANOVA.

All animals that received CBG+Hs766T tumor cells had similar tumor burden at 1-month post-tumor cell inoculation (Day 0 of T cell infusion), as measured by bioluminescence imaging, and animals were randomized to treatment groups. CART-TnMUC1 and CART-TnMUC1-BBz cell treated mice demonstrated a significant reduction in tumor growth compared to mice treated with CART-19 cells and NTD cells, indicating that 5E5-based CARs mediated TnMUC1-antigen specific eradication of Hs766T tumor cells. There was a non-significant trend towards more robust tumor clearance for the CART-TnMUC1 group, which was sustained throughout the study duration. This demonstrates anti-tumor efficacy of the CART-TnMUC1 in vivo.

Taken together, the nonclinical data for CART-TnMUC1 and the previous findings with CART-TnMUC1-BBz demonstrate antigen-dependent in vivo anti-tumor activity, with evidence for dose dependence of this activity.

Antigen-Dependent Proliferation: The propensity of CART-TnMUC1 cells to proliferate in response to cognate antigen was determined in two flow cytometry-based assay formats both based on the principle of the labelling of CART cells with a dye which is diluted between daughter cells during mitosis, and thus provides a measure of the degree of proliferation. In one assay format, T cells were labelled with CellTrace Violet, and in the other they were labeled with CFSE.

Figures 17A, 17B, 17C:
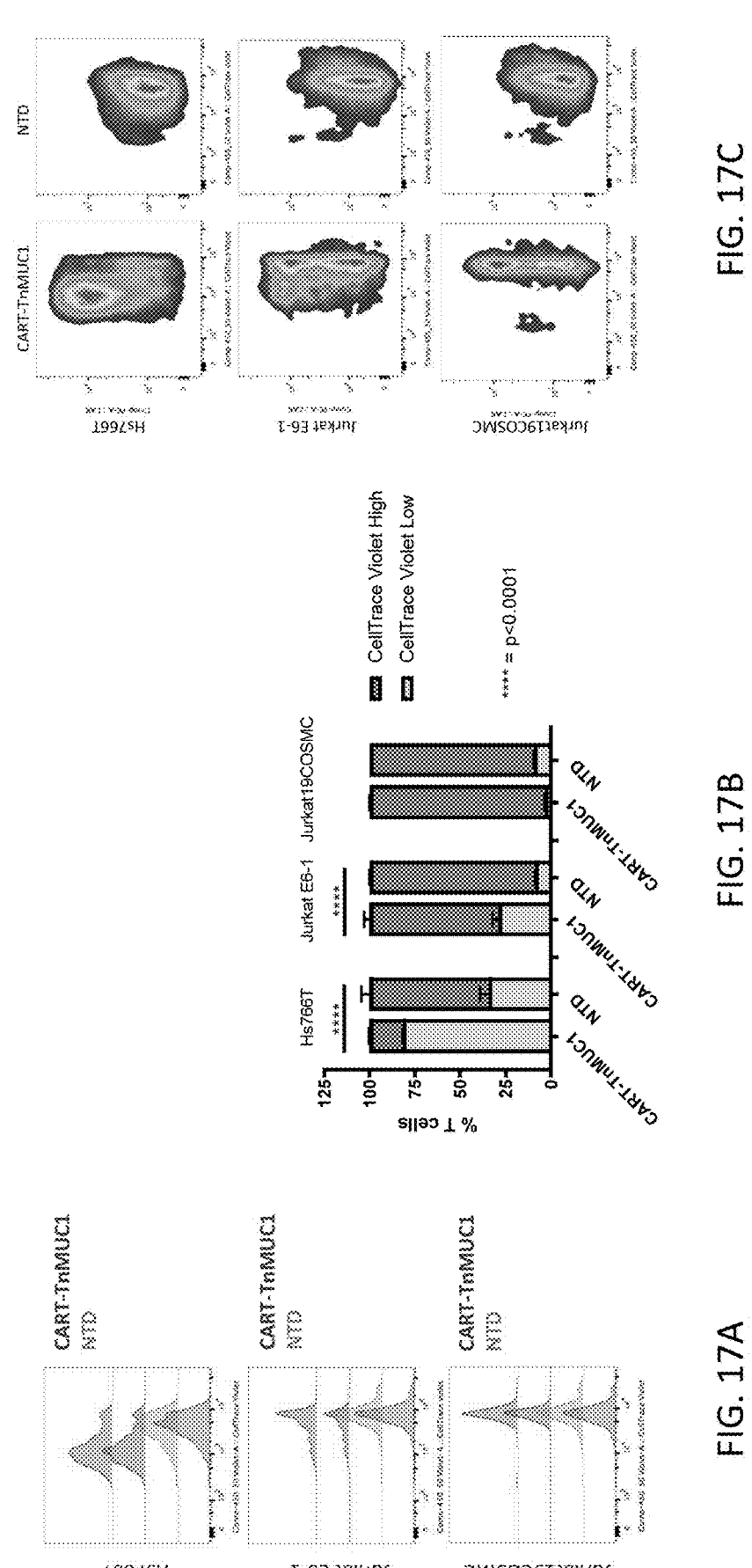
FIGS. 17A-17C are a series of graphs and images showing the proliferation of CART-TnMUC1 cells in response to antigen-expressing target cells.

In the CellTrace Violet assay, CART-TnMUC1 and control NTD cells were incubated with TnMUC1+Hs766T pancreatic tumor cells and Jurkat E6-1 leukemia cells, and with the control TnMUC1-Jurkat CD19t-P2A-COSMC cells (FIGS. 17A-17C).

CART-TnMUC1 cells underwent substantial proliferation in response to Hs766T cells, and modest proliferation in response to Jurkat E6-1 cells, but did not proliferate when exposed to the Jurkat CD19t-P2A-COSMC cells, which lack surface expressed TnMUC1 antigen, demonstrating antigen-specific proliferation. Proliferation was seen only in the CAR+ fraction of the T cells in the assay, further demonstrating the antigen-specificity of the response. In the carboxyfluorescein succinimidyl ester (CFSE) assay, proliferation was observed against TnMUC1+MCF7 breast cancer target cells.

FIGS. 17A-17C demonstrate the proliferation of CART-TnMUC1 cells in response to antigen-expressing target cells. Proliferation measured by decrease in CellTrace Violet signal and increase in the percentage of CellTrace Violet low T cells. (FIG. 17A) Histograms showing count versus Cell-Trace Violet signal. T cells are gated as GFP−, CD3+, L/D-near IR low lymphocytes. (FIG. 17B) The percent of T cells that fall within CellTrace Violet High (no proliferation) versus CellTrace Violet low (proliferation) groups. (FIG. 17C) Plots showing CAR expression versus CellTrace Violet signal. T cells are gated as GFP−, CD3+, L/D-near IR low lymphocytes. Statistical comparisons are between CART-TnMUC1 (5E5-CD2ζ) and NTD cells within CellTrace Violet high or CellTrace Violet low groups using a two way ANOVA test. *=p=0.0001, **=p<0.0001.

CART-TnMUC1 proliferative responses were noted against TnMUC1 positive MCF7, Hs766T, and Jurkat E6-1 cells but not TnMUC1 negative Jurkat CD19-P2A-COSMC cells, demonstrating antigen-dependent proliferation.

Figure 18:
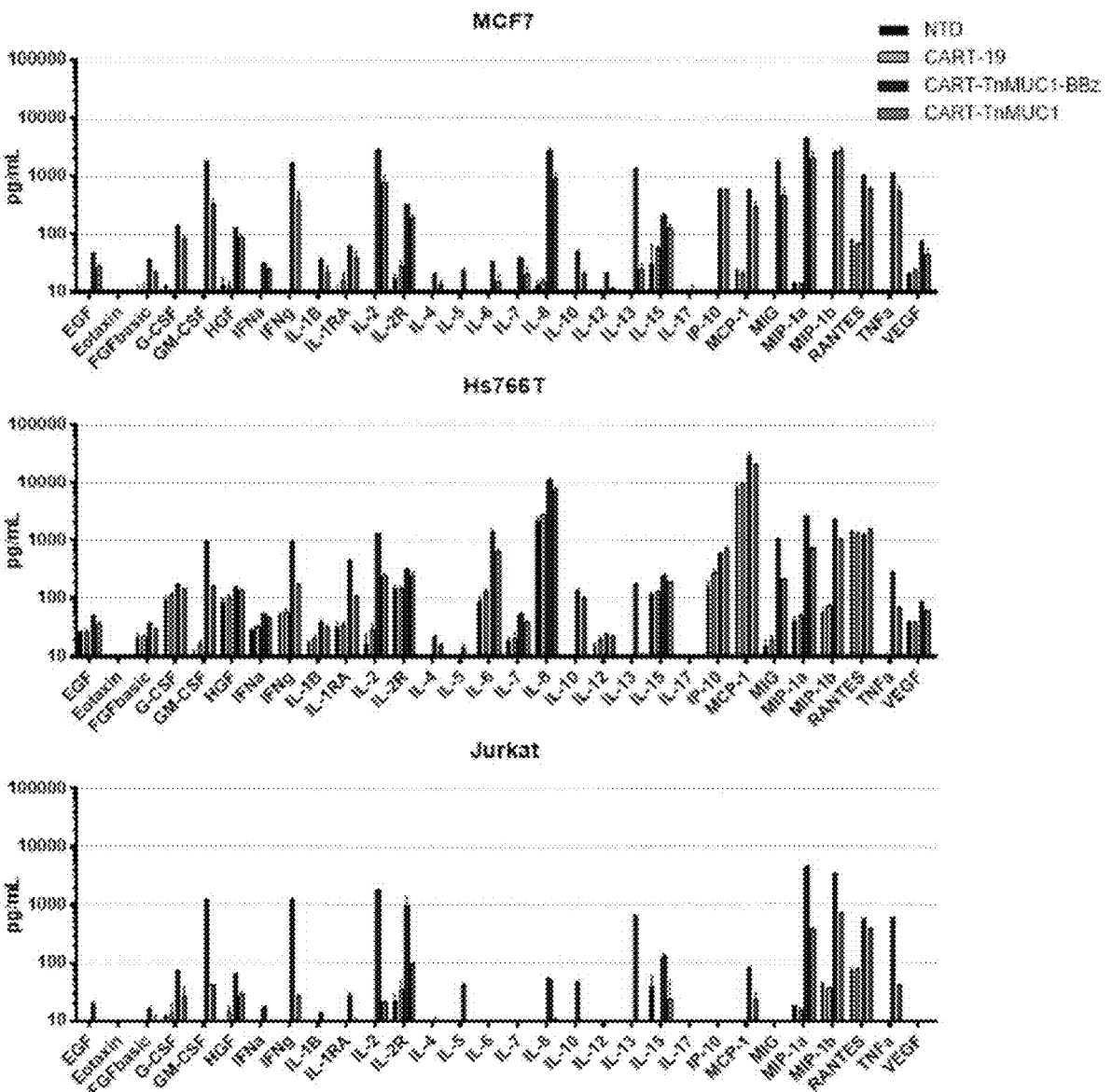
FIG. 18 is a series of graphs showing the production of cytokines and chemokines in various cell lines as indicated.

Antigen-Dependent Cytokine and Chemokine Production: The ability of CART-TnMUC1 cells to produce cytokines and chemokines in response to TnMUC1 was assessed by Luminex assay, a bead-based flow cytometry assay that simultaneously quantifies the production of a broad array of secreted factors (FIG. 18). Expanded CART-TnMUC1, analogue CART-TnMUC1-BBz, and the two negative control cell types CART-19 and NTD cells were thawed on Day 0 and incubated overnight to recover. On Day 1, cells were re stimulated with three TnMUC1+ target cell lines: MCF7 (breast cancer), Hs766T (pancreatic cancer), and Jurkat E6-1 (T cell leukemia) at a 2:1 effector to target ratio and cytokine profile in the cell growth media was assessed 24 hours later. The Luminex assay used specifically measures the following cytokines and soluble cytokine receptors: EGF, HGF, G-CSF, GM-CSF, IL-1B, IL-1R, IL-2, IL-2R, IL-4, IL-5, IL-6, IL-7, IL-10, IL-12, IL-13, IL-15, IFN-γ, TNF-α and VEGF; as well as the following chemokines: Eotaxin, IL-8, IP10, MCP-1, MIG, MIP-1α, MIP-1β, and RANTES.

FIG. 18 shows the production of cytokines and chemokines in various cell lines. Production of cytokines and chemokines by CART-TnMUC1, CART-TnMUC1-BBz analogue, and control cells (CART-19, and NTD) in response to TnMUC1+ targets as measured by Luminex. Supernatants were analyzed after 24 h coincubation of effector cells and targets at a 2:1 ratio.

The Luminex data demonstrate that CART-TnMUC1 cells produced numerous cytokines and chemokines in response to TnMUC1+ cell lines at levels superior to the negative controls and the two 5E5-based CART cells were broadly similar in their cytokine profile, albeit that overall levels of each factor trended lower with CART-TnMUC1 compared to CART-TnMUC1-BBz (FIG. 18). Without being bound by theory, this may be due to the lower CAR expression by CART-TnMUC1 and/or to differences in the signaling pathways. Specific cytokine production was evident against all three lines tested. Cytokine production favored a Th1-biased response, as the Th1-type cytokines including IFNg, TNFa, and IL-2 were secreted at much higher levels compared to Th17-type (IL-17) and Th2-type (IL-4, IL-5, IL-13, and IL-10) cytokines. In addition to trending towards lower production of each factor, CART-TnMUC1 cells differed from CART-TnMUC1-BBz cells in that production of IL 13 was minimal or absent with the former, whereas the latter secreted IL-13 against all three targets (FIG. 18). IL-13 has previously been observed as part of the cytokine profile of BBz-based CARs (Xue et al. (2017) *J Immunother Cancer,* 5:85).

Figure 19:
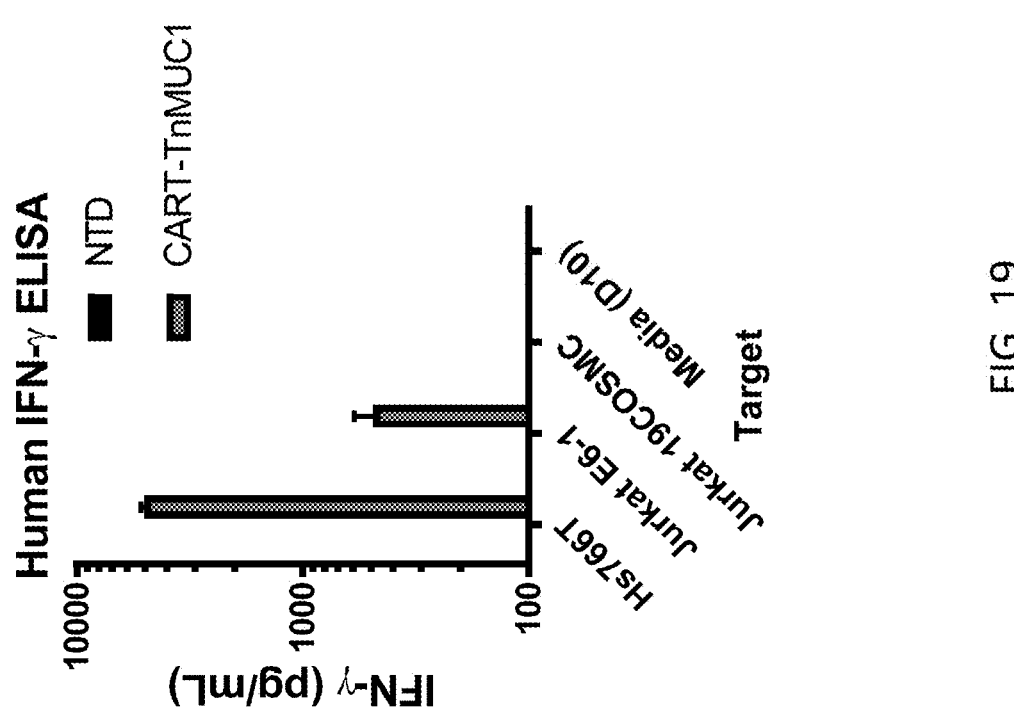
FIG. 19 is a graph showing data obtained from an IFNγ ELISA experiment.

The production of IFNγ was measured in an enzyme-linked immunosorbent assay (ELISA) following the coincubation of CART-TnMUC1 with TnMUC1+Hs766T, and Jurkat E6-1 cells and TnMUC1-Jurkat 19COSMC cells (FIG. 19). Significant IFNγ production was seen in response to TnMUC1+ but not TnMUC1-cell lines for CART-TnMUC1 but not for NTD control cells. These data further support the specificity and potential anti-tumor activity of CART-TnMUC1.

FIG. 19 shows data obtained from an IFNγ ELISA experiment. Cytokine secretion by CART-TnMUC1 cells or NTD cells was measured after 24 hour co-cultures at 2:1 E: T ratio with antigen positive (Hs766T, Jurkat E6-1) or antigen negative (Jurkat CD19-P2A-COSMC) cell lines or media alone. IFNγ in the co-culture supernatant was quantified in pg/mL.

Overall, these data demonstrate the specific production of cytokines and chemokines when CART-TnMUC1 or CART-TnMUC1-BBz cells are exposed to TnMUC1+ targets. Without being bound by theory, the profile is suggestive of a Th1-biased response due to the preponderance of IL-2, IFN-γ and TNF-α over IL-4, IL-5, IL-13 and IL-17, especially for CART-TnMUC1 cells which showed very little production of IL-13 compared to CART-TnMUC1-BBz cells. Th1-biased immune responses are known to support various aspects of anti-tumor immunity including the proliferation and cytotoxicity of CD8 T cells.

The monocyte/macrophage derived cytokines IL-6 and IL-1 may play a role in the pathogenesis of CART-related toxicities such as CRS. Monocyte/macrophages produce these cytokines in response to T cell cytokines and chemokines including GM-CSF, MIP 1a and IFNg, and potentially also through direct activation of monocytes/macrophages by CD4+ CART cells via the CD40L-CD40 interaction (Giavridis et al. (2018) *Nature Medicine,* 24:731-738; Norelli et al. (2018) *Nature Medicine* 24:739-748; Rooney et al. (2018) *Nature Medicine,* 24:705-706; Teachey et al. (2016) *Cancer Discov,* 6:664-679).

FIG. 18 shows that for each target cell line, CART-TnMUC1 cells elaborated lower amounts of GM-CSF, MIP-1a and IFNg (as well as IL-1B/IL-1RA and IL-6) when compared with CART-TnMUC1-BBz.

Together the nonclinical data for the two versions of CAR-T cells tested (CART-TnMUC1 and CART-TnMUC1-BBz) demonstrate antigen-specific production of Th1-biased cytokines and chemokines, which may support the in vivo function of CART cells as well as endogenous tumor-specific immune responses.

Antigen-Dependent CD40L Expression: The expression of CD40L by activated CD4 T cells can stimulate antigen-presenting cells including dendritic cells, B cells and macrophages via CD40 and contribute to an integrated immune response to the tumor. Indeed, the activation of antigen presenting cells via the CD40-CD40L pathway is a key mechanism of T cell 'help' for immune responses including the development of anti-tumor CD8 T cells (Toes et al. (1998) *Semin Immunol,* 10(6): 443-448). While activation of this pathway may be beneficial to tumor control, the activation of monocytes and macrophages by CD4+ CART cells may also contribute to toxicities such as CRS (Giavridis et al. (2018) *Nature Medicine,* 24:731-738; Norelli et al. (2018) *Nature Medicine* 24:739-748; Rooney et al. (2018) *Nature Medicine,* 24:705-706).

CD40L expression by CD4+ CART-TnMUC1 and CART-19 (BBz) cells was studied via flow cytometry after 24 hours of coincubation with TnMUC1 and CD19 positive and negative cell lines. Both CARTs upregulated CD40L in an antigen-specific manner. While basal levels of CD40L were similar, CART-19 showed approximately twice as much upregulation of CD40L in response to CD19 positive targets as CART-TnMUC1 did in response to TnMUC1 positive targets. The results demonstrate that CART-TnMUC1 and CART-19 are both able to upregulate CD40L expression by CD4 T cells in response to their respective antigens, and that CD40L expression levels were lower for CART-TnMUC1 than CART-19.

Pharmacokinetics and Product Metabolism in Animals

Expansion of CART-TnMUC1 in Murine Model: The expansion and persistence of CART-TnMUC1 cells was determined in the Hs766T pancreatic tumor NSG immuno-deficient mouse model. Since the murine MUC1 lacks the epitope for scFv 5E5 (Spicer et al. (1991) *Journal of Biological Chemistry*, 266:15099-15109), the expansion, persistence, and trafficking in this model reflects the background seen with NTD cells plus any specific signals derived from interaction with the TnMUC1+ tumor.

The levels of CART-TnMUC1 cells in the peripheral blood was measured in this experiment by retroorbital bleed at two time points: Day 21 and 42 post CART infusion (FIG. 20).

Figure 20:
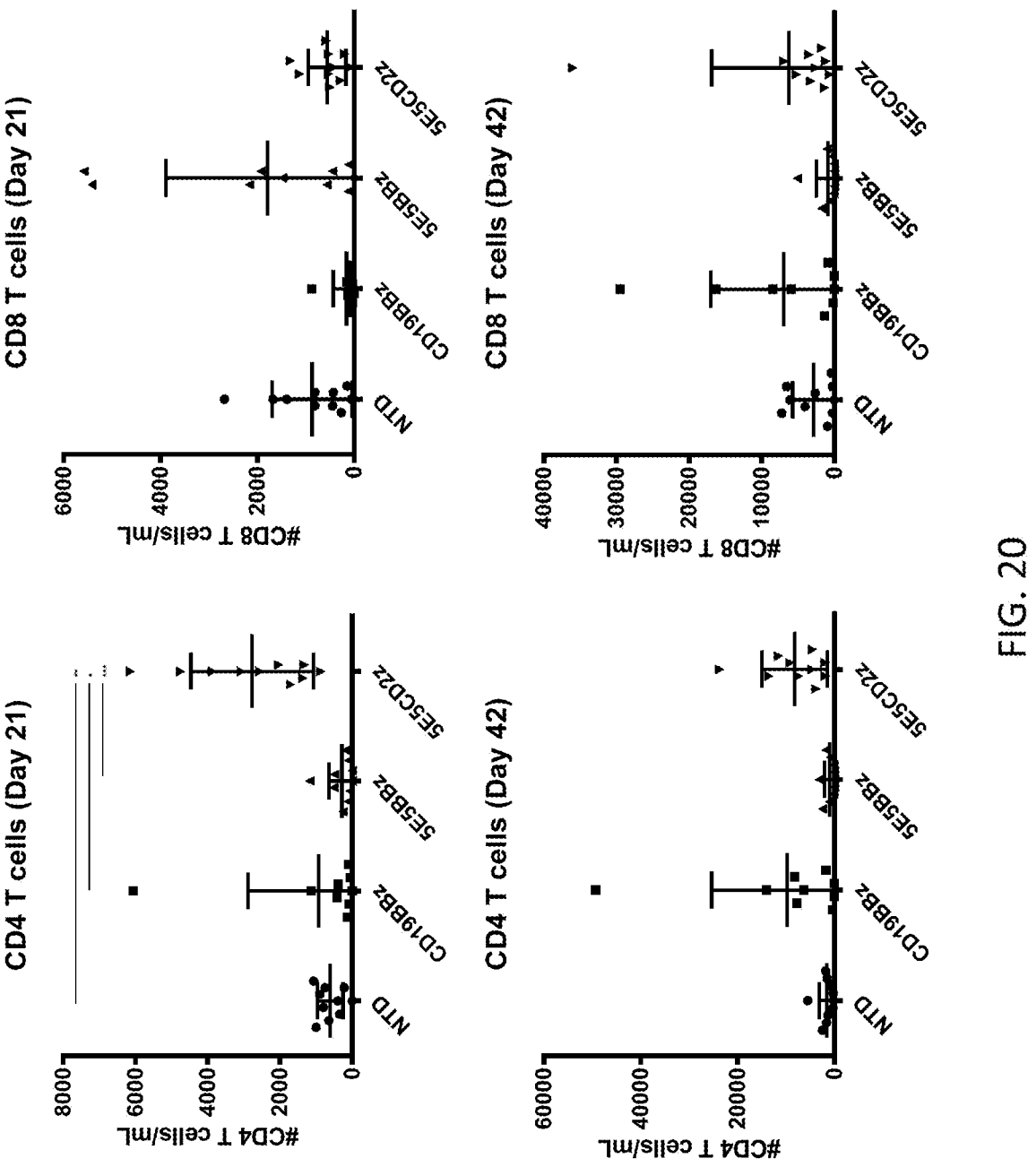
FIG. 20 is a series of graphs showing the quantitation of various T cells as indicated, in peripheral blood of mice at days 21 and 42 post-T cell infusion.

FIG. 20 shows the quantitation in peripheral blood of mice at Days 21 and 42 post-T cell infusion. NSG mice were injected with CBG+Hs766T cells and treated with CART-TnMUC1, CART-TnMUC1-BBz, CART-19, or NTD cells. Blood was collected via retro-orbital bleeding, lysed, and stained in order to detect human T cells. TruCount beads were used to quantify number of CD4+ and CD8+ T cells per microliter (μl) of blood. $*=p<0.005$; $**=p<0.01$; $*=p<0.05$ by one-way ANOVA with Tukey's multiple comparison test. Bars represent standard deviation.

At 21 days post infusion, mice treated with the CART-TnMUC1 had higher mean average numbers of human CD4+ T cells in the peripheral blood (2,774 cells/mL) as compared to all other groups, including the mice treated with CART-TnMUC1-BBz (290.4 cells/mL, ~10-fold difference) and the mice treated with NTD cells (614.8 cells/mL~4.5-fold difference). In the CD8 compartment there was an opposing trend to a smaller ~3-fold increase of CD8+ CART-TnMUC1-BBz cells versus CD8+ CART-TnMUC1 cells.

At Day 42 there were no significant differences in CD4 or CD8 T cells. With the exception of CD8+ CART-TnMUC1-BBz cells, the mean average cell number increased in each group between Day 21 and Day 42. Since the controls also expanded this may indicate a contribution of a nonspecific xeno-reactive response to the MHC of the mouse host, and potentially an allo-reactive response to any mismatched HLA alleles of the Hs766T tumor cell line. At Day 42, CART-19 and CART-TnMUC1 had the greatest mean average human T cell numbers in the peripheral blood at 9,767 CD4+ and 6,798 CD8+ for CART-19 and 8,254 CD4+ and 6,293 CD8+, at levels approximately 7-10-fold those seen with CART-TnMUC1-BBz at 975.3 CD4+ and 896.4 CD8+. Therefore, there was a trend for superior expansion and persistence of CART-TnMUC1 at Day 42.

Together, these data suggest that CART-TnMUC1 cells proliferate in response to TnMUC1+ target cells in vivo, and the expansion of the CD4 cell component of the CART-TnMUC1 product is significantly improved at Day 21 compared to the other test groups, with a trend to superior expansion of CART-TnMUC1 CD4 and CD8 cells compared to CART-TnMUC1-BBz at Day 42. Long-term effects were not followed as the experiment was terminated at Day 63, and alloreactive human T cells in all groups will continue to expand in NSG mice mediating xGVHD.

Toxicology

Specificity of mAb 5E5 and 5E5-based CART's: The 5E5 scFv was derived from mAb 5E5 which has previously been shown to bind an epitope comprised of Tn or STn glycans attached to the Ser and Thr residues of the GSTA amino acid sequence of the MUC1 variable number tandem repeat (VNTR) domain. The mAb 5E5 does not bind to other glycoforms of MUC1 including unglycosylated, other aberrant glycoforms or biosynthetic intermediates (T, ST, Core 3), or fully glycosylated forms, and shows minimal binding to Tn haptens at high hapten concentrations, with this specificity reproduced when the 5E5 scFv is used in the CART format (Posey et al. (2016) *Immunity*, 44:1444-1454; Sørensen et al. (2006) *Glycobiology*, 16:96-107; Tarp et al. (2007) *Glycobiology*, 17:197-209).

Immunoblot studies conducted on whole cell lysates of tumor cells further showed that mAb 5E5 binds only to a single band of >200 kDa in DU145 prostate cancer cells, which is also detected by anti-MUC1 mAb HMFG1, which is known to bind the APDTR amino acid sequence of the MUC1 VNTR and recognizes all MUC1 glycoforms (Price et al. (1997) *Tumor Biology*, 19:1-20; Taylor-Papadimitriou et al. (1981) *Biochim Biophys Acta*, 1455:301-313). The recognition by mAb 5E5 of a single band in the whole cell lysates supports a lack of cross-reactivity to other antigens in the proteome of DU145 cells, and thus limited off-target risk. CART-TnMUC1 cells were incubated with primary human cell types that strongly expressed MUC1 and minimal cytotoxicity or cytokine production was observed indicating that the normal glycoform of MUC1 is not recognized and TnMUC1 is an intracellular biosynthetic intermediated in healthy MUC1 positive cells.

Taken together, these lines of evidence indicate that CARs derived from mAb 5E5 retain specificity for Tn or STn glycoforms of the GSTA amino acid sequence of the VNTR domain of MUC1. In vitro cell line models not expressing the TnMUC1 antigen on the cell surface are not targeted by the CART-TnMUC1 cell based approach. The epitope for this antibody includes both the specific glycan haptens and the peptide backbone of MUC1, with minimal binding to Tn/STn haptens outside this context, and no binding to MUC1 where the glycans are either absent, restricted to T-, ST- or Core 3-glycans, or represent the normal complex glycans observed in healthy cells. No off-target reactivity of mAb 5E5 has been demonstrated. This specificity to an aberrant glycoform of MUC1 is expected to increase the selectivity for tumor cells.

Normal Tissue Cross-Reactivity of mAb 515: To identify potential target tissues for CART-TnMUC1 a Good Laboratory Practice (GLP) tissue cross-reactivity study was conducted using mAb 5E5 on a panel of 36 normal human tissues. This study utilized an average of four donors per tissue type, three concentrations of mAb 5E5 and isotype control. The panel of normal human tissues included: adrenal, bladder, blood vessels, bone marrow, brain (cerebellum, cerebral cortex, and pituitary gland), breast, cardiac muscle, esophagus, eye, fallopian tube, gastrointestinal tract (stomach, small intestine, colon), heart, kidney (cortex, medulla), liver, lung, lymph node, mesothelial cells, ovary, pancreas, placenta, prostate, salivary gland, skeletal muscle, skin, spinal cord, spleen, testis, thymus, thyroid gland, tonsil, ureter, and uterus (cervix, endometrium). The goal of the study was to determine the potential tissues that could be at risk in the clinic for the observation of on-target/off-tumor activity of the CART-TnMUC1. The study was designed to identify the tissues with either strong cytoplasmic expression and/or membranous expression.

At the highest concentration of antibody tested in the tissue cross reactivity study, five tissues were identified with TnMUC1 expression observed in more than 75% of the donors tested: (1) stomach, 100%; (2) kidney, 89%; (3) pancreas, 86%; (4) colon, 83%; and (5) lung, 75%. Only cytoplasmic expression is noted in all of these tissues, thought to have limited accessibility to the CART-TnMUC1, given the mechanism of action. Tissues that stained in a smaller proportion of cases also showed only cytoplasmic staining.

In summary, the studies performed with mAb 5E5 demonstrate that TnMUC1 expression by 5E5 IHC is evident in tissues reported to be MUC1 positive in protein expression ((Uhlen et al. (2015) *Science,* 347(6220)), Human Protein Atlas www.proteinatlas.org), and gene expression ((Carithers et al. (2015) *Biopreserve Biobank,* 13(5): 311-319) website: gtexportal.org/) databases, with the more intense cytoplasmic expression noted in the epithelial of the stomach and tubules of the kidneys. The expression pattern is largely intracellular with no definitive evidence for membranous expression, and this is supported by confocal microscopy and is consistent with the role of TnMUC1 as a biosynthetic intermediate in the synthesis of normal fully glycosylated MUC1.

In vitro Toxicology: CART-TnMUC1 cytotoxicity and cytokine expression in response to minimally cultured primary human cells was determined in vitro using a panel of cells selected on the basis of covering the range of MUC1 transcript and protein expression levels reported in public databases, and on the results of the GLP tissue cross-reactivity study. The tumor cell lines Hs766T (pancreatic cancer) and MCF7 (breast cancer) served as positive controls, while primary bladder smooth muscle cells served as an antigen negative control. All cells were assessed for MUC1 transcript expression via qPCR, and for TnMUC1 expression via immunocytochemistry using mAb 5E5, and produced the expected patterns of MUC1 and TnMUC1 expression.

In vitro Cytotoxicity: To measure cytotoxicity, the xCELLigence method over a 24-hour assessment was implemented, CART-TnMUC1 and NTD cells were then added at a range of E: T ratios and the impedance followed for a further 6 days. The detergent Triton™-X was used as a positive lysis control, and specific lysis signal determined as the percent lysis in comparison to Triton™-X once the background activity with NTD cells had been subtracted. Subtraction of the background activity at each E: T ratio controls for potential alloreactivity-mediated lysis and any disturbance in the culture due to effects of adding various amounts of T cells.

CART-TnMUC1 cells killed Hs766T tumor cells efficiently at high E: T ratios. They did not induce cytolysis or exhibited minimum reactivity against primary human stomach epithelial cells, esophageal epithelial cells, and colonic epithelial cells. CART-TnMUC1 cells lysed bladder smooth muscle cells and kidney epithelial cells, but only at high E: T ratios and to a lesser degree than Hs766T cells. Since the bladder smooth muscle cells were selected as a negative control, but had low levels of MUC1 RNA (70- to 870-fold less than the epithelial cells) and minimal 5E5 staining, and did not elicit many cytokines/chemokines at high levels, the lytic activity against this presumed negative control target is difficult to interpret. Low levels of CART cell-mediated cytolysis were observed with mammary and pancreatic epithelial cells at several different E: T ratios.

These data showed that while some lytic activity was seen for CART-TnMUC1 against kidney epithelial cells in the xCELLigence assay, it was similar in extent to the negative control bladder smooth muscle cells, and there was no lytic activity against kidney epithelial cells or kidney cortical epithelial cells in a classical 51Cr release assay using CART-TnMUC1-BBz.

In vitro Chemokine Cytokine Production: To measure cytokine and chemokine production, target cells, CART-TnMUC1 and NTD cells were coincubated at a 3:1 E: T ratio for 24 hours and the concentration of cytokines and chemokines in the supernatants determined by Luminex.

In general, low to intermediate levels of various cytokines, chemokines, and growth factors were produced by several primary normal human cell types following exposure to CART-TnMUC1 cells for 24 hours. CART-TnMUC1 cells were not as reactive against any of the primary normal human cells compared to positive control Hs766T cells, in terms of both the variety and levels of cytokines/chemokines produced. Similarly, CART-TnMUC1-BBz cells did not express levels of IL-2, TNFa or CD107a at levels above the background seen with CART-19 cells against the healthy cell panel in an intracellular cytokine staining assay.

Together, the in vitro toxicology data suggest that 5E5-based CART cells do not respond to normal healthy cells with appreciable levels of cytokines, and minimal cytotoxicity is seen against select cell types.

In vivo Toxicology in NSG Mice Tumor Model: The potential off-target toxicology of CART-TnMUC1 cells was determined in the Hs766T pancreatic tumor NSG immunodeficient mouse model as described. The clinical observations, body weight, and survival for each of the study animals were recorded. There were no unexpected toxicities reported after treatment with TnMUC1-targeting CART cell therapy. In all the animals, except for two in the NTD group, immune cell infiltrates (predominantly composed of lymphocytes) were observed in most of the examined organs and tissues. The severity and distribution of these infiltrates varied among the affected animals. Lesions were observed in nearly all mice who underwent necropsy, which showed the typical features of xenogeneic/allogeneic GvHD. This is a recognized artifact characteristic of the NSG mouse model (Garcia, et al. (1997) *Blood,* 89(1): 329-336), and is not a direct effect of treatment with CART-TnMUC1.

Example 8: TnMUC1 Clinical Trial Assay

A TnMUC1-specific Immunohistochemistry (IHC) prototype assay was developed using mAb 5E5, which was produced by the hybridoma method from mice immunized with a Tn glycosylated 60-mer MUC1 peptide containing 3 repeats of the VNTR domain (Sørensen et al. (2006) *Glycobiology,* 16:96-107).

Using this assay with positive (Jurkat) and negative (Jurkat CD19t-P2A-COSMC) control samples, an analysis was conducted to determine the proportion of cases in selected malignancies that had membranous staining. Results from this analysis and published studies indicate that TnMUC1 may be expressed in ~25%-40% of multiple myeloma cases (Andrulis et al. (2014) *Histopathology,* 64:799-806; Cloosen et al. (2006) *British Journal of Haematology,* 135:513-516), and at least 50% of cases of adenocarcinomas of the breast, lung, pancreas and ovary (Pinto et al. (2012) *J Cellular Mol Medicine*, 16:1474-1484; Sørensen et al. (2006) *Glycobiology*, 16:96-107).

Built upon the prototype assay, TnMUC1 CTA was developed on Thermo Scientific Lab Vision Autostainer and validated on DAKO Autostainer Link 48 to detect the TnMUC1 glycoprotein in FFPE tissue blocks derived from human carcinoma tissues. TnMUC1 CTA will be used as a Clinical Trial Assay (CTA) to aid the selection of patients enrolled into the first-in-human (FIH) phase 1 clinical study for the treatment of CART-TnMUC1 (see, Example 9).

As described herein, the FIH study will enroll TnMUC1-positive patients with ovarian cancer (including cancers of the fallopian tube), non-squamous non-small cell lung cancer (NSCLC), pancreatic adenocarcinoma, breast cancer and multiple myeloma. The Phase 1 portion of the trial is anticipated to enroll approximately 40 patients total (approximately 22 patients in Arm 1 and 18 patients in Arm 2). In the Phase 1a expansion with a Simon 2-stage design (Simon (1989) *Control Clin Trials*, 10:1-10), approximately 40 patients with platinum-resistant ovarian cancer are anticipated to be enrolled. TnMUC1 CTA will be used to support the phase 1 portion of the study and further developed to support the phase 1a portion of the study in ovarian cancer patients.

Materials and Reagents: The TnMUC1 CTA uses several reagents required to complete an IHC staining procedure for FFPE specimens on DAKO Autostainer Link 48 automated staining platform, as listed in Table 6:

priately to preserve the tissue for IHC staining. Standard methods of FFPE tissue processing are used for all specimens. Tissue sectioning, mounting on charged microscope slides and storage must follow the TnMUC1 CTA standard operating procedure (SOP). FFPE tissue blocks are cut into sections of 4 μm, mounted on charged microscope slides, baked for 2 hrs at 60° C. prior to staining and stored in the dark at 2-8° C. An aging study will be performed to determine slide stability as part of the TnMUC1 CTA development in supporting the development of CART-TnMUC1.

Figure 21:
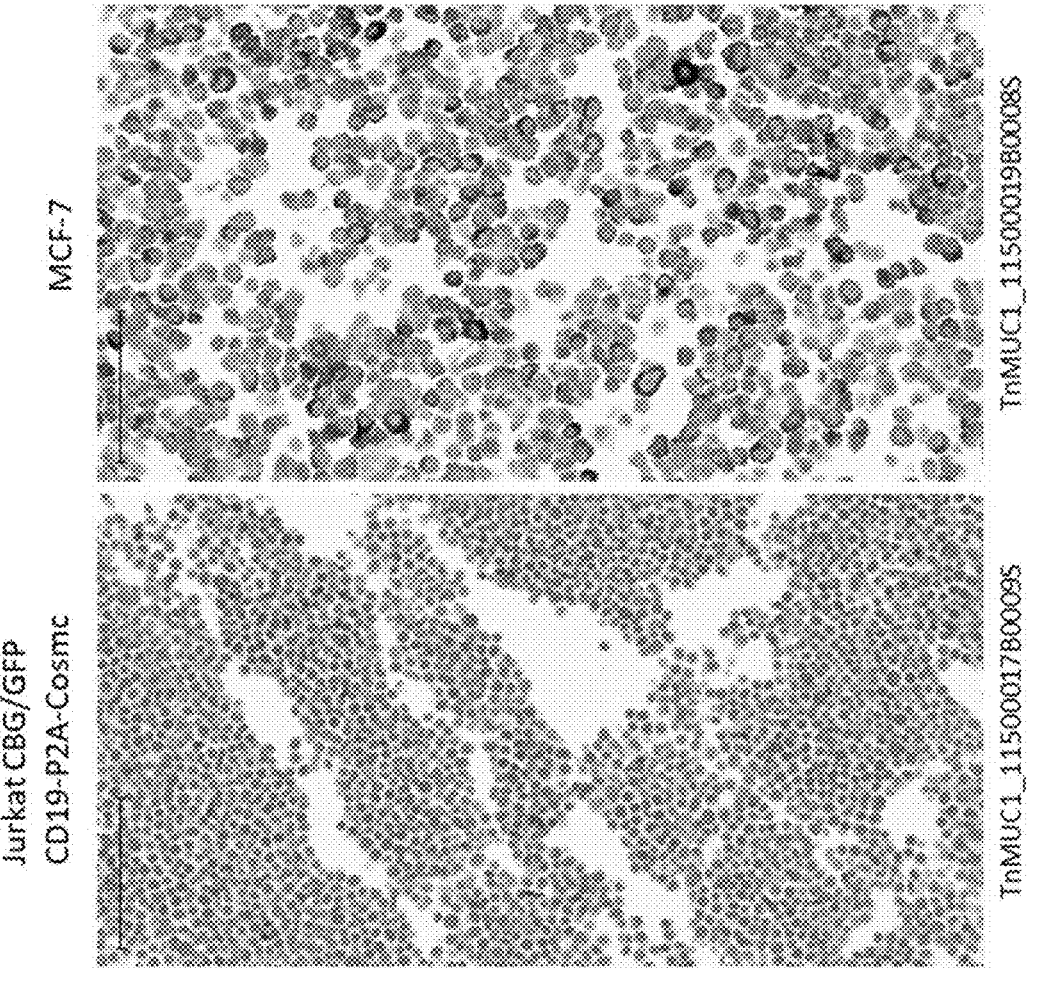
FIG. 21 are micrographs of Jurkat CBG/GFP CD19-P2A-Cosmc cells (left) and MCF-7 cells (right) stained with an anti-TnMUC1 antibody.

Assay Run Controls: One run control block containing a TnMUC1 positive and a TnMUC1 negative cell line, together with a TnMUC1-positive tumor with adjacent normal tissue (negative for TnMUC1) is used. Representative images of TnMUc1 positive and TnMUC1 negative cell lines are shown in FIG. 21.

In each run, 2 slides of the run controls are included, one stained with the primary antibody as the positive control and one with the IgG isotype as the negative control. The evaluation of the control slides indicates the validity of the staining run.

Principles of Operation: A Standard Operating Procedure (SOP) is established to describe the validated TnMUC1 CTA. The SOP provides details on the entire test system, including instrument, materials, reagents and step-by-step instructions for executing the staining protocol.

TABLE 6

List of materials and reagents for TnMUC1 CTA

| Process | Details |
|---|---|
| Sectioning | 4 μm from FFPE block |
| Deparaffinization and Epitope retrieval | EnVision ™ FLEX Target Retrieval Solution (TRS) Low pH (Agilent K8005) on DAKO PT Link Module |
| Blocking agent | EnVision ™ FLEX Peroxidase Block (SM801) |
| Primary antibody | Anti-TnMUC1 murine monoclonal antibody clone 5E5 (Wuxi Biologics) |
| | Murine IgG1, kappa monoclonal [MG1-45] - Isotype control (Abcam ab18448) |
| Antibody diluent | Dako REAL ™ Antibody Diluent (Agilent S2022) |
| Detection system and Visualization | EnVision ™ FLEX/HRP detection reagent (Agilent SM802), EnVision ™ FLEX DAB+ Chromogen (Agilent DM827), EnVision ™ FLEX Substrate Buffer (Agilent SM803) |
| Counterstaining | EnVision ™ FLEX Hematoxylin (Agilent K8008, SM806) |
| Wash Buffer | EnVision ™ FLEX Wash Buffer (Agilent K8007, DM831) |
| Dehydration | Ethanol 96% Ethanol absolute Xylene |
| Coverslipping | Sakura Tissue Tek Prisma automated slide stainer and film cover-slipper |

Instrumentation and Software: TnMUC1 CTA will be performed on DAKO Autostainer Link 48 automated staining system with embedded software that is designed to mimic the staining steps performed manually by a lab technician. The TnMUC1 CTA staining protocol is programmed to recognize and use all system reagents together.

A calibration certificate/data sheet is available for each DAKO Autostainer Link 48 instrument that certifies that the instrument has been tested and meets all specifications. After installation at the testing lab, all DAKO Autostainer Link 48 systems are internally qualified and maintained according to vendor specifications. The instruments are driven by Dako Link software version 4.0 installed on a dedicated PC.

Specimen Preparation: An archived tumor biopsy sample will be submitted to the central laboratory to determine the TnMUC1 status. Tumor specimens must be handled appro- The IHC staining procedure is performed using the Dako Autostainer Link 48 platform and an automated staining protocol validated for the TnMUC1 CTA assay. Deparaffinization, rehydration and target retrieval are performed in the PT Link module (Dako PT100) using a 3-in-1 procedure. After incubation with the monoclonal murine antibody, clone 5E5, or the negative control reagent (murine immunoglobulin G1 isotype control), specimens are first incubated with anti-mouse linker antibody specific to the host species of the primary antibody, and then with a ready-to-use visualization reagent consisting of secondary antibody molecules and horseradish peroxidase molecules coupled to a dextran polymer backbone. The enzymatic conversion of the subsequently added 3,3-diaminobenzidine tetrahydrochloride chromogen followed by 3,3-diaminobenzidine tetrahydrochloride enhancer results in the precipitation of a visible reaction product at the site of antigen. The specimens are then counterstained with hematoxylin and cover-slipped. Results are interpreted using a light microscope.

An outline of the staining protocol is provided in Table 7:

TnMUC1 CTA Validation: The processes for assay development and validation are documented and acceptance criteria for TnMUC1 CTA concerning specificity, sensitivity, repeatability and reproducibility are pre-specified.

TABLE 7

| Staining protocol outline | |
|---|---|
| 3-in-1 Specimen preparation on DAKO PT Link Module: | EnVision ™ FLEX Target Retrieval Solution (TRS) Low pH |
| Deparaffinization | Preheat at 65° C. |
| Re-hydratation | 20 minutes at 97° C. |
| Epitope pretreatment | Cool down to 65° C. |
| Slide staining on Dako Autostainer Link 48 (3 drop zones) | Rinse with EnVision ™ FLEX Wash Buffer |
| | EnVision ™ FLEX Peroxidase Block |
| | 5 minutes |
| | Rinse with EnVision ™ FLEX Wash Buffer |
| | Primary antibody - 30 minutes |
| | Rinse with EnVision ™ FLEX Wash Buffer |
| | Rinse with EnVision ™ FLEX Wash Buffer |
| | EnVision ™ FLEX/HRP detection reagent |
| | 30 minutes |
| | Rinse with EnVision ™ FLEX Wash Buffer |
| | Rinse with EnVision ™ FLEX Wash Buffer |
| | EnVision ™ FLEX DAB+ Chromogen, EnVision ™ FLEX Substrate Buffer |
| | 5 minutes |
| | EnVision ™ FLEX DAB+ Chromogen, EnVision ™ FLEX Substrate Buffer |
| | 5 minutes |
| | Rinse with EnVision ™ FLEX Was Buffer |
| | EnVision ™ FLEX Hematoxylin |
| | 5 minutes |
| | Rinse with DI water |
| | Rinse with EnVision ™ FLEX Wash Buffer |
| | Rinse with DI water |
| Manual dehydration | 1 min ± 10 sec in ethanol 96% vol |
| | 1 min ± 10 sec in ethanol 96% vol |
| | 1 min ± 10 sec in ethanol absolute |
| | 1 min ± 10 sec in ethanol absolute |
| | 2 min ± 20 sec in xylene |
| | 2 min ± 20 sec in xylene |
| Coverslipping on Sakura | Automated |

Interpretation of 5E5 Staining: Interpretation of TnMUC1 CTA staining results will be performed by a certified pathologist at the central lab, a CAP-CLIA certified and BELAC (ISO15189) accredited, global laboratory with a fully developed quality management system (QMS).

Only viable tumor cells are evaluated and included in the assessment. A minimum of 100 viable tumor cells must be present for the specimen to be considered adequate for evaluation. Specific cell types are excluded from scoring, including: (1) Tumor associated immune cells of any type (lymphocytes, macrophages, plasma cells, neutrophilic granulocytes, etc.); (2) Tumor associated stroma cells; (3) Areas of necrosis; and (4) Normal cells adjacent to tumor cells.

To successfully determine positive staining, the proper subcellular localization of the signal needs to be identified. Given the mechanism of action of CART-TnMUC1, the assessment of the TnMUC1 IHC images will focus on the membrane staining (partial or complete circumferential). The number of tumor cells (of 100 counted) with any membrane expression will be measured.

The cut-point for inclusion in the trial is based on the count/percent of tumor cells with membrane expression. At the commencement of the trial, a tumor specimen is considered TnMUC1-positive if at least 10% of tumor cells counted demonstrates membrane expression. As CART-TnMUC1 development progresses with more clinical data accumulating, the cut-point value will continue to be evaluated.

Specificity:

The specificity of mAb 5E5 was confirmed via Western Blot studies using whole cell lysates of the prostate cancer cell line DU145. mAb 5E5 stained a single band of >200 kDa representing mature TnMUC1, which was also stained with the anti-MUC1 VNTR protein backbone-directed mAb HMFG1.

The specificity of TnMUC1 CTA is demonstrated by tests performed on FFPE cell pellets with a known TnMUC1 expression pattern and on FFPE control tissues known to be TnMUC1 negative (adipose tissue) as well as TnMUC1 positive (healthy pancreas cytoplasmic staining).

Figure 22:
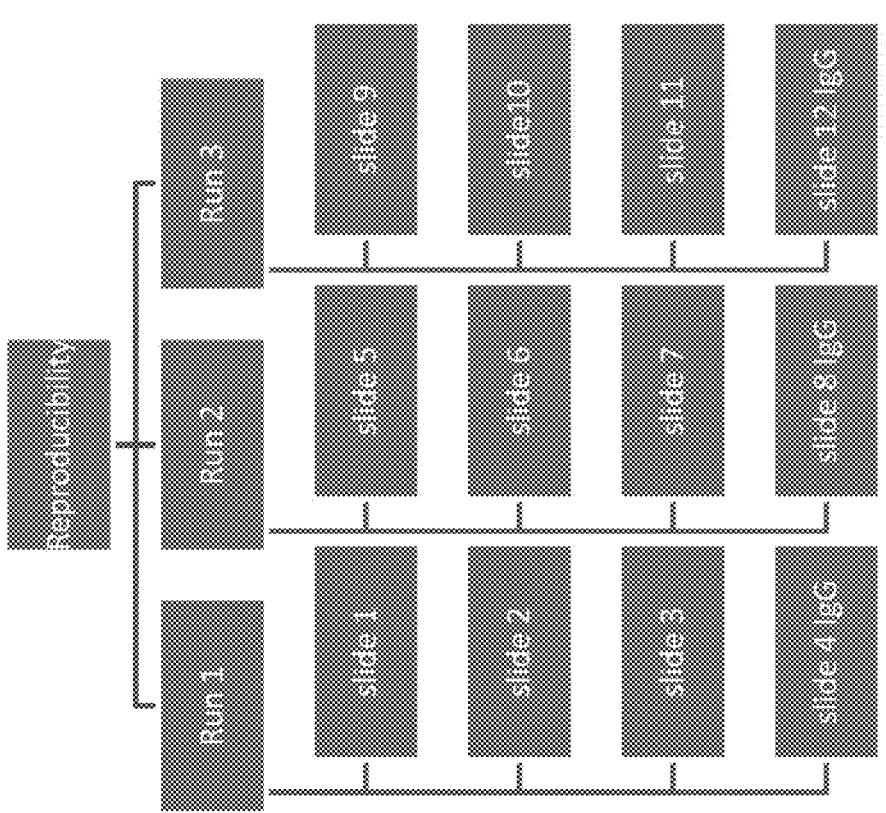
FIG. 22 is a schematic showing the experimental setup for testing the reproducibility of the TnMUC1 CTA assay.

Sensitivity: To test the sensitivity of the assay, a dilution series of the primary antibody has been tested to get the most optimal signal to noise ratio. Repeatability (intra-run variability) and reproducibility (inter-run variability):

Repeatability of the assay is assessed on five different tissue blocks over three different runs. The experimental set up is shown in FIG. 22.

In summary, the TnMUC1 CTA has been developed and analytically validated for the detection of TnMUC1 glycoprotein antigen in cancer tissues. The assay is intended as an aid in screening patients with an acceptable level of cell membrane TnMUC1 expression in a tumor sample. Patients with a defined TnMUC1+ tumor sample can be considered to participate in the CART-TnMUC1-01 FIH trial described herein and will be then assessed against the study inclusion/exclusion criteria as described herein.

Example 9: CART-TnMUC1-01 Clinical Study

Cloning Strategy

Figure 23:
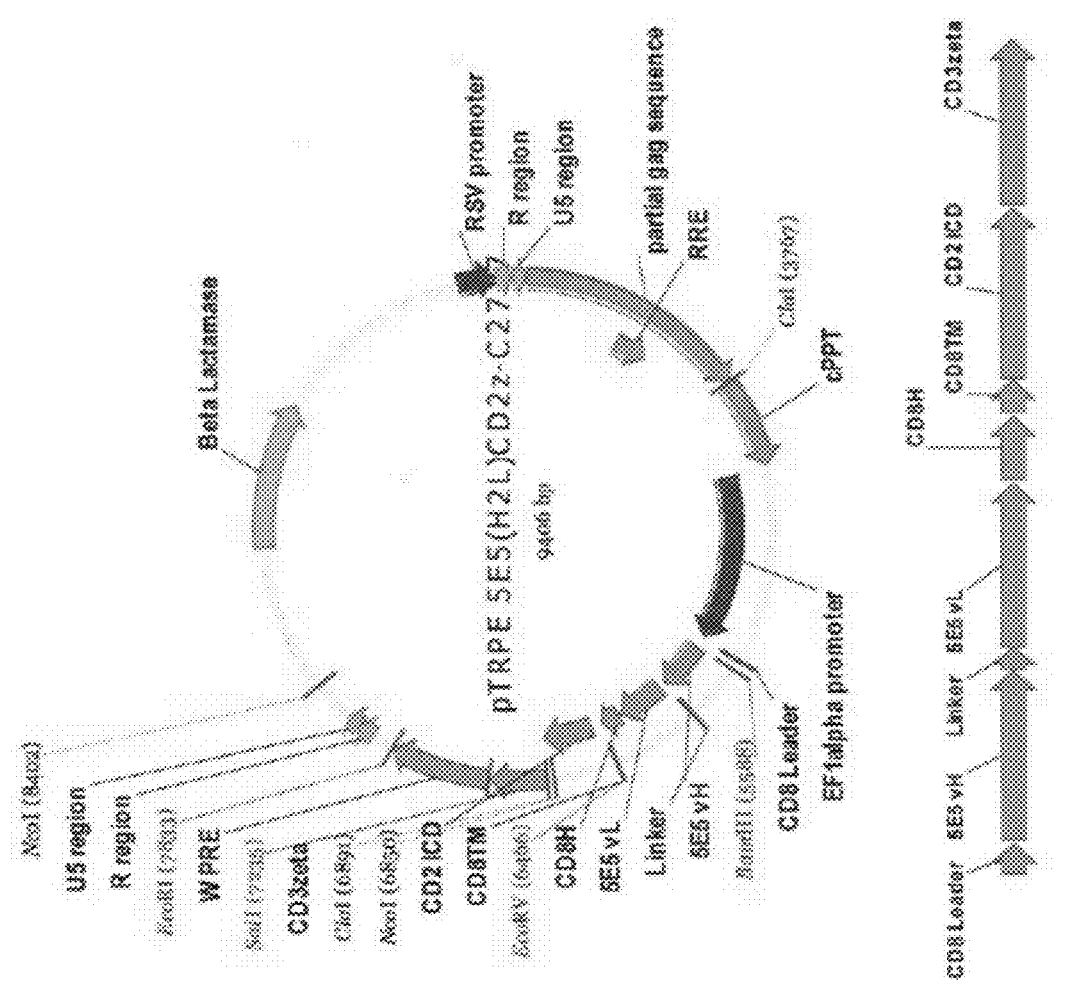
FIG. 23 is a schematic of the plasmid map of pTRPE_5E5 (H2L)_CD2z.

This section describes the cloning strategy performed to generate the lentiviral vector pTRPE_5E5 (H2L)_CD2z that is the source for GMP plasmid production to be used to transduce cells to create the CART-TnMUC1 cells used for clinical investigation. The pTRPE_5E5 (H2L)_CD2z vector was verified using open reading frame analysis, confirmatory restriction digests, and by sequencing the entire vector (see, FIG. 23 for a plasmid map of pTRPE_5E5 (H2L) _CD2z). Table 8 shows the transgene elements of the vector.

TABLE 8

Origin and Source of Transgene Elements

| Transgene element | Origin | Source |
|---|---|---|
| Human CD8a leader sequence | Human | de novo synthesized sequences of UPenn CD19 CAR construct (IND 13960) |
| 5E5 scFv | Murine | de novo synthesized from hybridoma sequences |
| Human CD8a hinge and transmembrane (TM) | Human | de novo synthesized from the sequences of UPenn CD19 CAR construct (IND 13960) |
| CD2 intracellular signaling domain (ICD) | Human | Originally amplified from normal donor human T cell cDNA and cloned through overlapping PCR into pGEM-SS1CD2z vector |
| CD3zeta signaling chain | Human | de novo synthesized from the sequences of UPenn CD19 CAR construct (IND 13960) |

The pTRPE lentiviral vector was de novo synthesized based on the pELPS lentiviral vector. pTRPE lentiviral vector is a derivative of the third generation, self-inactivating lentiviral expression vector pRRL-SIN-CMV-eGFP-WPRE (see, Dull et al. 1998) modified by replacing the CMV promoter with the EF-1alpha promoter and adding the cPPT sequence. The pTRPE lentiviral vector also contains the rev response element (RRE) for RNA transport, the woodchuck hepatitis virus posttranscriptional regulatory element (WPRE) for improved RNA translation, a 5' LTR and a 3' U3 deleted LTR, and the packing sequence.

The EF-1alpha promoter was selected over other eukaryotic promoters based on previous observations that reporter gene expression was higher under the control of the EF-1 alpha promoter in both lentivirally transduced primary CD4 and CD8 cells (see, Milone et al. (2009) *Mol Ther,* 17:1453-1464). The EF-1alpha promoter has been shown to be the most efficient in expression of transgenes in primary T cells in comparison to a panel of physiologic promoters (Milone et al. (2009) *Mol Ther,* 17:1453-1464). The EF-1alpha promoter was derived from the commercially available pTracer-CMV2 plasmid (Invitrogen Corporation, Carlsbad, CA) (Kim et al. 1990) and cloned into the Dull vector using PCR and standard molecular biology techniques.

A long form sequence in the gag gene called the central polypurine tract and central termination sequence (cppt/CTS) was amplified from the NL4-3 molecular clone and incorporated into the Dull vector backbone. The cppt/CTS sequence was found to be important for efficient reverse transcription and nuclear import (Sirven et al. 2000).

Figure 24:
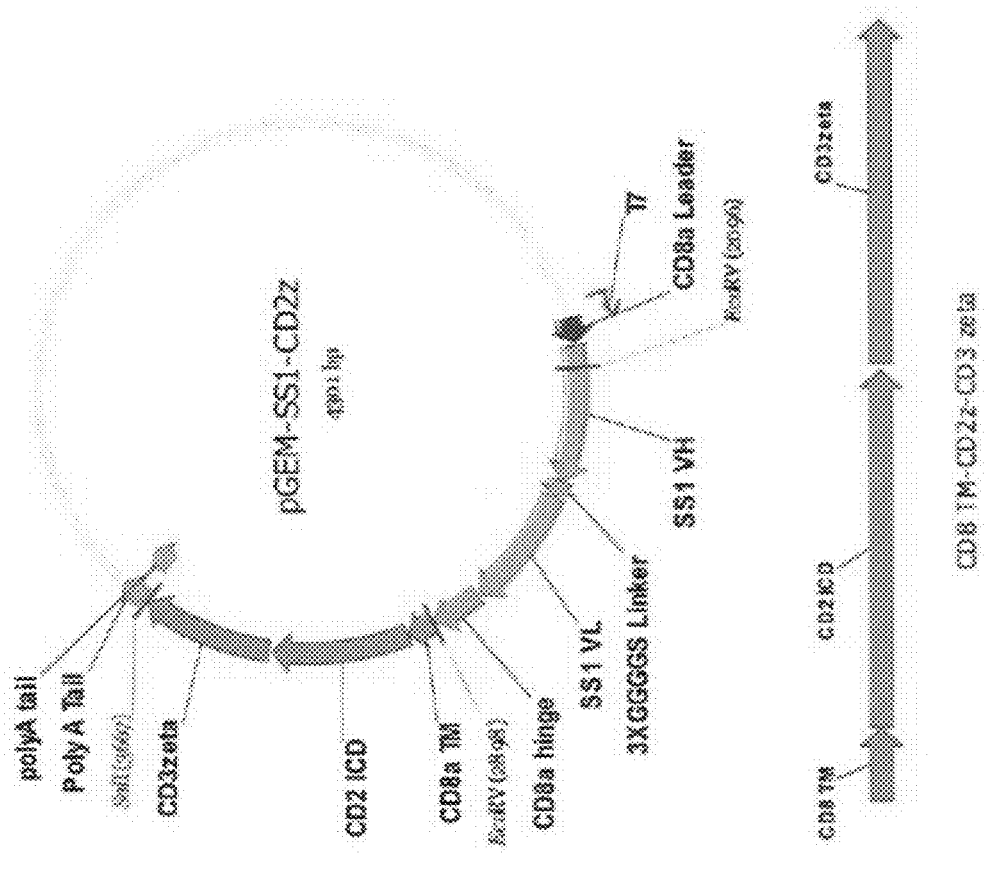
FIG. 24 is a schematic of the plasmid map of pGEM-SS1-CD2z.
Figure 25:
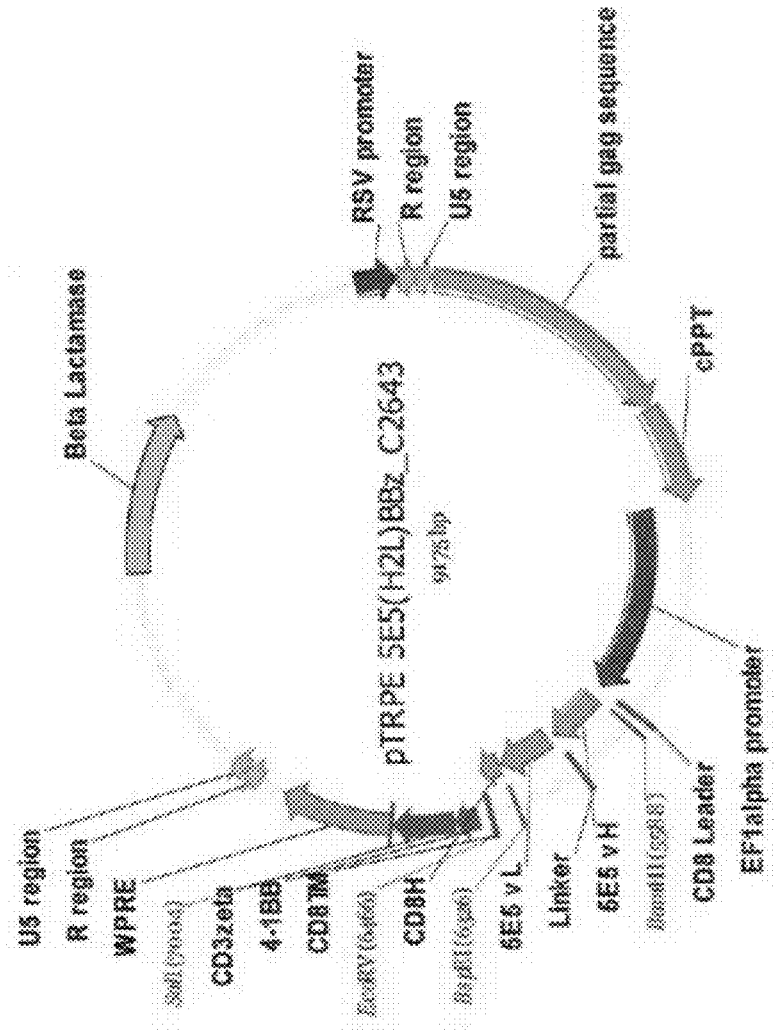
FIG. 25 is a schematic of the plasmid map of pTRPE_5E5-BBz.
Figure 26:
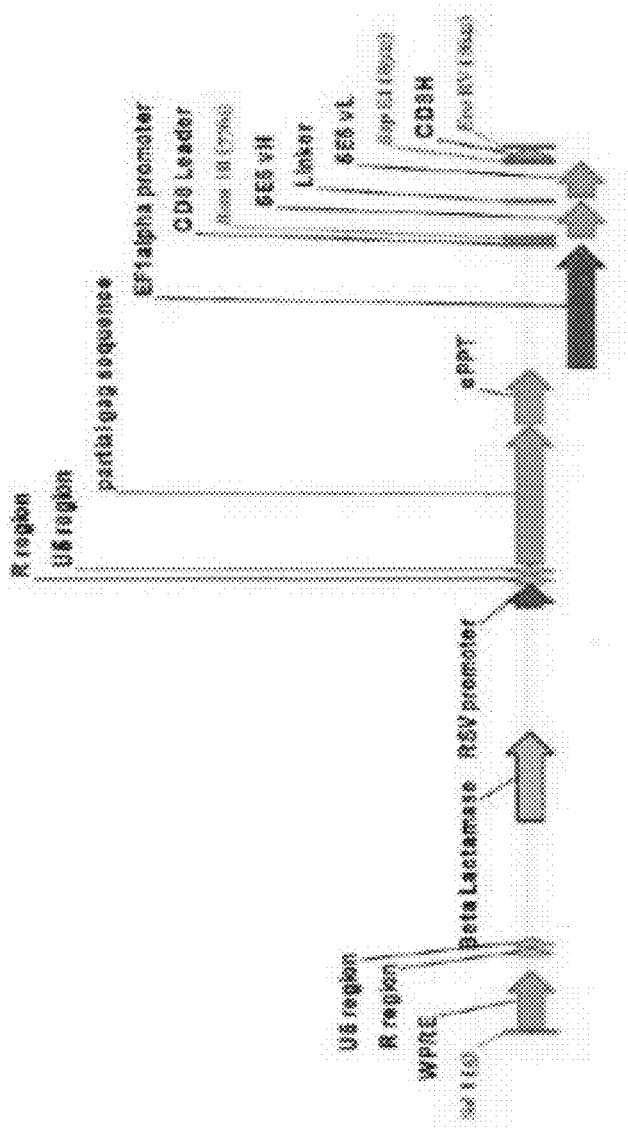
FIG. 26 is a schematic showing the pTRPE_5E5 (H2L) vector backbone.

The pTRPE_5E5 (H2L)_CD2z vector was generated from pGEM-SS1CD2z and pTRPE_5E5-BBz. A fragment containing the CD8TM, CD2 ICD and CD3zeta was digested from the pGEM-SS1CD2z vector and purified by gel extraction (see, FIG. 24 for plasmid map of pGEM-SS1-CD2z). A vector pTRPE_5E5 (H2L) vector backbone was generated from digesting pTRPE_5E5-BBz (see, FIG. 25 for plasmid map). The pTRPE_5E5 (H2L)_CD2z vector was generated by ligation of the CD8TM, CD2 ICD, and CD3zeta fragment into the pTRPE_5E5 (H2L) vector backbone (see, FIG. 26).

Study Design

The CART-TnMUC1-01 study is an open-label, multi-center first-in-human (FIH) Phase 1 study to assess the safety, tolerability, feasibility and preliminary efficacy of the administration of genetically modified autologous T cells (CART-TnMUC1 cells) engineered to express a chimeric antigen receptor (CAR) capable of recognizing the tumor antigen, TnMUC1 and activating the T cell.

In the Phase 1 dose escalation portion of the study, two parallel arms will be enrolled with the goal of identifying the recommended Phase 2 dose (RP2D) of CART-TnMUC1 following the LD chemotherapy regimen to test in further cohorts in two patient populations (1) patients with TnMUC1+ solid tumors and (2) patients with TnMUC1+ relapsed/refractory multiple myeloma (MM). The Phase 1 portion of the trial is anticipated to enroll approximately 40 patients (approximately 22 patients in Arm 1 and 18 patients in Arm 2; exact sample size of Phase 1 is determined by observed toxicity).

The Phase 1a expansion cohort is designed to assess the preliminary efficacy of CART-TnMUC1 cells dosing in patients with TnMUC1+ platinum-resistant ovarian cancer administered using an intravenous method following the LD chemotherapy administration. In the Phase 1a expansion approximately 40 patients are anticipated to be enrolled. This arm utilizes the Simon 2-Stage design, where Stage 1 enrolls 13 patients (provided the appropriate responses are observed), and following Stage 1 success, the total of Stage 1 and Stage 2 is approximately 40 patients to achieve 36 patients evaluable for the primary endpoint of ORR.

The period of patient accrual in the Phase 1 portion of the study is anticipated to last 12-16 months. Patient accrual in the Phase 1a expansion portion of the study is anticipated to last 12-16 months. Individual patients are expected to participate for approximately 24 months for treatment, and long-term safety follow-up assessments. Patients are followed for longer time periods for the final safety and overall survival (OS) analyses. The Phase 1 will be conducted at approximately 3-5 centers and the Phase 1a expansion cohort portion of the trial will add additional clinical trial sites (approximately 3-5 additional sites).

Figure 27:
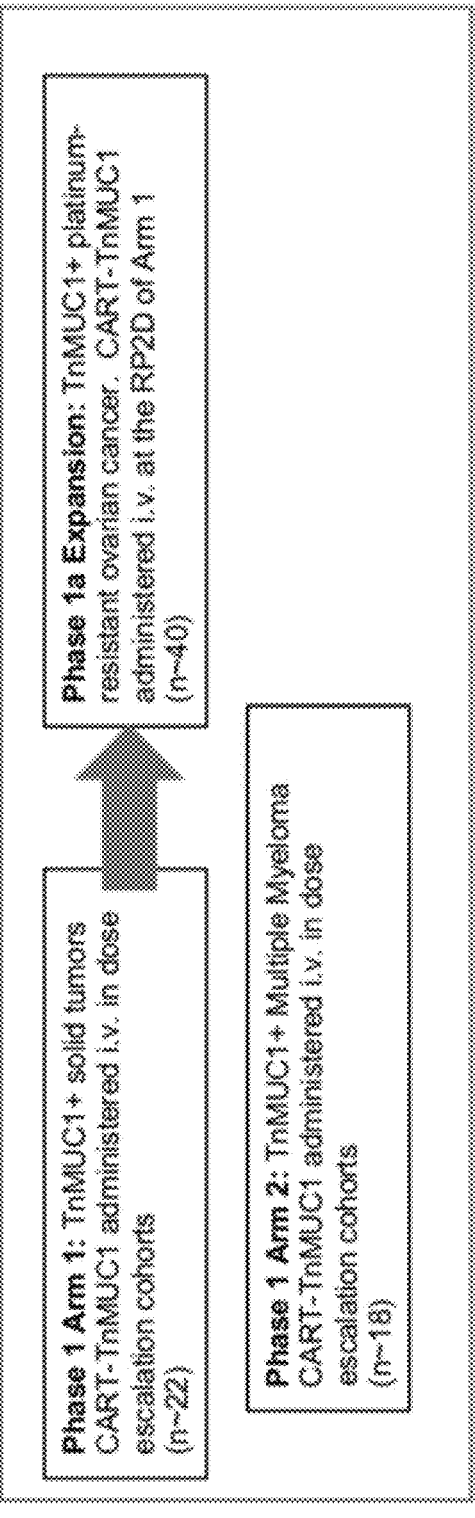
FIG. 27 is a schematic showing the study design of the Phase 1 and Phase 1a portions of the clinical trial.

The study design of the Phase 1 and Phase 1a portions is provided in FIG. 27. As shown in FIG. 27, the Phase 1 portion of the trial will be conducted in two parallel arms defined by disease setting. Arm 1: patients with TnMUC1+ solid tumors and Arm 2: patients with TnMUC1+ multiple myeloma. Arm 2 evaluation will begin with dose level 2, following the demonstration of safety in Arm 1 of dose level 1. The Phase 1a expansion cohort will enroll patients with TnMUC1+ platinum-resistant ovarian cancer. i.v. means intravenous; RP2D means recommended Phase 2 dose.

Patient Pathway

The patient pathway in Phase 1 and the expansion cohort of the trial will follow a similar pattern. Patients will first undergo Pre-screening after signing the Prescreening informed consent form to determine the TnMUC1 status of a tumor biopsy (all enrolled patients must have TnMUC1+ tumor sample as determined by the central IHC assay) prior to consent being obtained for the main study. Patients with a TnMUC1+ tumor sample determined centrally can then sign the main study informed consent form and undergo Screening. Patients meeting all relevant eligibility criteria will have eligibility form submitted to the Sponsor by email. If a cohort assignment is available in the Phase 1 portion of the trial, patients will be enrolled in the study and allocated to the assigned dose level cohort. At this time, patients will be scheduled for leukapheresis and lymphodepletion through to the CART-TnMUC1 infusion with the clinical trial site/study center.

After the leukapheresis procedure is completed at the designated apheresis center at the clinical trial site, the leukapheresis product is frozen and shipped to the manufacturing venue (University of Pennsylvania Clinical Cell and Vaccine Production Facility, CVPF). The period of manufacturing of the CART-TnMUC1 product takes approximately 4-6 weeks. During the ensuing 4-6 weeks of manufacturing timeframe, patients may be treated with bridging chemotherapy at the discretion of the principal investigator and following approval of the regimen by the Sponsor medical monitor. Following manufacturing, the frozen CART-TnMUC1 product is shipped to the treating institution.

Once the frozen CART-TnMUC1 product is received at the clinical trial site, the scheduled LD chemotherapy can commence. Patients in all cohorts with the exception of Cohort 1 (and any optional non-LD cohort recommended by the PSMC) will undergo the 3-day lymphodepletion (LD) chemotherapy regimen at Days −6 to Day −4 (with window of −1 day, i.e., commencing the 3 day LD regimen on Day −7 or −6). In all patients, the CART-TnMUC1 cell infusion is administered on Day 0. Follow-up visits to monitor safety and disease status will commence per protocol following the CART infusion. After disease progression or initiation of alternative anti-cancer therapy, patients will continue to be followed for long-term safety assessments and for the survival endpoint.

Figure 28:
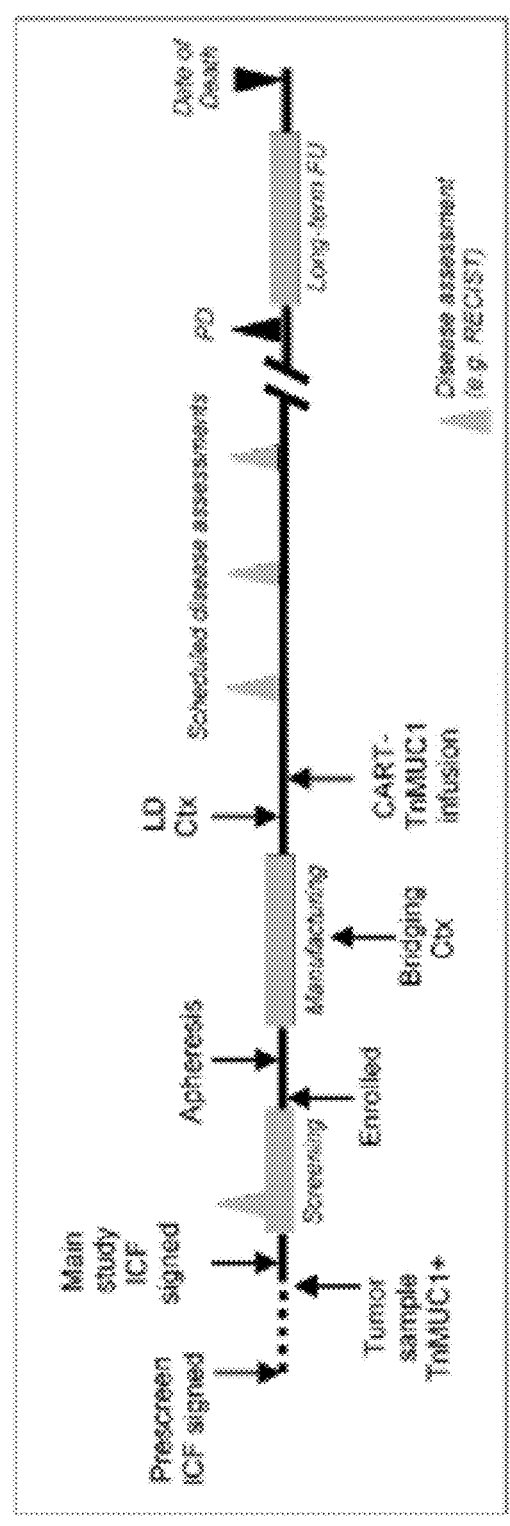
FIG. 28 is a schematic showing the overall patient pathway of the clinical trial.

FIG. 28 is a schematic showing the overall patient pathway. As shown, both the Phase 1 and Phase 2 portions of the trial commence with the determination of TnMUC1 status in a submitted tumor sample and end with the collection of the OS endpoint and date of death. Following CART-TnMUC1 infusion, patients will continue to be assessed for disease status according to the protocol. Upon demonstration of disease progression or commencement of new anti-cancer therapy, patients will enter the long-term FU period. Ctx means bridging chemotherapy; LD means lymphodepletion; FU means follow-up; PD means progressive disease.

Phase 1 Dose Escalation Design

The Phase 1 portion of the study will be a parallel two-arm dose escalation study designed to identify the maximum tolerated dose (MTD) and/or the recommended Phase 2 dose (RP2D) of CART-TnMUC1 cells that can be safely administered to patients in combination with the lymphodepletion regimen of fludarabine and cyclophosphamide. The two arms of the Phase 1 trial are comprised of two patient populations:

Arm 1: intravenous (i.v.) CART-TnMUC1 cells for patients with solid tumors including TnMUC1+ treatment-resistant ovarian cancer (including cancers of the fallopian tube), pancreatic adenocarcinoma, hormone receptor (HR)-negative and HER2-negative (triple negative) breast cancer (TNBC) and non-small cell lung cancer (NSCLC)

Arm 2: i.v. CART-TnMUC1 cells for TnMUC1+ relapsed/refractory multiple myeloma

Modified 3.3 Design: Patients enrolled in both arms will be dosed with CART-TnMUC1 cells in a modified 3+3 dose escalation design (Martin et al. (2018) *Cancer Chemother Pharmacol*, epub. Doi. 10.1007/s00280-018-3689-2; Crowley et al. (2017) CRC Press, Boca Raton, FL). The trial will begin with the first cohort at Dose Level 1 (Table 9) enrolling 3 patients with solid tumors (Arm 1). In this cohort, patients will be infused with CART-TnMUC1 without prior LD and no patients with multiple myeloma (Arm 2) will be enrolled in this first non-LD cohort. The safety of Cohort 1 (Dose Level 1, solid tumors) will be determined following the protocol specified process of a dose escalation teleconference with the Phase 1 Safety Monitoring Committee (PSMC) to determine the appropriate next step. If the safety of the first dose cohort is established following the dose escalation teleconference (DETC), then the next dose cohort (Dose Level 2, see Table 9) can be enrolled in both Arm 1 (solid tumors) and Arm 2 (multiple myeloma). At Dose Level 2, the LD regimen will be implemented at the same dose level tested in Dose Level 1. Dose level 2 is administered following the LD chemotherapy regimen, however Dose Level 1 is administered without the LD regimen.

TABLE 9

Dose levels of CART-TnMUC1-01

| Dose Level[a] | CART-TnMUC1 Dose | Lymphodepletion | Enrollment |
|---|---|---|---|
| 1[b] | $1\text{-}2 \times 10^{7}$ transduced cells | None | 3-6 |
| 2 | $1\text{-}2 \times 10^{7}$ transduced cells | Days −6 to −4 | 3-6 |
| 3 | $5\text{-}6 \times 10^{7}$ transduced cells | Days −6 to −4 | 3-6 |
| 4 | $1\text{-}2 \times 10^{8}$ transduced cells | Days −6 to −4 | 3-6 |
| 5 | $5\text{-}6 \times 10^{8}$ transduced cells | Days −6 to −4 | 3-6 |
| 6[c] | $1\text{-}2 \times 10^{9}$ transduced cells | Days −6 to −4 | 3-6 |

LD = lymphodepletion;
MTD = maximum tolerated dose;
PSMC = Phase 1 Safety Monitoring Committee
[a]At the discretion of the PSMC, individual dose level cohorts can be expanded in the absence of the LD regimen to assess observed on-target/off-tumor toxicity
[b]Dose Level 1 will only enroll in Arm 1 (solid tumors) and will not enroll in Arm 2 (multiple myeloma). Beginning with Dose Level 2, Arms 1 and 2 will enroll in parallel (see FIG. 29)
[c]In the absence of the identification of the MTD following dose level 5, the dose can be escalated in half log increments if recommended by the PSMC.

Figure 29:
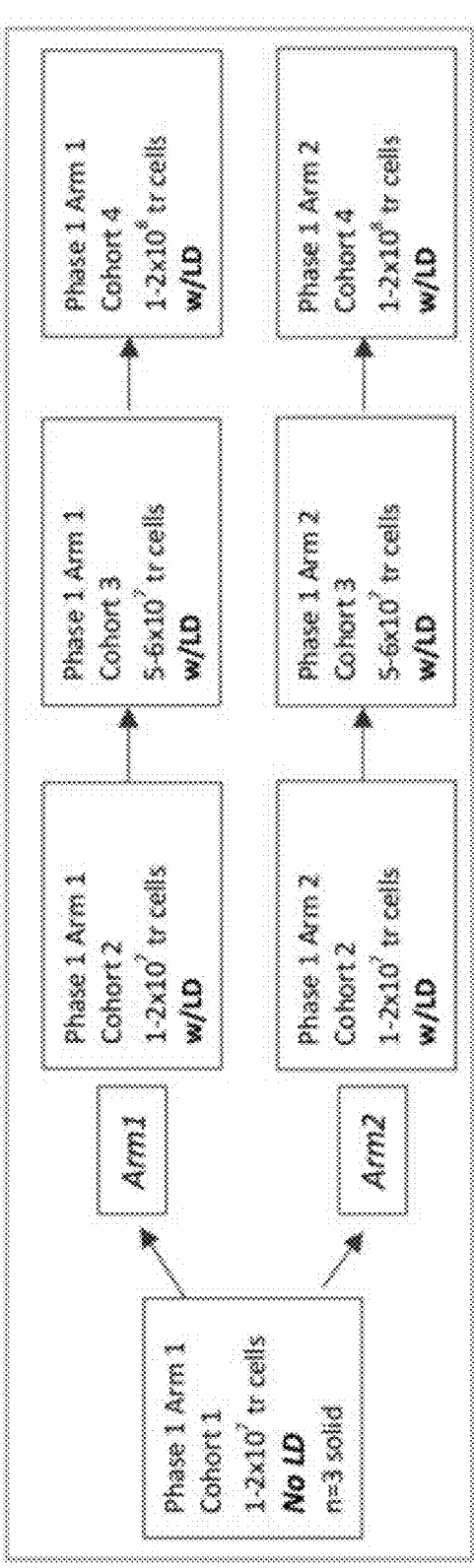
FIG. 29 is a schematic showing the dose escalation scheme of the clinical trial.

The two Phase 1 Arms will then continue to enroll in parallel (FIG. 29). FIG. 29 shows the dose escalation scheme. As shown, LD means lymphodepletion; MM means multiple myeloma; and tr cells means transduced cells. Dose escalation follows the steps from left to right. Cohort 1 is enrolled first with 3 patients with solid tumors and the CART-TnMUC1 is administered without the LD regimen. Arm 2 (MM) commences once the safety of Cohort 1 is established and begins with Cohort 2 (Dose level 2). Cohorts beyond the indicated Cohort 4 are enrolled according to the dose levels in Table 9.

Dose Escalation Guidelines: The dose limiting toxicity (DLT) observation period for each individual patient enrolled in Phase 1 will begin with the earlier of (1) the beginning of the LD chemotherapy regimen (in all patients receiving the LD regimen), or (2) the CART-TnMUC1 cell infusion (in all patients not receiving the LD regimen). The DLT period in all patients will conclude at 28 days following the CART-TnMUC1 cell infusion (Day 0). Thus, in all cohorts where the LD chemotherapy regimen is administered, the DLT observation period will include the timeframe of the LD chemotherapy (3 days of chemotherapy commencing on Day −6 to Day −4 with a window of −1 day). In contrast, in Cohort 1 (Arm 1) and all cohorts where the LD chemotherapy regimen is not administered, the DLT observation period begins with the administration of the CART-TnMUC1 cells. The DLT observation period for any given cohort concludes when the last patient enrolled in the cohort has completed the DLT observation period (28 days following the administration of the CART cells) or the patient experiences DLT (whichever event occurs earlier).

For the purpose of this study, the maximum tolerated dose (MTD) is defined as the highest dose level where the observed DLT rate is considered acceptable (0 patients with DLT of at least 3 evaluable patients or a maximum of 1 patient with DLT among 6 evaluable patients). Considering all available data in the Phase 1 portion of the trial, the PSMC will identify the dose that will be taken forward for further testing in the expansion cohort, defined as the recommended Phase 2 dose (RP2D) of the CART-TnMUC1 cells to be studied in the Phase 1a expansion portion of the trial. The RP2D may be the same dose as the MTD or a lower dose level studied in Phase 1. The RP2D identified in the two parallel Arms in Phase 1 may be different in the two Arms. In this case, the RP2D that is identified in Arm 1 (solid tumors, ST) is the RP2D-ST and the RP2D in Arm 2 (multiple myeloma, MM) is the RP2D-MM.

The process to determine the MTD will follow the protocol guidelines below for dose escalation or de-escalation until either the MTD is defined or the PSMC defines the RP2D.

The dose escalation decisions within the Phase 1 portion of the trial are the responsibility of the PSMC. The decision at each dose level will be to enact one of the following: (1) escalate to the next dose level; (2) de-escalate to a lower dose; (3) expand an individual dose level cohort; or (4) declare MTD and/or RP2D. The PSMC will consider all available safety, tolerability and feasibility data in the decision making for each individual dose level cohort decision process.

Dose escalation or de-escalation during the Phase 1 dose determining portion of the study will be at the discretion of the PSMC and implement the following:

If 1 DLT occurs among at least 3 evaluable patients (1 DLT/3 patients), then at the discretion of the PSMC, the cohort can be expanded to 6 evaluable patients at this dose level. After the cohort is expanded, if 2 DLT occur among the 6 evaluable patients, then the decision should be taken to de-escalate to the prior dose level by the PSMC.

If 0 DLT of the 3 evaluable patients or 1 DLT out of 6 evaluable patients occurs, the decision can be taken by the PSMC to escalate the dose to the next dose level cohort.

If 2 DLT occur within a given dose cohort, then enrollment in this cohort will be stopped and the dose will be de-escalated to the prior tolerated dose level.

Figure 30:
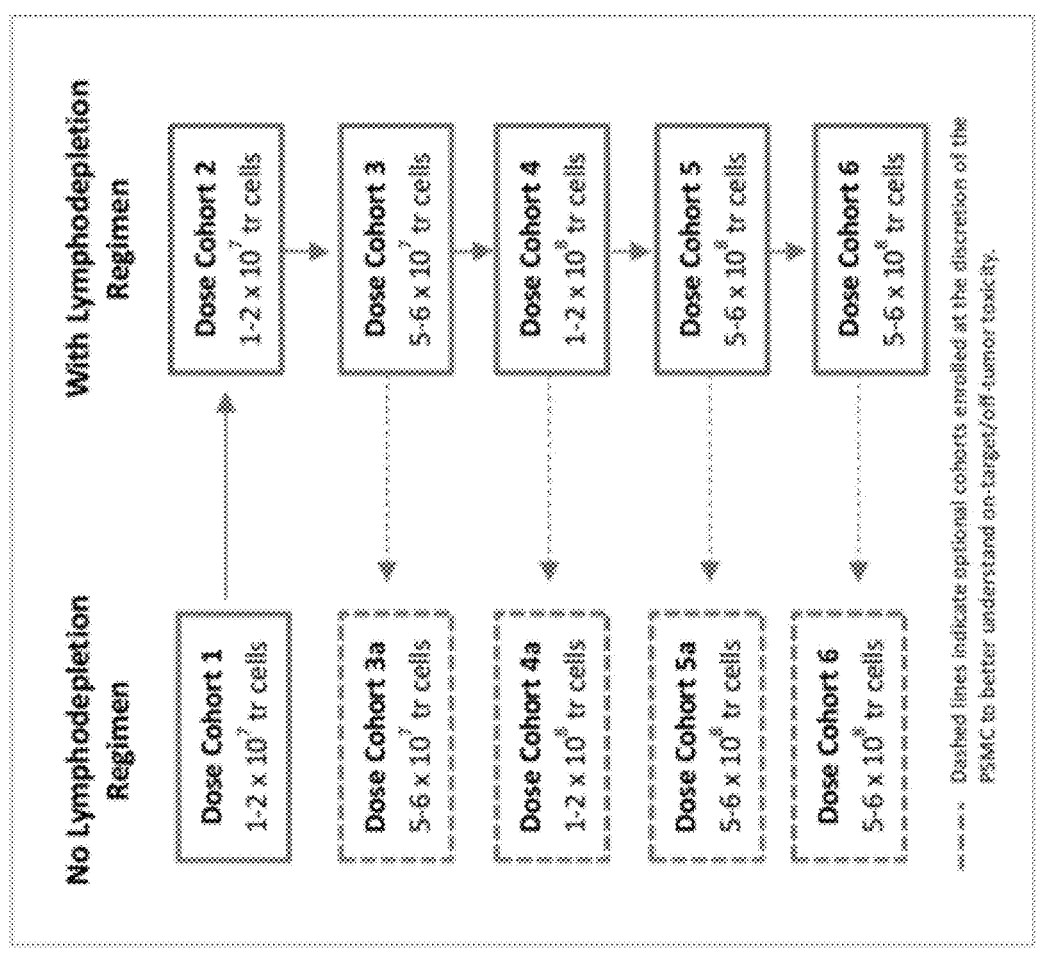
FIG. 30 is a schematic showing the dose escalation cohorts of the clinical trial.

At the discretion of the PSMC, following observation of DLT at a given dose level, the cohort can be expanded to include patients without lymphodepletion if deemed appropriate to better characterize on-target/off-tumor DLT observed (see "a" cohorts, FIG. 30). Patients treated in such non-lymphodepletion cohorts will not contribute to the dose decision making calculation. Patients treated at dose levels above dose level 1 without lymphodepletion (the "a" cohorts in FIG. 30) are to better understand the safety profile at a given dose level and not to the overall potential dose escalation.

At the discretion of the PSMC following identification of a potential RP2D, an additional cohort of 3-6 patients can be enrolled at the identified RP2D in one or both Arms of Phase 1 to further confirm the DLT rate and preliminary safety and tolerability prior to the formal identification of the RP2D-ST and/or RP2D-MM.

FIG. 30 shows the dose escalation cohorts. As shown, tr cells means transduced CART-TnMUC1 cells; and LD means lymphodepletion. The Phase 1 dose escalation portion of the trial will proceed as a modified 3+3 following the dose escalation cohorts as outlined. Optional cohorts can be enrolled without the administration of the LD regimen if determined to be appropriate by the PSMC to better assess observed on-target/off-tumor toxicity. Following the enrollment of cohorts without LD (the 'a' cohorts on the left), the PSMC can determine to continue with expansion of the cohort with the LD regimen or to de-escalate the dose.

Patients are considered evaluable for purposes of MTD/RP2D determination if either (1) the patient experiences a DLT or (2) the patient has been observed for the full 28 days following the CART-TnMUC1 cells administration without experiencing a DLT and they have received the protocol-specified dose level per cohort.

If for any reason, the protocol-specified dose cannot be manufactured for a given patient, but a lower dose of cells is produced and infused, then the patient will be considered evaluable for dose decision making in the following circumstances:

Patients who experience a DLT without having received the protocol-specified dose level but having received a lower dose level of the CART-TnMUC1 cells will be considered evaluable for the purpose of making a determination on the dose level with DLT.

Patients not experiencing a DLT but receiving a dose that is lower than the protocol-specified cohort dose level will be considered not evaluable for decision making purposes and will be replaced if required for dose decision making at the discretion of the PSMC.

Definition of Dose Limiting Toxicity: A DLT is defined in the CART-TnMUC1-01 study as any CART-treatment related non-hematologic adverse event of grade 3 or greater that does not resolve to grade 1 or 0 within 1 week with appropriate medical management and occurs within 28 days following the initial dose of the CART-TnMUC1 cells with the exception of the above criteria. Exceptions to the definition of the definition are described in Table 10 below.

In this study, AEs are graded according the CTCAE version 5.0 with the exception of CRS. Grading of CRS events is based on published criteria for CRS (Lee et al. (2014) *Blood*, 124(2): 188-195) and adapted in Table 11. CRS is a recognized complication of CART therapy.

The 28-day post-CART infusion window for DLT observation is inclusive of the LD chemotherapy regimen in patients receiving the LD regimen (thus the full DLT observation time will be approximately 35 days). In patients not treated with the LD regimen, the DLT observation period begins with the CART-TnMUC1 infusion (and the DLT observation is thus 28 days).

TABLE 10

Dose Limiting Toxicity Criteria

| Organ system | DLT criterion |
|---|---|
| Non-hematologic DLT criteria | |
| A DLT will consist of any Grade 3 or higher non-hematologic toxicity possibly or probably related to the treatment with CART-TnMUC1, with the following exceptions noted below. | |
| Any adverse event considered possibly or probably related to the treatment with CART-TnMUC1 that leads to the discontinuation of the treatment will be considered a DLT. | |
| Any patient experiencing a DLT will be removed from the study and will not be replaced. | |
| Neurologic | Any Grade 2 or higher neurotoxicity that does not resolve to grade 1 within 72 hours will be considered a DLT. |
| Gastrointestinal (pancreatitis) | Grade 3 or higher pancreatitis of any duration will be considered a DLT. Asymptomatic elevations of amylase and/or lipase of Grade 3 without symptoms of pancreatitis and with negative imaging$^a$ of the pancreas for inflammation will not be considered a DLT. |
| Hematologic DLT criteria | |
| A DLT will consist of any hematologic toxicity of Grade 4 possibly or probably related to the treatment with CART-TnMUC1. | |
| Any adverse event considered possibly or probably related to the treatment with CART-TnMUC1 that leads to the discontinuation of the treatment will be considered a DLT. | |
| Any patient experiencing a DLT will be removed from the study and will not be replaced. | |
| Thrombocytopenia | Grade 3 or higher thrombocytopenia with hemorrhage will be considered a DLT. |

CART means chimeric antigen receptor T cells; DLT means dose limiting toxicity
$^a$Imaging of the pancreas will be implemented in all patients with asymptomatic grade 2 or higher elevations in amylase and/or lipase

TABLE 11

Grading Scale for CRS Events

| Grade | Toxicity |
|---|---|
| Grade 1 | Symptoms of CRS are not life-threatening and require symptomatic treatment (fever, nausea, fatigue, headache, myalgias, malaise) |
| Grade 2 | Symptoms require and respond to moderate interventions Oxygen requirement <40% Hypotension responsive to fluids or single, low-dose vasopressor Grade 2 organ toxicity |
| Grade 3 | Symptoms require and respond to aggressive interventions Oxygen requirement ≥40% Hypotension requires high-dose or multiple vasopressors Grade 3 organ toxicity or Grade 4 transaminitis |
| Grade 4 | Life threatening symptoms Requirement for ventilator support Grade 4 organ toxicity |
| Grade 5 | Death |

CRS means cytokine release syndrome

Phase 1a Expansion Cohort Design

This part of the study will evaluate the preliminary efficacy and further characterize the safety, tolerability and feasibility of the recommended Phase 2 dose (RP2D) of CART-TnMUC1 cells administered i.v. following LD chemotherapy in patients with TnMUC1+ platinum-resistant ovarian cancer. The RP2D of CART-TnMUC1 cells will be identified based on safety and feasibility results of the different cohorts in Arm 1 (solid tumors) of the Phase 1 portion of the trial.

Patients will be enrolled serially in the single-arm Phase 1a expansion cohort of the trial. No delays will be imposed for the consideration of safety in the Phase 1a portion of the trial.

Patients enrolled in the Phase 1a expansion cohort will have TnMUC1+ platinum-resistant ovarian cancer.

Safety data in the Phase 1a expansion cohort will be monitored by an independent data monitoring committee (IDMC) consisting of 4 independent members, 3 medical oncologists and 1 statistician. The IDMC will monitor the conduct of the study with special emphasis on the assess of the safety concerns as well as observation of activity. The IDMC will be governed by the IDMC charter.

The primary responsibilities of the IDMC are to periodically review and evaluate the interim data with an emphasis on the safety of the patients enrolled in the trial, the overall conduct of the study, and the preliminary observations of efficacy.

The IDMC will review all safety data with emphasis on Grade 2 or greater toxicity as well as all cases of Grade 2 or greater neurologic toxicity and Grade 3 or greater CRS observed in the trial. The IDMC will monitor the safety data and assess the stopping rule of toxicities and enact the pause in enrollment. Briefly, a pause in enrollment will be implemented at the discretion of the IDMC for new Grade 4 toxicity (not observed during the Phase 1 portion of the trial) in a single patient considered at least possibly related to the CART-TnMUC1, any Grade 4 toxicities that were previously observed in Phase 1 considered at least possibly related to the infusion of the CART cells observed in two or more patients in Phase 1a (pending further evaluation of the cause of toxicity). Toxicities considered DLT in the protocol as well will be monitored and if the DLT rate is considered greater than 30%, the enrollment will be paused and IDMC convened. Any death within 30 days of the administration of the CART cells that is not attributed to disease progression and is considered at least possibly related to the CART cell infusion will result in a delay in enrollment for the IDMC to consider the safety of resuming enrollment.

Study Periods:

Patients who sign the Pre-screening informed consent form will have an archival tumor sample provided for central TnMUC1 testing by IHC. Patients without an archival sample can undergo biopsy using only non-significant risk procedures for Pre-screening tumor sample to be collected. Patients with TnMUC1+ tumors tested by central immunohistochemistry (IHC) assay can advance to Screening by signing the main study informed consent form. Patients with TnMUC1+ tumors by central assay who fail Screening will not need to submit a second tumor sample and go through the Pre-Screening process again to re-screen for the study.

Pre-screening: Patients who sign the Pre-screening informed consent form will have an archival tumor sample provided for central TnMUC1 testing by IHC. Patients without an archival sample can undergo biopsy using only non-significant risk procedures for Pre-screening tumor sample to be collected. Patients with TnMUC1+ tumors tested by central immunohistochemistry (IHC) assay can advance to Screening by signing the main study informed consent form. Patients with TnMUC1+ tumors by central assay who fail Screening will not need to submit a second tumor sample and go through the Pre-Screening process again to re-screen for the study.

Screening: Patients who meet all inclusion criteria and have none of the exclusion criteria will complete eligibility criteria and be submitted for cohort allocation. During Phase 1 dose escalation, patients are allocated to available slots within an open dosing cohort; patients are considered enrolled in the study at the time of cohort allocation. In the Phase 1a expansion, patients are allocated based on eligibility and manufacturing availability. At the time of enrollment, the patient is scheduled for the leukapheresis procedure and CART-TnMUC1 manufacturing.

Leukapheresis and CART Cell Manufacturing: Patients enrolled in the study (see above for definition) will be scheduled for the leukapheresis procedure, lymphodepletion chemotherapy (if protocol-specified) and CART-TnMUC1 infusion. The patients will then undergo the trial leukapheresis procedure according to the protocol and as detailed in the Apheresis and Infusion Manual for this study. With the procedure completed, the leukapheresis product is frozen and shipped to the manufacturing facility (University of Pennsylvania CVPF). The leukapheresis product is shipped to the CVPF for manufacturing process.

Bridging Anti-Cancer Therapy: In some patients, it is appropriate to offer a regimen of anti-cancer therapy following the leukapheresis procedure and before the LD chemotherapy regimen is administered (during the CART manufacturing process). In this instance, the Principal Investigator should consult with the Sponsor medical monitor regarding the proposed bridging therapy regimen selection and the timing of administration. In general, regimens with both (1) demonstrated activity in the specific disease setting and (2) that can be administered with no long-term toxicities interfering with the administration of the LD regimen are to be considered for administration as bridging therapy post-leukapheresis and pre-LD regimen in patients. Patients must have at least 2 weeks without any systemic therapy prior to the LD regimen administration. Consult the Sponsor medical monitor prior to the administration of bridging therapy.

Lymphodepletion Chemotherapy: As described, patients will receive the LD chemotherapy regimen beginning on Day −6 and completing on Day −4 prior to CART infusion (the window of time to administer the LD chemotherapy regimen can be extended to Day −7 to −5 with CART infusion fixed at Day 0). Prior to lymphodepletion (LD) regimen being administered, patients must be assessed against the Pre-LD Administration checklist (Table 12). Patients can be hospitalized for the LD chemotherapy at the discretion of the Principal Investigator. Patients enrolled in Cohort 1 in Phase 1 and in optional Phase 1 cohorts without LD (Table 12) will not receive the LD regimen and will proceed with the CART infusion (Day 0).

TABLE 12

| No. | Category | Description |
|---|---|---|
| | | Lymphodepletion Checklist |
| 1 | Disease Response | Patients must not have experienced new disease complications, tumor response or symptoms that would, in the opinion of the investigator, render it unsafe to receive the LD Regimen and CART infusion. Patients with anticipated Day 0 that is greater than 6 weeks since screening disease assessments must have repeat disease staging prior to LD chemotherapy or Day 0 CART infusion. |
| 2 | Anti-tumor therapy | Patients must not have received any anti-tumor therapy within 2 weeks prior to the administration of the LD regimen. Bridging anti-cancer therapy must be completed at least 2 weeks prior to LD chemotherapy administration. |
| 3 | ECOG status | Patients must not have experienced a significant change in performance or clinical status when compared to the status at Screening that would in the opinion of the investigator increase the risk of the CART cell infusion. |
| 4 | Respiratory viral panel | Patients must undergo the respiratory virus panel and results obtained within 10 days prior to the planned CART infusion. If the patient is positive for any virus on the viral panel, then treatment should be commenced, and the CART cell infusion delayed at least 7 days following treatment. If clinical symptoms are present, then the LD chemotherapy and CART cell infusion should be delayed until resolution. If patients cannot receive the CART infusion within 4 weeks from receiving the LD regimen, then the LD chemotherapy should be repeated. Consult with the Sponsor medical monitor in this setting. |
| 5 | Interval toxicity assessment | Patients must not have any of the following toxicities (as a result of the bridging chemotherapy): a. Pulmonary: Requirement for supplemental oxygen to maintain the oxygen saturation of greater than 95% or presence of new findings on pulmonary imaging studies (imaging studies are not required prior to LD or CART infusion unless needed to manage toxicity) |

TABLE 12-continued

| | | |
|---|---|---|
| | Lymphodepletion Checklist | |
| No. | Category | Description |
| | | b. Cardiac: no new cardiac arrhythmia |
| | | c. Hypotension requiring medical (inotropic) support |
| | | d. Active infection defined as positive cultures for bacteria, virus or fungus requiring antibiotics. Patients who require antibiotic therapy during the pre-infusion, pre-LD timeframe should complete the antibiotic therapy prior to LD chemotherapy and CART infusion |

CART means chimeric antigen receptor T cell;
ECOG means Eastern Cooperative Oncology Group;
LD means lymphodepletion CART-TnMUC1 Cell Infusion: CART infusion will begin approximately 3-4 days after completion of LD chemotherapy (where LD chemotherapy is administered). Patients will be assessed against the CART-TnMUC1 infusion checklist prior to the administration of the CART cells (Table 13). The infusion date of the CART-TnMUC1 is Study Day 0. Patients will be admitted for the CART infusion and managed as an inpatient following the CART cell infusion for at least 2 overnights as a mandatory observation period (minimum observation overnight Day 0 after infusion and overnight Day 1 with potential discharge Day 2). Additional inpatient management may be required for toxicities observed following the CART infusion. CART cell infusions will occur as an inpatient or in the cellular therapy unit with inpatient observation (minimum of 2 overnights observation).

TABLE 13

| | | |
|---|---|---|
| | CART-TnMUC1 Infusion Checklist | |
| No. | Category | Description |
| 1 | Disease Response | Patients must not have experienced new disease complications, tumor response or symptoms that would, in the opinion of the investigator, render it unsafe to receive the LD Regimen and CART infusion |
| | | Patients with anticipated Day 0 that is greater than 6 weeks since screening disease assessments must have repeat disease staging prior to LD chemotherapy or Day 0 CART infusion |
| 2 | Anti-tumor therapy | Patients must not have received any anti-tumor therapy within 2 weeks prior to the administration of the LD regimen. Bridging anti-cancer therapy must be completed at least 2 weeks prior to LD chemotherapy administration |
| 3 | ECOG status | Patients must not have experienced a significant change in performance or clinical status since LD chemotherapy when compared to the status at Screening that would in the opinion of the investigator increase the risk of the CART cell infusion |
| 4 | Respiratory viral panel | Patients must undergo the RVP and results obtained within 10 days prior to the planned CART infusion. If assessed prior to LD chemotherapy, the RVP does not need to be re-assessed following LD chemotherapy. If the patient is positive for any virus on the viral panel, then treatment should be commenced, and the CART cell infusion delayed at least 7 days following treatment. If clinical symptoms are present, then the LD chemotherapy and CART cell infusion should be delayed until resolution. If patients cannot receive the CART infusion within 4 weeks from receiving the LD regimen, then the LD chemotherapy should be repeated. Consult with the Sponsor medical monitor in this setting. |
| 5 | LD regimen toxicities | Patients must not have experienced the following toxicities during LD chemotherapy: a. Pulmonary: Requirement for supplemental oxygen to maintain the oxygen saturation of greater than 95% or presence of new findings on pulmonary imaging studies (no imaging studies are required prior to lymphodepletion or CART infusion) b. Cardiac: no new cardiac arrhythmia c. Hypotension requiring medical support d. Active infection defined as positive cultures for bacteria, virus or fungus requiring antibiotics. Patients requiring antibiotic therapy during the pre-infusion time period should complete therapy before lymphodepletion and CART infusion Patients experiencing toxicities from LD chemotherapy should have these toxicities managed and resolved to the investigator's discretion prior to the infusion of the CART cells. If patients cannot receive the CART infusion within 4 weeks, then LD chemotherapy should be repeated. Consult with the Sponsor medical monitor in this setting |

153

Patient Population

Inclusion Criteria:

The inclusion criteria for the Phase 1 and Phase 1a expansion portions of the study are outlined below. Patients enrolled must meet all of the respective inclusion criteria below for inclusion in the study.

1. Patients must be adults over 18 years of age and sign the main study informed consent form.
2. Patients must have a confirmed diagnosis of metastatic treatment-resistant ovarian cancer (including cancers of the fallopian tube), pancreatic adenocarcinoma, hormone receptor (HR)-negative and HER2-negative (triple negative) breast cancer (TNBC) or non-small cell lung cancer (NSCLC), or relapsed/refractory multiple myeloma.
3. Patients must have an ECOG score of 0 or 1.
4. Patients must have received the following prior therapy:
   a. Multiple myeloma: relapsed or refractory disease after either one of the following
   i. At least 3 prior regimens, which must have contained an alkylating agent, proteasome inhibitor, and thalidomide analog (lenalidomide or pomalidomide). OR
   ii. At least 2 prior regimens if 'double-refractory' to a proteasome inhibitor and thalidomide analog, defined as progression on or within 60 days of treatment with these agents.
   Note: Induction therapy, autologous stem cell transplant (ASCT), and maintenance therapy if given sequentially without intervening progression are considered 1 'regimen'.
   iii. Patients must be at least 90 days since ASCT, if performed.
   b. NSCLC
   iii. Patients must have received standard therapy, including both checkpoint inhibition (PD-1/PD-L1 directed therapy) and platinum-based chemotherapy or be intolerant of these standard therapies.
   iv. Patients with EGFR or ALK alterations must have received prior targeted therapy directed at the specific identified mutations in addition to the standard therapy classes described above.
   c. Pancreatic adenocarcinoma: Patients must have experienced disease progression following at least one standard of care systemic chemotherapy for metastatic or unresectable disease.
   d. Triple-negative Breast cancer (TNBC): Patients must have experienced disease progression following at least one prior systemic anti-cancer therapy regimen as part of their treatment for management of metastatic breast cancer.
   e. Ovarian cancer: Patients are eligible if considered platinum-resistant (initially sensitive to platinum therapy) and must have received at least two prior lines of therapy for metastatic ovarian cancer, including at least one prior line of therapy including a platinum-containing regimen.
5. Patients must have evaluable disease, qualified as to the following:
   a. Multiple Myeloma
   iii. Patients must have measurable disease on study entry, which must include at least one of the following
   1. Serum M spike ≥0.5 g/dL
   2. 24-hour urine M-spike ≥200 mg

154

3. Involved serum free light chain (FLC) ≥50 mg/L with abnormal ratio
   4. Measurable plasmacytoma on examination or imaging
   5. Bone marrow plasma cells ≥20%
   Note: Patients with IgA myeloma in whom serum protein electrophoresis is deemed unreliable, due to co-migration of normal serum proteins with the paraprotein in the beta region, may be considered eligible as long as total serum IgA level is elevated above normal range.
   b. Solid tumors: disease status will be assessed as per Response Evaluation Criteria In Solid Tumors Criteria (RECIST v.1.1, see, Eisenhauer et al. (2009) *Eur J Cancer*, 45(2): 228-247). Tumor imaging should be performed at least within 28 days before apheresis. Phase-specific criteria are mentioned below
   ii. Phase 1: Patients must have evaluable disease in Phase 1 per RECIST v.1.1
   iv. Phase 1a expansion: Patients must have measurable disease in Phase 1a expansion per RECISTv.1.1.
6. All patients must have TnMUC1+ disease, determined by centrally tested TnMUC1 expression in a prior or archival tumor biopsy. If an archival tumor biopsy sample is not available, then the patient may undergo an optional biopsy for the purposes of screening eligibility with only non-significant risk biopsy procedures.
7. Patients must have completed prior anti-cancer therapy at least 2 weeks prior to Screening and toxicities from any previous therapy must have recovered to grade 1 or 0 (with the exception of alopecia, well controlled electrolyte or endocrine abnormalities, well-controlled peripheral neuropathy, and vitiligo).
8. Life expectancy greater than 3 months.
9. Adequate vital organ function as defined by
   a. Serum creatinine ≤1.5 mg/dL or estimated creatinine clearance ≥30 ml/min (per Institutional standard calculation)
   b. Alanine aminotransferase (ALT) and aspartate aminotransferase (AST)≤3× the upper limit of normal (ULN) and total bilirubin≤2.0 mg/dL. No specific exclusions are made for patients with hepatic disease
   c. Serum total bilirubin <1.5×ULN
   d. Serum albumin ≥3.0 g/dL (solid tumor patients in Arm 1 and Phase 1a only, not applicable to patients with multiple myeloma)
   e. Left ventricular ejection fraction (LVEF) ≥45%. LVEF assessment must have been performed within 8 weeks of screening
10. Adequate hematologic reserve (without the use of supportive transfusion or hematopoietic growth factors within 4 weeks of apheresis), as defined by
   a. Hemoglobin ≥9 g/dL
   b. Absolute neutrophil count ≥1000/μL
   c. Platelet count ≥50,000/μL (≥30,000/μL if bone marrow plasma cells are ≥50% of cellularity for myeloma patients)
   d. Absolute lymphocyte count of >500/μL
   Note: patients must not be transfusion-dependent to maintain hematologic parameters
11. Patients of reproductive potential agree to use approved contraceptive methods per protocol.
   Exclusion Criteria: The exclusion criteria for both Phase 1 and Phase 1a expansion are described below. Patients being considered for enrollment in the study must not meet any of the criteria below.

1. Active invasive cancer other than the proposed cancers included in the study.
2. Current treatment with systemic high-dose corticosteroids (defined as a dose greater than the equivalent of prednisone 20 mg/day). Patients with multiple myeloma at the time of study entry must complete prior active high-dose corticosteroid therapy prior to apheresis and be maintained on low-dose corticosteroid therapy or no corticosteroid therapy. Low-dose physiologic replacement therapy with corticosteroids equivalent to prednisone 20 mg/day or lower is acceptable.
3. Active autoimmune disease (including connective tissue disease, uveitis, sarcoidosis, inflammatory bowel disease or multiple sclerosis) or have a history of severe autoimmune disease requiring prolonged immunosuppressive therapy (any immunosuppressive therapy should have been stopped within 6 weeks prior to screening visit).
4. Current, active HIV, HCV, HBV infections. Viral testing at Screening is required in all patients to rule out subclinical infections.
5. Other active or uncontrolled medical or psychiatric condition that would preclude participation in the opinion of the Sponsor or Principal Investigator.
6. Prior allogeneic stem cell transplant.
7. Active and untreated central nervous system (CNS) malignancy. Treated lesions may be considered inactive if they are stable for at least 1 month following definitive treatment. Patient must not require corticosteroid therapy or anti-epileptic medications for the management of brain metastases.
8. History of severe infusion reaction to monoclonal antibodies or biological therapies, or to study product excipients (e.g., human serum albumin, DMSO, dextran 40) that would preclude the patient safely receiving CART-TnMUC1 cells.
9. Active or recent (within the past 6 months prior to apheresis) cardiac disease, defined as (1) New York Heart Association (NYHA) Class III or IV heart failure, (2) unstable angina or (3) a history of recent (within 6 months) myocardial infarction or sustained (>30 second) ventricular tachyarrhythmias.
10. Have inadequate venous access for or contraindications for the apheresis procedure.
11. Pregnant or breastfeeding women.

In another embodiment, the patient population will meet the following criteria:

Key Inclusion Criteria:
1. Confirmed diagnosis of metastatic treatment-resistant ovarian cancer (including cancers of the fallopian tube), pancreatic adenocarcinoma, hormone receptor (HR)-negative and HER2-negative (triple negative) breast cancer (TNBC) or non-small cell lung cancer (NSCLC), or relapsed/refractory multiple myeloma.
2. Eastern Cooperative Oncology Group (ECOG) score of 0 or 1.
3. Prior therapies as defined by tumor type, as described herein.
4. Evaluable disease as defined by tumor type, as described herein.
5. TnMUC1+ disease, determined by centrally tested TnMUC1 expression in a prior or archival tumor biopsy.
6. Completed prior anti-cancer therapy at least 2 weeks prior to Screening and toxicities.
7. Life expectancy greater than 3 months.

8. Serum creatinine ≤1.2 mg/dL or calculated creatinine clearance ≥60 ml/min (using the Cockroft & Gault formula).
9. Asparatate aminotransferase (AST) or alinine aminotransferase (ALT)≤2.5× upper institutional limit of normal with the following exception: Patients with known hepatic metastases, AST or ALT ≤3× upper institutional limit of normal.
10. Serum total bilirubin <1.5 mg/dL with the following exception: patients with known Gilbert's disease, serum total bilirubin <3 mg/dL.
11. Serum albumin ≥3.0 g/dL (solid tumor patients in Arm 1 and Phase 1a only, not applicable to patients with multiple myeloma).
12. Left ventricular ejection fraction (LVEF) ≥50%. LVEF assessment must have been performed within 8 weeks of screening.
13. Hemoglobin ≥9 g/dL.
14. Absolute neutrophil count ≥1500/μL.
15. Platelet count ≥100,000/μL (≥30,000/μL if bone marrow plasma cells are >50% of cellularity for myeloma patients).
16. Absolute lymphocyte count of >500/μL.

Key Exclusion Criteria:
1. Active invasive cancer other than the proposed cancers included in the study.
2. Current treatment with systemic high-dose corticosteroids (defined as a dose greater than the equivalent of prednisone 20 mg/day).
3. Active autoimmune disease (including connective tissue disease, uveitis, sarcoidosis, inflammatory bowel disease or multiple sclerosis) or have a history of severe autoimmune disease requiring prolonged immunosuppressive therapy (any immunosuppressive therapy should have been stopped within 6 weeks prior to screening visit).
4. Current, active human immunodfifficiency virus (HIV), hepatitis C virus (HCV), hepatitis B virus (HBV) infections.
5. Prior allogeneic stem cell transplant.
6. Active and untreated central nervous system (CNS) malignancy.
7. History of severe infusion reaction to monoclonal antibodies or biological therapies, or to study product excipients (e.g., human serum albumin, dimethyl sulfoxide [DMSO], dextran 40) that would preclude the patient safely receiving CART-TnMUC1 cells.
8. Active or recent (within the past 6 months prior to apheresis) cardiac disease, defined as (1) New York Heart Association (NYHA) Class III or IV heart failure, (2) unstable angina or (3) a history of recent (within 6 months) myocardial infarction or sustained (>30 second) ventricular tachyarrhythmias.
9. Have inadequate venous access for or contraindications for the apheresis procedure.
10. Pregnant or breastfeeding women.

Study Treatment

Investigational Agents:

CART-TnMUC1 cells: autologous T cells transduced with a lentivirus encoding the anti-TnMUC1 CAR composed of a murine antihuman TnMUC1 scFv (derived from monoclonal Ab 5E5), CD8a hinge and transmembrane domain, CD2 and CD3ζ, CART-TnMUC1-cells are administered via the intravenous route.

Cyclophosphamide: a cytotoxic chemotherapy agent used for lymphodepletion prior to CART-TnMUC1 cell dosing administered intravenously in combination with fludarabine. Cyclophosphamide will be administered to all patients with the exception of patients in Cohort 1 (and patients enrolled in optional non-LD cohorts in Phase 1). Dosing of cyclophosphamide will be 300 mg/m²/day over 3 days in combination with fludarabine.

Fludarabine: a chemotherapy agent used for lymphodepletion prior to CART-TnMUC1 cell dosing in combination with cyclophosphamide. Fludarabine will be administered to all patients with the exception of patients in Cohort 1 (and patients enrolled in optional non-LD cohorts in Phase 1). Dosing of fludarabine will be 30 mg/m²/day for 3 days. Dosing of lymphodepletion chemotherapy will be scheduled on Days −6 to −4 (with a −1 day window, i.e., dosing on Days −7 to −5).

Lymphodepletion Regimen: In Phase 1 dose cohort level 2 and all patients in the Phase 1a expansion cohort, patients will be treated with the LD chemotherapy regimen on Days −6 to −4 (with a −1 day window, i.e., Day −7 to −5) and CART-TnMUC1 infusion on Day 0 (with the exception of dose escalation cohorts without the LD regimen at the discretion of the PSMC). All patients will receive the same LD regimen: cyclophosphamide: 300 mg/m²/day over 3 days in combination with fludarabine: 30 mg/m²/day over 3 days.

Premedication for cyclophosphamide/fludarabine: It is anticipated that patients receiving cyclophosphamide may experience nausea and vomiting as a side effect of the treatment. Anti-emetic prophylaxis premedication for nausea (including corticosteroids) can be administered prior to infusion of chemotherapy according to the institutional standards. Choice of specific agent will be left to the discretion of the investigator.

Cyclophosphamide: Cyclophosphamide is generally well-tolerated and should be administered according to Institutional practice, including with inpatient monitoring at the discretion of the Principal Investigator. Adverse events observed in patients with cyclophosphamide at the dose range utilized in the LD regimen are described in the Prescribing Information (Cyclophosphamide label). Adverse events anticipated at these doses include: (1) Dermatologic reactions (alopecia beginning 3-6 weeks); (2) Bone marrow toxicity observed as thrombocytopenia and anemia are less common than leukopenia and neutropenia with an onset at 7 days, nadir at 10-14 days, and recovery at approximately 21 days; (3) Nausea and vomiting occur more frequently with large doses, usually beginning 6-10 hours after administration; patients will be offered antiemetic prophylaxis and therapy according to the Institutional standards; and (4) Acute hemorrhagic cystitis, thought to be a result of chemical irritation of the bladder by a cyclophosphamide metabolite (acrolein) is observed in approximately 10% of patients and (up to 40% of patients in some series), adequate i.v. hydration with mesna is recommended according to Institutional practice.

Fludarabine: Fludarabine is administered in combination with cyclophosphamide in the LD chemotherapy regimen. Fludarabine is generally well-tolerated and should be administered according to Institutional practice, including with inpatient monitoring at the discretion of the Principal Investigator. Adverse events observed with dosing of fludarabine are described in the Prescribing Information (Fludarabine label). These AE generally include (1) myelosuppression, including anemia, thrombocytopenia, neutropenia, and lymphopenia. Patients can experience severe, but often reversible, although this typically occurs following cumulative dosing of fludarabine (administered for 3 consecutive days every 28 days). In this study, patients will receive a single 3-day administration of fludarabine. (2) Autoimmune hematologic adverse events, including hemolytic anemia or immune thrombocytopenia may occur following 1 or more cycles of fludarabine. Patients undergoing treatment with fludarabine will be evaluated and monitored closely for cytopenias and/or hemolysis. (3) Nausea and vomiting may occur with fludarabine, and patients will be offered anti-emetic prophylaxis and therapy according to Institutional practice.

Combination LD regimen (Flu/Cy): The combination of fludarabine and cyclophosphamide (Flu/Cy) is a generally accepted standard LD regimen in CAR-T trials. According to the above the more common potential AE with the combination include myelosuppression where low neutrophils/granulocytes or lymphocytes could lead to infection and/or thrombocytopenia may lead to an increase in bruising or bleeding. Other AE associated with the combination include neutropenic fever, hemorrhagic cystitis, fatigue, nausea, vomiting, and alopecia.

Administration of cyclophosphamide and fludarabine should follow the Institutional Standard practice and adhere to the supportive care guidance as indicated.

Preparation of CART-TnMUC1 Cells: Cell manufacturing is performed at the University of Pennsylvania Clinical Cell and Vaccine Production Facility (CVPF). The CART-TnMUC1 cell dose is formulated for administration according to the transduced cell dose in cryobags. The transduced cell dose is calculated using flow cytometry testing to determine the percentage of CD3+ T cells expressing the CAR. The total cell number contained in the infusion bag and the total volume of the cell suspension for infusion depends on the lentiviral transduction efficiency.

Each bag will contain an aliquot of cryomedia containing the following infusible grade reagents (% v/v):

31.25% (v/v) of PlasmaLyte-A
31.25% (v/v) of 5% Dextrose in 0.45% Sodium Chloride
10% (v/v) of 10% Dextran 40 in 5% Dextrose
20% (v/v) of 25% Human Serum Albumin (HSA)
7.5% (v/v) Dimethyl sulfoxide (DMSO)

Premedication and Supportive Care: Premedication: Side effects following T cell infusions include transient fever, chills, and/or nausea. It is recommended that the patient be pre-medicated with acetaminophen and an antihistamine prior to the CART-TnMUC1 cell infusion. These medications may be repeated every six hours as needed. A course of nonsteroidal anti-inflammatory medication may be prescribed if the patient continues to have fever not relieved by acetaminophen.

Corticosteroid therapy: Patients should receive systemic corticosteroids such as hydrocortisone, prednisone, prednisolone (methylprednisolone) or dexamethasone (Decadron) in the case of a life-threatening toxicity or toxicity that does not respond to the administration of tocilizumab. Administration of corticosteroid therapy for reasons other than anti-emetic prophylaxis with the LD chemotherapy regimen or life-threatening toxicity is not recommended, since this may have an adverse effect on CART-TnMUC1 cell expansion and function.

Supportive care: In patients who are neutropenic on the day of CAR-T infusion due to recent LD chemotherapy regimen administration, prophylactic antibiotics will be administered according to the Institutional Standard and/or as advised in Neelapu et al. (2018) Nat Rev Clin Oncology, 15:47, generally starting on the day of infusion and pending recovery of neutrophil counts, or until judged by the investigator to no longer be at increased risk of infection.

The on-site pharmacy must confirm that 2 doses of tocilizumab is on-site prior to infusion and available for administration in order to manage suspected toxicities. Emergency medical equipment (i.e., emergency trolley) must be available during the infusion in case the patient has an allergic/anaphylactic response, or severe hypotensive crisis, or any other reaction to the infusion.

CART-TnMUC1 Cell Intravenous Administration: The CART-TnMUC1 cell product will be administered via i.v. infusion on study Day 0 (no window) following the process outlined in the Apheresis and Infusion Manual. Study personnel at the infusion center should use precautions for immunosuppressed patients. T-cell infusions should be performed by a licensed Registered Nurse at the study centers in the presence of a study investigator or designated physician. CART cell infusions requiring delay in the infusion should be discussed with the Sponsor medical monitor for the study.

Vital signs are measured every 15 minutes (±5 minutes) for the first hour and then every 30 minutes (±10 minutes) for the next 2 hours following the CART infusion. If the patient's vital signs are not satisfactory and stable 3 hours post-CART-TnMUC1 cell infusion, vital signs will continue to be monitored every 30 minutes (±10 minutes) or as clinically indicated until stable. If vital signs are stable for the first 3 hours following the infusion, then patients should be monitored with vital signs every hour until 12 hours post-CART infusion. If vital signs continue to be stable, patients can be monitored with vital signs every 2-4 hours following the Institutional Standard until discharge. Patients are monitored as an inpatient for a period of 2 nights following the CART-TnMUC1 infusion. If this patient is stable following the second overnight observation period, then the patient can be discharged to home.

All patients must remain within the local geographic vicinity of the clinical trial site for at least 30 days following the CART-TnMUC1 infusion and return to the clinical trial site for assessment of any observation of toxicity, including (but not limited to) fever to 38° C., nausea, vomiting, dyspnea, malaise or any new neurologic symptoms. The local geographic vicinity is defined as a travel distance to the clinical trial site comprising no more than 60 minutes.

Additional assessments may be performed as necessary to evaluate specific adverse events until they resolve to baseline or CTCAE v5.0 Grade <1.

Outcome Measures

Primary Outcome Measures:

Primary outcome measures include (1) Phase 1: to identify incidence of dose limiting toxicity (DLT) in Arm 1 and Arm 2 cohorts for the purposes of dose identification; and (2) Phase 1a: to identify proportion of patients with platinum-resistant ovarian cancer having an objective response.

Secondary Outcome Measures:

Secondary outcome measures include (1) Safety, tolerability and feasibility of CART-TnMUC1: Incidence of treatment emergent adverse events (AEs), shifts, outliers and changes from baseline laboratory result, vital signs, and proportion of enrolled patients who did not receive CART-TnMUC1 cells; (2) Preliminary anti-tumor efficacy of CART: Overall survival (OS), progression-free survival (PFS), objective response rate (ORR), duration of response, and time to response; (3) Expression of TnMUC1: Correlation of the expression level of TnMUC1 with efficacy parameters; and (4) Peripheral expansion and persistence of CART-TnMUC1 cells: correlation with related efficacy and safety parameters.

Example 10: Transduction and T Cell Expansion Protocol

In one embodiment, CART-TnMUC1, CART-TnMUC1-BBz, CART-19, and NTD cells were generated using cells from Normal Donors ND473, ND474, ND502, and ND525.

Transduction: On Day 0, bulk T cells (CD4 and CD8) obtained from the Human Immunology Core were diluted to $1 \times 10^6$ cells/mL, and stimulated with CD3/28 beads at a cell:bead ratio of 1:3. T cells were cultured in R10 medium supplemented with 30 U/mL IL-2. Transductions of packaged lentiviral vectors (TnMUC1 CAR, TnMUC1-BBz CAR, CD19 CAR) were performed on Day 1 post-stimulation using a MOI of 3, and allowed to expand in a 37° C./5% CO2 incubator. NTD cells were cultured as a control.

T Cell Expansion: Cells were fed and split every 2 days to $0.75 \times 10^6$ cells/mL with fresh T cell culture medium. Cells were de-beaded on Day 5 and maintained in culture. At the end of the expansion phase, cells were rested, as determined by decreased rate of cell division and a decrease in mean cellular volume to around ~350 to ~300 fL. Cells were frozen in cryopreservation media in aliquots of $5 \times 10^7$ cells/mL (1 mL volume per vial) and stored in liquid nitrogen for later use.

Cell Counting: At various time-points throughout expansion, cells were gently mixed and a 40 µL aliquot of cells was collected from known culture volume and placed into accuvettes (Beckman Coulter) with 20 mL Isoton II Diluent Buffer for counting using a Coulter Multisizer 3 (Beckman Coulter) in accordance with the TRP laboratory Standard Operating Procedure. These assays determine cell concentration, total cell numbers, growth rates, and cell volumes and are used to calculate dilution volumes and to determine when cells are rested for freezing.

Viable cells were counted from Day 5 up to Day 23 post-stimulation. T cell expansions were ceased when mean corpuscular volume (MCV) reached near 300 fL for the cell product. The time from T cell activation to resting MCV can be influenced by CAR transduction as well as donor variability.

In another embodiment, CART-TnMUC1 and NTD cells were generated using cells from Normal Donor ND489.

Transduction: On Day 0, bulk T cells (CD4 and CD8) obtained from the Human Immunology Core were diluted to $1 \times 10^6$ cells/mL, and stimulated with CD3/28 beads at a cell:bead ratio of 1:3. T cells were cultured in CTS™ OpTmizer™ T Cell Expansion media supplemented with 100 U/mL IL-2. Transduction with the packaged lentiviral vector (TnMUC1 CAR) was performed on Day 1 post-stimulation using a MOI of 2.5, and allowed to expand in a 37° C./5% CO2 incubator. NTD cells were cultured as a control.

T Cell Expansion: Starting on Day 3, cells were fed and split every other day to 0.5×106 cells/mL using fresh T cell culture medium. Cells were maintained in culture through Day 9, at which point they were harvested and de-beaded. Cells were frozen in cryopreservation media in aliquots of $5 \times 10^7$ cells/mL (1 mL volume per vial) and stored in liquid nitrogen for later use.

Cell Counting: At various time-points throughout expansion, cells were gently mixed and an aliquot of cells was collected from a known culture volume and placed in a LUNA™ Cell counting slides (Logos Biosystems) following the addition of an acridine orange and propidium iodide cell viability dye. Cells were then counted using a Luna Automated Cell Counter (Logos Biosystems).

Flow Cytometry: Transgene expression of fresh cell aliquots was measured by flow cytometry. To determine transduction efficiency, the desired number of cells were centrifuged, resuspended in 100 μL fluorescence activated cell sorter (FACS) buffer (1× phosphate buffered saline [PBS] with 2% fetal bovine serum [FBS]), and stained for 20 minutes on ice with either 1.0 μg/100 μL biotinylated protein L or 5 μL/100 μL goat anti-mouse. Cells were washed 2 times with FACS buffer and stained with 1 μL/100 μL of streptavidin-PE for 20 minutes on ice. Cells were then washed in PBS and stained with L/D violet 0.1 μL/100 μL in PBS for 20 minutes at room temperature. After staining, cells were washed again, resuspended in 400 μL of FACS buffer, and acquired using a BD LSRFortessa.

T Cell Expansion:

Five different normal donors were used to generate CART-TnMUC1 cells with SIN lentiviral vectors. In brief, primary human T cells were isolated from mononuclear cells, cultured in medium supplemented with IL-2, and stimulated with CD3/CD28 beads (Invitrogen) at a 1:3 cell-to-bead ratio. Approximately 16 h after activation, T cells were transduced with lentivirus containing TnMUC1 CAR, TnMUC1-BBz CAR, or CD19 CAR and incubated overnight. NTD cells were cultured as a control. T cells were diluted with fresh culture medium every other day during expansion to maintain optimal growth.

Transduction with the TnMUC1 CAR did not negatively impact growth, as compared to the TnMUC1-BBz CAR, CD19 CAR, and NTD cells. Total cell numbers and population doubling levels (PDL) were calculated and plotted along with MCV. MCV was only determined for samples enumerated using the Multisizer 3 (ND473, ND474, ND502, ND525). Results are shown in FIGS. 31 and 32.

Figure 31:
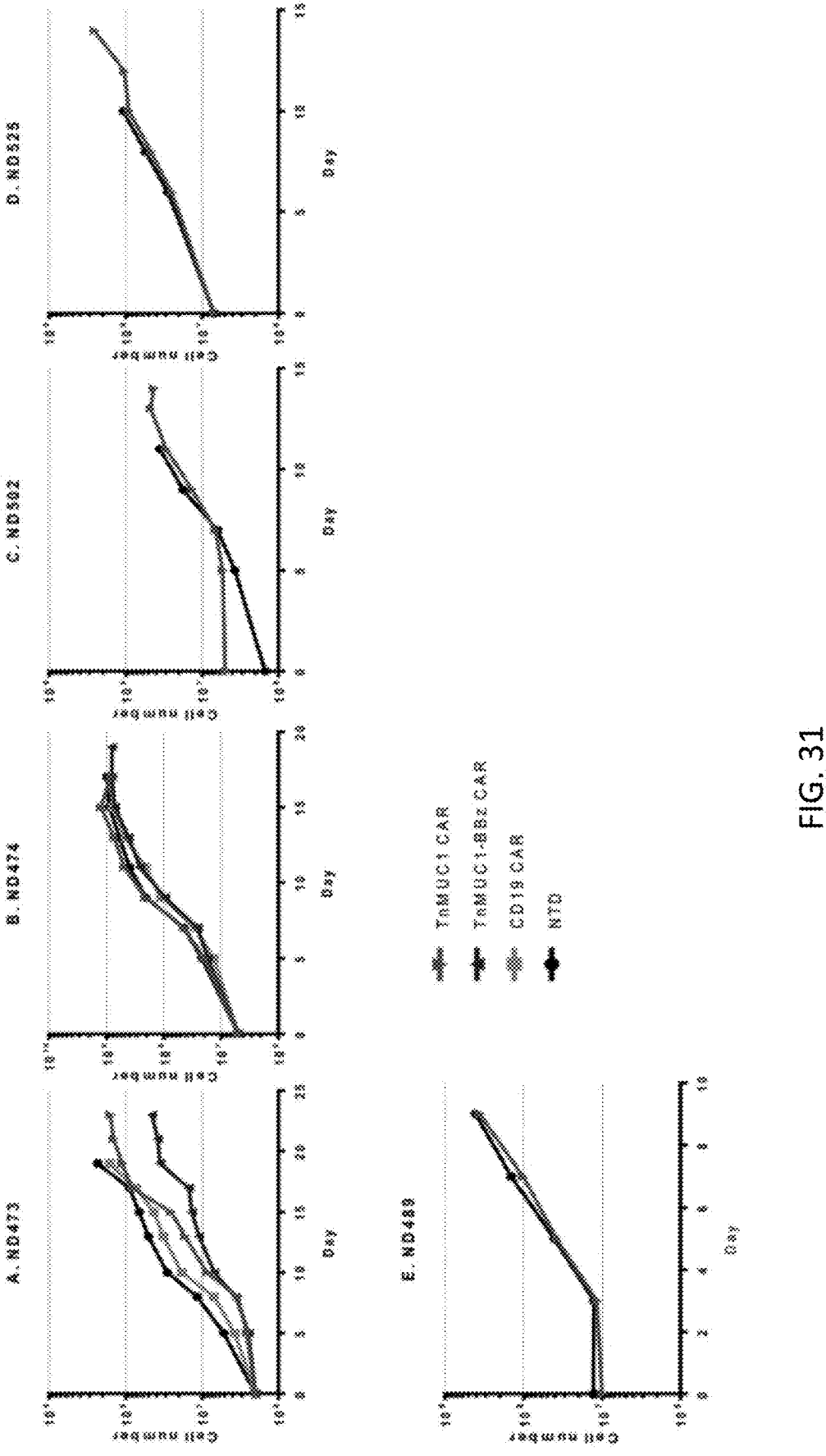
FIG. 31 is a series of graphs showing the total cell numbers for T cells from 5 different normal healthy donors transduced with the indicated CARs.

FIG. 31 shows the total cell numbers for T cells from 5 different normal healthy donors were transduced with the indicated CARs and expanded in vitro and viable cells were cultured. (A) ND473 (B) ND474, (C) ND502, (D) ND525, (E) ND489. Total cell numbers were calculated at each time-point and are plotted on the y-axis.

Figure 32:
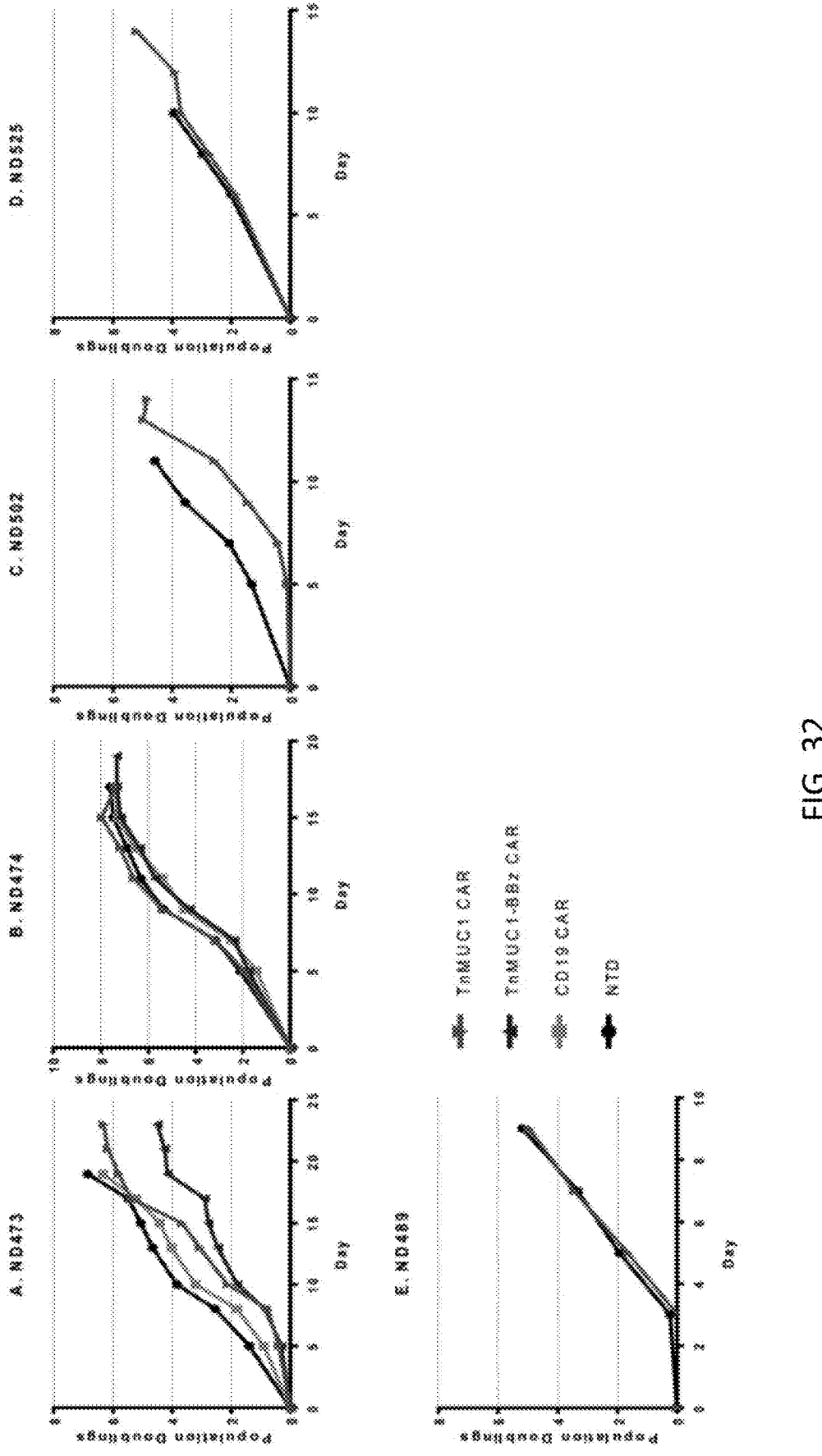
FIG. 32 is a series of graphs showing the population doublings of T cells from 5 different normal healthy donors transduced with the indicated CARs.

FIG. 32 shows the population doublings of T cells from 5 different normal healthy donors were transduced with the indicated CARs and expanded in vitro and viable cells were cultured. (A) ND473 (B) ND474, (C) ND502, (D) ND525, (E) ND489. Population doublings were calculated at each time-point and are plotted on the y-axis.

Figure 33:
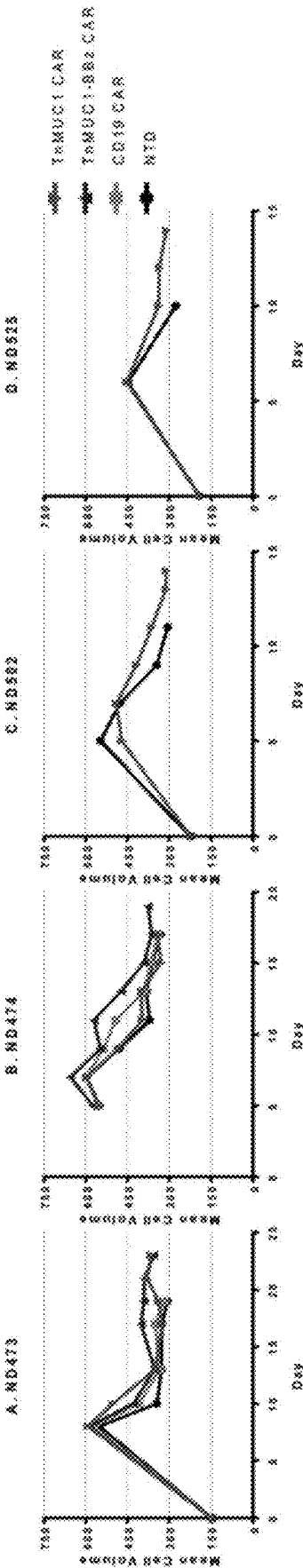
FIG. 33 is a series of graphs showing the mean cell volumes of T cells from 4 different normal healthy donors transduced with the indicated CARs.

FIG. 33 shows the mean cell volumes of T cells from 4 different normal healthy donors were transduced with the indicated CARs and expanded in vitro and viable cells were cultured. (A) ND473 (B) ND474, (C) ND502, (D) ND525. Mean cell volumes at each time point are plotted on the y axis. Mean cell volumes were not recorded for ND489.

For ND473, ND474, ND502, and ND525, culture duration was determined by decreased rate of cell division and a decrease in mean cellular volume to around ~350 to ~300 fL. CAR transduction can influence T cell activation state and increase the time that cell products remain above an MCV of 300 fL. Mean cell volumes peaked between days 5 to 8 and varied by donor. For ND473, cells were cryopreserved on day 23 for the TnMUC1 CAR and TnMUC1-BBz CAR groups and on day 19 for the CD19 CAR and NTD groups. For ND474, all groups were cryopreserved on day 17 except the TnMUC1-BBz CAR group, which was cryopreserved on day 19. For ND502 and ND525, the TnMUC1 CAR groups were cryopreserved on day 14, and the NTD groups were cryopreserved on day 11 and day 10, respectively.

In contrast, for ND489, both TnMUC1 CAR and NTD groups were cryopreserved on day 9. STIL prepares T cells over the course of 9-days to align with the 9-11 day CAR-T cell production.

At harvest, the TnMUC1 CAR-transduced group reached total fold expansions ranging from 8.7 (14 day culture, ND502) to 169.6 (17 day culture, ND474). The donor with the 9 day culture reached a total fold expansion of 36.3 (ND489). Harvest PDLs for the TnMUC1 CAR-transduced group ranged from 4.85 (14 day culture, ND502) to 7.4 (17 day culture, ND474). The donor with the 9 day culture had a harvest PDL of 4.97 (ND489). For all donors, harvest PDLs were not inhibited by more than 10% of donor-matched NTD cells at harvest.

Figure 34:
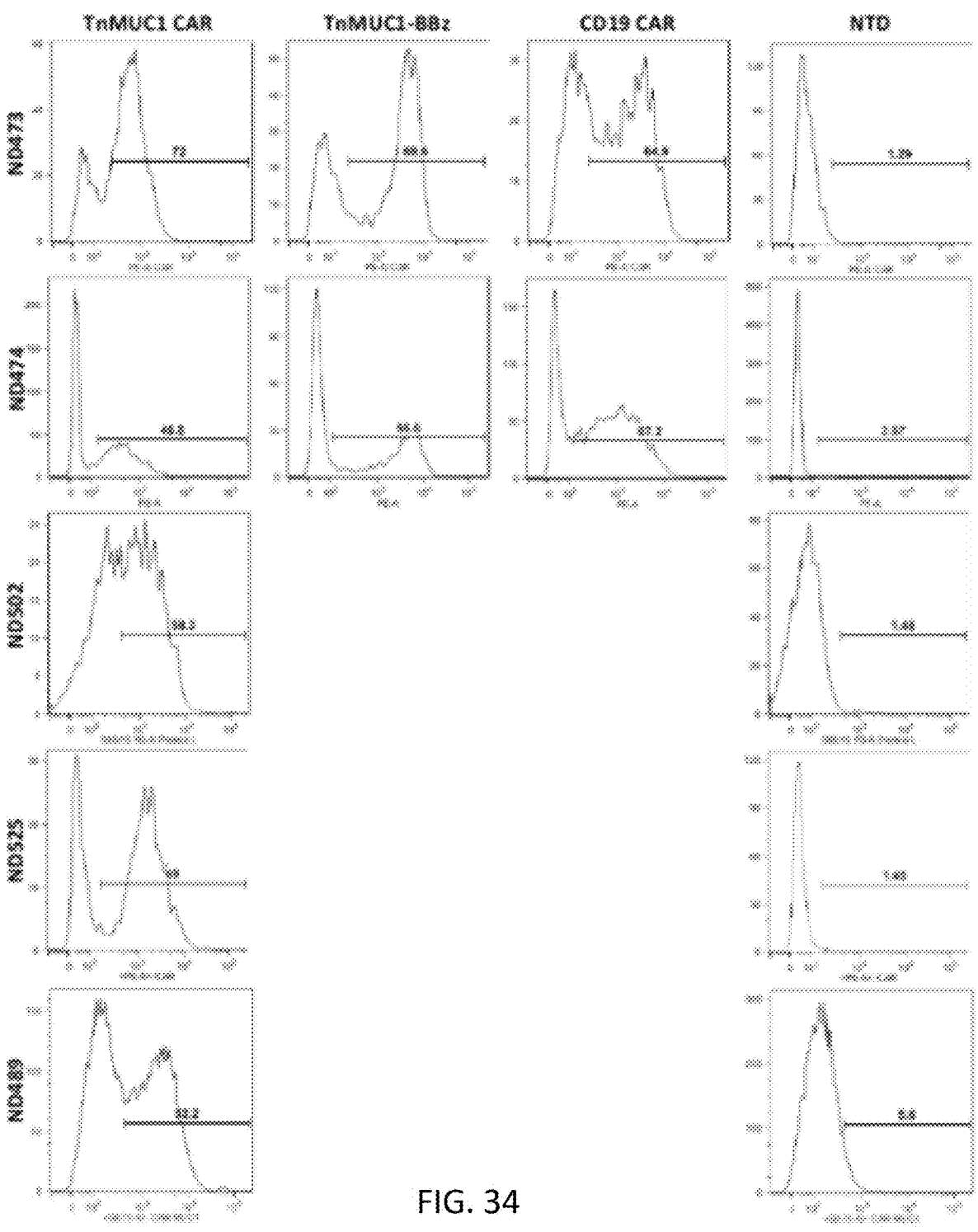
FIG. 34 is a set of flow cytometry plots showing the expression of the indicated CARs in T cells of 5 different normal healthy donors.

CAR Expression of Human T Cells:

Transgene expression was measured by flow cytometry using biotinylated protein L and streptavidin-PE or Biotin-Goat Anti-Mouse and streptavidin-PE. Expression is shown in FIG. 34. In FIG. 34, normal donor T cells were transduced with the indicated lentiviral expression vectors and the percentage of scFv+ T cells was measured by flow cytometry.

Transduction efficiencies for the TnMUC1 CAR were 72% (ND473; mean fluorescence intensity [MFI] 779), 46.8% (ND474; MFI 683), 58.3% (ND502; MFI 2617), 69.0% (ND525; MFI 2678), and 52.2% (ND489; MFI 2116). These results demonstrate that vector successfully drives expression of the TnMUC1 CAR transgene. Average transgene expression across the 5 normal donors was 59.7%, with an average MFI of 1775, while in the subset of 2 donors also used to produce CART-TnMUC1-BBz and CART-19 the average transduction efficiency was 59.4% with average MFI of 731.

Donor-matched transduction efficiencies for the TnMUC1-BBz CAR and CD19 CAR were 69.6% (MFI 4442) and 64.9% (MFI 2773), respectively, for ND473, and 55.6% (MFI 4342) and 67.2% (MFI 1971), respectively, for ND474. Average transduction efficiencies were 62.6% (average MFI 4392) for the TnMUC1-BBz CAR and 66.1% (average MFI 2372) for the CD19 CAR. ND502, ND525, and ND489 were not transduced with the TnMUC1-BBz CAR or CD19 CAR vector.

While the total percentage of donor-matched TnMUC1 CAR and TnMUC1-BBz CAR transduced cells was similar, differences in MFI indicate reduced intensity of the TnMUC1 CAR transgene.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A modified immune cell comprising:

(a) a chimeric antigen receptor (CAR) that specifically binds MUC1 on a target cell, wherein the CAR comprises a MUC1-specific antigen binding domain, a transmembrane domain, a costimulatory signaling domain, and an intracellular signaling domain of CD3 zeta, and wherein the CAR comprises the amino acid sequence set forth in SEQ ID NO: 47; and (b) a switch receptor comprising an extracellular domain of a signaling protein associated with a negative signal, a transmembrane domain, and an intracellular domain of a signaling protein associated with a positive signal; wherein the extracellular domain and the intracellular domain are respectively selected from PD-1 and CD28, PD-1$^{A132L}$ and CD28, PD-1 and 4-1BB, PD-1$^{A132L}$ and 4-1BB, PD-1 and IL12Rβ1, PD-1$^{A132L}$ and IL12Rβ1, PD-1 and IL12Rβ2, PD-1$^{A132L}$ and IL12Rβ2, TGFβRII and IL12Rβ1, TGFβRII and IL12Rβ2, TGFβRII and CD28, or TIM3 and CD28; and wherein the switch receptor is able to switch a negative signal to a positive signal upon activation, thereby enhancing an immune response.

2. The modified immune cell of claim 1, wherein the switch receptor is PD1-CTM-CD28 or TGFβR-IL12Rβ1.

3. The modified immune cell of claim 1, wherein the modified cell is a modified natural killer (NK) cell, a modified natural killer T (NKT) cell, or a modified T cell.

4. The modified immune cell of claim 3, wherein the modified immune cell is a modified T cell.

5. The modified immune cell of claim 1, wherein:

the switch receptor comprises an amino acid sequence selected from the group consisting of SEQ ID NO: 78, 80, 82, 84, 86, 88, 90, and 92.

6. An isolated nucleic acid comprising:

(a) a first nucleic acid sequence encoding a chimeric antigen receptor (CAR) that specifically binds MUC1 on a target cell, wherein the CAR comprises a MUC1-specific antigen binding domain, a transmembrane domain, a costimulatory signaling domain, and an intracellular signaling domain of CD3 zeta, and wherein the first nucleic acid sequence comprises SEQ ID NO: 46; and (b) a second nucleic acid sequence encoding a switch receptor comprising an extracellular domain of a signaling protein associated with a negative signal, a transmembrane domain, and an intracellular domain of a signaling protein associated with a positive signal;

wherein the extracellular domain and the intracellular domain are respectively selected from PD-1 and CD28, PD-1$^{4132L}$ and CD28, PD-1 and 4-1BB, PD-1$^{4132L}$ and 4-1BB, PD-1 and IL12Rβ1, PD-1$^{4132L}$ and IL12Rβ1, PD-1 and IL12Rβ2, PD-1$^{4132L}$ and IL12Rβ2, TGFβRII and IL12Rβ1, TGFβRII and IL12Rβ2, TGFβRII and CD28, or TIM3 and CD28;

wherein the switch receptor is able to switch the negative signal to the positive signal upon activation, thereby enhancing an immune response; and wherein the first and second nucleic acid sequences are separated by a nucleic acid sequence encoding a self-cleaving peptide.

7. The isolated nucleic acid of claim 6, wherein and the second nucleic acid sequence comprises a nucleic acid sequence selected from the group consisting of SEQ ID NO: 79, 81, 83, 85, 87, 89, 91, and 93.

8. An expression construct comprising the isolated nucleic acid of claim 6.

9. A method for generating a modified immune cell, comprising introducing into an immune cell the isolated nucleic acid of claim 6.

10. A method of treating a MUC1 associated cancer in a subject in need thereof, comprising administering to the subject a therapeutically effective amount of a composition comprising the modified immune of claim 1.

11. The method of claim 10, further comprising:

(a) administering to the subject a lymphodepleting chemotherapy; and/or (b) administering to the subject a cytokine release syndrome (CRS) management regimen.

12. The method of claim 11, wherein the lymphodepleting chemotherapy comprises administering to the subject a therapeutically effective amount of cyclophosphamide, and a therapeutically effective amount of fludarabine.

13. The method of claim 10, wherein the MUC1-associated cancer is:

(a) selected from the group consisting of multiple myeloma, non-small cell lung cancer, breast cancer, pancreatic adenocarcinoma, ovarian, and fallopian tube cancer;

and/or (b) characterized by abnormal glycosylation of MUC1.

14. The method of claim 13, wherein the breast cancer is selected from the group consisting of a hormone receptor-positive breast cancer, a hormone receptor-negative breast cancer, an estrogen receptor-negative breast cancer, a progesterone receptor-negative breast cancer, triple negative breast cancer, and a Her2 receptor-negative breast cancer.

* * * * *

SEQUENCE LISTING

<160> NUMBER OF SEQ ID NOS: 106

<210> SEQ ID NO 1
<211> LENGTH: 1476
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e5BBz)

<400> SEQUENCE: 1

```
atggccttac cagtgaccgc cttgctcctg ccgctggcct tgctgctcca cgccgccagg      60
ccgggatccc aggtgcagct gcagcagtct gatgccgagc tcgtgaagcc tggcagcagc     120
gtgaagatca gctgcaaggc cagcggctac accttcaccg accacgccat ccactgggtc     180
aagcagaagc ctgagcaggg cctggagtgg atcggccact tcagccccgg caacaccgac     240
atcaagtaca cgacaagtt caagggcaag gccaccctga ccgtggacag aagcagcagc     300
accgcctaca tgcagctgaa cagcctgacc agcgaggaca cgccgtgta cttctgcaag     360 accagcacct tcttttttcga ctactggggc caggcacaa ccctgacagt gtctagcgga     420
ggcggaggat ctggcggcgg aggaagtggc ggagggggat ctgaactcgt gatgacccag     480
agccccagct ctctgacagt gacagccggc gagaaagtga ccatgatctg caagtcctcc     540
cagagcctgc tgaactccgg cgaccagaag aactacctga cctggtatca gcagaaaccc     600
ggccagcccc ccaagctgct gatcttttgg gccagcaccc gggaaagcgg cgtgcccgat     660
agattcacag gcagcggctc cggcaccgac tttaccctga ccatcagctc cgtgcaggcc     720
gaggacctgg ccgtgtatta ctgccagaac gactacagct accccctgac cttcggagcc     780
ggcaccaagc tggaactgaa gtccggaacc acgacgccag cgccgcgacc accaacaccg     840
gcgcccacca tcgcgtcgca gcccctgtcc ctgcgcccag aggcgtgccg gccagcggcg     900
gggggcgcag tgcacacgag ggggctggac ttcgcctgtg atatctacat ctgggcgccc     960
ttggccggga cttgtggggt ccttctcctg tcactggtta tcacccttta ctgcaaacgg    1020
ggcagaaaga aactcctgta tatattcaaa caaccatta tgagaccagt acaaactact    1080
caagaggaag atggctgtag ctgccgattt ccagaagaag aagaaggagg atgtgaactg    1140
agagtgaagt tcagcaggag cgcagacgcc cccgcgtaca gcagggcca gaaccagctc    1200 tataacgagc tcaatctagg acgaagagag gagtacgatg ttttggacaa gagacgtggc    1260
cgggaccctg agatgggggg aaagccgaga aggaagaacc ctcaggaagg cctgtacaat    1320
gaactgcaga agataagat ggcggaggcc tacagtgaga ttgggatgaa aggcgagcgc    1380
cggaggggca aggggcacga tggcctttac caggtctca gtacagccac caaggacacc    1440
tacgacgccc ttcacatgca ggccctgccc cctcgc                             1476
```

<210> SEQ ID NO 2
<211> LENGTH: 492
<212> TYPE: PRT
<213> ORGANISM: Artificial Sequence
<220> FEATURE:
<223> OTHER INFORMATION: CAR
<220> FEATURE:
<223> OTHER INFORMATION: Tn-MUC1 (5e5BBz)

<400> SEQUENCE: 2

```
Met Ala Leu Pro Val Thr Ala Leu Leu Leu Pro Leu Ala Leu Leu Leu
1               5                   10                  15
```

```
His Ala Ala Arg Pro Gly Ser Gln Val Gln Leu Gln Gln Ser Asp Ala
             20              25              30

Glu Leu Val Lys Pro Gly Ser Ser Val Lys Ile Ser Cys Lys Ala Ser
         35              40              45

Gly Tyr Thr Phe Thr Asp His Ala Ile His Trp Val Lys Gln Lys Pro
     50              55              60

Glu Gln Gly Leu Glu Trp Ile Gly His Phe Ser Pro Gly Asn Thr Asp
65              70              75              80

Ile Lys Tyr Asn Asp Lys Phe Lys Gly Lys Ala Thr Leu Thr Val Asp
             85              90              95

Arg Ser Ser Ser Thr Ala Tyr Met Gln Leu Asn Ser Leu Thr Ser Glu
         100             105             110

Asp Ser Ala Val Tyr Phe Cys Lys Thr Ser Thr Phe Phe Phe Asp Tyr
     115             120             125

Trp Gly Gln Gly Thr Thr Leu Thr Val Ser Ser Gly Gly Gly Gly Ser
     130             135             140

Gly Gly Gly Gly Ser Gly Gly Gly Ser Glu Leu Val Met Thr Gln
145             150             155             160

Ser Pro Ser Ser Leu Thr Val Thr Ala Gly Glu Lys Val Thr Met Ile
             165             170             175

Cys Lys Ser Ser Gln Ser Leu Leu Asn Ser Gly Asp Gln Lys Asn Tyr
             180             185             190

Leu Thr Trp Tyr Gln Gln Lys Pro Gly Gln Pro Pro Lys Leu Leu Ile
         195             200             205

Phe Trp Ala Ser Thr Arg Glu Ser Gly Val Pro Asp Arg Phe Thr Gly
     210             215             220

Ser Gly Ser Gly Thr Asp Phe Thr Leu Thr Ile Ser Ser Val Gln Ala
225             230             235             240

Glu Asp Leu Ala Val Tyr Tyr Cys Gln Asn Asp Tyr Ser Tyr Pro Leu
             245             250             255

Thr Phe Gly Ala Gly Thr Lys Leu Glu Leu Lys Ser Gly Thr Thr Thr
             260             265             270

Pro Ala Pro Arg Pro Pro Thr Pro Ala Pro Thr Ile Ala Ser Gln Pro
         275             280             285

Leu Ser Leu Arg Pro Glu Ala Cys Arg Pro Ala Ala Gly Gly Ala Val
     290             295             300

His Thr Arg Gly Leu Asp Phe Ala Cys Asp Ile Tyr Ile Trp Ala Pro
305             310             315             320

Leu Ala Gly Thr Cys Gly Val Leu Leu Leu Ser Leu Val Ile Thr Leu
             325             330             335

Tyr Cys Lys Arg Gly Arg Lys Lys Leu Leu Tyr Ile Phe Lys Gln Pro
             340             345             350

Phe Met Arg Pro Val Gln Thr Thr Gln Glu Glu Asp Gly Cys Ser Cys
         355             360             365

Arg Phe Pro Glu Glu Glu Glu Gly Gly Cys Glu Leu Arg Val Lys Phe
     370             375             380

Ser Arg Ser Ala Asp Ala Pro Ala Tyr Lys Gln Gly Gln Asn Gln Leu
385             390             395             400

Tyr Asn Glu Leu Asn Leu Gly Arg Arg Glu Glu Tyr Asp Val Leu Asp
             405             410             415

Lys Arg Arg Gly Arg Asp Pro Glu Met Gly Gly Lys Pro Arg Arg Lys
             420             425             430

Asn Pro Gln Glu Gly Leu Tyr Asn Glu Leu Gln Lys Asp Lys Met Ala
```

```
          435                    440                    445
Glu Ala Tyr Ser Glu Ile Gly Met Lys Gly Glu Arg Arg Arg Gly Lys
    450                    455                    460

Gly His Asp Gly Leu Tyr Gln Gly Leu Ser Thr Ala Thr Lys Asp Thr
465                    470                    475                    480

Tyr Asp Ala Leu His Met Gln Ala Leu Pro Pro Arg
                485                    490
```

```
<210> SEQ ID NO 3
<211> LENGTH: 732
<212> TYPE: DNA
<213> ORGANISM: Artificial Sequence
<220> FEATURE:
<223> OTHER INFORMATION: scFv
<220> FEATURE:
<223> OTHER INFORMATION: 5e5

<400> SEQUENCE: 3
caggtgcagc tgcagcagtc tgatgccgag ctcgtgaagc ctggcagcag cgtgaagatc      60
agctgcaagg ccagcggcta caccttcacc gaccacgcca tccactgggt caagcagaag     120
cctgagcagg gcctggagtg gatcggccac ttcagccccg gcaacaccga catcaagtac     180
aacgacaagt tcaagggcaa ggccaccctg accgtggaca gaagcagcag caccgcctac     240
atgcagctga cagcctgac cagcgaggac agcgccgtgt acttctgcaa gaccagcacc     300 ttcttttttcg actactgggg ccagggcaca accctgacag tgtctagcgg aggcggagga     360
tctggcggcg aggaagtgg cggaggggga tctgaactcg tgatgaccca gagccccagc     420
tctctgacag tgacagccgg cgagaaagtg accatgatct gcaagtcctc ccagagcctg     480
ctgaactccg gcgaccagaa gaactacctg acctggtatc agcagaaacc cggccagccc     540
cccaagctgc tgatcttttg gccagcacc cgggaaagcg gcgtgcccga tagattcaca     600
ggcagcggct ccggcaccga ctttaccctg accatcagct ccgtgcaggc cgaggacctg     660
gccgtgtatt actgccagaa cgactacagc taccccctga ccttcggagc cggcaccaag     720
ctggaactga ag                                                        732
```

```
<210> SEQ ID NO 4
<211> LENGTH: 244
<212> TYPE: PRT
<213> ORGANISM: Artificial Sequence
<220> FEATURE:
<223> OTHER INFORMATION: scFv
<220> FEATURE:
<223> OTHER INFORMATION: 5e5

<400> SEQUENCE: 4

Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Phe Cys
                85                  90                  95
```

Lys Thr Ser Thr Phe Phe Phe Asp Tyr Trp Gly Gln Gly Thr Thr Leu
              100                     105                     110

Thr Val Ser Ser Gly Gly Gly Gly Ser Gly Gly Gly Ser Gly Gly
          115                     120                     125

Gly Gly Ser Glu Leu Val Met Thr Gln Ser Pro Ser Ser Leu Thr Val
          130                     135                     140

Thr Ala Gly Glu Lys Val Thr Met Ile Cys Lys Ser Ser Gln Ser Leu
145                     150                     155                     160

Leu Asn Ser Gly Asp Gln Lys Asn Tyr Leu Thr Trp Tyr Gln Gln Lys
                  165                     170                     175

Pro Gly Gln Pro Pro Lys Leu Leu Ile Phe Trp Ala Ser Thr Arg Glu
              180                     185                     190

Ser Gly Val Pro Asp Arg Phe Thr Gly Ser Gly Ser Gly Thr Asp Phe
          195                     200                     205

Thr Leu Thr Ile Ser Ser Val Gln Ala Glu Asp Leu Ala Val Tyr Tyr
      210                     215                     220

Cys Gln Asn Asp Tyr Ser Tyr Pro Leu Thr Phe Gly Ala Gly Thr Lys
225                     230                     235                     240

Leu Glu Leu Lys

<210> SEQ ID NO 5
<211> LENGTH: 116
<212> TYPE: PRT
<213> ORGANISM: Artificial Sequence
<220> FEATURE:
<223> OTHER INFORMATION: VH
<220> FEATURE:
<223> OTHER INFORMATION: 5e5

<400> SEQUENCE: 5

Gln Val Gln Leu Gln Gln Ser Asp Ala Glu Leu Val Lys Pro Gly Ser
1                     5                     10                     15

Ser Val Lys Ile Ser Cys Lys Ala Ser Gly Tyr Thr Phe Thr Asp His
              20                     25                     30

Ala Ile His Trp Val Lys Gln Lys Pro Glu Gln Gly Leu Glu Trp Ile
          35                     40                     45

Gly His Phe Ser Pro Gly Asn Thr Asp Ile Lys Tyr Asn Asp Lys Phe
      50                     55                     60

Lys Gly Lys Ala Thr Leu Thr Val Asp Arg Ser Ser Ser Thr Ala Tyr
65                     70                     75                     80

Met Gln Leu Asn Ser Leu Thr Ser Glu Asp Ser Ala Val Tyr Phe Cys
                  85                     90                     95

Lys Thr Ser Thr Phe Phe Phe Asp Tyr Trp Gly Gln Gly Thr Thr Leu
              100                     105                     110

Thr Val Ser Ser
          115

<210> SEQ ID NO 6
<211> LENGTH: 113
<212> TYPE: PRT
<213> ORGANISM: Artificial Sequence
<220> FEATURE:
<223> OTHER INFORMATION: VL
<220> FEATURE:
<223> OTHER INFORMATION: 5e5

<400> SEQUENCE: 6

Glu Leu Val Met Thr Gln Ser Pro Ser Ser Leu Thr Val Thr Ala Gly
1                     5                     10                     15

```
Glu Lys Val Thr Met Ile Cys Lys Ser Ser Gln Ser Leu Leu Asn Ser
                20                  25                  30

Gly Asp Gln Lys Asn Tyr Leu Thr Trp Tyr Gln Gln Lys Pro Gly Gln
            35                  40                  45

Pro Pro Lys Leu Leu Ile Phe Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys
```

<210> SEQ ID NO 7
<211> LENGTH: 24
<212> TYPE: PRT
<213> ORGANISM: Artificial Sequence
<220> FEATURE:
<223> OTHER INFORMATION: TM
<220> FEATURE:
<223> OTHER INFORMATION: CD8alpha

<400> SEQUENCE: 7

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 8
<211> LENGTH: 72
<212> TYPE: DNA
<213> ORGANISM: Artificial Sequence
<220> FEATURE:
<223> OTHER INFORMATION: TM
<220> FEATURE:
<223> OTHER INFORMATION: CD8alpha

<400> SEQUENCE: 8

```
atctacatct gggcgccctt ggccgggact tgtggggtcc ttctcctgtc actggttatc      60
accctttact gc                                                          72
```

<210> SEQ ID NO 9
<211> LENGTH: 42
<212> TYPE: PRT
<213> ORGANISM: Artificial Sequence
<220> FEATURE:
<223> OTHER INFORMATION: Domain
<220> FEATURE:
<223> OTHER INFORMATION: 4-1BB

<400> SEQUENCE: 9

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 10
<211> LENGTH: 126

```
<212> TYPE: DNA
<213> ORGANISM: Artificial Sequence
<220> FEATURE:
<223> OTHER INFORMATION: Domain
<220> FEATURE:
<223> OTHER INFORMATION: 4-1BB

<400> SEQUENCE: 10
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                               126

<210> SEQ ID NO 11
<211> LENGTH: 112
<212> TYPE: PRT
<213> ORGANISM: Artificial Sequence
<220> FEATURE:
<223> OTHER INFORMATION: Domain
<220> FEATURE:
<223> OTHER INFORMATION: CD3zeta

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 12
<211> LENGTH: 336
<212> TYPE: DNA
<213> ORGANISM: Artificial Sequence
<220> FEATURE:
<223> OTHER INFORMATION: Domain
<220> FEATURE:
<223> OTHER INFORMATION: CD3zeta

<400> SEQUENCE: 12
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac caggtctca gtacagccac caaggacacc      300
tacgacgccc ttcacatgca ggccctgccc cctcgc                              336

<210> SEQ ID NO 13
<211> LENGTH: 45
<212> TYPE: PRT
<213> ORGANISM: Artificial Sequence
<220> FEATURE:
<223> OTHER INFORMATION: Hinge
```

-continued

```
<220> FEATURE:
<223> OTHER INFORMATION: CD8

<400> SEQUENCE: 13

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 14
<211> LENGTH: 135
<212> TYPE: DNA
<213> ORGANISM: Artificial Sequence
<220> FEATURE:
<223> OTHER INFORMATION: Hinge
<220> FEATURE:
<223> OTHER INFORMATION: CD8

<400> SEQUENCE: 14
accacgacgc cagcgccgcg accaccaaca ccggcgccca ccatcgcgtc gcagcccctg      60
tccctgcgcc cagaggcgtg ccggccagcg gcggggggcg cagtgcacac gaggggctg     120 gacttcgcct gtgat                                                     135

<210> SEQ ID NO 15
<211> LENGTH: 27
<212> TYPE: PRT
<213> ORGANISM: Artificial Sequence
<220> FEATURE:
<223> OTHER INFORMATION: TM
<220> FEATURE:
<223> OTHER INFORMATION: CD28

<400> SEQUENCE: 15

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 16
<211> LENGTH: 81
<212> TYPE: DNA
<213> ORGANISM: Artificial Sequence
<220> FEATURE:
<223> OTHER INFORMATION: TM
<220> FEATURE:
<223> OTHER INFORMATION: CD28

<400> SEQUENCE: 16
ttttgggtgc tggtggtggt tggtggagtc ctggcttgct atagcttgct agtaacagtg      60
gcctttatta ttttctgggt g                                               81

<210> SEQ ID NO 17
<211> LENGTH: 41
<212> TYPE: PRT
<213> ORGANISM: Artificial Sequence
<220> FEATURE:
<223> OTHER INFORMATION: Domain
<220> FEATURE:
<223> OTHER INFORMATION: CD28

<400> SEQUENCE: 17

Arg Ser Lys Arg Ser Arg Leu Leu His Ser Asp Tyr Met Asn Met Thr
```

```
1                5              10             15

Pro Arg Arg Pro Gly Pro Thr Arg Lys His Tyr Gln Pro Tyr Ala Pro
             20              25             30

Pro Arg Asp Phe Ala Ala Tyr Arg Ser
      35              40
```

<210> SEQ ID NO 18
<211> LENGTH: 123
<212> TYPE: DNA
<213> ORGANISM: Artificial Sequence
<220> FEATURE:
<223> OTHER INFORMATION: Domain
<220> FEATURE:
<223> OTHER INFORMATION: CD28

<400> SEQUENCE: 18

```
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                    123
```

<210> SEQ ID NO 19
<211> LENGTH: 14
<212> TYPE: PRT
<213> ORGANISM: Artificial Sequence
<220> FEATURE:
<223> OTHER INFORMATION: LC
<220> FEATURE:
<223> OTHER INFORMATION: CDR1

<400> SEQUENCE: 19

```
Gln Ser Leu Leu Asn Ser Gly Asp Gln Lys Asn Tyr Leu Thr
1                5                  10
```

<210> SEQ ID NO 20
<211> LENGTH: 11
<212> TYPE: PRT
<213> ORGANISM: Artificial Sequence
<220> FEATURE:
<223> OTHER INFORMATION: LC
<220> FEATURE:
<223> OTHER INFORMATION: CDR2

<400> SEQUENCE: 20

```
Leu Leu Ile Phe Trp Ala Ser Thr Arg Glu Ser
1                5                  10
```

<210> SEQ ID NO 21
<211> LENGTH: 8
<212> TYPE: PRT
<213> ORGANISM: Artificial Sequence
<220> FEATURE:
<223> OTHER INFORMATION: LC
<220> FEATURE:
<223> OTHER INFORMATION: CDR3

<400> SEQUENCE: 21

```
Gln Asn Asp Tyr Ser Tyr Pro Leu
1                5
```

<210> SEQ ID NO 22
<211> LENGTH: 9
<212> TYPE: PRT
<213> ORGANISM: Artificial Sequence
<220> FEATURE:
<223> OTHER INFORMATION: HC
<220> FEATURE:

<223> OTHER INFORMATION: CDR1

<400> SEQUENCE: 22

Tyr Thr Phe Thr Asp His Ala Ile His
1               5

<210> SEQ ID NO 23
<211> LENGTH: 14
<212> TYPE: PRT
<213> ORGANISM: Artificial Sequence
<220> FEATURE:
<223> OTHER INFORMATION: HC
<220> FEATURE:
<223> OTHER INFORMATION: CDR2

<400> SEQUENCE: 23

Trp Ile Gly His Phe Ser Pro Gly Asn Thr Asp Ile Lys Tyr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: HC
<220> FEATURE:
<223> OTHER INFORMATION: CDR3

<400> SEQUENCE: 24

Lys Thr Ser Thr Phe Phe Phe Asp Tyr
1               5

<210> SEQ ID NO 25
<211> LENGTH: 35
<212> TYPE: PRT
<213> ORGANISM: Artificial Sequence
<220> FEATURE:
<223> OTHER INFORMATION: Domain
<220> FEATURE:
<223> OTHER INFORMATION: ICOS

<400> SEQUENCE: 25

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 26
<211> LENGTH: 105
<212> TYPE: DNA
<213> ORGANISM: Artificial Sequence
<220> FEATURE:
<223> OTHER INFORMATION: Domain
<220> FEATURE:
<223> OTHER INFORMATION: ICOS

<400> SEQUENCE: 26
acaaaaaaga agtattcatc cagtgtgcac gaccctaacg gtgaatacat gttcatgaga        60
gcagtgaaca cagccaaaaa atctagactc acagatgtga cccta                       105

<210> SEQ ID NO 27
<211> LENGTH: 105
<212> TYPE: DNA
<213> ORGANISM: Artificial Sequence

```
<220> FEATURE:
<223> OTHER INFORMATION: Domain
<220> FEATURE:
<223> OTHER INFORMATION: ICOS

<400> SEQUENCE: 27
acaaaaaaga agtattcatc cagtgtgcac gaccctaacg gtgaatacat gttcatgaga        60
gcagtgaaca cagccaaaaa atccagactc acagatgtga cccta                       105

<210> SEQ ID NO 28
<211> LENGTH: 117
<212> TYPE: PRT
<213> ORGANISM: Artificial Sequence
<220> FEATURE:
<223> OTHER INFORMATION: Domain
<220> FEATURE:
<223> OTHER INFORMATION: CD2

<400> SEQUENCE: 28

Thr Lys Arg Lys Lys Gln Arg Ser Arg Arg Asn Asp Glu Glu Leu Glu
1               5                   10                  15

Thr Arg Ala His Arg Val Ala Thr Glu Glu Arg Gly Arg Lys Pro His
                20                  25                  30

Gln Ile Pro Ala Ser Thr Pro Gln Asn Pro Ala Thr Ser Gln His Pro
            35                  40                  45

Pro Pro Pro Pro Gly His Arg Ser Gln Ala Pro Ser His Arg Pro Pro
        50                  55                  60

Pro Pro Gly His Arg Val Gln His Gln Pro Gln Lys Arg Pro Pro Ala
65                  70                  75                  80

Pro Ser Gly Thr Gln Val His Gln Gln Lys Gly Pro Pro Leu Pro Arg
                85                  90                  95

Pro Arg Val Gln Pro Lys Pro Pro His Gly Ala Ala Glu Asn Ser Leu
            100                 105                 110

Ser Pro Ser Ser Asn
        115

<210> SEQ ID NO 29
<211> LENGTH: 351
<212> TYPE: DNA
<213> ORGANISM: Artificial Sequence
<220> FEATURE:
<223> OTHER INFORMATION: Domain
<220> FEATURE:
<223> OTHER INFORMATION: CD2

<400> SEQUENCE: 29
accaaaagga aaaacagag gagtcggaga aatgatgagg agctggagac aagagcccac        60
agagtagcta ctgaagaaag gggccggaag ccccaccaaa ttccagcttc aacccctcag       120
aatccagcaa cttcccaaca tcctcctcca ccacctggtc atcgttccca ggcacctagt       180
catcgtcccc cgcctcctgg acaccgtgtt cagcaccagc ctcagaagag gcctcctgct       240
ccgtcgggca cacaagttca ccagcagaaa ggcccgcccc tccccagacc tcgagttcag       300
ccaaaacctc cccatggggc agcagaaaac tcattgtccc cttcctctaa t                351

<210> SEQ ID NO 30
<211> LENGTH: 112
<212> TYPE: PRT
<213> ORGANISM: Artificial Sequence
<220> FEATURE:
<223> OTHER INFORMATION: Domain
<220> FEATURE:
```

<223> OTHER INFORMATION: CD3zeta (Q14K)

<400> SEQUENCE: 30

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 31
<211> LENGTH: 336
<212> TYPE: DNA
<213> ORGANISM: Artificial Sequence
<220> FEATURE:
<223> OTHER INFORMATION: Domain
<220> FEATURE:
<223> OTHER INFORMATION: CD3zeta (Q14K)

<400> SEQUENCE: 31

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336
```

<210> SEQ ID NO 32
<211> LENGTH: 41
<212> TYPE: PRT
<213> ORGANISM: Artificial Sequence
<220> FEATURE:
<223> OTHER INFORMATION: Domain
<220> FEATURE:
<223> OTHER INFORMATION: CD28 (YMFM)

<400> SEQUENCE: 32

```
Arg Ser Lys Arg Ser Arg Leu Leu His Ser Asp Tyr Met Phe Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 33
<211> LENGTH: 123
<212> TYPE: DNA
<213> ORGANISM: Artificial Sequence
<220> FEATURE:
<223> OTHER INFORMATION: Domain
<220> FEATURE:
<223> OTHER INFORMATION: CD28 (YMFM)

-continued

<400> SEQUENCE: 33
aggagtaaga ggagcaggct cctgcacagt gactacatgt tcatgactcc ccgccgcccc          60
gggcccaccc gcaagcatta ccagccctat gccccaccac gcgacttcgc agcctatcgc         120
tcc                                                                       123

<210> SEQ ID NO 34
<211> LENGTH: 48
<212> TYPE: PRT
<213> ORGANISM: Artificial Sequence
<220> FEATURE:
<223> OTHER INFORMATION: Domain
<220> FEATURE:
<223> OTHER INFORMATION: CD27

<400> SEQUENCE: 34

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 35
<211> LENGTH: 144
<212> TYPE: DNA
<213> ORGANISM: Artificial Sequence
<220> FEATURE:
<223> OTHER INFORMATION: Domain
<220> FEATURE:
<223> OTHER INFORMATION: CD27

<400> SEQUENCE: 35
caacgaagga aatatagatc aaacaaagga gaaagtcctg tggagcctgc agagccttgt          60
cgttacagct gccccaggga ggaggagggc agcaccatcc ccatccagga ggattaccga         120
aaaccggagc ctgcctgctc cccc                                                144

<210> SEQ ID NO 36
<211> LENGTH: 42
<212> TYPE: PRT
<213> ORGANISM: Artificial Sequence
<220> FEATURE:
<223> OTHER INFORMATION: Domain
<220> FEATURE:
<223> OTHER INFORMATION: OX40

<400> SEQUENCE: 36

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 37
<211> LENGTH: 126
<212> TYPE: DNA
<213> ORGANISM: Artificial Sequence
<220> FEATURE:
<223> OTHER INFORMATION: Domain
<220> FEATURE:
<223> OTHER INFORMATION: OX40

```
<400> SEQUENCE: 37
gccctgtacc tgctccgcag ggaccagagg ctgccccccg atgcccacaa gccccctggg      60
ggaggcagtt tcaggacccc catccaagag gagcaggccg acgcccactc caccctggcc     120
aagatc                                                                126

<210> SEQ ID NO 38
<211> LENGTH: 1482
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e528z)

<400> SEQUENCE: 38
atggccttac cagtgaccgc cttgctcctg ccgctggcct tgctgctcca cgccgccagg      60
ccgggatccc aggtgcagct gcagcagtct gatgccgagc tcgtgaagcc tggcagcagc     120
gtgaagatca gctgcaaggc cagcggctac accttcaccg accacgccat ccactgggtc     180
aagcagaagc ctgagcaggg cctggagtgg atcggccact tcagccccgg caacaccgac     240
atcaagtaca cgacaagtt caagggcaag gccaccctga ccgtggacag aagcagcagc     300
accgcctaca tgcagctgaa cagcctgacc agcgaggaca cgccgtgta cttctgcaag     360 accagcacct tcttttttcga ctactggggc agggcacaa ccctgacagt gtctagcgga     420
ggcggaggat ctggcggcgg aggaagtggc ggaggggggat ctgaactcgt gatgacccag     480
agccccagct ctctgacagt gacagccggc gagaaagtga ccatgatctg caagtcctcc     540
cagagcctgc tgaactccgg cgaccagaag aactacctga cctggtatca gcagaaaccc     600
ggccagcccc ccaagctgct gatcttttgg gccagcaccc gggaaagcgg cgtgcccgat     660
agattcacag gcagcggctc cggcaccgac tttaccctga ccatcagctc cgtgcaggcc     720
gaggacctgg ccgtgtatta ctgccagaac gactacagct accccctgac cttcggagcc     780
ggcaccaagc tggaactgaa gtccggaacc acgacgccag cgccgcgacc accaacaccg     840
gcgcccacca tcgcgtcgca gcccctgtcc ctgcgcccag aggcgtgccg gccagcggcg     900
gggggcgcag tgcacacgag ggggctggac ttcgcctgtg atttttgggt gctggtggtg     960
gttggtggag tcctggcttg ctatagcttg ctagtaacag tggcctttat tattttctgg    1020
gtgaggagta agaggagcag gctcctgcac agtgactaca tgaacatgac tccccgccgc    1080
cccgggccca cccgcaagca ttaccagccc tatgccccac cacgcgactt cgcagcctat    1140
cgctccagag tgaagttcag caggagcgca gacgcccccg cgtacaagca gggccagaac    1200
cagctctata cgagctcaa tctaggacga agagaggagt acgatgtttt ggacaagaga    1260
cgtggccggg accctgagat ggggggaaag ccgagaagga agaaccctca ggaaggcctg    1320
tacaatgaac tgcagaaaga taagatggcg gaggcctaca gtgagattgg gatgaaaggc    1380
gagcgccgga ggggcaaggg gcacgatggc ctttaccagg gtctcagtac agccaccaag    1440
gacacctacg acgcccttca catgcaggcc ctgccccctc gc                       1482

<210> SEQ ID NO 39
<211> LENGTH: 494
<212> TYPE: PRT
<213> ORGANISM: Artificial Sequence
<220> FEATURE:
<223> OTHER INFORMATION: CAR
<220> FEATURE:
<223> OTHER INFORMATION: Tn-MUC1 (5e528z)
```

-continued

<400> SEQUENCE: 39

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Asp Ala
            20                  25                  30

Glu Leu Val Lys Pro Gly Ser Ser Val Lys Ile Ser Cys Lys Ala Ser
        35                  40                  45

Gly Tyr Thr Phe Thr Asp His Ala Ile His Trp Val Lys Gln Lys Pro
    50                  55                  60

Glu Gln Gly Leu Glu Trp Ile Gly His Phe Ser Pro Gly Asn Thr Asp
65                  70                  75                  80

Ile Lys Tyr Asn Asp Lys Phe Lys Gly Lys Ala Thr Leu Thr Val Asp
                85                  90                  95

Arg Ser Ser Ser Thr Ala Tyr Met Gln Leu Asn Ser Leu Thr Ser Glu
            100                 105                 110

Asp Ser Ala Val Tyr Phe Cys Lys Thr Ser Thr Phe Phe Phe Asp Tyr
            115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Glu Leu Val Met Thr Gln
145                 150                 155                 160

Ser Pro Ser Ser Leu Thr Val Thr Ala Gly Glu Lys Val Thr Met Ile
                165                 170                 175

Cys Lys Ser Ser Gln Ser Leu Leu Asn Ser Gly Asp Gln Lys Asn Tyr
            180                 185                 190

Leu Thr Trp Tyr Gln Gln Lys Pro Gly Gln Pro Pro Lys Leu Leu Ile
            195                 200                 205

Phe Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Ser Tyr Pro Leu
            245                 250                 255

Thr Phe Gly Ala Gly Thr Lys Leu Glu Leu Lys Ser Gly Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
            340                 345                 350

Tyr Met Asn Met Thr Pro Arg Arg Pro Gly Pro Thr Arg Lys His Tyr
            355                 360                 365

Gln Pro Tyr Ala Pro Pro Arg Asp Phe Ala Ala Tyr Arg Ser Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val

-continued

```
                405                 410                 415
Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 40
<211> LENGTH: 1482
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e528z YMFM)

<400> SEQUENCE: 40

```
atggccttac cagtgaccgc cttgctcctg ccgctggcct tgctgctcca cgccgccagg      60
ccgggatccc aggtgcagct gcagcagtct gatgccgagc tcgtgaagcc tggcagcagc     120
gtgaagatca gctgcaaggc cagcggctac accttcaccg accacgccat ccactgggtc     180
aagcagaagc ctgagcaggg cctggagtgg atcggccact tcagccccgg caacaccgac     240
atcaagtaca cgacaagtt caagggcaag gccaccctga ccgtggacag aagcagcagc     300
accgcctaca tgcagctgaa cagcctgacc agcgaggaca cgccgtgta cttctgcaag     360 accagcacct tcttttttcga ctactggggc cagggcacaa ccctgacagt gtctagcgga     420
ggcggaggat ctggcggcgg aggaagtggc ggaggggggat ctgaactcgt gatgacccag     480
agccccagct ctctgacagt gacagccggc gagaaagtga ccatgatctg caagtcctcc     540
cagagcctgc tgaactccgg cgaccagaag aactacctga cctggtatca gcagaaaccc     600
ggccagcccc ccaagctgct gatcttttgg gccagcaccc gggaaagcgg cgtgcccgat     660
agattcacag gcagcggctc cggcaccgac tttaccctga ccatcagctc cgtgcaggcc     720
gaggacctgc ccgtgtatta ctgccagaac gactacagct accccctgac cttcggagcc     780
ggcaccaagc tggaactgaa gtccggaacc acgacgccag cgccgcgacc accaacaccg     840
gcgcccacca tcgcgtcgca gcccctgtcc ctgcgcccag aggcgtgccg gccagcggcg     900
gggggcgcag tgcacacgag ggggctggac ttcgcctgtg attttgggt gctggtggtg     960 gttggtggag tcctggcttg ctatagcttg ctagtaacag tggcctttat tattttctgg    1020
gtgaggagta agaggagcag gctcctgcac agtgactaca tgttcatgac tccccgccgc    1080
cccgggccca cccgcaagca ttaccagccc tatgcccac cacgcgactt cgcagcctat    1140
cgctccagag tgaagttcag caggagcgca gacgcccccg cgtacaagca gggccagaac    1200
cagctctata cgagctcaa tctaggacga agagaggagt acgatgtttt ggacaagaga    1260
cgtggccggg accctgagat ggggggaaag ccgagaagga agaaccctca ggaaggcctg    1320
tacaatgaac tgcagaaaga taagatggcg gaggcctaca gtgagattgg gatgaaaggc    1380
gagcgccgga ggggcaaggg gcacgatggc ctttaccagg gtctcagtac agccaccaag    1440
gacacctacg acgcccttca catgcaggcc ctgccccctc gc                        1482
```

-continued

```
<210> SEQ ID NO 41
<211> LENGTH: 494
<212> TYPE: PRT
<213> ORGANISM: Artificial Sequence
<220> FEATURE:
<223> OTHER INFORMATION: CAR
<220> FEATURE:
<223> OTHER INFORMATION: Tn-MUC1 (5e528z YMFM)

<400> SEQUENCE: 41

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Asp Ala
                20                  25                  30

Glu Leu Val Lys Pro Gly Ser Ser Val Lys Ile Ser Cys Lys Ala Ser
            35                  40                  45

Gly Tyr Thr Phe Thr Asp His Ala Ile His Trp Val Lys Gln Lys Pro
        50                  55                  60

Glu Gln Gly Leu Glu Trp Ile Gly His Phe Ser Pro Gly Asn Thr Asp
65                  70                  75                  80

Ile Lys Tyr Asn Asp Lys Phe Lys Gly Lys Ala Thr Leu Thr Val Asp
                85                  90                  95

Arg Ser Ser Ser Thr Ala Tyr Met Gln Leu Asn Ser Leu Thr Ser Glu
                100                 105                 110

Asp Ser Ala Val Tyr Phe Cys Lys Thr Ser Thr Phe Phe Phe Asp Tyr
            115                 120                 125

Trp Gly Gln Gly Thr Thr Leu Thr Val Ser Ser Gly Gly Gly Gly Ser
        130                 135                 140

Gly Gly Gly Gly Ser Gly Gly Gly Ser Glu Leu Val Met Thr Gln
145                 150                 155                 160

Ser Pro Ser Ser Leu Thr Val Thr Ala Gly Glu Lys Val Thr Met Ile
                165                 170                 175

Cys Lys Ser Ser Gln Ser Leu Leu Asn Ser Gly Asp Gln Lys Asn Tyr
                180                 185                 190

Leu Thr Trp Tyr Gln Gln Lys Pro Gly Gln Pro Pro Lys Leu Leu Ile
            195                 200                 205

Phe Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Ser Tyr Pro Leu
                245                 250                 255

Thr Phe Gly Ala Gly Thr Lys Leu Glu Leu Lys Ser Gly Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
        290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
            340                 345                 350

Tyr Met Phe Met Thr Pro Arg Arg Pro Gly Pro Thr Arg Lys His Tyr
```

-continued

```
             355                 360                 365
Gln Pro Tyr Ala Pro Pro Arg Asp Phe Ala Ala Tyr Arg Ser Arg Val
        370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
        450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

```
<210> SEQ ID NO 42
<211> LENGTH: 1494
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e527z)

<400> SEQUENCE: 42
atggccttac cagtgaccgc cttgctcctg ccgctggcct tgctgctcca cgccgccagg      60
ccgggatccc aggtgcagct gcagcagtct gatgccgagc tcgtgaagcc tggcagcagc     120
gtgaagatca gctgcaaggc cagcggctac accttcaccg accacgccat ccactgggtc     180
aagcagaagc ctgagcaggg cctggagtgg atcggccact tcagccccgg caacaccgac     240
atcaagtaca cgacaagtt caagggcaag gccaccctga ccgtggacag aagcagcagc     300
accgcctaca tgcagctgaa cagcctgacc agcgaggaca cgccgtgta cttctgcaag     360 accagcacct tcttttttcga ctactggggc cagggcacaa ccctgacagt gtctagcgga     420
ggcggaggat ctggcggcgg aggaagtggc ggaggggggat ctgaactcgt gatgacccag     480
agccccagct ctctgacagt gacagccggc gagaaagtga ccatgatctg caagtcctcc     540
cagagcctgc tgaactccgg cgaccagaag aactacctga cctggtatca gcagaaaccc     600
ggccagcccc ccaagctgct gatcttttgg gccagcaccc gggaaagcgg cgtgcccgat     660
agattcacag gcagcggctc cggcaccgac tttacccctga ccatcagctc cgtgcaggcc     720
gaggacctgg ccgtgtatta ctgccagaac gactacagct accccctgac cttcggagcc     780
ggcaccaagc tggaactgaa gtccggaacc acgacgccag cgccgcgacc accaacaccg     840
gcgcccacca tcgcgtcgca gccccctgtcc ctgcgcccag aggcgtgccg gccagcggcg     900
gggggcgcag tgcacacgag ggggctggac ttcgcctgtg atatctacat ctgggcgccc     960
ttggccggga cttgtggggt ccttctcctg tcactggtta tcacccttta ctgccaacga    1020
aggaaatata gatcaaacaa aggagaaagt cctgtggagc ctgcagagcc ttgtcgttac    1080
agctgcccca gggaggagga gggcagcacc atccccatcc aggaggatta ccgaaaaccg    1140
gagcctgcct gctccccccag agtgaagttc agcaggagcg cagacgcccc cgcgtacaag    1200
cagggccaga accagctcta taacgagctc aatctaggac gaagagagga gtacgatgtt    1260
```

```
ttggacaaga gacgtggccg ggaccctgag atgggggggaa agccgagaag gaagaaccct       1320
caggaaggcc tgtacaatga actgcagaaa gataagatgg cggaggccta cagtgagatt       1380
gggatgaaag gcgagcgccg gaggggcaag gggcacgatg gcctttacca gggtctcagt       1440
acagccacca aggacaccta cgacgccctt cacatgcagg ccctgcccccc tcgc            1494
```

```
<210> SEQ ID NO 43
<211> LENGTH: 498
<212> TYPE: PRT
<213> ORGANISM: Artificial Sequence
<220> FEATURE:
<223> OTHER INFORMATION: CAR
<220> FEATURE:
<223> OTHER INFORMATION: Tn-MUC1 (5e527z)

<400> SEQUENCE: 43

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Asp Ala
                20                  25                  30

Glu Leu Val Lys Pro Gly Ser Ser Val Lys Ile Ser Cys Lys Ala Ser
            35                  40                  45

Gly Tyr Thr Phe Thr Asp His Ala Ile His Trp Val Lys Gln Lys Pro
        50                  55                  60

Glu Gln Gly Leu Glu Trp Ile Gly His Phe Ser Pro Gly Asn Thr Asp
65                  70                  75                  80

Ile Lys Tyr Asn Asp Lys Phe Lys Gly Lys Ala Thr Leu Thr Val Asp
                85                  90                  95

Arg Ser Ser Ser Thr Ala Tyr Met Gln Leu Asn Ser Leu Thr Ser Glu
            100                 105                 110

Asp Ser Ala Val Tyr Phe Cys Lys Thr Ser Thr Phe Phe Phe Asp Tyr
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Glu Leu Val Met Thr Gln
145                 150                 155                 160

Ser Pro Ser Ser Leu Thr Val Thr Ala Gly Glu Lys Val Thr Met Ile
                165                 170                 175

Cys Lys Ser Ser Gln Ser Leu Leu Asn Ser Gly Asp Gln Lys Asn Tyr
            180                 185                 190

Leu Thr Trp Tyr Gln Gln Lys Pro Gly Gln Pro Pro Lys Leu Leu Ile
        195                 200                 205

Phe Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Ser Tyr Pro Leu
                245                 250                 255

Thr Phe Gly Ala Gly Thr Lys Leu Glu Leu Lys Ser Gly Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
```

-continued

```
305             310             315             320
Leu Ala Gly Thr Cys Gly Val Leu Leu Leu Ser Leu Val Ile Thr Leu
            325             330             335

Tyr Cys Gln Arg Arg Lys Tyr Arg Ser Asn Lys Gly Glu Ser Pro Val
            340             345             350

Glu Pro Ala Glu Pro Cys Arg Tyr Ser Cys Pro Arg Glu Glu Glu Gly
            355             360             365

Ser Thr Ile Pro Ile Gln Glu Asp Tyr Arg Lys Pro Glu Pro Ala Cys
    370             375             380

Ser Pro Arg Val Lys Phe Ser Arg Ser Ala Asp Ala Pro Ala Tyr Lys
385             390             395             400

Gln Gly Gln Asn Gln Leu Tyr Asn Glu Leu Asn Leu Gly Arg Arg Glu
            405             410             415

Glu Tyr Asp Val Leu Asp Lys Arg Arg Gly Arg Asp Pro Glu Met Gly
            420             425             430

Gly Lys Pro Arg Arg Lys Asn Pro Gln Glu Gly Leu Tyr Asn Glu Leu
            435             440             445

Gln Lys Asp Lys Met Ala Glu Ala Tyr Ser Glu Ile Gly Met Lys Gly
    450             455             460

Glu Arg Arg Arg Gly Lys Gly His Asp Gly Leu Tyr Gln Gly Leu Ser
465             470             475             480

Thr Ala Thr Lys Asp Thr Tyr Asp Ala Leu His Met Gln Ala Leu Pro
            485             490             495

Pro Arg
```

```
<210> SEQ ID NO 44
<211> LENGTH: 1476
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e5Ox40z)

<400> SEQUENCE: 44
atggccttac cagtgaccgc cttgctcctg ccgctggcct tgctgctcca cgccgccagg      60
ccgggatccc aggtgcagct gcagcagtct gatgccgagc tcgtgaagcc tggcagcagc     120
gtgaagatca gctgcaaggc cagcggctac accttcaccg accacgccat ccactgggtc     180
aagcagaagc ctgagcaggg cctggagtgg atcggccact tcagccccgg caacaccgac     240
atcaagtaca cgacaagtt caagggcaag gccaccctga ccgtggacag aagcagcagc     300
accgcctaca tgcagctgaa cagcctgacc agcgaggaca cgccgtgta cttctgcaag     360 accagcacct tcttttcga ctactgggc caggcacaa ccctgacagt gtctagcgga     420
ggcggaggat ctggcggcgg aggaagtggc ggagggggat ctgaactcgt gatgacccag     480
agccccagct ctctgacagt gacagccggc gagaaagtga ccatgatctg caagtcctcc     540
cagagcctgc tgaactccgg cgaccagaag aactacctga cctggtatca gcagaaaccc     600
ggccagcccc ccaagctgct gatcttttgg gccagcaccc gggaaagcgg cgtgcccgat     660
agattcacag gcagcggctc cggcaccgac tttacccctga ccatcagctc cgtgcaggcc     720
gaggacctgg ccgtgtatta ctgccagaac gactacagct accccctgac cttcggagcc     780
ggcaccaagc tggaactgaa gtccggaacc acgacgccag cgccgcgacc accaacaccg     840
gcgcccacca tcgcgtcgca gcccctgtcc ctgcgcccag aggcgtgccg gccagcggcg     900
```

-continued

```
ggggcgcag tgcacacgag ggggctggac ttcgcctgtg atatctacat ctgggcgccc      960
ttggccggga cttgtggggt ccttctcctg tcactggtta tcacccttta ctgcgccctg     1020
tacctgctcc gcagggacca gaggctgccc cccgatgccc acaagccccc tggggggaggc    1080 agtttcagga cccccatcca agaggagcag gccgacgccc actccaccct ggccaagatc     1140
agagtgaagt tcagcaggag cgcagacgcc cccgcgtaca agcagggcca gaaccagctc     1200
tataacgagc tcaatctagg acgaagagag gagtacgatg ttttggacaa agacgtggc     1260 cgggaccctg agatggggggg aaagccgaga aggaagaacc ctcaggaagg cctgtacaat    1320
gaactgcaga aagataagat ggcggaggcc tacagtgaga ttgggatgaa aggcgagcgc     1380 cggagggggca aggggcacga tggcctttac cagggtctca gtacagccac caaggacacc    1440
tacgacgccc ttcacatgca ggccctgccc cctcgc                              1476
```

<210> SEQ ID NO 45
<211> LENGTH: 492
<212> TYPE: PRT
<213> ORGANISM: Artificial Sequence
<220> FEATURE:
<223> OTHER INFORMATION: CAR
<220> FEATURE:
<223> OTHER INFORMATION: Tn-MUC1 (5e50x40z)

<400> SEQUENCE: 45

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Asp Ala
            20                  25                  30

Glu Leu Val Lys Pro Gly Ser Ser Val Lys Ile Ser Cys Lys Ala Ser
        35                  40                  45

Gly Tyr Thr Phe Thr Asp His Ala Ile His Trp Val Lys Gln Lys Pro
    50                  55                  60

Glu Gln Gly Leu Glu Trp Ile Gly His Phe Ser Pro Gly Asn Thr Asp
65                  70                  75                  80

Ile Lys Tyr Asn Asp Lys Phe Lys Gly Lys Ala Thr Leu Thr Val Asp
                85                  90                  95

Arg Ser Ser Ser Thr Ala Tyr Met Gln Leu Asn Ser Leu Thr Ser Glu
            100                 105                 110

Asp Ser Ala Val Tyr Phe Cys Lys Thr Ser Thr Phe Phe Phe Asp Tyr
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Glu Leu Val Met Thr Gln
145                 150                 155                 160

Ser Pro Ser Ser Leu Thr Val Thr Ala Gly Glu Lys Val Thr Met Ile
                165                 170                 175

Cys Lys Ser Ser Gln Ser Leu Leu Asn Ser Gly Asp Gln Lys Asn Tyr
            180                 185                 190

Leu Thr Trp Tyr Gln Gln Lys Pro Gly Gln Pro Pro Lys Leu Leu Ile
        195                 200                 205

Phe Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Ser Tyr Pro Leu
                245                 250                 255
```

-continued

```
Thr Phe Gly Ala Gly Thr Lys Leu Glu Leu Lys Ser Gly Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Ala Leu Tyr Leu Leu Arg Arg Asp Gln Arg Leu Pro Pro Asp
            340                 345                 350

Ala His Lys Pro Pro Gly Gly Gly Ser Phe Arg Thr Pro Ile Gln Glu
            355                 360                 365

Glu Gln Ala Asp Ala His Ser Thr Leu Ala Lys Ile Arg Val Lys Phe
            370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 46
<211> LENGTH: 1707
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e5 CD2z)

<400> SEQUENCE: 46

```
atggccttac cagtgaccgc cttgctcctg ccgctggcct tgctgctcca cgccgccagg      60
ccgggatccc aggtgcagct gcagcagtct gatgccgagc tcgtgaagcc tggcagcagc     120
gtgaagatca gctgcaaggc cagcggctac accttcaccg accacgccat ccactgggtc     180
aagcagaagc ctgagcaggg cctggagtgg atcggccact tcagccccgg caacaccgac     240
atcaagtaca cgacaagtt caagggcaag gccaccctga ccgtggacag aagcagcagc     300
accgcctaca tgcagctgaa cagcctgacc agcgaggaca cgccgtgta cttctgcaag     360 accagcacct tctttttcga ctactggggc caggcacaa ccctgacagt gtctagcgga     420
ggcggaggat ctggcggcgg aggaagtggc ggagggggat ctgaactcgt gatgacccag     480
agccccagct ctctgacagt gacagccggc gagaaagtga ccatgatctg caagtcctcc     540
cagagcctgc tgaactccgg cgaccagaag aactacctga cctggtatca gcagaaaccc     600
ggccagcccc ccaagctgct gatcttttgg gccagcaccc gggaaagcgg cgtgcccgat     660
```

```
agattcacag gcagcggctc cggcaccgac tttaccctga ccatcagctc cgtgcaggcc     720
gaggacctgg ccgtgtatta ctgccagaac gactacagct accccctgac cttcggagcc     780
ggcaccaagc tggaactgaa gtccggaacc acgacgccag cgccgcgacc accaacaccg     840
gcgcccacca tcgcgtcgca gccccctgtcc ctgcgcccag aggcgtgccg gccagcggcg     900
gggggcgcag tgcacacgag ggggctggac ttcgcctgtg atatctacat ctgggcgccc     960
ttggccggga cttgtggggt ccttctcctg tcactggtta tcacccttta ctgcaccaaa    1020
aggaaaaaac agaggagtcg gagaaatgat gaggagctgg agacaagagc ccacagagta    1080
gctactgaag aaaggggccg gaagccccac caaattccag cttcaacccc tcagaatcca    1140
gcaacttccc aacatcctcc tccaccacct ggtcatcgtt cccaggcacc tagtcatcgt    1200
cccccgcctc ctggacaccg tgttcagcac cagcctcaga agaggcctcc tgctccgtcg    1260
ggcacacaag ttcaccagca gaaaggcccg cccctcccca gacctcgagt tcagccaaaa    1320
cctccccatg gggcagcaga aaactcattg tccccttcct ctaatatcga tagagtgaag    1380
ttcagcagga gcgcagacgc ccccgcgtac aagcagggcc agaaccagct ctataacgag    1440
ctcaatctag gacgaagaga ggagtacgat gttttggaca gagacgtggg ccgggaccct    1500
gagatggggg gaaagccgag aaggaagaac cctcaggaag gcctgtacaa tgaactgcag    1560
aaagataaga tggcggaggc ctacagtgag attgggatga aggcgagcg ccggagggggc    1620 aagggggcacg atggccttta ccagggtctc agtacagcca ccaaggacac ctacgacgcc    1680
cttcacatgc aggccctgcc ccctcgc                                        1707
```

<210> SEQ ID NO 47
<211> LENGTH: 569
<212> TYPE: PRT
<213> ORGANISM: Artificial Sequence
<220> FEATURE:
<223> OTHER INFORMATION: CAR
<220> FEATURE:
<223> OTHER INFORMATION: Tn-MUC1 (5e5 CD2z)

<400> SEQUENCE: 47

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Asp Ala
            20                  25                  30

Glu Leu Val Lys Pro Gly Ser Ser Val Lys Ile Ser Cys Lys Ala Ser
        35                  40                  45

Gly Tyr Thr Phe Thr Asp His Ala Ile His Trp Val Lys Gln Lys Pro
    50                  55                  60

Glu Gln Gly Leu Glu Trp Ile Gly His Phe Ser Pro Gly Asn Thr Asp
65                  70                  75                  80

Ile Lys Tyr Asn Asp Lys Phe Lys Gly Lys Ala Thr Leu Thr Val Asp
                85                  90                  95

Arg Ser Ser Ser Thr Ala Tyr Met Gln Leu Asn Ser Leu Thr Ser Glu
            100                 105                 110

Asp Ser Ala Val Tyr Phe Cys Lys Thr Ser Thr Phe Phe Phe Asp Tyr
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Gly Ser Glu Leu Val Met Thr Gln
145                 150                 155                 160
```

-continued

```
Ser Pro Ser Ser Leu Thr Val Thr Ala Gly Glu Lys Val Thr Met Ile
            165                 170                 175

Cys Lys Ser Ser Gln Ser Leu Leu Asn Ser Gly Asp Gln Lys Asn Tyr
            180                 185                 190

Leu Thr Trp Tyr Gln Gln Lys Pro Gly Gln Pro Pro Lys Leu Leu Ile
            195                 200                 205

Phe Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Ser Tyr Pro Leu
                245                 250                 255

Thr Phe Gly Ala Gly Thr Lys Leu Glu Leu Lys Ser Gly Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Thr Lys Arg Lys Lys Gln Arg Ser Arg Arg Asn Asp Glu Glu
            340                 345                 350

Leu Glu Thr Arg Ala His Arg Val Ala Thr Glu Glu Arg Gly Arg Lys
            355                 360                 365

Pro His Gln Ile Pro Ala Ser Thr Pro Gln Asn Pro Ala Thr Ser Gln
    370                 375                 380

His Pro Pro Pro Pro Gly His Arg Ser Gln Ala Pro Ser His Arg
385                 390                 395                 400

Pro Pro Pro Pro Gly His Arg Val Gln His Gln Pro Gln Lys Arg Pro
                405                 410                 415

Pro Ala Pro Ser Gly Thr Gln Val His Gln Gln Lys Gly Pro Pro Leu
            420                 425                 430

Pro Arg Pro Arg Val Gln Pro Lys Pro Pro His Gly Ala Ala Glu Asn
            435                 440                 445

Ser Leu Ser Pro Ser Ser Asn Ile Asp Arg Val Lys Phe Ser Arg Ser
    450                 455                 460

Ala Asp Ala Pro Ala Tyr Lys Gln Gly Gln Asn Gln Leu Tyr Asn Glu
465                 470                 475                 480

Leu Asn Leu Gly Arg Arg Glu Glu Tyr Asp Val Leu Asp Lys Arg Arg
                485                 490                 495

Gly Arg Asp Pro Glu Met Gly Gly Lys Pro Arg Arg Lys Asn Pro Gln
            500                 505                 510

Glu Gly Leu Tyr Asn Glu Leu Gln Lys Asp Lys Met Ala Glu Ala Tyr
            515                 520                 525

Ser Glu Ile Gly Met Lys Gly Glu Arg Arg Gly Lys Gly His Asp
    530                 535                 540

Gly Leu Tyr Gln Gly Leu Ser Thr Ala Thr Lys Asp Thr Tyr Asp Ala
545                 550                 555                 560

Leu His Met Gln Ala Leu Pro Pro Arg
                565
```

-continued

<210> SEQ ID NO 48
<211> LENGTH: 21
<212> TYPE: PRT
<213> ORGANISM: Artificial Sequence
<220> FEATURE:
<223> OTHER INFORMATION: Leader
<220> FEATURE:
<223> OTHER INFORMATION: CD8alpha

<400> SEQUENCE: 48

Met Ala Leu Pro Val Thr Ala Leu Leu Leu Pro Leu Ala Leu Leu Leu
1               5                   10                  15

His Ala Ala Arg Pro
            20

<210> SEQ ID NO 49
<211> LENGTH: 485
<212> TYPE: PRT
<213> ORGANISM: Artificial Sequence
<220> FEATURE:
<223> OTHER INFORMATION: CAR
<220> FEATURE:
<223> OTHER INFORMATION: Tn-MUC1 (5e5ICOSz)

<400> SEQUENCE: 49

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Asp Ala
            20                  25                  30

Glu Leu Val Lys Pro Gly Ser Ser Val Lys Ile Ser Cys Lys Ala Ser
        35                  40                  45

Gly Tyr Thr Phe Thr Asp His Ala Ile His Trp Val Lys Gln Lys Pro
    50                  55                  60

Glu Gln Gly Leu Glu Trp Ile Gly His Phe Ser Pro Gly Asn Thr Asp
65                  70                  75                  80

Ile Lys Tyr Asn Asp Lys Phe Lys Gly Lys Ala Thr Leu Thr Val Asp
                85                  90                  95

Arg Ser Ser Ser Thr Ala Tyr Met Gln Leu Asn Ser Leu Thr Ser Glu
            100                 105                 110

Asp Ser Ala Val Tyr Phe Cys Lys Thr Ser Thr Phe Phe Phe Asp Tyr
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Glu Leu Val Met Thr Gln
145                 150                 155                 160

Ser Pro Ser Ser Leu Thr Val Thr Ala Gly Glu Lys Val Thr Met Ile
                165                 170                 175

Cys Lys Ser Ser Gln Ser Leu Leu Asn Ser Gly Asp Gln Lys Asn Tyr
            180                 185                 190

Leu Thr Trp Tyr Gln Gln Lys Pro Gly Gln Pro Pro Lys Leu Leu Ile
            195                 200                 205

Phe Trp Ala Ser Thr Arg Glu Ser Gly Val Pro Asp Arg Phe Thr Gly
        210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Ser Tyr Pro Leu
                245                 250                 255

Thr Phe Gly Ala Gly Thr Lys Leu Glu Leu Lys Ser Gly Thr Thr Thr
            260                 265                 270

```
Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
        290                 295                 300

His Thr Arg Gly Leu Asp Phe Ala Cys Asp Phe Trp Leu Pro Ile Gly
305                 310                 315                 320

Cys Ala Ala Phe Val Val Val Cys Ile Leu Gly Cys Ile Leu Ile Cys
                325                 330                 335

Trp Leu Thr Lys Lys Lys Tyr Ser Ser Ser Val His Asp Pro Asn Gly
            340                 345                 350

Glu Tyr Met Phe Met Arg Ala Val Asn Thr Ala Lys Lys Ser Arg Leu
        355                 360                 365

Thr Asp Val Thr Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

```
<210> SEQ ID NO 50
<211> LENGTH: 1455
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e5ICOSz)

<400> SEQUENCE: 50
atggccttac cagtgaccgc cttgctcctg ccgctggcct tgctgctcca cgccgccagg      60
ccgggatccc aggtgcagct gcagcagtct gatgccgagc tcgtgaagcc tggcagcagc     120
gtgaagatca gctgcaaggc cagcggctac accttcaccg accacgccat ccactgggtc     180
aagcagaagc ctgagcaggg cctggagtgg atcggccact tcagccccgg caacaccgac     240
atcaagtaca cgacaagtt caagggcaag gccaccctga ccgtggacag aagcagcagc     300
accgcctaca tgcagctgaa cagcctgacc agcgaggaca cgccgtgta cttctgcaag     360 accagcacct tcttttttcga ctactggggc cagggcacaa ccctgacagt gtctagcgga     420
ggcggaggat ctggcggcgg aggaagtggc ggagggggat ctgaactcgt gatgacccag     480
agccccagct ctctgacagt gacagccggc gagaaagtga ccatgatctg caagtcctcc     540
cagagcctgc tgaactccgg cgaccagaag aactacctga cctggtatca gcagaaaccc     600
ggccagcccc ccaagctgct gatcttttgg gccagcaccc gggaaagcgg cgtgcccgat     660
agattcacag gcagcggctc cggcaccgac tttaccctga ccatcagctc cgtgcaggcc     720
```

```
gaggacctgg ccgtgtatta ctgccagaac gactacagct accccctgac cttcggagcc     780
ggcaccaagc tggaactgaa gtccggaacc acgacgccag cgccgcgacc accaacaccg     840
gcgcccacca tcgcgtcgca gcccctgtcc ctgcgcccag aggcgtgccg gccagcggcg     900
gggggcgcag tgcacacgag ggggctggac ttcgcctgtg atttctggtt acccatagga     960
tgtgcagcct ttgttgtagt ctgcattttg ggatgcatac ttatttgttg gcttacaaaa    1020
aagaagtatt catccagtgt gcacgaccct aacggtgaat acatgttcat gagagcagtg    1080
aacacagcca aaaaatccag actcacagat gtgaccctaa gagtgaagtt cagcaggagc    1140
gcagacgccc ccgcgtacaa gcagggccag aaccagctct ataacgagct caatctagga    1200
cgaagagagg agtacgatgt tttggacaag agacgtggcc gggaccctga gatggggggga    1260 aagccgagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct acgacgccct tcacatgcag    1440
gccctgcccc ctcgc                                                     1455
```

```
<210> SEQ ID NO 51
<211> LENGTH: 1456
<212> TYPE: DNA
<213> ORGANISM: Artificial Sequence
<220> FEATURE:
<223> OTHER INFORMATION: CAR
<220> FEATURE:
<223> OTHER INFORMATION: Tn-MUC1 (5e5ICOSz-2)

<400> SEQUENCE: 51
```

```
atggccttac cagtgaccgc cttgctcctg ccgctggcct tgctgctcca cgccgccagg     60
ccgggatccc aggtgcagct gcagcagtct gatgccgagc tcgtgaagcc tggcagcagc    120
gtgaagatca gctgcaaggc cagcggctac accttcaccg accacgccat ccactgggtc    180
aagcagaagc ctgagcaggg cctggagtgg atcggccact tcagccccgg caacaccgac    240
atcaagtaca cgacaagtt caagggcaag gccacccctga ccgtggacag aagcagcagc    300
accgcctaca tgcagctgaa cagcctgacc agcgaggaca cgccgtgta cttctgcaag    360 accagcacct tcttttttcga ctactggggc cagggcacaa ccctgacagt gtctagcgga    420
ggcggaggat ctggcggcgg aggaagtggc ggaggggat ctgaactcgt gatgacccag    480
agccccagct ctctgacagt gacagccggc gagaaagtga ccatgatctg caagtcctcc    540
cagagcctgc tgaactccgg cgaccagaag aactacctga cctggtattc agcagaaacc    600
cggccagccc cccaagctgc tgatcttttg ggccagcacc cgggaaagcg gcgtgcccga    660
tagattcaca ggcagcggct ccggcaccga ctttaccctg accatcagct ccgtgcaggc    720
cgaggacctg gccgtgtatt actgccagaa cgactacagc taccccctga ccttcggagc    780
cggcaccaag ctggaactga gtccggaac acgacgccca gcgccgcgac caccaacacc    840
ggcgcccacc atcgcgtcgc agcccctgtc cctgcgccca gaggcgtgcc ggccagcggc    900 gggggcgca gtgcacacga ggggctgga cttcgcctgt gatttctggt tacccatagg    960
atgtgcagcc tttgttgtag tctgcattt gggatgcata cttatttgtt ggcttacaaa    1020
aaagaagtat tcatccagtg tgcacgaccc taacggtgaa tacatgttca tgagagcagt    1080
gaacacagcc aaaaaatcta gactcacaga tgtgaccta agagtgaagt tcagcaggag    1140
cgcagacgcc cccgcgtaca agcagggcca gaaccagctc tataacgagc tcaatctagg    1200
acgaagagag gagtacgatg ttttggacaa gagacgtggc cgggaccctg agatggggggg    1260
```

-continued

```
aaagccgaga aggaagaacc ctcaggaagg cctgtacaat gaactgcaga aagataagat    1320
ggcggaggcc tacagtgaga ttgggatgaa aggcgagcgc cggaggggca aggggcacga    1380
tggcctttac cagggtctca gtacagccac caaggacacc tacgacgccc ttcacatgca    1440
ggccctgccc cctcgc                                                    1456
```

```
<210> SEQ ID NO 52
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 1

<400> SEQUENCE: 52

Gly Ser Gly Gly Ser
1               5
```

```
<210> SEQ ID NO 53
<211> LENGTH: 4
<212> TYPE: PRT
<213> ORGANISM: Artificial Sequence
<220> FEATURE:
<223> OTHER INFORMATION: Linker
<220> FEATURE:
<223> OTHER INFORMATION: 2

<400> SEQUENCE: 53

Gly Gly Gly Ser
1
```

```
<210> SEQ ID NO 54
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 3

<400> SEQUENCE: 54

Gly Gly Gly Gly Ser
1               5
```

```
<210> SEQ ID NO 55
<211> LENGTH: 4
<212> TYPE: PRT
<213> ORGANISM: Artificial Sequence
<220> FEATURE:
<223> OTHER INFORMATION: Linker
<220> FEATURE:
<223> OTHER INFORMATION: 4

<400> SEQUENCE: 55

Gly Gly Ser Gly
1
```

```
<210> SEQ ID NO 56
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 5
```

```
<400> SEQUENCE: 56

Gly Gly Ser Gly Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 6

<400> SEQUENCE: 57

Gly Ser Gly Ser Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 7

<400> SEQUENCE: 58

Gly Ser Gly Gly Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 8

<400> SEQUENCE: 59

Gly Gly Gly Ser Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 9

<400> SEQUENCE: 60

Gly Ser Ser Ser Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Linker
<220> FEATURE:
<223> OTHER INFORMATION: 10

<400> SEQUENCE: 61

Gly Gly Gly Gly Ser
1               5
```

<210> SEQ ID NO 62
<211> LENGTH: 15
<212> TYPE: PRT
<213> ORGANISM: Artificial Sequence
<220> FEATURE:
<223> OTHER INFORMATION: Linker
<220> FEATURE:
<223> OTHER INFORMATION: 11

<400> SEQUENCE: 62

Gly Gly Gly Gly Ser Gly Gly Gly Gly Ser Gly Gly Gly Gly Ser
1               5                   10                  15

<210> SEQ ID NO 63
<211> LENGTH: 45
<212> TYPE: DNA
<213> ORGANISM: Artificial Sequence
<220> FEATURE:
<223> OTHER INFORMATION: Linker
<220> FEATURE:
<223> OTHER INFORMATION: 11

<400> SEQUENCE: 63
ggtggcggtg gctcgggcgg tggtgggtcg ggtggcggcg gatct                          45

<210> SEQ ID NO 64
<211> LENGTH: 5
<212> TYPE: PRT
<213> ORGANISM: Artificial Sequence
<220> FEATURE:
<223> OTHER INFORMATION: Hinge
<220> FEATURE:
<223> OTHER INFORMATION: 1

<400> SEQUENCE: 64

Asp Lys Thr His Thr
1               5

<210> SEQ ID NO 65
<211> LENGTH: 4
<212> TYPE: PRT
<213> ORGANISM: Artificial Sequence
<220> FEATURE:
<223> OTHER INFORMATION: Hinge
<220> FEATURE:
<223> OTHER INFORMATION: 2

<400> SEQUENCE: 65

Cys Pro Pro Cys
1

<210> SEQ ID NO 66
<211> LENGTH: 15
<212> TYPE: PRT
<213> ORGANISM: Artificial Sequence
<220> FEATURE:
<223> OTHER INFORMATION: Hinge
<220> FEATURE:
<223> OTHER INFORMATION: 3

<400> SEQUENCE: 66

Cys Pro Glu Pro Lys Ser Cys Asp Thr Pro Pro Pro Cys Pro Arg
1               5                   10                  15

<210> SEQ ID NO 67
<211> LENGTH: 12
<212> TYPE: PRT

```
<213> ORGANISM: Artificial Sequence
<220> FEATURE:
<223> OTHER INFORMATION: Hinge
<220> FEATURE:
<223> OTHER INFORMATION: 4

<400> SEQUENCE: 67

Glu Leu Lys Thr Pro Leu Gly Asp Thr Thr His Thr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Hinge
<220> FEATURE:
<223> OTHER INFORMATION: 5

<400> SEQUENCE: 68

Lys Ser Cys Asp Lys Thr His Thr Cys Pro
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Hinge
<220> FEATURE:
<223> OTHER INFORMATION: 6

<400> SEQUENCE: 69

Lys Cys Cys Val Asp Cys Pro
1               5

<210> SEQ ID NO 70
<211> LENGTH: 7
<212> TYPE: PRT
<213> ORGANISM: Artificial Sequence
<220> FEATURE:
<223> OTHER INFORMATION: Hinge
<220> FEATURE:
<223> OTHER INFORMATION: 7

<400> SEQUENCE: 70

Lys Tyr Gly Pro Pro Cys Pro
1               5

<210> SEQ ID NO 71
<211> LENGTH: 15
<212> TYPE: PRT
<213> ORGANISM: Artificial Sequence
<220> FEATURE:
<223> OTHER INFORMATION: Hinge
<220> FEATURE:
<223> OTHER INFORMATION: Hu IgG1

<400> SEQUENCE: 71

Glu Pro Lys Ser Cys Asp Lys Thr His Thr Cys Pro Pro Cys Pro
1               5                   10                  15

<210> SEQ ID NO 72
<211> LENGTH: 12
<212> TYPE: PRT
<213> ORGANISM: Artificial Sequence
<220> FEATURE:
<223> OTHER INFORMATION: Hinge
<220> FEATURE:
```

<223> OTHER INFORMATION: Hu IgG2

<400> SEQUENCE: 72

Glu Arg Lys Cys Cys Val Glu Cys Pro Pro Cys Pro
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Hinge
<220> FEATURE:
<223> OTHER INFORMATION: Hu IgG3

<400> SEQUENCE: 73

Glu Leu Lys Thr Pro Leu Gly Asp Thr Thr His Thr Cys Pro Arg Cys
1               5                   10                  15

Pro

<210> SEQ ID NO 74
<211> LENGTH: 12
<212> TYPE: PRT
<213> ORGANISM: Artificial Sequence
<220> FEATURE:
<223> OTHER INFORMATION: Hinge
<220> FEATURE:
<223> OTHER INFORMATION: Hu IgG4

<400> SEQUENCE: 74

Ser Pro Asn Met Val Pro His Ala His His Ala Gln
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Hinge
<220> FEATURE:
<223> OTHER INFORMATION: Hu IgG1 H229Y

<400> SEQUENCE: 75

Glu Pro Lys Ser Cys Asp Lys Thr Tyr Thr Cys Pro Pro Cys Pro
1               5                   10                  15

<210> SEQ ID NO 76
<211> LENGTH: 201
<212> TYPE: PRT
<213> ORGANISM: Artificial Sequence
<220> FEATURE:
<223> OTHER INFORMATION: Receptor
<220> FEATURE:
<223> OTHER INFORMATION: TGFbRII-DN

<400> SEQUENCE: 76

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro

```
        65                    70                    75                    80
Gln Glu Val Cys Val Ala Val Trp Arg Lys Asn Asp Glu Asn Ile Thr
                    85                    90                    95

Leu Glu Thr Val Cys His Asp Pro Lys Leu Pro Tyr His Asp Phe Ile
                    100                   105                   110

Leu Glu Asp Ala Ala Ser Pro Lys Cys Ile Met Lys Glu Lys Lys Lys
                    115                   120                   125

Pro Gly Glu Thr Phe Phe Met Cys Ser Cys Ser Ser Asp Glu Cys Asn
        130                   135                   140

Asp Asn Ile Ile Phe Ser Glu Glu Tyr Asn Thr Ser Asn Pro Asp Leu
145                   150                   155                   160

Leu Leu Val Ile Phe Gln Val Thr Gly Ile Ser Leu Leu Pro Pro Leu
                    165                   170                   175

Gly Val Ala Ile Ser Val Ile Ile Ile Phe Tyr Cys Tyr Arg Val Asn
                    180                   185                   190

Arg Gln Gln Lys Leu Ser Ser Ser Gly
        195                   200
```

<210> SEQ ID NO 77
<211> LENGTH: 603
<212> TYPE: DNA
<213> ORGANISM: Artificial Sequence
<220> FEATURE:
<223> OTHER INFORMATION: Receptor
<220> FEATURE:
<223> OTHER INFORMATION: TGFbRII-DN

<400> SEQUENCE: 77

```
atgggtcggg ggctgctcag gggcctgtgg ccgctgcaca tcgtcctgtg gacgcgtatc      60
gccagcacga tccccaccgca cgttcagaag tcggttaata cgacatgat agtcactgac     120 aacaacggtg cagtcaagtt tccacaactg tgtaaatttt gtgatgtgag attttccacc     180
tgtgacaacc agaaatcctg catgagcaac tgcagcatca cctccatctg tgagaagcca     240
caggaagtct gtgtggctgt atggagaaag aatgacgaga acataacact agagacagtt     300
tgccatgacc ccaagctccc ctaccatgac tttattctgg aagatgctgc ttctccaaag     360
tgcattatga aggaaaaaaa aaagcctggt gagactttct tcatgtgttc ctgtagctct     420
gatgagtgca atgacaacat catcttctca gaagaatata acaccagcaa tcctgacttg     480
ttgctagtca tatttcaagt gacaggcatc agcctcctgc caccactggg agttgccata     540
tctgtcatca tcatcttcta ctgctaccgc gttaaccggc agcagaagct gagttcatcc     600
gga                                                                    603
```

<210> SEQ ID NO 78
<211> LENGTH: 238
<212> TYPE: PRT
<213> ORGANISM: Artificial Sequence
<220> FEATURE:
<223> OTHER INFORMATION: Receptor
<220> FEATURE:
<223> OTHER INFORMATION: PD1-CTM-CD28

<400> SEQUENCE: 78

```
Met Gln Ile Pro Gln Ala Pro Trp Pro Val Val Trp Ala Val Leu Gln
1                   5                     10                    15

Leu Gly Trp Arg Pro Gly Trp Phe Leu Asp Ser Pro Asp Arg Pro Trp
                    20                    25                    30

Asn Pro Pro Thr Phe Ser Pro Ala Leu Leu Val Val Thr Glu Gly Asp
```

-continued

```
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Phe Trp Val Leu Val Val
                165                 170                 175

Val Gly Gly Val Leu Ala Cys Tyr Ser Leu Leu Val Thr Val Ala Phe
                180                 185                 190

Ile Ile Phe Trp Val Arg Ser Lys Arg Ser Arg Leu Leu His Ser Asp
                195                 200                 205

Tyr Met Asn Met Thr Pro Arg Arg Pro Gly Pro Thr Arg Lys His Tyr
    210                 215                 220

Gln Pro Tyr Ala Pro Pro Arg Asp Phe Ala Ala Tyr Arg Ser
225                 230                 235
```

```
<210> SEQ ID NO 79
<211> LENGTH: 714
<212> TYPE: DNA
<213> ORGANISM: Artificial Sequence
<220> FEATURE:
<223> OTHER INFORMATION: Receptor
<220> FEATURE:
<223> OTHER INFORMATION: PD1-CTM-CD28

<400> SEQUENCE: 79
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg tcagggccc  ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccacccag  ccctcaccc     480 aggccagccg gccagttcca aaccctggtg ttttgggtgc tggtggtggt tggtggagtc    540
ctggcttgct atagcttgct agtaacagtg gcctttatta ttttctgggt gaggagtaag    600
aggagcaggc tcctgcacag tgactacatg aacatgactc ccgccgccc  cgggcccacc    660 cgcaagcatt accagcccta tgccccacca cgcgacttcg cagcctatcg ctcc          714
```

```
<210> SEQ ID NO 80
<211> LENGTH: 232
<212> TYPE: PRT
<213> ORGANISM: Artificial Sequence
```

```
<220> FEATURE:
<223> OTHER INFORMATION: Receptor
<220> FEATURE:
<223> OTHER INFORMATION: PD1-PTM-CD28

<400> SEQUENCE: 80

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Leu Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
            180                 185                 190

Ser Lys Arg Ser Arg Leu Leu His Ser Asp Tyr Met Asn Met Thr Pro
            195                 200                 205

Arg Arg Pro Gly Pro Thr Arg Lys His Tyr Gln Pro Tyr Ala Pro Pro
        210                 215                 220

Arg Asp Phe Ala Ala Tyr Arg Ser
225                 230

<210> SEQ ID NO 81
<211> LENGTH: 696
<212> TYPE: DNA
<213> ORGANISM: Artificial Sequence
<220> FEATURE:
<223> OTHER INFORMATION: Receptor
<220> FEATURE:
<223> OTHER INFORMATION: PD1-PTM-CD28

<400> SEQUENCE: 81
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccacccccag ccctcaccc     480
```

-continued

```
aggccagccg gccagttcca aaccctggtg gttggtgtcg tgggcggcct gctgggcagc      540
ctggtgctgc tagtctgggt cctggccgtc atcaggagta agaggagcag gctcctgcac      600
agtgactaca tgaacatgac tccccgccgc cccgggccca cccgcaagca ttaccagccc      660
tatgccccac cacgcgactt cgcagcctat cgctcc                                696
```

```
<210> SEQ ID NO 82
<211> LENGTH: 232
<212> TYPE: PRT
<213> ORGANISM: Artificial Sequence
<220> FEATURE:
<223> OTHER INFORMATION: Receptor
<220> FEATURE:
<223> OTHER INFORMATION: PD1A132L-PTM-CD28

<400> SEQUENCE: 82

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
            180                 185                 190

Ser Lys Arg Ser Arg Leu Leu His Ser Asp Tyr Met Asn Met Thr Pro
        195                 200                 205

Arg Arg Pro Gly Pro Thr Arg Lys His Tyr Gln Pro Tyr Ala Pro Pro
    210                 215                 220

Arg Asp Phe Ala Ala Tyr Arg Ser
225                 230
```

```
<210> SEQ ID NO 83
<211> LENGTH: 693
<212> TYPE: DNA
<213> ORGANISM: Artificial Sequence
<220> FEATURE:
<223> OTHER INFORMATION: Receptor
<220> FEATURE:
<223> OTHER INFORMATION: PD1A132L-PTM-CD28

<400> SEQUENCE: 83
atgcagatcc cacaggcgcc ctggccagtc gtctgggcgg tgctacaact gggctggcgg      60
```

-continued

```
ccaggatggt tcttagactc cccagacagg ccctggaacc cccccacctt ctccccagcc      120
ctgctcgtgg tgaccgaagg ggacaacgcc accttcacct gcagcttctc caacacatcg      180
gagagcttcg tgctaaactg gtaccgcatg agccccagca accagacgga caagctggcc      240
gccttccccg aggaccgcag ccagcccggc caggactgcc gcttccgtgt cacacaactg      300
cccaacgggc gtgacttcca catgagcgtg gtcagggccc ggcgcaatga cagcggcacc      360
tacctctgtg gggccatctc cctggccccc aagctgcaga tcaaagagag cctgcgggca      420
gagctcaggg tgacagagag aagggcagaa gtgcccacag cccacccccag ccctcaccc     480 aggccagccg gccagttcca aaccctggtg gttggtgtcg tgggcggcct gctgggcagc      540
ctggtgctgc tagtctgggt cctggccgtc atcaggagta agaggagcag gctcctgcac      600
agtgactaca tgaacatgac tccccgccgc cccgggccca cccgcaagca ttaccagccc      660
tatgccccac cacgcgactt cgcagcctat cgc                                    693
```

```
<210> SEQ ID NO 84
<211> LENGTH: 237
<212> TYPE: PRT
<213> ORGANISM: Artificial Sequence
<220> FEATURE:
<223> OTHER INFORMATION: Receptor
<220> FEATURE:
<223> OTHER INFORMATION: PD1-4-1BB

<400> SEQUENCE: 84

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
            180                 185                 190

Tyr Cys Lys Lys Arg Gly Arg Lys Lys Leu Leu Tyr Ile Phe Lys Gln
            195                 200                 205

Pro Phe Met Arg Pro Val Gln Thr Thr Gln Glu Glu Asp Gly Cys Ser
        210                 215                 220

Cys Arg Phe Pro Glu Glu Glu Glu Gly Gly Cys Glu Leu
225                 230                 235
```

<210> SEQ ID NO 85
<211> LENGTH: 711
<212> TYPE: DNA
<213> ORGANISM: Artificial Sequence
<220> FEATURE:
<223> OTHER INFORMATION: Receptor
<220> FEATURE:
<223> OTHER INFORMATION: PD1-4-1BB

<400> SEQUENCE: 85

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcaggaccc ggcgcaatga cagcggcacc     360
tacctctgtg gggccatctc cctggccccc aaggcgcaga tcaaagagag cctgcgggca     420
gagctcaggt gacagagag aagggcagaa gtgcccacag cccaccccag cccctcaccc     480
aggccagccg gccagttcca aaccctggtt atctacatct gggcgccctt ggccgggact     540
tgtggggtcc ttctcctgtc actggttatc acccttact gcaaaaaacg gggcagaaag     600
aaactcctgt atatattcaa acaaccattt atgagaccag tacaaactac tcaagaggaa     660
gatggctgta gctgccgatt tccagaagaa gaagaaggag gatgtgaact g            711
```

<210> SEQ ID NO 86
<211> LENGTH: 237
<212> TYPE: PRT
<213> ORGANISM: Artificial Sequence
<220> FEATURE:
<223> OTHER INFORMATION: Receptor
<220> FEATURE:
<223> OTHER INFORMATION: PD1A132L-4-1BB

<400> SEQUENCE: 86

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160
```

-continued

```
Arg Pro Ala Gly Gln Phe Gln Thr Leu Val Ile Tyr Ile Trp Ala Pro
            165                 170                 175

Leu Ala Gly Thr Cys Gly Val Leu Leu Leu Ser Leu Val Ile Thr Leu
            180                 185                 190

Tyr Cys Lys Lys Arg Gly Arg Lys Lys Leu Leu Tyr Ile Phe Lys Gln
            195                 200                 205

Pro Phe Met Arg Pro Val Gln Thr Thr Gln Glu Glu Asp Gly Cys Ser
        210                 215                 220

Cys Arg Phe Pro Glu Glu Glu Glu Gly Gly Cys Glu Leu
225                 230                 235
```

```
<210> SEQ ID NO 87
<211> LENGTH: 711
<212> TYPE: DNA
<213> ORGANISM: Artificial Sequence
<220> FEATURE:
<223> OTHER INFORMATION: Receptor
<220> FEATURE:
<223> OTHER INFORMATION: PD1A132L-4-1BB

<400> SEQUENCE: 87
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggcccc aagctgcaga tcaaagagag cctgcgggca     420
gagctcaggg tgacagagag aaagggcagaa gtgcccacag cccaccccag cccctcaccc     480
aggccagccg gccagttcca aaccctggtt atctacatct gggcgccctt ggccgggact     540
tgtgggttcc ttctcctgtc actggttatc acccttact gcaaaaaacg gggcagaaag     600
aaactcctgt atatattcaa acaaccattt atgagaccag tacaaactac tcaagaggaa     660
gatggctgta gctgccgatt ccagaagaa gaagaaggag gatgtgaact g               711
```

```
<210> SEQ ID NO 88
<211> LENGTH: 238
<212> TYPE: PRT
<213> ORGANISM: Artificial Sequence
<220> FEATURE:
<223> OTHER INFORMATION: Receptor
<220> FEATURE:
<223> OTHER INFORMATION: TGFbR-IL12Rb1

<400> SEQUENCE: 88

Met Glu Ala Ala Val Ala Ala Pro Arg Pro Arg Leu Leu Leu Leu Val
1               5                   10                  15

Leu Ala Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
```

```
                    85              90              95
Thr Thr Tyr Cys Cys Asn Gln Asp His Cys Asn Lys Ile Glu Leu Pro
            100             105             110

Thr Thr Val Lys Ser Ser Pro Gly Leu Gly Pro Val Glu Leu Ala Ala
        115             120             125

Val Ile Ala Gly Pro Val Cys Phe Val Cys Ile Ser Leu Met Leu Met
    130             135             140

Val Tyr Ile Arg Ala Ala Arg His Leu Cys Pro Pro Leu Pro Thr Pro
145             150             155             160

Cys Ala Ser Ser Ala Ile Glu Phe Pro Gly Gly Lys Glu Thr Trp Gln
            165             170             175

Trp Ile Asn Pro Val Asp Phe Gln Glu Glu Ala Ser Leu Gln Glu Ala
            180             185             190

Leu Val Val Glu Met Ser Trp Asp Lys Gly Glu Arg Thr Glu Pro Leu
        195             200             205

Glu Lys Thr Glu Leu Pro Glu Gly Ala Pro Glu Leu Ala Leu Asp Thr
    210             215             220

Glu Leu Ser Leu Glu Asp Gly Asp Arg Cys Lys Ala Lys Met
225             230             235
```

<210> SEQ ID NO 89
<211> LENGTH: 714
<212> TYPE: DNA
<213> ORGANISM: Artificial Sequence
<220> FEATURE:
<223> OTHER INFORMATION: Receptor
<220> FEATURE:
<223> OTHER INFORMATION: TGFbR-IL12Rb1

<400> SEQUENCE: 89

```
atggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc     120
tgtacaaaag acaattttac ttgtgtgaca gatgggctct gctttgtctc tgtcacagag     180
accacagaca aagttataca caacagcatg tgtatagctg aaattgactt aattcctcga     240
gataggccgt ttgtatgtgc accctcttca aaaactgggc tgtgactac aacatattgc     300 tgcaatcagg accattgcaa taaaatagaa cttccaacta ctgtaaagtc atcacctggc     360
cttggtcctg tggaactggc agctgtcatt gctggaccag tgtgcttcgt ctgcatctca     420
ctcatgttga tggtctatat cagggccgca cggcacctgt gcccgccgct gcccacaccc     480
tgtgccagct ccgccattga gttccctgga gggaaggaga cttggcagtg gatcaaccca     540
gtggacttcc aggaagaggc atccctgcag gaggccctgg tggtagagat gtcctgggac     600
aaaggcgaga ggactgagcc tctcgagaag acagagctac ctgagggtgc ccctgagctg     660
gccctggata cagagttgtc cttggaggat ggagacaggt gcaaggccaa gatg          714
```

<210> SEQ ID NO 90
<211> LENGTH: 403
<212> TYPE: PRT
<213> ORGANISM: Artificial Sequence
<220> FEATURE:
<223> OTHER INFORMATION: Receptor
<220> FEATURE:
<223> OTHER INFORMATION: TGFbR-IL12Rb2

<400> SEQUENCE: 90

```
Met Gly Arg Gly Leu Leu Arg Gly Leu Trp Pro Leu His Ile Val Leu
1               5               10              15
```

-continued

Trp Thr Arg Ile Ala Ser Thr Ile Pro Pro His Val Gln Lys Ser Val
        20                  25              30

Asn Asn Asp Met Ile Val Thr Asp Asn Asn Gly Ala Val Lys Phe Pro
        35                  40              45

Gln Leu Cys Lys Phe Cys Asp Val Arg Phe Ser Thr Cys Asp Asn Gln
    50                  55              60

Lys Ser Cys Met Ser Asn Cys Ser Ile Thr Ser Ile Cys Glu Lys Pro
65                  70              75              80

Gln Glu Val Cys Val Ala Val Trp Arg Lys Asn Asp Glu Asn Ile Thr
                85              90              95

Leu Glu Thr Val Cys His Asp Pro Lys Leu Pro Tyr His Asp Phe Ile
            100             105             110

Leu Glu Asp Ala Ala Ser Pro Lys Cys Ile Met Lys Glu Lys Lys Lys
            115             120             125

Pro Gly Glu Thr Phe Phe Met Cys Ser Cys Ser Ser Asp Glu Cys Asn
        130             135             140

Asp Asn Ile Ile Phe Ser Glu Glu Tyr Asn Thr Ser Asn Pro Asp Leu
145             150             155             160

Leu Leu Val Ile Phe Gln Val Thr Gly Ile Ser Leu Leu Pro Pro Leu
            165             170             175

Gly Val Ala Ile Ser Val Ile Ile Ile Phe Tyr Gln Gln Lys Val Phe
        180             185             190

Val Leu Leu Ala Ala Leu Arg Pro Gln Trp Cys Ser Arg Glu Ile Pro
        195             200             205

Asp Pro Ala Asn Ser Thr Cys Ala Lys Lys Tyr Pro Ile Ala Glu Glu
    210             215             220

Lys Thr Gln Leu Pro Leu Asp Arg Leu Leu Ile Asp Trp Pro Thr Pro
225             230             235             240

Glu Asp Pro Glu Pro Leu Val Ile Ser Glu Val Leu His Gln Val Thr
            245             250             255

Pro Val Phe Arg His Pro Pro Cys Ser Asn Trp Pro Gln Arg Glu Lys
        260             265             270

Gly Ile Gln Gly His Gln Ala Ser Glu Lys Asp Met Met His Ser Ala
        275             280             285

Ser Ser Pro Pro Pro Arg Ala Leu Gln Ala Glu Ser Arg Gln Leu
    290             295             300

Val Asp Leu Tyr Lys Val Leu Glu Ser Arg Gly Ser Asp Pro Lys Pro
305             310             315             320

Glu Asn Pro Ala Cys Pro Trp Thr Val Leu Pro Ala Gly Asp Leu Pro
            325             330             335

Thr His Asp Gly Tyr Leu Pro Ser Asn Ile Asp Asp Leu Pro Ser His
            340             345             350

Glu Ala Pro Leu Ala Asp Ser Leu Glu Glu Leu Glu Pro Gln His Ile
            355             360             365

Ser Leu Ser Val Phe Pro Ser Ser Ser Leu His Pro Leu Thr Phe Ser
    370             375             380

Cys Gly Asp Lys Leu Thr Leu Asp Gln Leu Lys Met Arg Cys Asp Ser
385             390             395             400

Leu Met Leu

<210> SEQ ID NO 91
<211> LENGTH: 1209
<212> TYPE: DNA

```
<213> ORGANISM: Artificial Sequence
<220> FEATURE:
<223> OTHER INFORMATION: Receptor
<220> FEATURE:
<223> OTHER INFORMATION: TGFbR-IL12Rb2

<400> SEQUENCE: 91
atgggtcggg ggctgctcag gggcctgtgg ccgctgcaca tcgtcctgtg gacgcgtatc      60
gccagcacga tcccaccgca cgttcagaag tcggttaata cgacatgat agtcactgac       120 aacaacggtg cagtcaagtt tccacaactg tgtaaatttt gtgatgtgag attttccacc      180
tgtgacaacc agaaatcctg catgagcaac tgcagcatca cctccatctg tgagaagcca      240
caggaagtct gtgtggctgt atggagaaag aatgacgaga acataacact agagacagtt      300
tgccatgacc ccaagctccc ctaccatgac tttattctgg aagatgctgc ttctccaaag      360
tgcattatga aggaaaaaaa aaagcctggt gagactttct tcatgtgttc ctgtagctct      420
gatgagtgca atgacaacat catcttctca gaagaatata acaccagcaa tcctgacttg      480
ttgctagtca tatttcaagt gacaggcatc agcctcctgc caccactggg agttgccata      540
tctgtcatca tcatcttcta ccagcaaaag gtgtttgttc cctagcagc cctcagacct       600 cagtggtgta gcagagaaat tccagatcca gcaaatagca cttgcgctaa gaaatatccc      660
attgcagagg agaagacaca gctgcccttg acaggctcc tgatagactg gcccacgcct        720
gaagatcctg aaccgctggt catcagtgaa gtccttcatc aagtgacccc agttttcaga       780 catccccct gctccaactg gccacaaagg gaaaaaggaa tccaaggtca tcaggcctct         840
gagaaagaca tgatgcacag tgcctcaagc ccaccacctc caagagctct ccaagctgag        900
agcagacaac tggtggatct gtacaaggtg ctggagagca ggggctccga cccaaagcca        960
gaaaacccag cctgtccctg gacggtgctc ccagcaggtg accttcccac ccatgatggc       1020
tacttaccct ccaacataga tgacctcccc tcacatgagg cacctctcgc tgactctctg      1080
gaagaactgg agcctcagca catctccctt tctgtttcc cctcaagttc tcttcacca         1140 ctcaccttct cctgtggtga taagctgact ctggatcagt aaagatgag gtgtgactcc        1200 ctcatgctc                                                             1209

<210> SEQ ID NO 92
<211> LENGTH: 268
<212> TYPE: PRT
<213> ORGANISM: Artificial Sequence
<220> FEATURE:
<223> OTHER INFORMATION: Receptor
<220> FEATURE:
<223> OTHER INFORMATION: Tim3-CD28

<400> SEQUENCE: 92

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95
```

-continued

```
Ile Glu Asn Val Thr Leu Ala Asp Ser Gly Ile Tyr Cys Cys Arg Ile
        100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
                180                 185                 190

Arg Asp Ser Gly Ala Thr Ile Arg Phe Trp Val Leu Val Val Val Gly
            195                 200                 205

Gly Val Leu Ala Cys Tyr Ser Leu Leu Val Thr Val Ala Phe Ile Ile
        210                 215                 220

Phe Trp Val Arg Ser Lys Arg Ser Arg Leu Leu His Ser Asp Tyr Met
225                 230                 235                 240

Asn Met Thr Pro Arg Arg Pro Gly Pro Thr Arg Lys His Tyr Gln Pro
                245                 250                 255

Tyr Ala Pro Pro Arg Asp Phe Ala Ala Tyr Arg Ser
            260                 265
```

```
<210> SEQ ID NO 93
<211> LENGTH: 804
<212> TYPE: DNA
<213> ORGANISM: Artificial Sequence
<220> FEATURE:
<223> OTHER INFORMATION: Receptor
<220> FEATURE:
<223> OTHER INFORMATION: Tim3-CD28

<400> SEQUENCE: 93
atgttttcac atcttccctt tgactgtgtc ctgctgctgc tgctgctact acttacaagg      60
tcctcagaag tggaatacag agcggaggtc ggtcagaatg cctatctgcc ctgcttctac     120
accccagccg ccccagggaa cctcgtgccc gtctgctggg gcaaaggagc ctgtcctgtg     180
tttgaatgtg gcaacgtggt gctcaggact gatgaaaggg atgtgaatta ttggacatcc     240
agatactggc taaatgggga tttccgcaaa ggagatgtgt ccctgaccat agagaatgtg     300
actctagcag acagtgggat ctactgctgc gaatccaaa tcccaggcat aatgaatgat      360
gaaaaattta acctgaagtt ggtcatcaaa ccagccaagg tcaccctgc accgactcgg      420 cagagagact tcactgcagc ctttccaagg atgcttacca ccaggggaca tggcccagca     480
gagacacaga cactggggag cctccctgac ataaatctaa cacaaatatc cacattggcc     540
aatgagttac gggactctag gttggccaat gacttacggg actccggagc aaccatcaga     600
ttttgggtgc tggtggtggt tggtggagtc ctggcttgct atagcttact agtaacagtg     660
gcctttatta ttttctgggt gaggagtaag aggagcaggc tcctgcacag tgactacatg     720
aacatgactc cccgccgccc cgggcccacc cgcaagcatt accagcccta tgccccacca     780
cgcgacttcg cagcctatcg ctcc                                            804
```

```
<210> SEQ ID NO 94
<211> LENGTH: 18
<212> TYPE: PRT
<213> ORGANISM: Artificial Sequence
```

-continued

<220> FEATURE:
<223> OTHER INFORMATION: Linker
<220> FEATURE:
<223> OTHER INFORMATION: T2A

<400> SEQUENCE: 94

Glu Gly Arg Gly Ser Leu Leu Thr Cys Gly Asp Val Glu Glu Asn Pro
1               5                   10                  15

Gly Pro

<210> SEQ ID NO 95
<211> LENGTH: 54
<212> TYPE: DNA
<213> ORGANISM: Artificial Sequence
<220> FEATURE:
<223> OTHER INFORMATION: Linker
<220> FEATURE:
<223> OTHER INFORMATION: T2A

<400> SEQUENCE: 95
gagggcagag gaagtcttct aacatgcggt gacgtggagg agaatcccgg ccct          54

<210> SEQ ID NO 96
<211> LENGTH: 7
<212> TYPE: PRT
<213> ORGANISM: Artificial Sequence
<220> FEATURE:
<223> OTHER INFORMATION: Spacer
<220> FEATURE:
<223> OTHER INFORMATION: T2A

<400> SEQUENCE: 96

Ser Gly Arg Ser Gly Gly Gly
1               5

<210> SEQ ID NO 97
<211> LENGTH: 21
<212> TYPE: DNA
<213> ORGANISM: Artificial Sequence
<220> FEATURE:
<223> OTHER INFORMATION: Spacer
<220> FEATURE:
<223> OTHER INFORMATION: T2A

<400> SEQUENCE: 97
tccggaagat ctggcggcgg a                                              21

<210> SEQ ID NO 98
<211> LENGTH: 22
<212> TYPE: PRT
<213> ORGANISM: Artificial Sequence
<220> FEATURE:
<223> OTHER INFORMATION: Linker
<220> FEATURE:
<223> OTHER INFORMATION: F2A

<400> SEQUENCE: 98

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 99
<211> LENGTH: 66
<212> TYPE: DNA
<213> ORGANISM: Artificial Sequence
<220> FEATURE:

```
<223> OTHER INFORMATION: Linker
<220> FEATURE:
<223> OTHER INFORMATION: F2A

<400> SEQUENCE: 99
gtgaaacaga ctttgaattt tgaccttctc aagttggcgg gagacgtgga gtccaaccca      60
gggccg                                                                 66

<210> SEQ ID NO 100
<211> LENGTH: 4
<212> TYPE: PRT
<213> ORGANISM: Artificial Sequence
<220> FEATURE:
<223> OTHER INFORMATION: Furin Cleavage
<220> FEATURE:
<223> OTHER INFORMATION: 1
<220> FEATURE:
<221> NAME/KEY: misc_feature
<222> LOCATION: (2)..(2)
<223> OTHER INFORMATION: Xaa can be any naturally occurring amino acid

<400> SEQUENCE: 100

Arg Xaa Lys Arg
1

<210> SEQ ID NO 101
<211> LENGTH: 4
<212> TYPE: PRT
<213> ORGANISM: Artificial Sequence
<220> FEATURE:
<223> OTHER INFORMATION: Furin Cleavage
<220> FEATURE:
<223> OTHER INFORMATION: 2
<220> FEATURE:
<221> NAME/KEY: misc_feature
<222> LOCATION: (2)..(2)
<223> OTHER INFORMATION: Xaa can be any naturally occurring amino acid

<400> SEQUENCE: 101

Arg Xaa Arg Arg
1

<210> SEQ ID NO 102
<211> LENGTH: 4
<212> TYPE: PRT
<213> ORGANISM: Artificial Sequence
<220> FEATURE:
<223> OTHER INFORMATION: Furin Cleavage
<220> FEATURE:
<223> OTHER INFORMATION: 3
<220> FEATURE:
<221> NAME/KEY: misc_feature
<222> LOCATION: (2)..(3)
<223> OTHER INFORMATION: Xaa can be any naturally occurring amino acid

<400> SEQUENCE: 102

Arg Xaa Xaa Arg
1

<210> SEQ ID NO 103
<211> LENGTH: 4
<212> TYPE: PRT
<213> ORGANISM: Artificial Sequence
<220> FEATURE:
<223> OTHER INFORMATION: Furin Cleavage
<220> FEATURE:
<223> OTHER INFORMATION: 4

<400> SEQUENCE: 103
```

Arg Gly Lys Arg
1

<210> SEQ ID NO 104
<211> LENGTH: 5
<212> TYPE: PRT
<213> ORGANISM: Artificial Sequence
<220> FEATURE:
<223> OTHER INFORMATION: Furin Cleavage
<220> FEATURE:
<223> OTHER INFORMATION: 5
<220> FEATURE:
<221> NAME/KEY: Xaa
<222> LOCATION: (1)..(1)
<223> OTHER INFORMATION: Xaa is K or R
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: Xaa
<222> LOCATION: (4)..(4)
<223> OTHER INFORMATION: Xaa is K or R

<400> SEQUENCE: 104

Xaa Arg Xaa Xaa Arg
1               5

<210> SEQ ID NO 105
<211> LENGTH: 96
<212> TYPE: DNA
<213> ORGANISM: Artificial Sequence
<220> FEATURE:
<223> OTHER INFORMATION: Linker
<220> FEATURE:
<223> OTHER INFORMATION: F-GS2-T2A

<400> SEQUENCE: 105
cgtgcgaaga ggggcggcgg gggctccggc gggggaggca gtgagggccg cggctccctg        60
ctgacctgcg gagatgtaga agagaaccca ggcccc                                  96

<210> SEQ ID NO 106
<211> LENGTH: 32
<212> TYPE: PRT
<213> ORGANISM: Artificial Sequence
<220> FEATURE:
<223> OTHER INFORMATION: Linker
<220> FEATURE:
<223> OTHER INFORMATION: F-GS2-T2A

<400> SEQUENCE: 106

Arg Ala Lys Arg Gly Gly Gly Gly Ser Gly Gly Gly Gly Ser Glu Gly
1               5               10              15

Arg Gly Ser Leu Leu Thr Cys Gly Asp Val Glu Glu Asn Pro Gly Pro
            20              25              30